(12) United States Patent
Naef et al.

(10) Patent No.: US 11,905,293 B2
(45) Date of Patent: *Feb. 20, 2024

(54) DUAL MODE OF ACTION SOLUBLE GUANYLATE CYCLASE ACTIVATORS AND PHOSPHODIESTERASE INHIBITORS AND USES THEREOF

(71) Applicant: TOPADUR PHARMA AG, Schlieren (CH)

(72) Inventors: Reto Naef, Rheinfelden (CH); Hermann Tenor, Constance (DE)

(73) Assignee: TOPADUR PHARMA AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/477,122

(22) Filed: Sep. 16, 2021

(65) Prior Publication Data

US 2022/0073529 A1 Mar. 10, 2022

Related U.S. Application Data

(63) Continuation of application No. 16/615,283, filed as application No. PCT/EP2018/063339 on May 22, 2018, now Pat. No. 11,155,558.

(30) Foreign Application Priority Data

May 22, 2017 (EP) ..................................... 17172193

(51) Int. Cl.
*C07D 487/04* (2006.01)
*A61P 15/10* (2006.01)
*A61P 25/00* (2006.01)
*A61P 3/10* (2006.01)

(52) U.S. Cl.
CPC ............ *C07D 487/04* (2013.01); *A61P 15/10* (2018.01); *A61P 3/10* (2018.01); *A61P 25/00* (2018.01)

(58) Field of Classification Search
CPC .................................................. C07D 487/04
See application file for complete search history.

(56) References Cited

U.S. PATENT DOCUMENTS

| | | | |
|---|---|---|---|
| 6,362,178 B1 | 3/2002 | Niewöhner et al. | |
| 2002/0182162 A1 | 12/2002 | Shahinpoor et al. | |
| 2002/0193388 A1 | 12/2002 | Maw et al. | |
| 2006/0106019 A1 | 5/2006 | Greenpharma | |

FOREIGN PATENT DOCUMENTS

| | | |
|---|---|---|
| CN | 102292340 B | 5/2015 |
| EP | 0995751 A2 | 4/2000 |
| JP | 2002-523450 A5 | 10/2006 |
| WO | 1999/24433 A1 | 5/1999 |
| WO | 2000/012076 A1 | 3/2000 |
| WO | 2001/60825 A1 | 8/2001 |
| WO | 2010/081647 A2 | 7/2010 |
| WO | 2010/084438 A1 | 7/2010 |
| WO | 2011/075655 A1 | 7/2011 |

OTHER PUBLICATIONS

Any references not provided herewith were previously submitted in U.S. Appl. No. 16/615,283, to which this application claims priority.
Beedimani et al., "Current and Emerging Uses of Phosphodiesterase 5 Inhibitors," International Journal of Pharma and Bio Sciences 5(2):530-539 (2014).
Dobhal et al., "Current Status and Future Prospects of PDE5 Inhibitors for Various Therapeutic Implications," Clinical Review in Pharmaceutical Sciences 1(3):13-27 (2012).
Mónica et al., "Modulating cGMP levels as therapeutic drug targets in cardiovascular and non-cardiovascular diseases," OA Biochemistry 2(1):1-12 (2014).
Nossaman et al., "Stimulators and Activators of Soluble Guanylate Cyclase: Review and Potential Therapeutic Indications," Critical Care Research and Practice vol. 2012:1-13 (2012).
Palit et al., "An update on new oral PDE5 inhibitors for treatment of erectile dysfunction," Nat. Rev. Urol. 7:603-609 (2010).
Papapetropoulos et al., "Extending the translational potential of targeting NO/cGMP-regulated pathways in the CVS," British Journal of Pharmacology 172:1397-1414 (2015).
Wroński et al., "The new horizons of pharmacotherapy. Unexpected pharmacological actions and a new therapeutic strategy of phosphodiesterase-5 inhibitors," Central European Journal of Urology 67:314-318 (2014).
The International Search Report issued in International Application No. PCT/EP2018/063339 dated Jul. 17, 2018.
Flores Toque, Haroldo A. et al., "Synthesis and Pharmacological Evaluations of Sildenafil Analogues for Treatment of Erectile Dysfunction," Journal of Medicinal Chemistry, 2008, vol. 51, pp. 2807-2815.

(Continued)

*Primary Examiner* — Susanna Moore
(74) *Attorney, Agent, or Firm* — MEDLER FERRO WOODHOUSE & MILLS PLLC

(57) ABSTRACT

The present invention relates to compounds of formula I or pharmaceutically acceptable salt, solvate or hydrate thereof and their use in methods of treating or preventing a disease alleviated by inhibition of PDE5 in a human or in a non-human mammal.

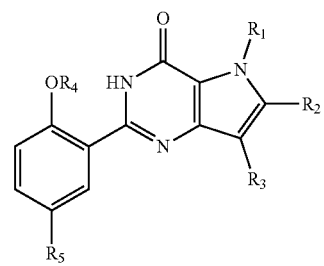

21 Claims, 2 Drawing Sheets

(56) References Cited

OTHER PUBLICATIONS

Ohwada, Tomohiko et al., "Structual Design and Synthesis of Nitric Oxide Donors Aimed to Controlled Release," Journal of the Society of Synthetic Organic Chemistry, Japan, 2003, vol. 61, No. 3, pp. 45-57.

DUAL MODE OF ACTION SOLUBLE GUANYLATE CYCLASE ACTIVATORS AND PHOSPHODIESTERASE INHIBITORS AND USES THEREOF

The present invention relates to pharmaceutically useful compounds, in particular to compounds which are activators of the enzyme soluble guanylate cyclase (sGC) and at the same time inhibit cyclic guanosine 3',5'-monophosphate phosphodiesterases (cGMP PDEs), in particular type 5 cyclic guanosine 3',5'-monophosphate phosphodiesterase (cGMP PDE5). The compounds of the present invention have utility in a variety of therapeutic areas, including male erectile dysfunction (MED), priapism, female sexual dysfunction, Alzheimer's disease, pulmonary artery hypertension (PAH), chronic thromboembolic pulmonary hypertension, livedoid vasculopathy, thromboangitis obliterans, chronic anal fissure, skin fibrosis, glaucoma, endothelial dysfunction (ED), benign prostatic hyperplasia (BPH) and lower urinary tract symptoms (LUTS), priapism, hair loss, cystic fibrosis, peripheral vascular disease, vascular disorders such as Raynaud's disease, systemic sclerosis (SSc), scleroderma, diabetes, and in particular for pulmonary artery hypertension (PAH), chronic thromboembolic pulmonary hypertension, male erectile dysfunction, priapism, female sexual dysfunction, wound healing, in particular chronic wound healing, diabetic foot, diabetic foot ulcer, leg ulcer, diabetic neuropathy and pressure ulcer.

RELATED ART

Phosphodiesterases (PDEs) are enzymes that catalyzes the hydrolysis and thus the degradation of cyclic adenosine monophosphate (cAMP) and cyclic guanosine monophosphate (cGMP) and thereby regulates intracellular levels of second messengers. Inhibition of PDEs leads to increasing intracellular concentrations of endogenous cAMP/cGMP. Therefore, inhibition of PDE can mediate a variety of physiological mechanisms at different cell and organ levels.

Phosphodiesterase type 5 (PDE5) hydrolyses cyclic guanylate monophosphate (cGMP) specifically to 5' GMP. The selective inhibition of PDE5 has been validated as a relevant approach and strategies directed to promote inhibition of PDE5 activity have been applied as therapeutic tools, in particular, in neuronal and cardiovascular conditions. Moreover, the introduction of PDE5 inhibitors has revolutionized the treatment of male erectile dysfunction (MED) (Dobhal T, Kaur S, Prakash Sharma O, Hari Kumar S L, Critical Review in Pharmaceutical Sciences (2012) 1(3):13-27; Palit V, Eardley I, Nature Reviews Urology (2010) 7(11):603-609). Several PDE5 inhibitors are on the market and are characterized particularly for MED or pulmonary hypertension (PH), in particular pulmonary artery hypertension (PAH) (Papapetropoulos A, Hobbs A J, Topouzis S, British Journal of Pharmacology (2015) 172:1397-1414; Monica F Z, Murad F, Bian K, OA Biochemistry (2014) March 11; 2(1):3; Beedimani R S, Kalmath B, Int J Pharm Bio Sci (2014) 5(2): 530-539; Wronski S, Cent European J Urol (2014) 67: 314-318; and references cited therein). Most prominent examples of PDE5 inhibitors are Sildenafil, Tadalafil, Vardenafil and Mirodenafil which have been described among others, for example, in WO 99/24433, WO 01/60825, EP 995'751 and WO 2011/075655.

Beside the success of the known PDE5 inhibitors, there is still a need for further and in particular more effective drugs and their pharmaceutical compositions for use in the therapeutic treatment or prophylaxis of diseases associated with a disturbed cGMP balance. Moreover, and in general, there is still a need for compounds and their pharmaceutical compositions being beneficial for use in the therapeutic treatment or prophylaxis of diseases associated with a disturbed cGMP balance.

Endothelial dysfunction leads to an imbalance of vasodilator and vasoconstrictor mediators shifted towards the latter. One key mechanism remains impaired endothelial NO generation and associated, reduced activation of soluble guanylyl cyclase (sGC) in adjacent smooth muscle cells. Strategies to increase disturbed cGMP levels by enhancing cGMP in vascular smooth muscle by improving cGMP synthesis and inhibiting its degradation have been described. Examples are combinations of sGC stimulators or activators in combination with PDE5 inhibitors, for example WO 2010/081647 or US2002/0182162. Compounds however, which stimulate sGC and inhibit PDE5 at the same time however have not been described.

SUMMARY OF THE INVENTION

We have surprisingly found that the compounds of the present invention are dual-pharmacology NO-releasing PDE5 inhibitors believed to release NO in addition to its PDE5 inhibition in a more than additive, thus, synergistic fashion. We have further surprisingly found that the compounds of the present invention are highly bound to plasma proteins when they reach blood circulation. Such strongly bound compounds cannot exhibit their biological activity, making them especially prone to local application and local action. The synergistic increase of cGMP results in highly potent vasodilatation, angiogenesis and inhibition of endothelial dysfunction (see FIG. 1). Thus, the dual-pharmacology NO-releasing PDE5 inhibitors of the present invention are expected to be especially beneficial in treating disorders where NO production is diminished such as in conditions of endothelial dysfunction. Furthermore, the inventive dual-pharmacology NO-releasing PDE5 inhibitors are further believed to be highly beneficial for the treatment of diabetic patients.

Moreover, we have surprisingly found that the compounds of the present invention show even a significantly higher efficacy to elevate intracellular cGMP. as compared to known PDE5 inhibitors such as sildenafil or mirodenafil. In addition we discovered a very high plasma protein binding with several compounds of the invention, making them especially prone to local applications and local actions. As a consequence, the novel pyrrolo pyrimidone compounds of the present invention are useful in the therapy and prophylaxis of diseases which are associated with a disturbed cGMP balance.

Due to the potent and selective PDE5 inhibition in combination with stimulation of soluble guanylate cyclase exhibited by compounds of the present invention, cGMP levels are elevated, which in turn can give rise to beneficial vasodilatory, anti-vasospastic, anti-platelet, natriuretic and diuretic activities. Furthermore, the dual-pharmacology NO-releasing PDE5 inhibitors allows the release of nitric oxide for activating the soluble guanylate cyclase as well as the PDE5 inhibition in a more than additive fashion. Thus, the compounds of the present invention have utility in variety of therapeutic areas where a disturbed cGMP balance occurred and/or PDE5 inhibition is thought to be beneficial. Some of the preferred therapeutic areas are pulmonary artery hypertension (PAH), chronic thromboembolic pulmonary hypertension, male erectile dysfunction, priapism, female sexual dysfunction, wound healing, in particular chronic wound healing, diabetic foot, diabetic foot ulcer, leg ulcer, Raynaud's, male erectile dysfunction, Alzheimer's disease, livedoid vasculopathy, thromboangitis obliterans, chronic anal fissure, skin fibrosis, diabetes, hair loss, skin aging, vascular aging, pulmonary artery hypertension and chronic heart failure. The compounds of the invention are especially suited for local drug application as depicted in FIG. 2.

Thus, in a first aspect, the present invention provides for a compound of formula I

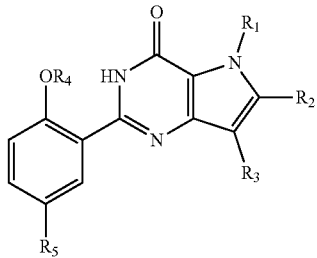

or pharmaceutically acceptable salt, solvate or hydrate thereof, wherein
at least one of $R_1$, $R_2$, $R_3$, $R_4$, or $R_5$ independently of each other comprises at least one $ONO_2$ or ONO moiety, and wherein preferably said $R_1$, $R_2$, $R_3$, $R_4$, and $R_5$ comprise together at least two moieties selected from $ONO_2$ or ONO moieties;

$R_1$ is $C_1$-$C_3$alkyl optionally substituted with F, $C_3$-$C_6$cycloalkyl, $C_1$-$C_3$alkoxy, ONO, $ONO_2$;

$R_2$ is H, $C_1$-$C_3$alkyl optionally substituted with OH, ONO, $ONO_2$; C(O)OH, C(O)O$C_1$-$C_3$alkyl, CHO, CN, C(O)N($R_6$)$OR_7$, $CR_8$=N—$OR_9$, $CR_8$=N—$NR_{10}R_{11}$, $CR_8$=$NR_{12}$, $CR_8$=N—$ONO_2$, $C_1$-$C_3$alkoxy; $C_1$-$C_3$alkylene-Y, wherein Y is ONO, $ONO_2$, C(O)OH, C(O)O$C_1$-$C_3$alkyl, CHO, CN, OH, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)O$C_1$-$C_3$alkyl, $OC_1$-$C_3$alkylene-C(O)N($R_6$)$OR_7$, S($O_{0-2}$)$C_1$-$C_3$alkyl, $CR_8$=N—$OR_9$, $CR_8$=N—$NR_{10}R_{11}$, $CR_8$=$NR_{12}$ or $CR_8$=N—$ONO_2$;

$R_3$ is $C_1$-$C_4$alkyl optionally substituted with F, OH, ONO, $ONO_2$, $C_1$-$C_3$alkoxy, $C_3$-$C_6$cycloalkyl; $C_3$-$C_6$cycloalkyl, $C_2$-$C_6$alkenyl, $C_2$-$C_6$alkynyl;

$R_4$ is $C_1$-$C_6$alkyl optionally substituted with $C_3$-$C_6$cycloalkyl, $C_1$-$C_6$alkoxy, F, ONO, $ONO_2$; $C_2$-$C_6$alkenyl, $C_2$-$C_6$alkynyl, $C_3$-$C_6$cycloalkyl;

$R_5$ is H, $SO_2NR_{13}R_{14}$, $NHSO_2NR_{13}R_{14}$;

$R_6$ is H or $C_1$-$C_3$alkyl;

$R_7$ is H, $C_1$-$C_3$alkyl, $C_1$-$C_3$alkoxy, $C_1$-$C_3$alkyl substituted with phenyl, benzyl or a heterocyclic ring, wherein said phenyl, benzyl or said heterocyclic ring are independently optionally substituted by $C_1$-$C_3$alkyl, F;

$R_8$ is H, $CH_3$ or $C_2H_5$;

$R_9$ is H, $C_1$-$C_3$alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)O$C_1$-$C_3$alkyl, $OC_1$-$C_3$alkylene-C(O)N($R_6$)$OR_7$, S($O_{0-2}$)$C_1$-$C_3$alkyl;

$R_{10}$ and $R_{11}$ are each independently H, $C_1$-$C_3$alkyl optionally substituted with OH, ONO, $ONO_2$, CN, COOH, COO$C_1$-$C_3$, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)O$C_1$-$C_3$alkyl, $OC_1$-$C_3$alkylene-C(O)N($R_6$)$OR_7$, S($O_{0-2}$)$C_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl;

$R_{12}$ is $C_1$-$C_3$ alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)O$C_1$-$C_3$alkyl, $OC_1$-$C_3$alkylene-C(O)N($R_6$)$OR_7$, S($O_{0-2}$)$C_1$-$C_3$alkyl;

$R_{13}$ and $R_{14}$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with $R_{15}$;

$R_{15}$ is $C_1$-$C_6$alkyl optionally substituted with halogen, OH, ONO, $ONO_2$, $C_1$-$C_3$alkoxy, $C_1$-$C_3$haloalkoxy, $COOR_{16}$, $NR_{17}R_{18}$, C=$NR_{19}$, or with a tetrazole moiety which is optionally substituted with $C_1$-$C_3$alkyl; or a heteroaryl ring which is optionally substituted with F, wherein the at least one heteroatom of said heteroaryl ring is nitrogen;

$R_{16}$ is H, or $C_1$-$C_4$alkyl optionally substituted with F, OH, ONO, $ONO_2$, $NR_{17}R_{18}$, or with a heteroaryl ring, wherein the at least one heteroatom of said heteroaryl ring is nitrogen, and wherein preferably said heteroaryl ring is selected from pyrrolidine, piperidine, piperazine, morpholine, pyrrole, and imidazole, wherein nitrogen atom is directly bound to $C_1$-$C_4$ alkyl;

$R_{17}$ and $R_{18}$ are each independently H or $C_1$-$C_4$alkyl optionally substituted with ONO, $ONO_2$;

$R_{19}$ is $C_1$-$C_4$alkyl optionally substituted with F, ONO, $ONO_2$; $C_3$-$C_6$cycloalkyl.

In a further aspect, the present invention provides for a pharmaceutical composition comprising at least one of the inventive compound of formula I, or a pharmaceutically acceptable salt, solvate or hydrate thereof, and a pharmaceutically acceptable excipient, adjuvant, or carrier.

In another aspect, the present invention provides for a compound of formula I, or a pharmaceutical composition, or a pharmaceutically acceptable salt, solvate or hydrate thereof, for use as a medicament.

In another aspect, the present invention provides for a compound of formula I, or a pharmaceutical composition, or a pharmaceutically acceptable salt, solvate or hydrate thereof, for use in a method of treating or preventing a disease alleviated by inhibition of PDE5 in a human or in a non-human mammal, preferably in a human, wherein preferably said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure.

In another aspect, the present invention provides for a compound of formula I, or a pharmaceutical composition, or a pharmaceutically acceptable salt, solvate or hydrate thereof, for use in a method of treating or preventing a disease in a human or in a non-human mammal, preferably in a human, wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

Further aspects and embodiments of the present invention will be become apparent as this description continues.

DETAILED DESCRIPTION OF THE INVENTION

Figure 1:
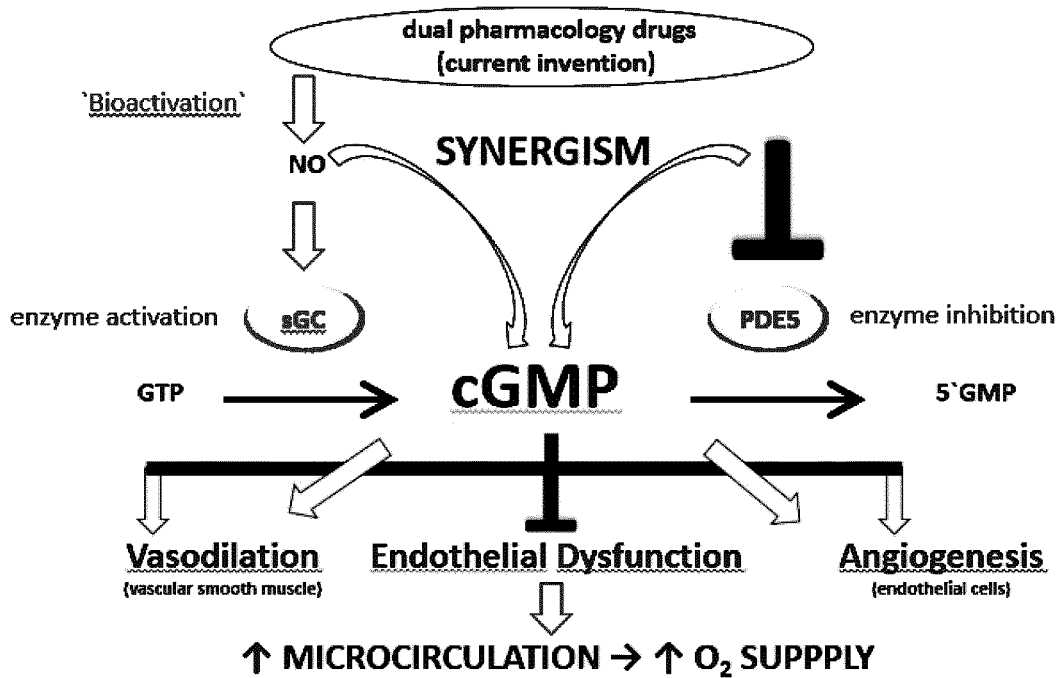
FIG. 1: PDE5 inhibition and activation of soluble guanylate cyclase from one molecule

Unless defined otherwise, all technical and scientific terms used herein have the same meanings as commonly understood by one of ordinary skill in the art to which this invention belongs.

We have surprisingly found that the compounds of the present invention are dual-pharmacology NO-releasing PDE5 inhibitors believed to release NO in addition to its PDE5 inhibition resulting in a more than additive stimulation of intracellular cGMP elevation. Moreover, the compounds of the present invention show even a significantly higher efficacy to stimulate cGMP as compared to known single pharmacology PDE5 inhibitors such as sildenafil or mirodenafil. Furthermore, the compounds of the present invention are highly bound to plasma proteins when they reach blood circulation making them especially prone to local application and local action.

Thus, in a first aspect, the present invention provides for a compound of formula I,

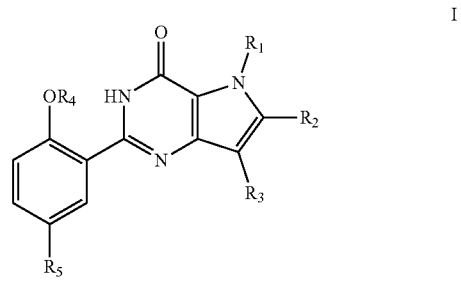

or pharmaceutically acceptable salt, solvate or hydrate thereof, wherein at least one of $R_1$, $R_2$, $R_3$, $R_4$, or $R_5$ independently of each other comprises at least one $ONO_2$ or ONO moiety, and wherein preferably said $R_1$, $R_2$, $R_3$, $R_4$, and $R_5$ comprise together at least two moieties selected from $ONO_2$ or ONO moieties;

$R_1$ is $C_1$-$C_3$alkyl optionally substituted with F, $C_3$-$C_6$cycloalkyl, $C_1$-$C_3$alkoxy, ONO, $ONO_2$;

$R_2$ is H, $C_1$-$C_3$alkyl optionally substituted with OH, ONO, $ONO_2$; C(O)OH, C(O)O$C_1$-$C_3$alkyl, CHO, CN, C(O)N($R_6$)O$R_7$, $CR_8$=N—O$R_9$, $CR_8$=N—N$R_{10}R_{11}$, $CR_8$=N$R_{12}$, $CR_8$=N—$ONO_2$, $C_1$-$C_3$alkoxy; $C_1$-$C_3$alkylene-Y, wherein Y is ONO, $ONO_2$, C(O)OH, C(O)O$C_1$-$C_3$alkyl, CHO, CN, OH, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl, $CR_8$=N—O$R_9$, $CR_8$=N—N$R_{10}R_{11}$, $CR_8$=N$R_{12}$ or $CR_8$=N—$ONO_2$;

$R_3$ is $C_1$-$C_4$alkyl optionally substituted with F, OH, ONO, $ONO_2$, $C_1$-$C_3$alkoxy, $C_3$-$C_6$cycloalkyl; $C_3$-$C_6$cycloalkyl, $C_2$-$C_6$alkenyl, $C_2$-$C_6$alkynyl;

$R_4$ is $C_1$-$C_6$alkyl optionally substituted with $C_3$-$C_6$cycloalkyl, $C_1$-$C_6$alkoxy, F, ONO, $ONO_2$; $C_2$-$C_6$alkenyl, $C_2$-$C_6$alkynyl, $C_3$-$C_6$cycloalkyl;

$R_5$ is H, $SO_2NR_{13}R_{14}$, $NHSO_2NR_{13}R_{14}$;

$R_6$ is H or $C_1$-$C_3$alkyl;

$R_7$ is H, $C_1$-$C_3$alkyl, $C_1$-$C_3$alkoxy, $C_1$-$C_3$alkyl substituted with phenyl, benzyl or a heterocyclic ring, wherein said phenyl, benzyl or said heterocyclic ring are independently optionally substituted by $C_1$-$C_3$alkyl, F;

$R_8$ is H, $CH_3$ or $C_2H_5$;

$R_9$ is H, $C_1$-$C_3$alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl; $R_{10}$ and $R_{11}$ are each independently H, $C_1$-$C_3$alkyl optionally substituted with OH, ONO, $ONO_2$, CN, COOH, COO$C_1$-$C_3$, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl;

$R_{12}$ is $C_1$-$C_3$ alkyl optionally substituted with OH, ONO, ONO$_2$, CN, COOH, COOC$_1$-$C_3$alkyl, $C_1$-$C_3$alkoxy, OC(O)H, OC(O)—C$_1$-$C_3$alkyl, C(O)N(R$_6$)OR$_7$, OC$_1$-$C_3$alkylene-C(O)OH, OC$_1$-$C_3$alkylene-C(O)OC$_1$-$C_3$alkyl, OC$_1$-$C_3$alkylene-C(O)N(R$_6$)OR$_7$, S(O$_{0-2}$)C$_1$-$C_3$alkyl;

$R_{13}$ and $R_{14}$ are each independently H or $C_1$-$C_6$alkyl optionally substituted with F, OH, ONO, ONO$_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with $R_{15}$;

$R_{15}$ is $C_1$-$C_6$alkyl optionally substituted with halogen, OH, ONO, ONO$_2$, $C_1$-$C_3$alkoxy, $C_1$-$C_3$haloalkoxy, COOR$_{16}$, NR$_{17}$R$_{18}$, C=NR$_{19}$, or with a tetrazole moiety which is optionally substituted with $C_1$-$C_3$alkyl; or a heteroaryl ring which is optionally substituted with F, wherein the at least one heteroatom of said heteroaryl ring is nitrogen;

$R_{16}$ is H, or $C_1$-$C_4$alkyl optionally substituted with F, OH, ONO, ONO$_2$, NR$_{17}$R$_{18}$, or with a heteroaryl ring, wherein the at least one heteroatom of said heteroaryl ring is nitrogen, and wherein preferably said heteroaryl ring is selected from pyrrolidine, piperidine, piperazine, morpholine, pyrrole, and imidazole, wherein nitrogen atom is directly bound to $C_1$-$C_4$ alkyl;

$R_{17}$ and $R_{18}$ are each independently H or $C_1$-$C_4$alkyl optionally substituted with ONO, ONO$_2$;

$R_{19}$ is $C_1$-$C_4$alkyl optionally substituted with F, ONO, ONO$_2$; $C_3$-$C_6$cycloalkyl.

Thus, in a further aspect, the present invention provides for a compound of formula I

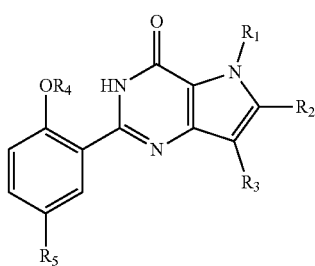

I wherein at least one of $R_1$, $R_2$, $R_3$, $R_4$, or $R_5$ independently of each other comprises at least one ONO$_2$ or ONO moiety, and wherein preferably said $R_1$, $R_2$, $R_3$, $R_4$, and $R_5$ comprise together at least two moieties selected from ONO$_2$ or ONO moieties;

$R_1$ is $C_1$-$C_3$alkyl optionally substituted with F, $C_3$-$C_6$cycloalkyl, $C_1$-$C_3$alkoxy, ONO, ONO$_2$;

$R_2$ is H, $C_1$-$C_3$alkyl optionally substituted with OH, ONO, ONO$_2$; C(O)OH, C(O)OC$_1$-$C_3$alkyl, CHO, CN, C(O)N(R$_6$)OR$_7$, CR$_8$=N—OR$_9$, CR$_8$=N—NR$_{10}$R$_{11}$, CR$_8$=NR$_{12}$, CR$_8$=N—ONO$_2$, $C_1$-$C_3$alkoxy; $C_1$-$C_3$alkylene-Y, wherein Y is ONO, ONO$_2$, C(O)OH, C(O)OC$_1$-$C_3$alkyl, CHO, CN, OH, OC(O)H, OC(O)—C$_1$-$C_3$alkyl, C(O)N(R$_6$)OR$_7$, OC$_1$-$C_3$alkylene-C(O)OH, OC$_1$-$C_3$alkylene-C(O)OC$_1$-$C_3$alkyl, OC$_1$-$C_3$alkylene-C(O)N(R$_6$)OR$_7$, S(O$_{0-2}$)C$_1$-$C_3$alkyl, CR$_8$=N—OR$_9$, CR$_8$=N—NR$_{10}$R$_{11}$, CR$_8$=NR$_{12}$ or CR$_8$=N—ONO$_2$;

$R_3$ is $C_1$-$C_4$alkyl optionally substituted with F, OH, ONO, ONO$_2$, $C_1$-$C_3$alkoxy, $C_3$-$C_6$cycloalkyl; $C_3$-$C_6$cycloalkyl, $C_2$-$C_6$alkenyl, $C_2$-$C_6$alkynyl;

$R_4$ is $C_1$-$C_6$alkyl optionally substituted with $C_3$-$C_6$cycloalkyl, $C_1$-$C_6$alkoxy, F, ONO, ONO$_2$; $C_2$-$C_6$alkenyl, $C_2$-$C_6$alkynyl, $C_3$-$C_6$cycloalkyl;

$R_5$ is H, SO$_2$NR$_{13}$R$_{14}$, NHSO$_2$NR$_{13}$R$_{14}$;

$R_6$ is H or $C_1$-$C_3$alkyl;

$R_7$ is H, $C_1$-$C_3$alkyl, $C_1$-$C_3$alkoxy, $C_1$-$C_3$alkyl substituted with phenyl, benzyl or a heterocyclic ring, wherein said phenyl, benzyl or said heterocyclic ring are independently optionally substituted by $C_1$-$C_3$alkyl, F;

$R_8$ is H, CH$_3$ or C$_2$H;

$R_9$ is H, $C_1$-$C_3$alkyl optionally substituted with OH, ONO, ONO$_2$, CN, COOH, COOC$_1$-$C_3$alkyl, $C_1$-$C_3$alkoxy, OC(O)H, OC(O)—C$_1$-$C_3$alkyl, C(O)N(R$_6$)OR$_7$, OC$_1$-$C_3$alkylene-C(O)OH, OC$_1$-$C_3$alkylene-C(O)OC$_1$-$C_3$alkyl, OC$_1$-$C_3$alkylene-C(O)N(R$_6$)OR$_7$, S(O$_{0-2}$)C$_1$-$C_3$alkyl; $R_{10}$ and $R_{11}$ are each independently H, $C_1$-$C_3$alkyl optionally substituted with OH, ONO, ONO$_2$, CN, COOH, COOC$_1$-$C_3$, $C_1$-$C_3$alkoxy, OC(O)H, OC(O)—C$_1$-$C_3$alkyl, C(O)N(R$_6$)OR$_7$, OC$_1$-$C_3$alkylene-C(O)OH, OC$_1$-$C_3$alkylene-C(O)OC$_1$-$C_3$alkyl, OC$_1$-$C_3$alkylene-C(O)N(R$_6$)OR$_7$, S(O$_{0-2}$)C$_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl;

$R_{12}$ is $C_1$-$C_3$ alkyl optionally substituted with OH, ONO, ONO$_2$, CN, COOH, COOC$_1$-$C_3$alkyl, $C_1$-$C_3$alkoxy, OC(O)H, OC(O)—C$_1$-$C_3$alkyl, C(O)N(R$_6$)OR$_7$, OC$_1$-$C_3$alkylene-C(O)OH, OC$_1$-$C_3$alkylene-C(O)OC$_1$-$C_3$alkyl, OC$_1$-$C_3$alkylene-C(O)N(R$_6$)OR$_7$, S(O$_{0-2}$)C$_1$-$C_3$alkyl;

$R_{13}$ and $R_{14}$ are each independently H or $C_1$-$C_6$alkyl optionally substituted with F, OH, ONO, ONO$_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with $R_{15}$;

$R_{15}$ is $C_1$-$C_6$alkyl optionally substituted with halogen, OH, ONO, ONO$_2$, $C_1$-$C_3$alkoxy, $C_1$-$C_3$haloalkoxy, COOR$_{16}$, NR$_{17}$R$_{18}$, C=NR$_{19}$, or with a tetrazole moiety which is optionally substituted with $C_1$-$C_3$alkyl; or a heteroaryl ring which is optionally substituted with F, wherein the at least one heteroatom of said heteroaryl ring is nitrogen;

$R_{16}$ is H, or $C_1$-$C_4$alkyl optionally substituted with F, OH, ONO, ONO$_2$, NR$_{17}$R$_{18}$, or with a heteroaryl ring, wherein the at least one heteroatom of said heteroaryl ring is nitrogen, and wherein preferably said heteroaryl ring is selected from pyrrolidine, piperidine, piperazine, morpholine, pyrrole, and imidazole, wherein nitrogen atom is directly bound to $C_1$-$C_4$ alkyl;

$R_{17}$ and $R_{18}$ are each independently H or $C_1$-$C_4$alkyl optionally substituted with ONO, ONO$_2$;

$R_{19}$ is $C_1$-$C_4$alkyl optionally substituted with F, ONO, ONO$_2$; $C_3$-$C_6$cycloalkyl.

The term "alkyl", as used herein, refers to a straight or branched hydrocarbon chain radical consisting solely of carbon and hydrogen atoms, containing no unsaturation, having typically and preferably from one to six carbon atoms (e.g., (C$_{1-6}$alkyl), and which typically is attached to the rest of the molecule by a single bond. Whenever it appears herein, a numerical range such as "1 to 6" refers to each integer in the given range. For example, "1 to 6 carbon atoms" means that the alkyl group may consist of 1 carbon atom, 2 carbon atoms, 3 carbon atoms, etc., up to and including 6 carbon atoms, although the definition is also intended to cover the occurrence of the term "alkyl" where no numerical range is specifically designated. Typical alkyl groups include, but are not limited to methyl, ethyl, n-propyl, prop-2-yl, n-butyl, but-2-yl, 2-methyl-prop-1-yl or 2-methyl-prop-2-yl. Examples of an alkoxy include methoxy, ethoxy, propoxy, iso-propoxy, n-butoxy, sec-butoxy, tert-butoxy, n-pentoxy, neo-pentoxy, n-hexoxy.

The term "alkylene", as used herein, refers to a straight or branched hydrocarbon chain bi-radical derived from alkyl, as defined herein, wherein one hydrogen of said alkyl is cleaved off generating the second radical of said alkylene. Examples of alkylene are, by way of illustration, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—.

Each cycloalkyl moiety can be in mono- or bi-cyclic form, typically and preferably in mono-cyclic form, and preferably contains 3 to 8 carbon atoms, more preferably 3 to 7 carbon atoms. Examples of monocyclic cycloalkyl moieties include cyclopropyl, cyclobutyl and cyclohexyl.

Each alkenyl moiety either alone or as part of a larger moiety such as alkenyloxy or alkenylene is a straight or branched chain and is preferably $C_2$-$C_6$alkenyl, more preferably $C_2$-$C_4$alkenyl. Each moiety can be of either the (E)- or (Z)-configuration. Examples include vinyl and allyl. A compound of the present invention comprising an alkenyl moiety thus may include, if applicable, either said compound with said alkenyl moiety in its (E)-configuration, said compound with said alkenyl moiety in its (Z)-configuration and mixtures thereof in any ratio.

Each alkynyl moiety either alone or as part of a larger moiety such as alkynyloxy is a straight or branched chain and is preferably $C_2$-$C_6$alkynyl, more preferably $C_2$-$C_4$alkynyl. Examples are ethynyl and propargyl.

The term "ONO2" refers to the nitrate moiety *—O—$NO_2$ as described herein, wherein the * indicates the attachment to the parent structure and rest of the molecule. Preferably, said ONO2 is a terminal ONO2 substituent.

The term "ONO" refers to the nitrite moiety *—O—NO as described herein, wherein the * indicates the attachment to the parent structure and rest of the molecule. Preferably, said ONO is a terminal ONO substituent.

The term "alkoxy" refers to the group —O-alkyl, including typically from 1 to 6 carbon atoms of a straight, branched configuration and combinations thereof attached to the parent structure through an oxygen, also referred to as $C_{1-6}$alkoxy or O—$C_{1-6}$alkyl. Examples include, but are not limited to, methoxy, ethoxy, propoxy, isopropoxy, cyclopropyloxy and cyclohexyloxy. As described herein, alkoxy may include further substitutents such as halogen atoms leading to haloalkoxy moieties.

Halogen is fluorine, chlorine, bromine, or iodine.

Each haloalkyl moiety either alone or as part of a larger moiety such as haloalkoxy is an alkyl moiety substituted by one or more of the same or different halogen atoms. Examples include difluoromethyl, trifluoromethyl, chlorodifluoromethyl and 2,2,2-trifluoro-ethyl.

The term "heterocyclic ring" refers to a saturated or partially unsaturated carbocyclic ring containing one to four heteroatoms selected from nitrogen, oxygen and sulfur as ring members. Such rings do not contain adjacent oxygen atoms, adjacent sulfur atoms, or adjacent oxygen and sulfur atoms within the ring. Preferred examples are aziridine, azetidine, pyrollidine, piperidine, morpholine, piperazine, homopiperazine, tetrahydrofurane, dioxane, 2,5-diazabicyclo[2,2,1]heptane and 3,7-diazabicyclo[3,3,0]octane, and further preferred are aziridine, azetidine, pyrollidine, piperidine, morpholine, piperazine, homopiperazine, 2,5-diazabicyclo[2,2,1]heptane and 3,7-diazabicyclo[3,3,0]octane.

The term "heteroaryl" refers to an aromatic ring system containing at least one heteroatom, and preferably up to three heteroatoms selected from nitrogen, oxygen and sulfur as ring members. Heteroaryl rings do not contain adjacent oxygen atoms, adjacent sulfur atoms, or adjacent oxygen and sulfur atoms within the ring. Preferred examples are include pyrrolidine, piperidine, piperazine, morpholine, pyridine, pyrimidine, pyrazine, pyridazine, pyrrole, pyrazole, imidazole, triazole, isoxazole, oxazole, isothiazole, thiazole, tetrazole, furane, and thiophenyl, and further preferred are pyrrolidine, piperidine, piperazine, morpholine, pyrrole, and imidazole.

Where a moiety is said to be optionally substituted, preferably there are optionally 1-5 substituents, more preferably optionally 1-3 substituents, again more preferably optionally 1 or 2 substituents. Where a moiety is said to be optionally substituted, and where there are more than one substituents for said optional substitution of said moiety, said more than one substituents can either be the same or different.

Certain compounds of formula I of the present invention may contain one or two or more centers of chirality and such compounds may be provided as pure enantiomers or pure diastereoisomers as well as mixtures thereof in any ratio. The compounds of the invention also include all tautomeric forms of the compounds of formula I. The compounds of formula I may also be solvated, especially hydrated, which are also included in the compounds of formula I. Solvation and hydration may take place during the preparation process.

As a consequence, the compounds of the present invention and, thus, the compounds of formula I include stereoisomers, geometric isomers and tautomers. Furthermore, the compounds of the present invention and, thus, the compounds of formula I include solvates or hydrates, pharmaceutically acceptable salts, and solvates or hydrates of the salts thereof.

Compounds of formula I of the present invention include pharmaceutically acceptable salts of said compounds. In particular, the term "pharmaceutically acceptable salt" as used herein, refers to pharmaceutically acceptable organic or inorganic salts of a compound of the present invention, in particular acid addition salts. Exemplary salts include, but are not limited to, salts of physiologically acceptable mineral acids, such as hydrochloric acid, sulfuric acid, nitric acid and phosphoric acid, or salts of organic acids, such as methane-sulfonic acid, p-toluenesulfonic acid, lactic acid, malic acid, tartaric acid, acetic acid, trifluoroacetic acid, citric acid, succinic acid, fumaric acid, maleic acid and salicylic acid. Further examples of pharmacologically acceptable salts of the compounds of formula I are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts. Further examples of pharmaceutically acceptable salts of the compounds of formula I include the hydrochloride, hydrobromide, sulfate, bisulfate, phosphate, hydrogen phosphate, nitrate, acetate, benzoate, succinate, fumarate, maleate, lactate, citrate, benzenesulphonate, p-toluenesulphonate or the like.

A "solvate" refers to an association or complex of one or more solvent molecules and a compound of the present invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

In a preferred embodiment of the present invention, said compound of formula I comprises exactly one $ONO_2$ moiety. In another preferred embodiment of the present invention, said compound of formula I comprises exactly one ONO moiety. In a preferred embodiment of the present invention, said compound of formula I comprises at least two moieties selected from $ONO_2$ or ONO moieties. In another preferred embodiment of the present invention, said compound of formula I comprises exactly two $ONO_2$ or two ONO moieties. In another preferred embodiment of the present invention, said compound of formula I comprises exactly one $ONO_2$ moiety and one ONO moiety. In another preferred embodiment of the present invention, said compound of formula I comprises at least three moieties selected from $ONO_2$ or ONO moieties. In another preferred embodiment of the present invention, said compound of formula I comprises exactly three $ONO_2$ or three ONO moieties. In another preferred embodiment of the present invention, said compound of formula I comprises exactly three moieties selected from $ONO_2$ or ONO moieties.

In a preferred embodiment of the present invention, $R_1$ is $C_1$-$C_3$alkyl substituted with $ONO_2$. In a further preferred embodiment of the present invention, $R_1$ is $C_1$-$C_3$alkyl. In a further preferred embodiment, $R_1$ is $CH_3$ or $C_2H_5$. In a further very preferred embodiment, $R_1$ is $CH_3$. In a further very preferred embodiment, $R_1$ is $C_2H$.

In a further preferred embodiment, said $R_2$ is H, $C_1$-$C_3$alkyl optionally substituted with OH, ONO, $ONO_2$; C(O)OH, C(O)O$C_1$-$C_3$alkyl, CHO, CN, C(O)N($R_6$)O$R_7$, $CR_8$=N—$OR_9$, $CR_8$=N—$NR_{10}R_{11}$, $CR_8$=$NR_{12}$, $CR_8$=N—$ONO_2$, $C_1$-$C_3$alkoxy; $C_1$-$C_3$alkylene-Y, wherein Y is ONO, $ONO_2$, C(O)OH, C(O)O$C_1$-$C_3$alkyl, CHO, CN, OH, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl, $CR_8$=N—$OR_9$, $CR_8$=N—$NR_{10}R_{11}$, $CR_8$=$NR_{12}$ or $CR_8$=N—$ONO_2$;

In a further preferred embodiment, $R_7$ is H, $C_1$-$C_3$alkyl, $C_1$-$C_3$alkoxy, $C_1$-$C_3$alkyl substituted with phenyl, benzyl or a heterocyclic ring selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said phenyl, benzyl or said heterocyclic ring are independently optionally substituted by $C_1$-$C_3$alkyl, F. In a further preferred embodiment, $R_7$ is H, $C_1$-$C_3$alkyl, $C_1$-$C_3$alkoxy, $C_1$-$C_3$alkyl substituted with phenyl, benzyl or a heterocyclic ring selected from pyrollidine, piperidine, morpholine, piperazine, homopiperazine, wherein said phenyl, benzyl or said heterocyclic ring are independently optionally substituted by $C_1$-$C_3$alkyl.

In a further preferred embodiment, said $R_9$ is H, $C_1$-$C_3$alkyl substituted with OH, CN, COOH, COO$C_1$-$C_3$alkyl, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl. In a further preferred embodiment, said $R_9$ is H, $C_1$-$C_3$alkyl substituted with OH, CN, COOH, COO$C_1$-$C_3$alkyl, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$.

In a further preferred embodiment, said $R_{10}$ and $R_{11}$ are each independently H, $C_1$-$C_3$alkyl optionally substituted with OH, CN, COOH, COO$C_1$-$C_3$, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl. In a further preferred embodiment, said $R_{10}$ and $R_{11}$ are each independently H, $C_1$-$C_3$alkyl optionally substituted with OH, CN, COOH, COO$C_1$-$C_3$, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl; or together with the nitrogen atom to which they are attached form a heterocyclic ring, wherein preferably said heterocyclic ring is selected from pyrollidine, piperidine, morpholine, piperazine and homopiperazine, wherein said heterocyclic ring is optionally substituted with $C_1$-$C_3$ alkyl.

In a further preferred embodiment, said $R_2$ is H, $C_1$-$C_3$alkyl optionally substituted with OH, ONO, $ONO_2$; C(O)OH, C(O)O$C_1$-$C_3$alkyl, CHO, CN, $CR_8$=N—$OR_9$, $CR_8$=N—$NR_{10}R_{11}$, $CR_8$=$NR_{12}$, $CR_8$=N—$ONO_2$, $C_1$-$C_3$alkoxy; $C_1$-$C_3$alkylene-Y, wherein Y is ONO, $ONO_2$, CHO, CN, OH, OC(O)H, O$C_1$-$C_3$alkylene-C(O)OH, O$C_1$-$C_3$alkylene-C(O)O$C_1$-$C_3$alkyl, OC(O)—$C_1$-$C_3$alkyl, C(O)O$C_1$-$C_3$alkyl, C(O)N($R_6$)O$R_7$, $CR_8$=N—$OR_9$, $CR_8$=N—$NR_{10}R_{11}$, $CR_8$=$NR_{12}$ or $CR_8$=N—$ONO_2$, wherein preferably said $R_6$ and $R_8$ are independently of each other H or $CH_3$.

In a further preferred embodiment, said $R_2$ is H, $C_1$-$C_3$alkyl optionally substituted with OH, ONO, $ONO_2$; CHO, CN, $CR_8$=N—$OR_9$, $CR_8$=N—$NR_{10}R_{11}$, $C_1$-$C_3$alkoxy; $C_1$-$C_3$alkylene-Y, wherein Y is ONO, $ONO_2$, CHO, CN, OH, OC(O)H, C(O)O$C_1$-$C_3$alkyl, $CR_8$=N—$OR_9$, $CR_8$=N—$NR_{10}R_{11}$, or $CR_8$=N—$ONO_2$.

In a further preferred embodiment, said $R_2$ is H, $C_1$-$C_3$alkyl optionally substituted with OH, ONO, $ONO_2$; CHO, CN, $CR_8$=N—$OR_9$, $CR_8$=N—$NR_{10}R_{11}$, $C_1$-$C_3$alkoxy; $C_1$-$C_3$alkylene-Y, wherein Y is ONO, $ONO_2$, CHO, CN, OH, OC(O)H, C(O)O$C_1$-$C_3$alkyl, $CR_8$=N—$OR_9$, $CR_8$=N—$NR_{10}R_{11}$, or $CR_8$=N—$ONO_2$, wherein $R_6$ and $R_8$ are independently of each other H or $CH_3$; $R_9$ is H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl; $R_{10}$ and $R_{11}$ are each independently H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl.

In a further very preferred embodiment, said $R_2$ is H, CHO, CN, $C_1$-$C_3$alkoxy, $C_1$-$C_3$alkoxy optionally substituted with $ONO_2$; $CR_8$=N—$OR_9$, preferably (E)-$CR_8$=N—$OR_9$, wherein said $R_8$ is H or $CH_3$, preferably wherein said $R_8$ is H, and wherein said $R_9$ is H or $C_1$-$C_3$ alkyl optionally substituted with OH or $C_1$-$C_3$ alkyl optionally substituted with OH, ONO, $ONO_2$, CN, COOH, COO$C_1$-$C_3$alkyl, OC(O)H, OC(O)—$C_1$-$C_3$alkyl.

In a further very preferred embodiment, said $R_2$ is H, CHO, CN, $C_1$-$C_3$alkoxy, $C_1$-$C_3$alkoxy optionally substituted with $ONO_2$; CH=N—$OR_9$, preferably (E)-CH=N—$OR_9$, wherein $R_9$ is H, $C_1$-$C_3$alkyl optionally substituted with OH, ONO, $ONO_2$, CN, COOH, COO$C_1$-$C_3$alkyl, OC(O)H, OC(O)—$C_1$-$C_3$alkyl.

In a further very preferred embodiment, said $R_2$ is H, CHO, CN, $C_1$-$C_3$alkoxy, $C_1$-$C_3$alkoxy optionally substituted with $ONO_2$; CH=N—$OR_9$, preferably (E)-CH=N—$OR_9$, wherein $R_9$ is H, $C_1$-$C_3$alkyl substituted with OH, ONO, $ONO_2$, CN.

In a further very preferred embodiment, said $R_2$ is H, CHO, $C_1$-$C_3$alkoxy, $C_1$-$C_3$alkoxy optionally substituted with $ONO_2$; CH=N—$OR_9$, preferably (E)-CH=N—$OR_9$, wherein $R_9$ is H, $C_1$-$C_3$alkyl optionally substituted with $ONO_2$.

In a further very preferred embodiment, said $R_2$ is H.

In a further very preferred embodiment, said $R_2$ is CHO.

In a further very preferred embodiment, said $R_2$ is $C_1$-$C_3$alkoxy. In a further very preferred embodiment, said $R_2$ is $C_1$-$C_3$alkoxy optionally substituted with $ONO_2$.

In a further very preferred embodiment, said $R_2$ is methoxy ($CH_2OH$) or ethoxy ($C_2H_5OH$).

In a further very preferred embodiment, said $R_2$ is methoxy.

In a further very preferred embodiment, said $R_2$ is CH=N—$OR_9$, preferably (E)-CH=N—$OR_9$, wherein $R_9$ is H, $C_1$-$C_3$alkyl optionally substituted with OH, ONO, $ONO_2$, CN, COOH, $COOC_1$-$C_3$alkyl, OC(O)H, OC(O)—$C_1$-$C_3$alkyl.

In a further very preferred embodiment, said $R_2$ is CH=N—$OR_9$, preferably (E)-CH=N—$OR_9$, wherein $R_9$ is H, $C_1$-$C_3$alkyl optionally substituted with OH, $ONO_2$.

In a further very preferred embodiment, said $R_2$ is CH=N—$OR_9$, preferably (E)-CH=N—$OR_9$, wherein $R_9$ is H, $C_1$-$C_3$alkyl optionally substituted with $ONO_2$.

In a further very preferred embodiment, said $R_2$ is CH=N—$OR_9$, preferably (E)-CH=N—$OR_9$, wherein $R_9$ is H.

In another preferred embodiment, $R_3$ is $C_1$-$C_4$alkyl optionally substituted with OH, ONO, $ONO_2$, $C_1$-$C_3$alkoxy; $C_2$-$C_4$alkenyl. In another preferred embodiment, $R_3$ is $C_1$-$C_4$alkyl optionally substituted with F, OH, ONO, $ONO_2$, $C_1$-$C_3$alkoxy, $C_3$-$C_6$cycloalkyl. In a further preferred embodiment, $R_3$ is $C_2$-$C_3$alkyl optionally substituted with F, OH, ONO, $ONO_2$, $C_1$-$C_3$alkoxy, $C_3$-$C_6$cycloalkyl, $C_2$-$C_4$alkenyl. In a further preferred embodiment, $R_3$ is $C_1$-$C_4$alkyl optionally substituted with ONO, $ONO_2$ or $C_3$-$C_5$cycloalkyl. In a further preferred embodiment, $R_3$ is $C_1$-$C_4$alkyl optionally substituted with $ONO_2$ or $C_3$-$C_5$cycloalkyl. In a further preferred embodiment, $R_3$ is $C_1$-$C_4$alkyl optionally substituted with $ONO_2$. In a further preferred embodiment, $R_3$ is $C_1$-$C_4$alkyl, very preferably $R_3$ is $C_2$-$C_3$alkyl. In a very preferred embodiment, $R_3$ is n-propyl.

In another preferred embodiment, $R_4$ is $C_1$-$C_4$alkyl optionally substituted with $C_3$-$C_6$cycloalkyl, $C_1$-$C_6$alkoxy, F, ONO, $ONO_2$; $C_2$-$C_4$alkenyl. In a further preferred embodiment, $R_4$ is $C_1$-$C_4$alkyl optionally substituted with ONO, $ONO_2$, $C_1$-$C_6$alkoxy, or $C_3$-$C_5$cycloalkyl. In a further preferred embodiment, $R_4$ is $C_1$-$C_4$alkyl optionally substituted with ONO, $ONO_2$ or $C_1$-$C_6$alkoxy. In a further preferred embodiment, $R_4$ is $C_1$-$C_4$alkyl optionally substituted with $ONO_2$ or $C_1$-$C_6$alkoxy. In a further preferred embodiment, $R_4$ is $C_1$-$C_4$alkyl substituted with $ONO_2$. In a further preferred embodiment, $R_4$ is $C_2$-$C_3$alkyl substituted with $ONO_2$. In a further preferred embodiment, $R_4$ is ethyl or n-propyl. In a further very preferred embodiment, $R_4$ is ethyl. In a further very preferred embodiment, $R_4$ is n-propyl.

In a further preferred embodiment, said $R_1$ is $C_1$-$C_3$alkyl; $R_3$ is $C_1$-$C_4$alkyl optionally substituted with F, OH, ONO, $ONO_2$, $C_1$-$C_3$alkoxy, $C_3$-$C_6$cycloalkyl, $C_2$-$C_4$alkenyl; and $R_4$ is $C_1$-$C_4$alkyl optionally substituted with $C_3$-$C_6$cycloalkyl, $C_1$-$C_3$alkoxy, F, ONO, $ONO_2$; $C_2$-$C_4$alkenyl.

In a further preferred embodiment, said $R_1$ is $CH_3$ or $C_2H_5$, preferably $R_1$ is $CH_3$; $R_3$ is $C_1$-$C_4$alkyl optionally substituted with $ONO_2$ or $C_3$-$C_5$cycloalkyl, preferably $R_3$ is n-propyl; and $R_4$ is $C_1$-$C_4$alkyl optionally substituted with $ONO_2$ or $C_3$-$C_5$cycloalkyl, preferably $R_4$ is ethyl or n-propyl.

In a further preferred embodiment, said $R_5$ is $SO_2NR_{13}R_{14}$, $NHSO_2NR_{13}R_{14}$. In a further preferred embodiment, said $R_{13}$ and $R_{14}$ together with the nitrogen atom to which they are attached form a heterocyclic ring, wherein said heterocyclic ring is selected from aziridine, azetidine, pyrollidine, piperidine, morpholine, piperazine, homopiperazine, 2,5-diazabicyclo-[2,2,1]heptane and 3,7-diazabicyclo[3,3,0]octane, wherein said heterocyclic ring is optionally substituted with $R_{15}$; $R_{15}$ is $C_1$-$C_4$alkyl optionally substituted with halogen, OH, ONO, $ONO_2$, $C_1$-$C_3$alkoxy, $C_1$-$C_3$haloalkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; $R_{17}$ and $R_{18}$ are each independently H or $C_1$-$C_4$alkyl optionally substituted with ONO, $ONO_2$, preferably $R_{17}$ and $R_{18}$ are each independently H or $C_1$-$C_4$alkyl optionally substituted with $ONO_2$; $R_{19}$ is $C_1$-$C_4$alkyl optionally substituted with F, ONO, $ONO_2$, preferably $R_{19}$ is $C_1$-$C_4$alkyl optionally substituted with $ONO_2$.

In a further preferred embodiment, said $R_5$ is $SO_2NR_{13}R_{14}$, $NHSO_2NR_{13}R_{14}$; said $R_{13}$ and $R_{14}$ together with the nitrogen atom to which they are attached form a heterocyclic ring, wherein said heterocyclic ring is selected from aziridine, azetidine, pyrollidine, piperidine, morpholine, piperazine, homopiperazine, 2,5-diazabicyclo-[2,2,1]heptane and 3,7-diazabicyclo[3,3,0]octane, wherein said heterocyclic ring is optionally substituted with $R_{15}$; said $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; said $R_{17}$ and $R_{18}$ are each independently H or $C_1$-$C_4$alkyl optionally substituted with ONO, $ONO_2$; said $R_{19}$ is $C_1$-$C_4$alkyl optionally substituted with F, ONO, $ONO_2$.

In a further preferred embodiment, said $R_5$ is $SO_2NR_{13}R_{14}$, wherein $R_{13}$ and $R_{14}$ are each independently H or together with the nitrogen atom to which they are attached form a mono-cyclic ring selected from imidazol, aziridine, azetidine, pyrrolidine, piperidine, morpholine, piperazine and homopiperazine optionally substituted with $R_{15}$; said $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; said $R_{17}$ and $R_{18}$ are each independently H or $C_1$-$C_4$alkyl optionally substituted with ONO, $ONO_2$; said $R_{19}$ is $C_1$-$C_4$alkyl optionally substituted with F, ONO, $ONO_2$.

In a further preferred embodiment, said $R_5$ is $SO_2NR_{13}R_{14}$, wherein $R_{13}$ and $R_{14}$ together with the nitrogen atom to which they are attached form a mono-cyclic ring selected from imidazol, aziridine, azetidine, pyrrolidine, piperidine, morpholine, piperazine and homopiperazine optionally substituted with $R_{15}$; said $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, $C=NR_{19}$; $R_{16}$ is H, or $C_1$-$C_4$alkyl optionally substituted with OH, ONO, $ONO_2$; said $R_{17}$ and $R_{18}$ are each independently H or $C_1$-$C_4$alkyl optionally substituted with ONO, $ONO_2$; said $R_{19}$ is $C_1$-$C_4$alkyl optionally substituted with ONO, $ONO_2$.

In a further preferred embodiment, said $R_5$ is $SO_2NR_{13}R_{14}$, wherein $R_{13}$ and $R_{14}$ together with the nitrogen atom to which they are attached form a mono-cyclic ring selected from imidazol, aziridine, azetidine, pyrrolidine, piperidine, morpholine, piperazine and homopiperazine optionally substituted with $R_{15}$; said $R_{15}$ is $C_1$-$C_4$alkyl optionally substituted with halogen, OH, $ONO_2$, $C_1$-$C_3$alkoxy, $COOR_{16}$, $NR_{17}R_{18}$, $C=NR_{19}$; $R_{16}$ is H, or $C_1$-$C_4$alkyl optionally substituted with OH, $ONO_2$; said $R_{17}$ and $R_{18}$ are each independently H or $C_1$-$C_4$alkyl optionally substituted with $ONO_2$; said $R_{19}$ is $C_1$-$C_4$alkyl optionally substituted with $ONO_2$.

In a further preferred embodiment, said $R_5$ is $SO_2NR_{13}R_{14}$, wherein $R_{13}$ and $R_{14}$ together with the nitrogen atom to which they are attached form a mono-cyclic ring selected from imidazol, pyrrolidine, piperidine, morpholine, piperazine and homopiperazine optionally substituted with $R_{15}$; said $R_{15}$ is $C_1$-$C_4$alkyl optionally substituted with OH, $ONO_2$, $C_1$-$C_3$alkoxy, $COOR_{16}$, $NR_{17}R_{18}$, $C=NR_{19}$; $R_{16}$ is H, or $C_1$-$C_4$alkyl optionally substituted with OH, $ONO_2$; said $R_{17}$ and $R_{18}$ are each independently H or $C_1$-$C_4$alkyl optionally substituted with $ONO_2$; said $R_{19}$ is $C_1$-$C_4$alkyl optionally substituted with $ONO_2$.

In a further very preferred embodiment, said $R_5$ is $SO_2NR_{13}R_{14}$, wherein $R_{13}$ and $R_{14}$ together with the nitrogen atom to which they are attached form a mono-cyclic ring selected from piperidine, and piperazine optionally substituted with $R_{15}$; said $R_{15}$ is $C_1$-$C_4$alkyl optionally substituted with OH, ONO or ONO.

In a further very preferred embodiment, said $R_5$ is $SO_2NR_{13}R_{14}$, wherein $R_{13}$ and $R_{14}$ together with the nitrogen atom to which they are attached form a mono-cyclic ring selected from piperidine, and piperazine optionally substituted with $R_{15}$; said $R_{15}$ is $C_1$-$C_3$alkyl optionally substituted with OH, ONO or $ONO_2$.

In a further very preferred embodiment, said $R_5$ is $SO_2NR_{13}R_{14}$, wherein $R_{13}$ and $R_{14}$ together with the nitrogen atom to which they are attached form a mono-cyclic ring selected from piperidine, and piperazine optionally substituted with $R_{15}$; said $R_{15}$ is $C_1$-$C_3$alkyl optionally substituted with OH or $ONO_2$.

In a further very preferred embodiment, said $R_5$ is $SO_2NR_{13}R_{14}$, wherein $R_{13}$ and $R_{14}$ together with the nitrogen atom to which they are attached form a mono-cyclic ring selected from piperidine, and piperazine optionally substituted with $R_{15}$; said $R_{15}$ is $C_1$-$C_3$alkyl substituted with $ONO_2$.

In a further very preferred embodiment, said $R_5$ is $SO_2NR_{13}R_{14}$, wherein $R_{13}$ and $R_{14}$ together with the nitrogen atom to which they are attached form a mono-cyclic ring selected from piperidine, and piperazine optionally substituted with $R_{15}$; said $R_{15}$ is $C_1$-$C_3$alkyl substituted with ONO.

In a further very preferred embodiment, said compound of formula I is a compound of formula I*, or pharmaceutically acceptable salt, solvate or hydrate thereof;

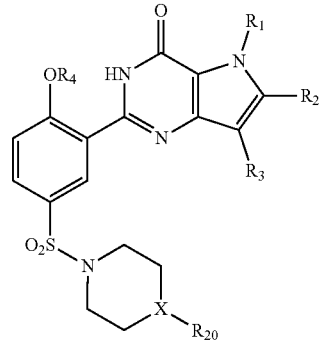

wherein $R_1$, $R_2$, $R_3$, and $R_4$, are as defined herein; and wherein X is $CR_{21}$ or N; and wherein at least one of $R_1$, $R_2$, $R_3$, $R_4$, $R_{20}$ or $R_{21}$ independently of each other comprises at least one $ONO_2$ or ONO moiety, and wherein preferably said $R_1$, $R_2$, $R_3$, $R_4$, $R_{20}$ and $R_{21}$ comprise together at least two moieties selected from $ONO_2$ or ONO moieties;

$R_{20}$ is $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, $C=NR_{28}$;

$R_{21}$ is H or $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, $C=NR_{28}$;

$R_{25}$ is H, or $C_1$-$C_4$alkyl optionally substituted with F, OH, ONO, $ONO_2$;

$R_{26}$ and $R_{27}$ are each independently H or $C_1$-$C_4$alkyl optionally substituted with ONO, $ONO_2$;

$R_{28}$ is $C_1$-$C_4$alkyl optionally substituted with F, ONO, $ONO_2$.

In a further very preferred embodiment, said $R_{20}$ or $R_{21}$ independently of each other comprises at least one $ONO_2$ or ONO moiety. In a further very preferred embodiment, said $R_{20}$ or said $R_{21}$ comprises exactly one $ONO_2$ moiety. In a further very preferred embodiment, said $R_{20}$ comprises exactly one $ONO_2$ moiety. In a further very preferred embodiment, said $R_{21}$ comprises exactly one $ONO_2$ moiety. In a further very preferred embodiment, said $R_{20}$ and said $R_{21}$ comprise together at least two moieties selected from $ONO_2$ or ONO moieties. In a further very preferred embodiment, said $R_{20}$ and said $R_{21}$ comprise together exactly two moieties selected from $ONO_2$ or ONO moieties. In a further very preferred embodiment, said $R_{20}$ and said $R_{21}$ comprise together exactly two moieties, one $ONO_2$ moiety and one ONO moiety. In a further very preferred embodiment, said $R_{20}$ comprises exactly two $ONO_2$ moieties. In a further very preferred embodiment, said $R_{20}$ comprises exactly two ONO moieties. In a further very preferred embodiment, said $R_{20}$ and said $R_{21}$ each comprises exactly one moiety selected from $ONO_2$ or ONO. In a further very preferred embodiment, said $R_{20}$ and said $R_{21}$ each comprises exactly one $ONO_2$ moiety. In a further very preferred embodiment, said $R_{20}$ and said $R_{21}$ comprise together at least three moieties selected from $ONO_2$ or ONO moieties. In a further very preferred embodiment, said $R_{20}$ and said $R_{21}$ comprise together exactly three $ONO_2$ or three ONO moieties. In a further very preferred embodiment, said $R_{20}$ and said $R_{21}$ comprise together exactly three moieties selected from $ONO_2$ or ONO moieties. In a further very preferred embodiment, said $R_{20}$ comprises exactly three ONO moieties. In a very preferred embodiment, said $R_{21}$ is H.

In a further very preferred embodiment, said compound of formula I is a compound of formula I*, or pharmaceutically acceptable salt, solvate or hydrate thereof, wherein at least one of $R_1$, $R_2$, $R_3$, $R_4$, or $R_{20}$ independently of each other comprises at least one $ONO_2$ or ONO moiety, and wherein preferably said $R_1$, $R_2$, $R_3$, $R_4$, and $R_{20}$ comprise together at least two moieties selected from $ONO_2$ or ONO moieties;

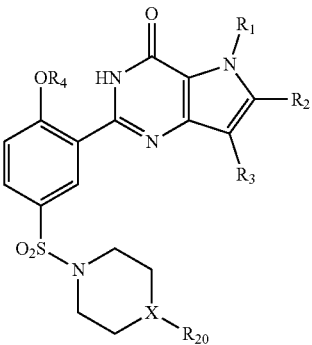

I* wherein $R_1$, $R_2$, $R_3$, and $R_4$, are as defined herein; and wherein X is CH or N;
$R_{20}$ is $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, $C=NR_{28}$;
$R_{25}$ is H, or $C_1$-$C_4$alkyl optionally substituted with F, OH, ONO, $ONO_2$;
$R_{26}$ and $R_{27}$ are each independently H or $C_1$-$C_4$alkyl optionally substituted with ONO, $ONO_2$;
$R_{28}$ is $C_1$-$C_4$alkyl optionally substituted with F, ONO, $ONO_2$.

In a further very preferred embodiment, said compound of formula I is a compound of formula I**, or pharmaceutically acceptable salt, solvate or hydrate thereof, wherein at least one of $R_1$, $R_2$, $R_3$, $R_4$, $R_{22}$, $R_{23}$ or $R_{24}$ independently of each other comprises at least one $ONO_2$ or ONO moiety, and wherein preferably said $R_1$, $R_2$, $R_3$, $R_4$, $R_{22}$, $R_{23}$ and $R_{24}$ comprise together at least two moieties selected from $ONO_2$ or ONO moieties;

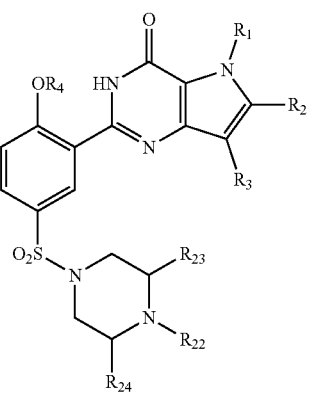

II* wherein $R_1$, $R_2$, $R_3$, and $R_4$, are as defined herein;
$R_{22}$ is H or $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, $C=NR_{28}$;

$R_{23}$ and $R_{24}$ are each independently $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, $C=NR_{28}$;
$R_{25}$ is H, or $C_1$-$C_4$alkyl optionally substituted with F, OH, ONO, $ONO_2$;
$R_{26}$ and $R_{27}$ are each independently H or $C_1$-$C_4$alkyl optionally substituted with ONO, $ONO_2$;
$R_{28}$ is $C_1$-$C_4$alkyl optionally substituted with F, ONO, $ONO_2$.

In a further very preferred embodiment, said $R_{22}$, $R_{23}$ or $R_{24}$ independently of each other comprises at least one $ONO_2$ or ONO moiety. In a further very preferred embodiment, said $R_{22}$, $R_{23}$ and $R_{24}$ comprise together at least two moieties selected from $ONO_2$ or ONO moieties. In a further very preferred embodiment, said $R_{22}$, $R_{23}$ and $R_{24}$ comprise together exactly two moieties selected from $ONO_2$ or ONO moieties. In a further very preferred embodiment, said $R_{23}$ and said $R_{24}$ comprise together exactly two $ONO_2$ or two ONO moieties. In a further very preferred embodiment, said $R_{23}$ and said $R_{24}$ comprise together exactly one $ONO_2$ moiety and one ONO moiety. In a further very preferred embodiment, said $R_{23}$ and said $R_{24}$ comprise exactly one $ONO_2$ moiety. In a further very preferred embodiment, said $R_{23}$ and said $R_{24}$ comprise exactly one ONO moiety.

In a further very preferred embodiment, said compound of formula I is a compound of formula I*, wherein $R_1$ is $C_1$-$C_3$alkyl; and
$R_2$ is H, $C_1$-$C_3$alkyl optionally substituted with OH, ONO, $ONO_2$; CHO, CN, $CR_8=N-OR_9$, $CR_8=N-NR_{10}R_{11}$, $C_1$-$C_3$alkoxy; $C_1$-$C_3$alkylene-Y, wherein Y is ONO, $ONO_2$, CHO, CN, OH, OC(O)H, C(O)O$C_1$-$C_3$alkyl, $CR_8=N-OR_9$, $CR_8=N-NR_{10}R_{11}$, or $CR_8=N-ONO_2$, wherein $R_6$ and $R_8$ are independently of each other H or $CH_3$; $R_9$ is H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl;
$R_{10}$ and $R_{11}$ are each independently H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl;
$R_3$ is $C_1$-$C_4$alkyl optionally substituted with OH, ONO, $ONO_2$, $C_1$-$C_3$alkoxy;
$R_4$ is $C_1$-$C_4$alkyl optionally substituted with $C_1$-$C_3$alkoxy, F, ONO, $ONO_2$;
$R_{20}$ is $C_1$-$C_4$alkyl optionally substituted with halogen, OH, ONO, $ONO_2$, $C_1$-$C_3$alkoxy, $COOR_{25}$, $NR_{26}R_{27}$; wherein $R_{25}$ is H, or $C_1$-$C_4$alkyl optionally substituted with OH, ONO, $ONO_2$;
$R_{26}$ and $R_{27}$ are each independently H or $C_1$-$C_4$alkyl optionally substituted with ONO, $ONO_2$.

In a further very preferred embodiment, said compound of formula I is a compound of formula I*, wherein $R_1$ is $C_1$-$C_3$alkyl; and
$R_2$ is H, $C_1$-$C_3$alkyl optionally substituted with OH, ONO, $ONO_2$; CHO, CN, $CR_8=N-OR_9$, $CR_8=N-NR_{10}R_{11}$, $C_1$-$C_3$alkoxy; $C_1$-$C_3$alkylene-Y, wherein Y is ONO, $ONO_2$, CHO, CN, OH, OC(O)H, C(O)O$C_1$-$C_3$alkyl, $CR_8=N-OR_9$, $CR_8=N-NR_{10}R_{11}$, or $CR_8=N-ONO_2$, wherein $R_6$ and $R_8$ are independently of each other H or $CH_3$; $R_9$ is H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl;
$R_{10}$ and $R_{11}$ are each independently H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl;
$R_3$ is $C_1$-$C_4$alkyl optionally substituted with OH, ONO, $ONO_2$, $C_1$-$C_3$alkoxy;
$R_4$ is $C_1$-$C_4$alkyl optionally substituted with $C_1$-$C_3$alkoxy, F, ONO, $ONO_2$;

$R_{20}$ is $C_1$-$C_4$alkyl optionally substituted with halogen, OH, ONO, $ONO_2$, $C_1$-$C_3$alkoxy, $COOR_{25}$, $NR_{26}R_{27}$; wherein $R_{25}$ is H, or $C_1$-$C_4$alkyl optionally substituted with OH, ONO, $ONO_2$;
$R_{21}$ is H or $C_1$-$C_4$alkyl optionally substituted with halogen, OH, ONO, $ONO_2$, $C_1$-$C_3$alkoxy, $COOR_{25}$, $NR_{26}R_{27}$; wherein $R_{25}$ is H, or $C_1$-$C_4$alkyl optionally substituted with OH, ONO, $ONO_2$;
$R_{26}$ and $R_{27}$ are each independently H or $C_1$-$C_4$alkyl optionally substituted with ONO, $ONO_2$.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_1$-$C_3$alkyl substituted with at least one substituent selected from OH, ONO and $ONO_2$;
$R_{21}$ is H or $C_1$-$C_3$alkyl substituted with at least substituent selected from OH, ONO and $ONO_2$.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_1$-$C_3$alkyl substituted with one, two or three substituents selected from OH, ONO and $ONO_2$;
$R_{21}$ is H or $C_1$-$C_3$alkyl substituted with one or two substituents selected from OH, ONO and $ONO_2$.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_1$-$C_3$alkyl substituted with one or two substituents selected from ONO and $ONO_2$ and optionally substituted with OH;
$R_{21}$ is H.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;

$R_4$ is $C_2$-$C_3$alkyl optionally substituted with ONO, $ONO_2$;
$R_{20}$ is $C_2$-$C_3$alkyl substituted with one or two substituents selected from ONO and $ONO_2$ and optionally substituted with one OH; $R_{21}$ is H.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is selected from $CH_2ONO_2$, $CH_2ONO$, $CH_2CH_2ONO$, $CH_2CH_2ONO_2$, $CH(OH)CH_2ONO_2$, $CH(OH)CH_2ONO$, $CH_2CH_2CH_2ONO_2$, $CH_2CH_2CH_2ONO$, $CH(ONO_2)CH_2OH$, $CH(ONO)CH_2OH$, $CH(ONO_2)CH_2ONO_2$, $CH(ONO)CH_2ONO_2$, $CH(ONO_2)CH_2ONO$, $C(OH)(CH_2ONO_2)CH_2ONO$, $C(OH)(CH_2ONO)CH_2ONO_2$, $C(OH)(CH_2ONO_2)CH_2ONO_2$, $C(OH)(CH_2CH_2ONO)CH_2CH_2ONO_2$, $C(OH)(CH_2CH_2ONO_2)CH_2CH_2ONO$, $C(OH)(CH_2CH_2ONO_2)CH_2CH_2ONO_2$, and wherein preferably $R_{20}$ is selected from $CH_2ONO_2$, $CH_2CH_2ONO_2$, $CH(OH)CH_2ONO_2$, $CH_2CH_2CH_2ONO_2$, $CH(ONO_2)CH_2OH$, $CH(ONO_2)CH_2ONO_2$, $C(OH)(CH_2ONO_2)CH_2ONO_2$, $C(OH)(CH_2CH_2ONO_2)CH_2CH_2ONO_2$; $R_2$ is H.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is selected from $CH_2ONO_2$, $CH_2ONO$, $CH_2CH_2ONO$, $CH_2CH_2ONO_2$, and wherein preferably $R_{20}$ is selected from $CH_2ONO_2$ or $CH_2CH_2ONO_2$;
$R_{21}$ is selected from $CH_2ONO_2$, $CH_2ONO$, $CH_2CH_2ONO$, $CH_2CH_2ONO_2$, and wherein preferably $R_{21}$ is selected from $CH_2ONO_2$ or $CH_2CH_2ONO_2$.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_2$-$C_3$alkyl substituted with OH, ONO, $ONO_2$.

In a further very preferred embodiment, said compound of formula I is a compound of formula I*, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;

$R_4$ is $C_2$-$C_3$alkyl optionally substituted with ONO, $ONO_2$;
$R_{20}$ is $C_2$-$C_3$alkyl substituted with $ONO_2$, preferably $C_2$-$C_3$alkyl substituted with one, two or three $ONO_2$, further preferably $C_2$-$C_3$alkyl substituted with one or two $ONO_2$.

In a further very preferred embodiment, said compound of formula I is a compound of formula I*, wherein $R_1$ is methyl or ethyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or $CR_8$=N—$OR_9$, wherein $R_8$ is H or $CH_3$; $R_9$ is H, $C_1$-$C_3$alkyl optionally substituted with OH, ONO, $ONO_2$;
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_2$-$C_3$alkyl substituted with $ONO_2$, preferably $C_2$-$C_3$alkyl substituted with one, two or three $ONO_2$, further preferably $C_2$-$C_3$alkyl substituted with one or two $ONO_2$.

In a further very preferred embodiment, said compound of formula I is a compound of formula I*, wherein $R_1$ is methyl or ethyl;
$R_2$ is H, CHO, CN, $C_1$-$C_3$alkoxy, $C_1$-$C_3$alkoxy optionally substituted with $ONO_2$; CH=N—$OR_9$, preferably (E)-CH=N—$OR_9$, wherein $R_9$ is H, $C_1$-$C_3$alkyl optionally substituted with OH, ONO, $ONO_2$, CN, COOH, $COOC_1$-$C_3$alkyl, OC(O)H, OC(O)—$C_1$-$C_3$alkyl.
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_2$-$C_3$alkyl substituted with $ONO_2$, preferably $C_2$-$C_3$alkyl substituted with one, two or three $ONO_2$, further preferably $C_2$-$C_3$alkyl substituted with one or two $ONO_2$.

In a further very preferred embodiment, said compound of formula I is a compound of formula I*, wherein $R_1$ is methyl or ethyl;
$R_2$ is H, CHO, CN, $C_1$-$C_3$alkoxy, $C_1$-$C_3$alkoxy optionally substituted with $ONO_2$; CH=N—$OR_9$, preferably (E)-CH=N—$OR_9$, wherein $R_9$ is H, $C_1$-$C_3$alkyl substituted with OH, ONO, $ONO_2$.
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_2$-$C_3$alkyl substituted with $ONO_2$, preferably $C_2$-$C_3$alkyl substituted with one, two or three $ONO_2$, further preferably $C_2$-$C_3$alkyl substituted with one or two $ONO_2$.

In a further very preferred embodiment, said compound of formula I is a compound of formula I*, wherein $R_1$ is methyl or ethyl;
$R_2$ is H, CHO, $C_1$-$C_3$alkoxy, $C_1$-$C_3$alkoxy optionally substituted with $ONO_2$; CH=N—$OR_9$, preferably (E)-CH=N—$OR_9$, wherein $R_9$ is H, $C_1$-$C_3$alkyl optionally substituted with $ONO_2$.
$R_3$ is $C_2$-$C_3$alkyl optionally substituted with OH, ONO, $ONO_2$;
$R_4$ is $C_2$-$C_3$alkyl optionally substituted with ONO, $ONO_2$;
$R_{20}$ is $C_2$-$C_3$alkyl substituted with $ONO_2$, preferably $C_2$-$C_3$alkyl substituted with one, two or three $ONO_2$, further preferably $C_2$-$C_3$alkyl substituted with one or two $ONO_2$.

In a further very preferred embodiment, said compound of formula I is a compound of formula I**, or pharmaceutically acceptable salt, solvate or hydrate thereof, wherein at least one of $R_1$, $R_2$, $R_3$, $R_4$, $R_{22}$, $R_{23}$ or $R_{24}$ independently of each other comprises at least one $ONO_2$ or ONO moiety, and wherein preferably said $R_1$, $R_2$, $R_3$, $R_4$, $R_{22}$, $R_{23}$ and $R_{24}$ comprise together at least two moieties selected from $ONO_2$ or ONO moieties;

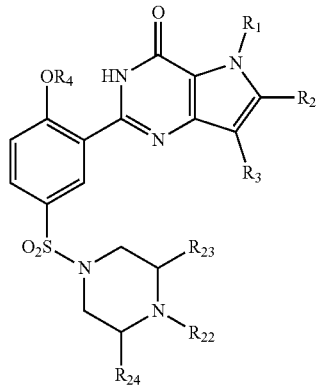

II* wherein $R_1$, $R_2$, $R_3$, and $R_4$, are as defined herein;
$R_{22}$ is H or $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, C=$NR_{28}$;
$R_{23}$ and $R_{24}$ are each independently $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, C=$NR_{28}$;
$R_{25}$ is H, or $C_1$-$C_4$alkyl optionally substituted with F, OH, ONO, $ONO_2$;
$R_{26}$ and $R_{27}$ are each independently H or $C_1$-$C_4$alkyl optionally substituted with ONO, $ONO_2$;
$R_{28}$ is $C_1$-$C_4$alkyl optionally substituted with F, ONO, $ONO_2$.

In a further very preferred embodiment, said compound of formula I is a compound of formula I**, wherein $R_1$ is $C_1$-$C_3$alkyl;
$R_2$ is H, $C_1$-$C_3$alkyl optionally substituted with OH, ONO, $ONO_2$; CHO, CN, $CR_8$=N—$OR_9$, $CR_8$=N—$NR_{10}R_{11}$, $C_1$-$C_3$alkoxy; $C_1$-$C_3$alkylene-Y, wherein Y is ONO, $ONO_2$, CHO, CN, OH, OC(O)H, C(O)O$C_1$-$C_3$alkyl, $CR_8$=N—$OR_9$, $CR_8$=N—$NR_{10}R_{11}$, or $CR_8$=N—$ONO_2$, wherein $R_6$ and $R_8$ are independently of each other H or $CH_3$; $R_9$ is H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl;
$R_{10}$ and $R_{11}$ are each independently H, $C_1$-$C_3$alkyl optionally substituted with OH, ONO, $ONO_2$, CN, COOH, $C_1$-$C_3$alkoxy, OC(O)H, OC(O)—$C_1$-$C_3$alkyl;
$R_3$ is $C_1$-$C_4$alkyl optionally substituted with OH, ONO, $ONO_2$, $C_1$-$C_3$alkoxy;
$R_4$ is $C_1$-$C_4$alkyl optionally substituted with $C_1$-$C_3$alkoxy, F, ONO, $ONO_2$;
$R_{22}$ is H or $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, C=$NR_{28}$;
$R_{23}$ and $R_{24}$ are each independently $C_1$-$C_4$alkyl optionally substituted with halogen, OH, ONO, $ONO_2$, $C_1$-$C_3$alkoxy, $C_1$-$C_3$haloalkoxy, $COOR_{25}$, $NR_{26}R_{27}$, C=$NR_{28}$;
$R_{25}$ is H, or $C_1$-$C_4$alkyl optionally substituted with F, OH, ONO, $ONO_2$;
$R_{26}$ and $R_{27}$ are each independently H or $C_1$-$C_4$alkyl optionally substituted with ONO, $ONO_2$;
$R_{28}$ is $C_1$-$C_4$alkyl optionally substituted with F, ONO, $ONO_2$.

In a further very preferred embodiment, said compound of formula I is a compound of formula I**, wherein $R_1$ is $C_1$-$C_2$alkyl;
$R_2$ is H, $C_1$-$C_3$alkyl optionally substituted with OH, ONO, $ONO_2$; CHO, $CR_8$=N—$OR_9$, $C_1$-$C_3$alkoxy; $C_1$-$C_3$alkylene-Y, wherein Y is ONO, $ONO_2$, CN, or CR$_8$=N—OR$_9$, wherein R$_8$ is H or CH$_3$; R$_9$ is H, C$_1$-C$_3$alkyl optionally substituted with OH, ONO, ONO$_2$;
R$_3$ is C$_2$-C$_3$alkyl optionally substituted with OH, ONO, ONO$_2$;
R$_4$ is C$_2$-C$_3$alkyl optionally substituted with ONO, ONO$_2$;
R$_{22}$ is H or C$_1$-C$_4$alkyl optionally substituted with halogen, OH, ONO, ONO$_2$;
R$_{23}$ and R$_{24}$ are each independently C$_1$-C$_4$alkyl optionally substituted with halogen, OH, ONO, ONO$_2$.

In a further very preferred embodiment, said compound of formula I is a compound of formula I**, wherein R$_1$ is C$_1$-C$_2$alkyl;
R$_2$ is H, C$_1$-C$_3$alkyl optionally substituted with OH, ONO, ONO$_2$; CHO, CR$_8$=N—OR$_9$, C$_1$-C$_3$alkoxy; C$_1$-C$_3$alkylene-Y, wherein Y is ONO, ONO$_2$, CN, or CR$_8$=N—OR$_9$, wherein R$_8$ is H or CH$_3$; R$_9$ is H, C$_1$-C$_3$alkyl optionally substituted with OH, ONO, ONO$_2$;
R$_3$ is C$_2$-C$_3$alkyl optionally substituted with OH, ONO, ONO$_2$;
R$_4$ is C$_2$-C$_3$alkyl optionally substituted with ONO, ONO$_2$;
R$_{22}$ is C$_1$-C$_2$alkyl, preferably methyl R$_{23}$ and R$_{24}$ are each independently C$_1$-C$_3$alkyl substituted with OH, ONO, ONO$_2$, wherein preferably R$_{23}$ and R$_{24}$ are each independently C$_1$-C$_3$alkyl substituted with ONO, ONO$_2$.

In a further very preferred embodiment, said compound of formula I is a compound of formula I**, wherein R$_1$ is C$_1$-C$_2$alkyl;
R$_2$ is H, C$_1$-C$_3$alkyl optionally substituted with OH, ONO, ONO$_2$; CHO, CR$_8$=N—OR$_9$, C$_1$-C$_3$alkoxy; C$_1$-C$_3$alkylene-Y, wherein Y is ONO, ONO$_2$, CN, or CR$_8$=N—OR$_9$, wherein R$_8$ is H or CH$_3$; R$_9$ is H, C$_1$-C$_3$alkyl optionally substituted with OH, ONO, ONO$_2$;
R$_3$ is C$_2$-C$_3$alkyl optionally substituted with OH, ONO, ONO$_2$;
R$_4$ is C$_2$-C$_3$alkyl optionally substituted with ONO, ONO$_2$;
R$_{22}$ is C$_1$-C$_2$alkyl, preferably methyl R$_{23}$ and R$_{24}$ are each independently C$_1$-C$_2$alkyl substituted with ONO, ONO$_2$, wherein preferably R$_{23}$ and R$_{24}$ are each independently C$_1$-C$_2$alkyl substituted with ONO$_2$.

In a further very preferred embodiment, said R$_1$ is C$_1$-C$_3$alkyl.

In a further very preferred embodiment, said R$_1$ is CH$_3$ or C$_2$H$_5$, preferably R$_1$ is CH$_3$.

In a further preferred embodiment, said R$_3$ is C$_1$-C$_4$alkyl optionally substituted with F, OH, ONO, ONO$_2$, C$_1$-C$_3$alkoxy, C$_3$-C$_6$cycloalkyl, C$_2$-C$_4$alkenyl.

In a further very preferred embodiment, said R$_3$ is C$_1$-C$_4$alkyl optionally substituted with ONO$_2$ or C$_3$-C$_5$cycloalkyl.

In a further very preferred embodiment, said R$_3$ is n-propyl.

In a further very preferred embodiment, said R$_4$ is C$_1$-C$_4$alkyl optionally substituted with C$_3$-C$_6$cycloalkyl, C$_1$-C$_3$alkoxy, F, ONO, ONO$_2$; C$_2$-C$_4$alkenyl.

In a further preferred embodiment, said R$_4$ is C$_1$-C$_4$alkyl optionally substituted with ONO$_2$ or C$_3$-C$_5$cycloalkyl.

In a further preferred embodiment, said R$_4$ is ethyl or n-propyl.

Further very preferred embodiments of the present invention are represented by individual compounds of formula I or pharmaceutically acceptable salts, solvates or hydrates thereof.

Thus, in another very preferred embodiment, said compound of formula I is selected from
(E)-2-(4-((3-(5-ethyl-6-((hydroxyimino) methyl)-4-oxo-7-propyl-4,5-dihydro-3H-pyrrolo[3,2-d]pyrimidin-2-yl)-4-propoxyphenyl)sulfonyl)piperazin-1-yl)ethyl nitrate

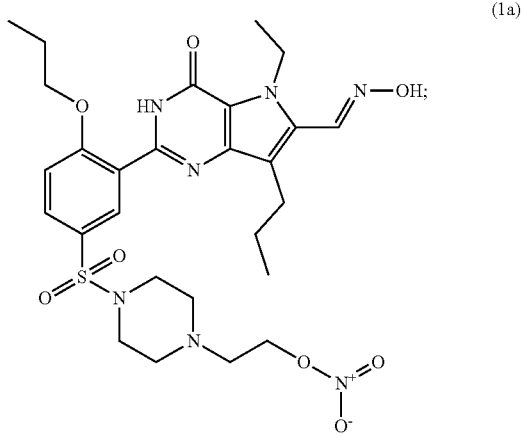 [SMILES: CCCOc1ccc(S(=O)(=O)N2CCN(CCO[N+](=O)[O-])CC2)cc1-c1nc2c(CCC)c(/C=N/O)n(CC)c2c(=O)[nH]1]

2-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethyl nitrate

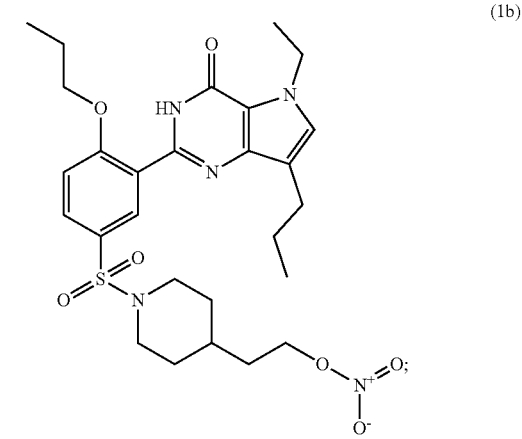 [SMILES: CCCOc1ccc(S(=O)(=O)N2CCC(CCO[N+](=O)[O-])CC2)cc1-c1nc2c(CCC)cn(CC)c2c(=O)[nH]1]

(E)-2-(1-((3-(5-ethyl-6-((hydroxyimino) methyl)-4-oxo-7-propyl-4,5-dihydro-3H-pyrrolo[3,2-d]pyrimidin-2-yl)-4-propoxyphenyl)sulfonyl)piperidin-4-yl)ethyl nitrate

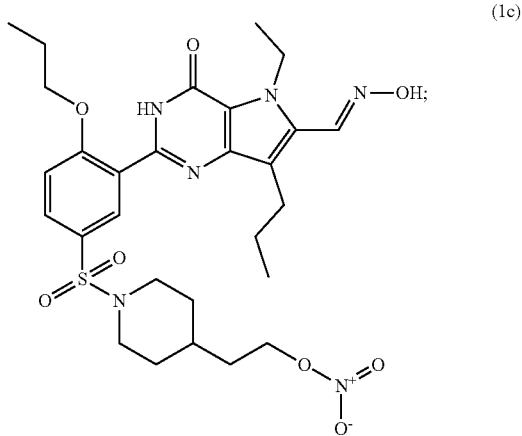

3-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)propyl nitrate (1d)

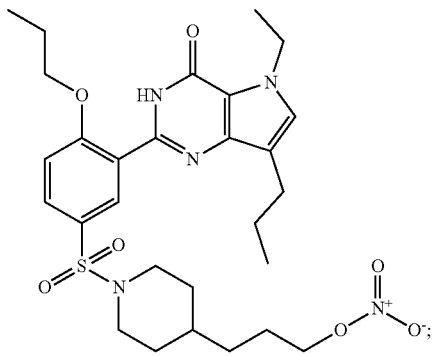

(E)-3-(1-((3-(5-ethyl-6-((hydroxyimino) methyl)-4-oxo-7-propyl-4,5-dihydro-3H-pyrrolo[3,2-d]pyrimidin-2-yl)-4-propoxyphenyl)sulfonyl)piperidin-4-yl)propyl nitrate (1e)

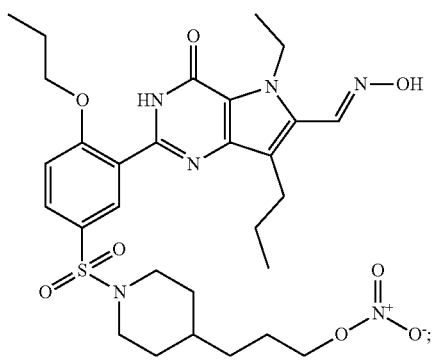

2-(4-((3-(5-ethyl-6-formyl-4-oxo-7-propyl-4,5-dihydro-3H-pyrrolo[3,2-d]pyrimidin-2-yl)-4-propoxyphenyl)sulfonyl)piperazin-1-yl)ethyl nitrate (1f)

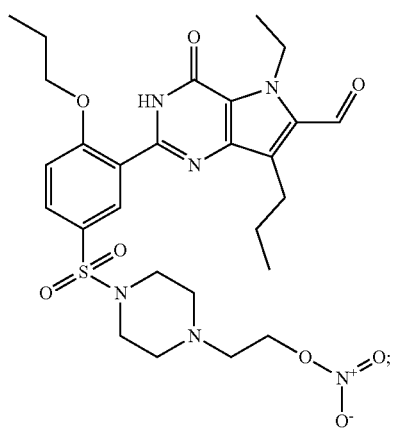

2-(1-((3-(5-ethyl-6-formyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (1g)

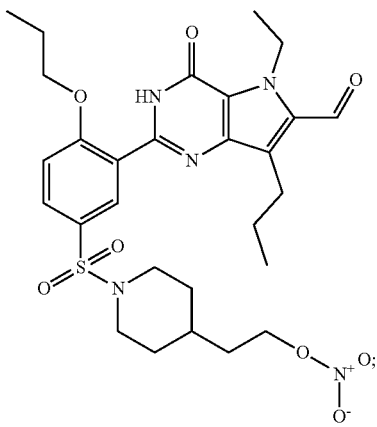

3-(1-((3-(5-ethyl-6-formyl-4-oxo-7-propyl-4,5-dihydro-3H-pyrrolo[3,2-d]pyrimidin-2-yl)-4-propoxyphenyl)sulfonyl)piperidin-4-yl)propyl nitrate (1h)

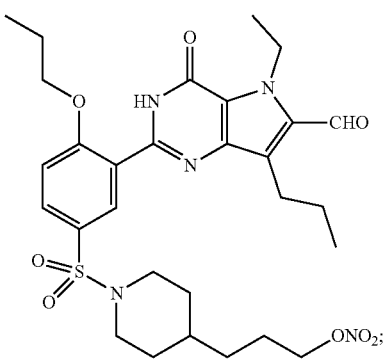

2-(4-((3-(5-ethyl-4-oxo-7-propyl-4,5-dihydro-3H-pyrrolo[3,2-d]pyrimidin-2-yl)-4-propoxyphenyl)sulfonyl)piperazin-1-yl)ethyl nitrate (1i)

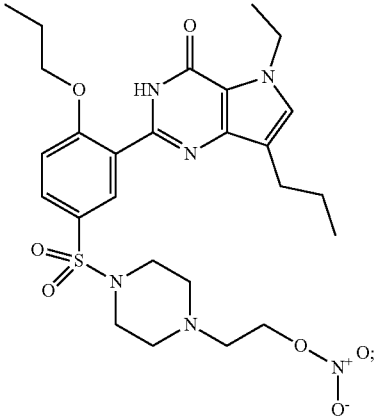

(R)-1-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate

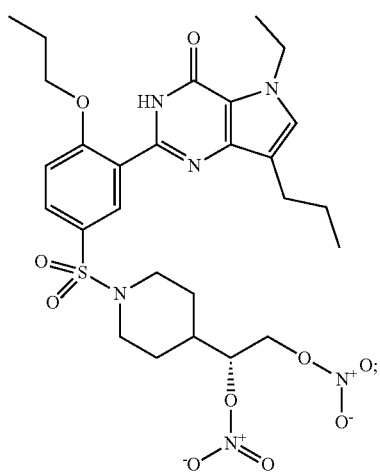

(S)-1-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (1k)

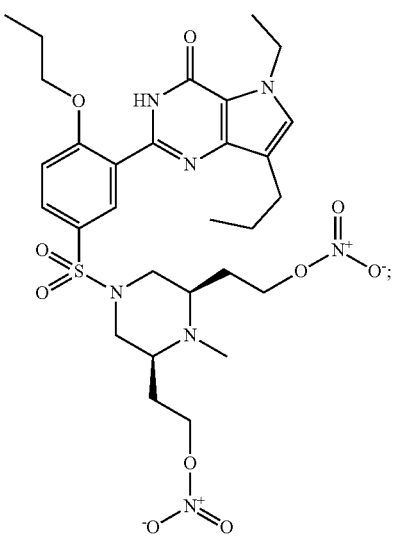

(1-((3-(5-ethyl-4-oxo-7-propyl-4,5-dihydro-3H-pyrrolo[3,2-d]pyrimidin-2-yl)-4-propoxyphenyl)sulfonyl)piperidine-4,4-diyl)bis(ethane-2,1-diyl) dinitrate (1m)

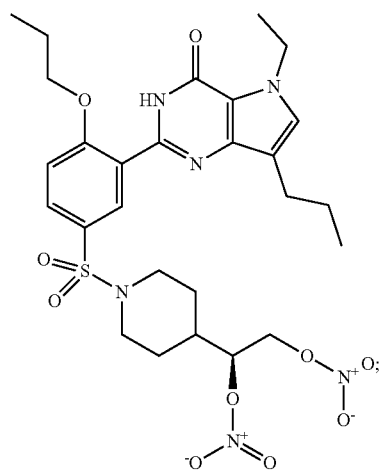

((2R,6S)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)bis(ethane-2,1-diyl) dinitrate (1l)

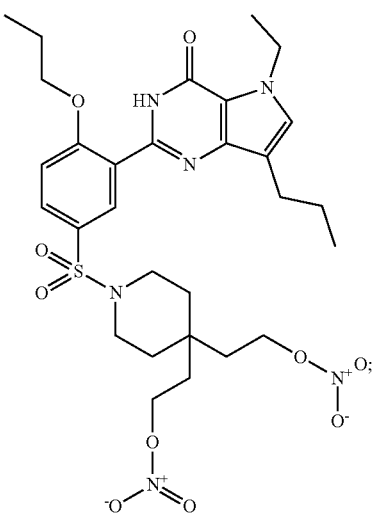

((2S,6S)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)bis(ethane-2,1-diyl) dinitrate (1n)

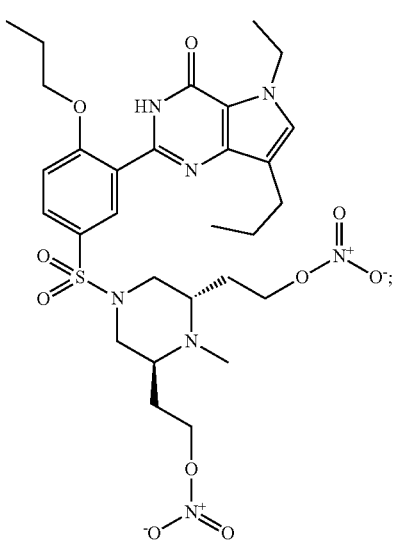

3-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)-3-hydroxypentane-1,5-diyl dinitrate

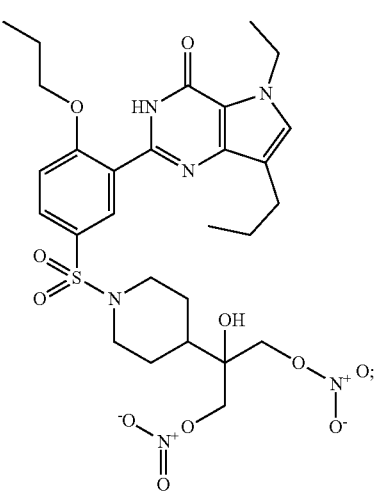

(E)-2-(1-((4-ethoxy-3-(6-((hydroxyimino) methyl)-5-methyl-4-oxo-7-propyl-4,5-dihydro-3H-pyrrolo[3,2-d]pyrimidin-2-yl)phenyl)sulfonyl)piperidin-4-yl)ethyl nitrate

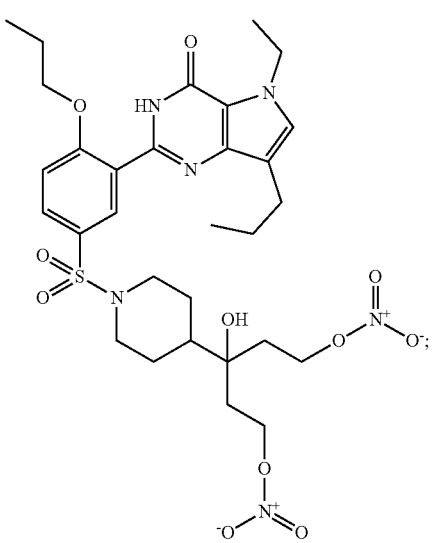

2-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)-2-hydroxypropane-1,3-diyl dinitrate

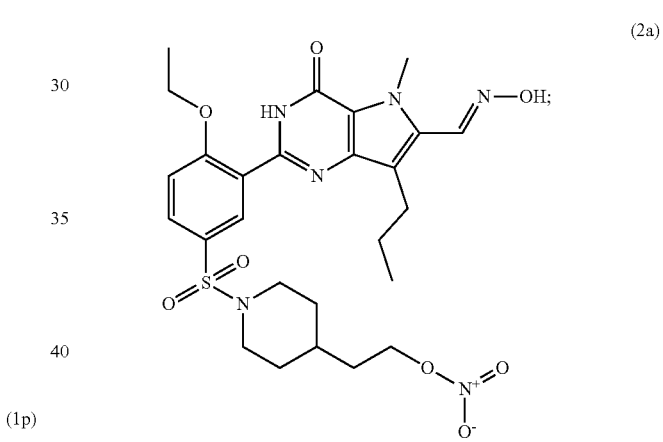

3-(1-((4-ethoxy-3-(5-methyl-4-oxo-7-propyl-4,5-dihydro-3H-pyrrolo[3,2-d]pyrimidin-2-yl)phenyl)sulfonyl)piperidin-4-yl)propyl nitrate

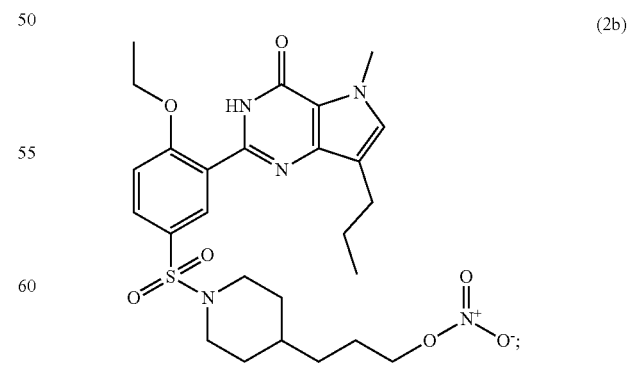

2-(1-((4-ethoxy-3-(5-methyl-4-oxo-7-propyl-4,5-dihydro-3H-pyrrolo[3,2-d]pyrimidin-2-yl)phenyl)sulfonyl)piperidin-4-yl)ethyl nitrate

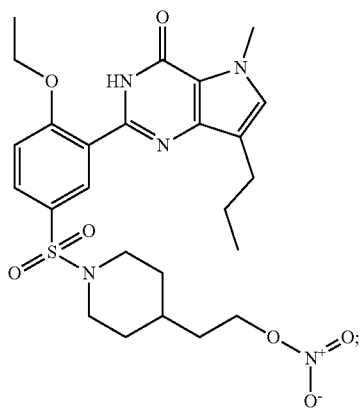

2-(4-((4-ethoxy-3-(5-methyl-4-oxo-7-propyl-4,5-dihydro-3H-pyrrolo[3,2-d]pyrimidin-2-yl)phenyl)sulfonyl)piperazin-1-yl)ethyl nitrate

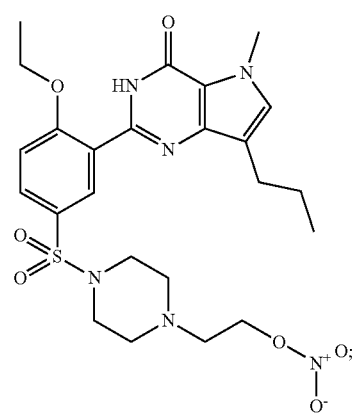

2-(1-((4-ethoxy-3-(6-formyl-5-methyl-4-oxo-7-propyl-4,5-dihydro-3H-pyrrolo[3,2-d]pyrimidin-2-yl)phenyl)sulfonyl)piperidin-4-yl)ethyl nitrate

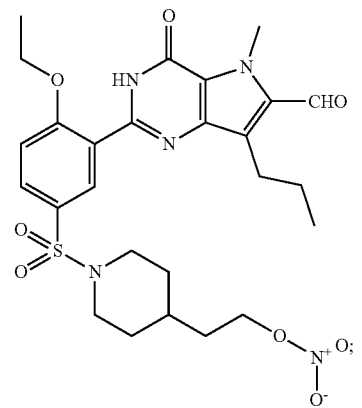

(E)-3-(4-((4-ethoxy-3-(6-((hydroxyimino)methyl)-5-methyl-4-oxo-7-propyl-4,5-dihydro-3H-pyrrolo[3,2-d]pyrimidin-2-yl)phenyl)sulfonyl)piperazin-1-yl)propyl nitrate

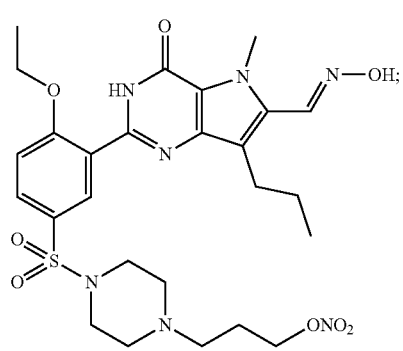

(E)-2-(4-((4-ethoxy-3-(6-((hydroxyimino)methyl)-5-methyl-4-oxo-7-propyl-4,5-dihydro-3H-pyrrolo[3,2-d]pyrimidin-2-yl)phenyl)sulfonyl)piperazin-1-yl)ethyl nitrate

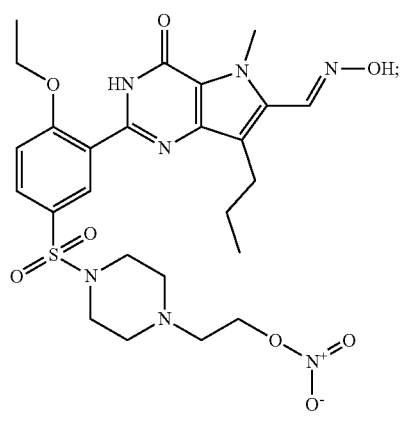

2-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate

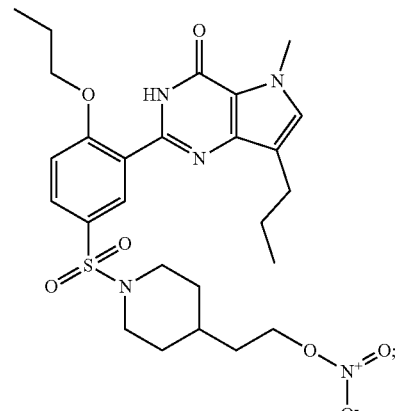

2-(4-((3-(5-methyl-4-oxo-7-propyl-4,5-dihydro-3H-pyrrolo[3,2-d]pyrimidin-2-yl)-4-propoxyphenyl)sulfonyl)piperazin-1-yl)ethyl nitrate

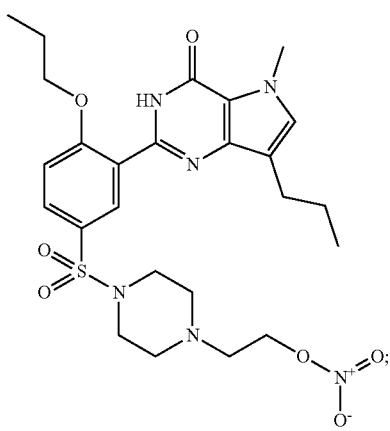

(E)-2-(1-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate

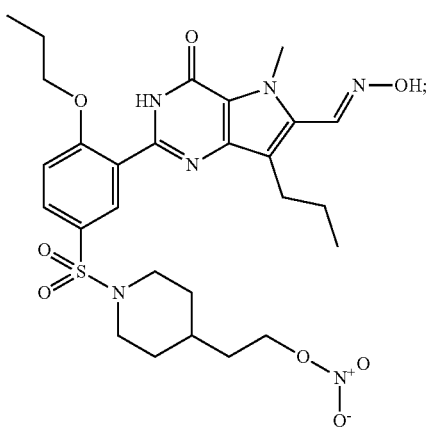

3-(4-((3-(5-methyl-4-oxo-7-propyl-4,5-dihydro-3H-pyrrolo[3,2-d]pyrimidin-2-yl)-4-propoxyphenyl)sulfonyl)piperazin-1-yl)propyl nitrate

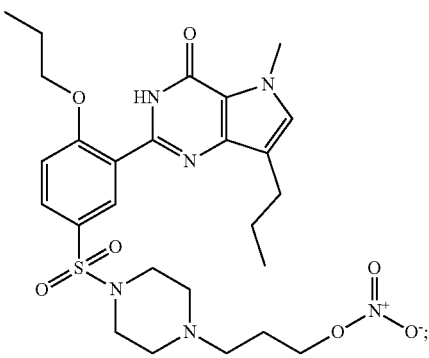

(E)-2-(4-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperazin-1-yl)ethyl nitrate

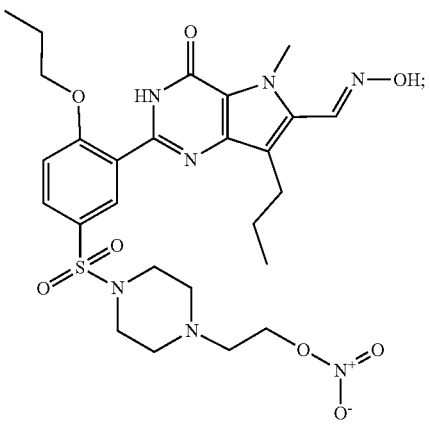

(E)-3-(4-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfon 1)piperazin-1-yl)propyl nitrate

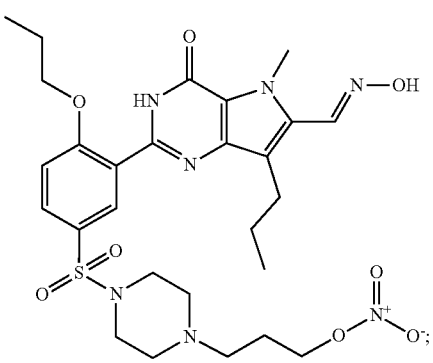

(R)-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate

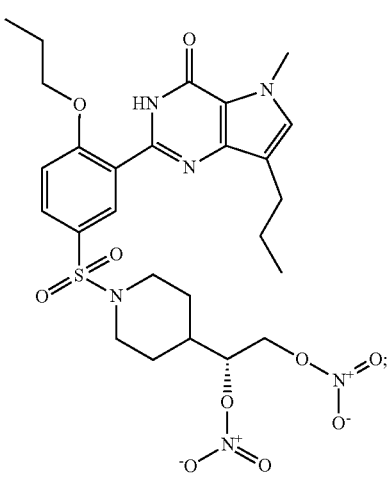

(S)-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate

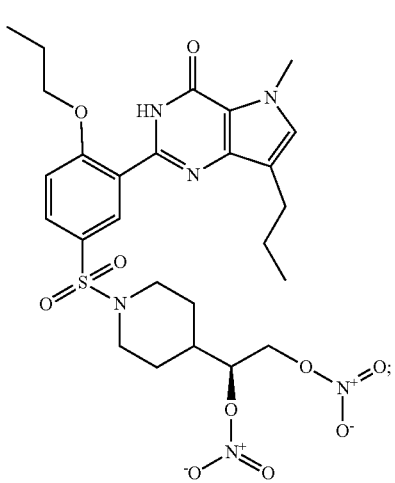

(1-((3-(5-methyl-4-oxo-7-propyl-4,5-dihydro-3H-pyrrolo[3,2-d]pyrimidin-2-yl)-4-propoxyphenyl)sulfonyl)piperidine-4,4-diyl)bis(methylene) dinitrate

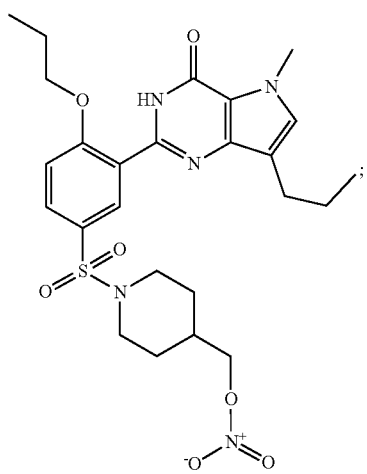

(R)-2-hydroxy-2-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate

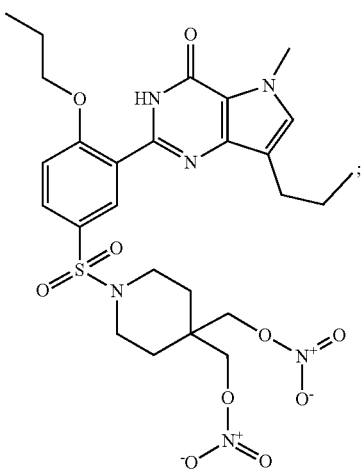

(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)methyl nitrate

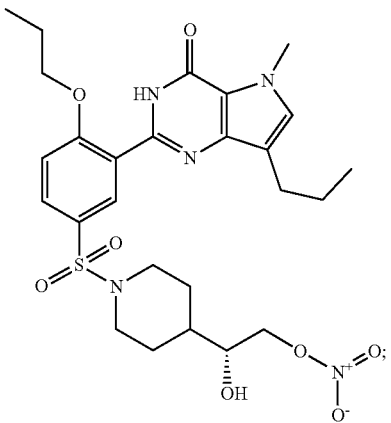

2-hydroxy-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate isomer a

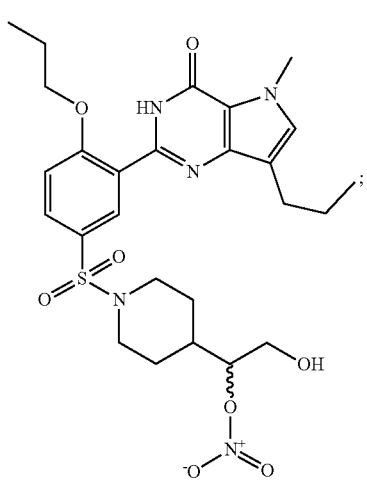

2-hydroxy-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate isomer b

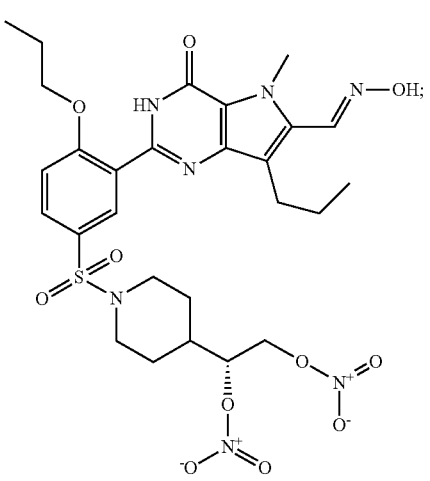

(S)-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate

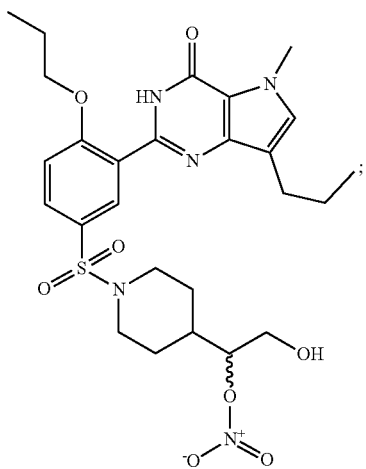

(R,E)-1-(1-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate

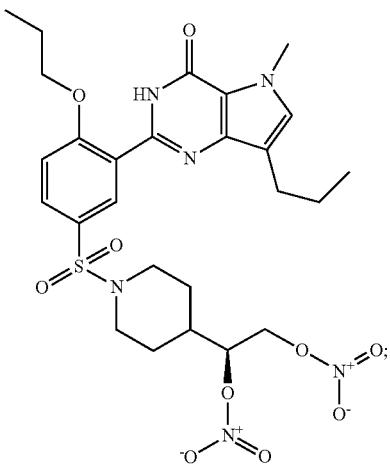

(S)-2-hydroxy-2-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate

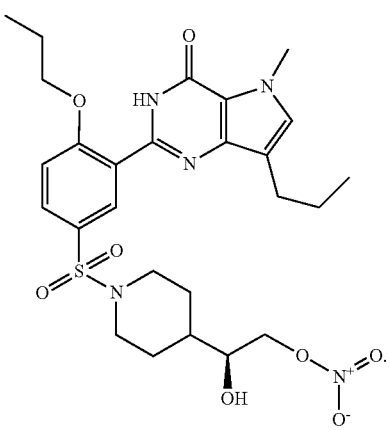

(3q)

In a further very preferred embodiment, said compound of formula I is selected from
(E)-2-(4-((3-(5-ethyl-6-((hydroxyimino) methyl)-4-oxo-7-propyl-4,5-dihydro-3H-pyrrolo[3,2-d]pyrimidin-2-yl)-4-propoxyphenyl)sulfonyl)piperazin-1-yl)ethyl nitrate (1a);
2-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (1b);
(E)-2-(1-((3-(5-ethyl-6-((hydroxyimino) methyl)-4-oxo-7-propyl-4,5-dihydro-3H-pyrrolo[3,2-d]pyrimidin-2-yl)-4-propoxyphenyl)sulfonyl)piperidin-4-yl)ethyl nitrate (1c);
3-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)propyl nitrate (1d);
(E)-3-(1-((3-(5-ethyl-6-((hydroxyimino) methyl)-4-oxo-7-propyl-4,5-dihydro-3H-pyrrolo[3,2-d]pyrimidin-2-yl)-4-propoxyphenyl)sulfonyl)piperidin-4-yl)propyl nitrate (1e);
2-(4-((3-(5-ethyl-6-formyl-4-oxo-7-propyl-4,5-dihydro-3H-pyrrolo[3,2-d]pyrimidin-2-yl)-4-propoxyphenyl)sulfonyl)piperazin-1-yl)ethyl nitrate (1f);
2-(1-((3-(5-ethyl-6-formyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (1g);
3-(1-((3-(5-ethyl-6-formyl-4-oxo-7-propyl-4,5-dihydro-3H-pyrrolo[3,2-d]pyrimidin-2-yl)-4-propoxyphenyl)sulfonyl)piperidin-4-yl)propyl nitrate (1h);
2-(4-((3-(5-ethyl-4-oxo-7-propyl-4,5-dihydro-3H-pyrrolo[3,2-d]pyrimidin-2-yl)-4-propoxyphenyl)sulfonyl)piperazin-1-yl)ethyl nitrate (1H);
(R)-1-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (1k);
(S)-1-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (1l);
((2R,6S)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)bis(ethane-2,1-diyl) dinitrate (1m);
(1-((3-(5-ethyl-4-oxo-7-propyl-4,5-dihydro-3H-pyrrolo[3,2-d]pyrimidin-2-yl)-4-propoxyphenyl)sulfonyl)piperidine-4,4-diyl)bis(ethane-2,1-diyl) dinitrate (1n);
((2S,6S)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)bis(ethane-2,1-diyl) dinitrate (1O);
3-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)-3-hydroxypentane-1,5-diyl dinitrate (1p); and
2-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)-2-hydroxypropane-1,3-diyl dinitrate (1q).

In a further very preferred embodiment, said compound is selected from In a further preferred embodiment, said compound is selected from
2-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (1b);
(E)-2-(1-((4-ethoxy-3-(6-((hydroxyimino) methyl)-5-methyl-4-oxo-7-propyl-4,5-dihydro-3H-pyrrolo[3,2-d]pyrimidin-2-yl)phenyl)sulfonyl)piperidin-4-yl)ethyl nitrate (2a);
2-(1-((4-ethoxy-3-(5-methyl-4-oxo-7-propyl-4,5-dihydro-3H-pyrrolo[3,2-d]pyrimidin-2-yl)phenyl)sulfonyl)piperidin-4-yl)ethyl nitrate (2c); and
2-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (3a).

Figure 2:
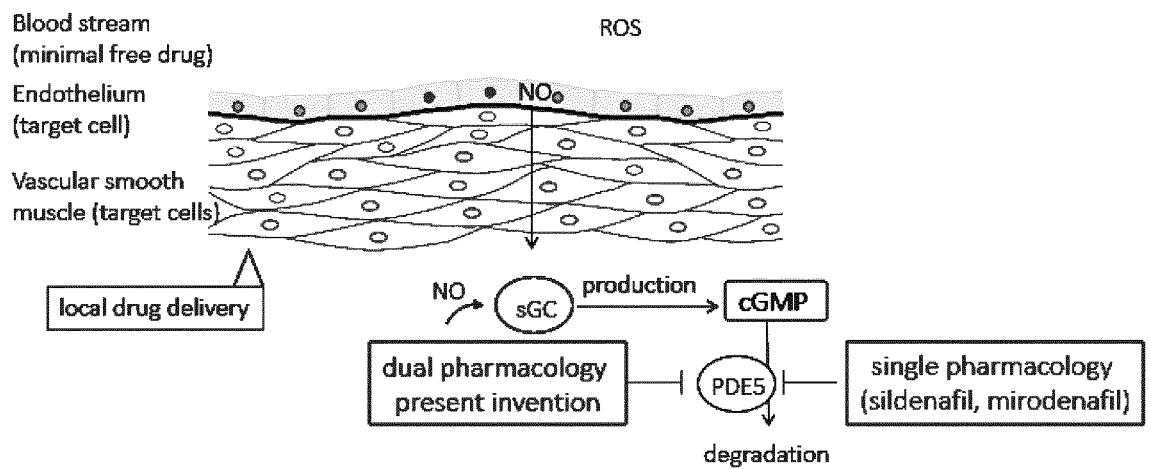
FIG. 2: Dual-pharmacology NO-releasing PDE5 inhibitors addressing disturbed cGMP balance in diseases with disturbed cGMP balance

It has been shown that compounds of the present invention are potent and selective inhibitors of cGMP specific PDE. Furthermore, it has been found that the compounds of the present invention are dual-pharmacology NO-releasing PDE5 inhibitors believed to release NO in addition to its PDE5 inhibition in a more than additive fashion. Thus, compounds of formula I are of interest for use in therapy, specifically for the treatment of a variety of conditions where inhibition of cGMP specific PDE is thought to be beneficial. Given the discovery of strong plasma protein binding the compounds of the present invention are especially suited for local action after local application (see FIG. 2).

Thus, in a further aspect, the present invention provides for a pharmaceutical composition comprising at least one of the inventive compound of formula I, or a pharmaceutically acceptable salt, solvate or hydrate thereof, and a pharmaceutically acceptable excipient, adjuvant, or carrier.

In another aspect, the present invention provides for a pharmaceutical composition comprising exactly one inventive compound of formula I, or a pharmaceutically acceptable salt, solvate or hydrate thereof, and a pharmaceutically acceptable excipient, adjuvant, or carrier. Pharmaceutically acceptable excipient, adjuvant, or carrier are known to the skilled person.

In another aspect, the present invention provides for a compound of formula I, or a pharmaceutical composition, or a pharmaceutically acceptable salt, solvate or hydrate thereof, for use as a medicament.

In another aspect, the present invention provides for a compound of formula I, or a pharmaceutically acceptable salt, solvate or hydrate thereof, for use as a pharmaceutical. In again another aspect, the present invention provides for a compound of formula I, or a pharmaceutically acceptable salt, solvate or hydrate thereof, for use as an animal medicament.

It has surprisingly been found that the compounds of the present invention are dual-pharmacology NO-releasing PDE5 inhibitors believed to release NO in addition to its PDE5 inhibition in a more than additive fashion. As a consequence, the novel pyrrolo pyrimidine compounds of the present invention are useful in the therapy and prophylaxis of diseases which are associated with a disturbed cGMP balance. In particular, the compounds of the present invention are activators of soluble guanylyl cyclase (sGC)

potent and at the same time selective inhibitors of cyclic guanosine 3'-5'-monophosphate specific phosphodiesterase 5 (cGMP specific PDE5) and thus have utility in variety of therapeutic areas where such inhibition is beneficial.

Some of the preferred therapeutic areas are wound healing, in particular chronic wound healing, diabetic foot, diabetic foot ulcer, leg ulcer, Raynaud's, male erectile dysfunction, female sexual dysfunction, diabetes, hair loss, skin aging, vascular aging, pulmonary artery hypertension and livedoid vasculopathy, thromboangitis obliterans, chronic anal fissure, skin fibrosis.

As a consequence of the selective PDE5 inhibition exhibited by compounds of the present invention, cGMP levels are expected to be elevated, which in turn can give rise to beneficial anti-platelet, anti-vasospastic, vasodilatory, natriuretic and diuretic activities as well as potentiation of the effects of endothelium-derived relaxing factor (EDRF) nitric oxide (NO), nitrovasodilators, atrial natriuretic factor (ANF), brain natriuretic peptide (BNP), C-type natriuretic peptide (CNP) and endothelium-dependent relaxing agents such as bradykinin, acetylcholine and 5-HT$_1$. The compounds of formula I therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, diabetes, glaucoma and diseases characterized by disorders of gut motility like irritable bowel syndrome, wound healing, in particular chronic wound healing, diabetic foot, diabetic foot ulcer, leg ulcer, Alzheimer's disease, hair loss, skin aging, vascular aging, pulmonary artery hypertension and chronic heart failure.

Thus, in another aspect, the present invention provides for a compound of formula I, or a pharmaceutical composition, or a pharmaceutically acceptable salt, solvate or hydrate thereof, for use in a method of treating or preventing a disease alleviated by inhibition of PDE5 in a human or in a non-human mammal, preferably in a human. Preferably, said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure. wherein further preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism and female sexual dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for the inventive compound of formula I, or the inventive pharmaceutical composition, or a pharmaceutically acceptable salt, solvate or hydrate thereof, for use in a method of treating or preventing a disease in a human or in a non-human mammal, preferably in a human, wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism and female sexual dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for a compound of formula I, or a pharmaceutical composition, or a pharmaceutically acceptable salt, solvate or hydrate thereof, for use in a method of treating or preventing a disease by activation of soluble guanylyl cyclase (sGC) and inhibition of PDE5 in a human or in a non-human mammal, preferably in a human. In again another aspect, the present invention provides for a compound of formula I, or a pharmaceutical composition, or a pharmaceutically acceptable salt, solvate or hydrate thereof, for use in a method of treating or preventing a disease by activation of soluble guanylyl cyclase (sGC) or inhibition of PDE5 in a human or in a non-human mammal, preferably in a human. In again another aspect, the present invention provides for a compound of formula I, or a pharmaceutical composition, or a pharmaceutically acceptable salt, solvate or hydrate thereof, for use in a method of treating a medical condition in a human or in a non-human mammal, preferably in a human, wherein for said medical condition inhibition of PDE5 and/or activation of soluble guanylyl cyclase (sGC) is desired. Very preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides use of a compound of formula I, or a pharmaceutical composition, or a pharmaceutically acceptable salt, solvate or hydrate thereof, for the manufacture of a medicament for the treatment or prevention of a disease by activation of soluble guanylyl cyclase (sGC) and/or inhibition of PDE5 in a human or in a non-human mammal, preferably in a human. In again another aspect, the present invention provides use of a compound of formula I, or a pharmaceutical composition, or a pharmaceutically acceptable salt, solvate or hydrate thereof, for the manufacture of a medicament for the treatment or prevention of a disease alleviated by activation of soluble guanylyl cyclase (sGC) and/or inhibition of PDE5 in a human or in a non-human mammal, preferably in a human. In again another aspect, the present invention provides use of a compound of formula I, or a pharmaceutical composition, or a pharmaceutically acceptable salt, solvate or hydrate thereof, for the manufacture of a medicament for the treatment a medical condition in a human or in a non-human mammal, preferably in a human, wherein for said medical condition activation of soluble guanylyl cyclase (sGC) and/or inhibition of PDE5 is desired. In again another aspect, the present invention provides use of a compound of formula I, or a pharmaceutical composition, or a pharmaceutically acceptable salt, solvate or hydrate thereof, for the manufacture of a medicament for the treatment or prevention of a disease, wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure. wherein further preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism and female sexual dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In again another aspect, the present invention provides for a method of treating or preventing a disease by activation of soluble guanylyl cyclase (sGC) and/or inhibition of PDE5 in a human or in a non-human mammal, preferably in a human, comprising administering to said human or said non-human mammal, preferably to said human an effective amount of a compound of formula I, or a pharmaceutical composition, or a pharmaceutically acceptable salt, solvate or hydrate thereof. In again another aspect, the present invention provides for a method of treating or preventing a disease alleviated by activation of soluble guanylyl cyclase (sGC) and/or inhibition of PDE5 in a human or in a non-human mammal, preferably in a human, comprising administering to said human or said non-human mammal, preferably to said human an effective amount of a compound of formula I, or a pharmaceutical composition, or a pharmaceutically acceptable salt, solvate or hydrate thereof. In again another aspect, the present invention provides for a method of treating a medical condition in a human or in a non-human mammal, preferably in a human, wherein for said medical condition activation of soluble guanylyl cyclase (sGC) and/or inhibition of PDE5 is desired, comprising administering to said human or said non-human mammal, preferably to said human an effective amount of a compound of formula I, or a pharmaceutical composition, or a pharmaceutically acceptable salt, solvate or hydrate thereof. In again another aspect, the present invention provides for a method of treating or preventing a disease in a human or in a non-human mammal, preferably in a human, comprising administering to said human or said non-human mammal, preferably to said human, an effective amount of a compound of formula I, or a pharmaceutical composition, or a pharmaceutically acceptable salt, solvate or hydrate thereof, and wherein said disease is selected from wound healing, chronic wound healing, diabetic foot, diabetic foot ulcer, leg ulcer, Raynaud's disease, male erectile dysfunction, priapism, female sexual dysfunction, hair loss, skin aging, vascular aging, pulmonary artery hypertension; livedoid vasculopathy, thromboangitis obliterans, chronic anal fissure, skin fibrosis, stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure. wherein further preferably said disease is selected from wound healing, chronic wound healing, diabetic foot, diabetic foot ulcer, leg ulcer, diabetic neuropathy, peripheral vascular disease, vascular disorders such as Raynaud's disease, livedoid vasculopathy, thromboangitis obliterans, chronic anal fissure, skin fibrosis, systemic sclerosis (SSc), scleroderma, pulmonary artery hypertension (PAH), chronic thromboembolic pulmonary hypertension, male erectile dysfunction, priapism and female sexual dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In a preferred embodiment of the present invention, said disease or said a medical condition is selected from livedoid vasculopathy, thromboangitis obliterans, chronic anal fissure, skin fibrosis, wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from livedoid vasculopathy, thromboangitis obliterans, chronic anal fissure, skin fibrosis, wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

There is thus provided as a further aspect of the present invention a compound of formula I for use in the treatment of wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

According to another aspect of the invention, there is provided the use of a compound of formula I for the manufacture of a medicament for the treatment of wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In a further aspect, the invention provides a method of treating wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension (PAH), chronic thromboembolic pulmonary hypertension, diabetes, male erectile dysfunction, and wherein again further preferably said disease is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer, in a human or in non-human mammal, preferably in a human, said method comprises administering to said human or said non-human mammal, preferably to said human, an effective amount of a compound of formula I.

In a very preferred embodiment of the present invention, said disease or said a medical condition is selected from pulmonary artery hypertension (PAH), chronic thromboembolic pulmonary hypertension, male erectile dysfunction, priapism and female sexual dysfunction, livedoid vasculopathy, thromboangitis obliterans, chronic anal fissure, skin fibrosis, wound healing, chronic wound healing, diabetic foot, diabetic foot ulcer, leg ulcer, diabetic neuropathy and pressure ulcer.

In a very preferred embodiment of the present invention, said disease or said a medical condition is selected from wound healing, preferably chronic wound healing, diabetic foot, diabetic foot ulcer and leg ulcer, pulmonary artery hypertension and male erectile dysfunction and livedoid vasculopathy, thromboangitis obliterans, chronic anal fissure, skin fibrosis.

Chronic, non-healing skin wounds such as in diabetes mellitus are governed by complex disease mechanisms including impaired angiogenesis, defective microcirculation, and endothelial dysfunction. Diabetic foot ulcer and chronic wounds are a major source of morbidity and is a leading cause of hospitalizations in diabetic patients. It afflicts 15% of diabetes patients (275 Mio) and is a huge burden to patients and payers (12 billion $/year). 3-4% of all diabetic patients will get lower limb amputations every year. Ultra-potent PDE5 inhibitors or compounds integrating highly potent activation of soluble guanylyl cyclase (sGC) and/or inhibition of PDE5 and activation of nitric oxide dependent soluble guanylate cyclase as the ones of the present invention can be expected to accelerate wound healing.

As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment. Preferably, beneficial or desired clinical results of said treatment include, but are not limited to, alleviation of symptoms, diminishment of extent of disease or medical condition, stabilized (i.e., not worsening) state of disease or medical condition, delay or slowing of disease or medical condition progression, amelioration or palliation of the disease or medical condition state.

As used herein, the term "effective amount" refers to an amount necessary or sufficient to realize a desired biologic effect. Preferably, the term "effective amount" refers to an amount of a compound of formula I of the present invention that (i) treats or prevents the particular disease, medical condition, or disorder, (ii) attenuates, ameliorates, or eliminates one or more symptoms of the particular disease, medical condition, or disorder, or (iii) prevents or delays the onset of one or more symptoms of the particular disease, medical condition, or disorder described herein.

An effective amount of the inventive compound of formula I, or said pharmaceutical composition, would be the amount that achieves this selected result, and such an amount could be determined as a matter of routine by a person skilled in the art. Further preferably, the term "effective amount", as used herein, refers to an amount necessary or sufficient to be effective to activation of soluble guanylyl cyclase (sGC) and/or increase the inhibition of PDE5, typically and preferably as determined in Example 54, or to increase the formation of cGMP, typically and preferably as determined in Example 56. The effective amount can vary depending on the particular composition being administered and the size of the subject. One of ordinary skill in the art can empirically determine the effective amount of a particular composition of the present invention without necessitating undue experimentation.

The term "mammal", as used herein, includes, but is not limited to, humans, mice, rats, guinea pigs, monkeys, dogs, cats, horses, cows, pigs, and sheep. The term "mammal", as used herein, preferably refers to humans.

The compounds of formula I and the pharmaceutical compositions of the present invention may be administered by any suitable route, for example by oral, buccal, sublingual, rectal, vaginal, intranasal, nasal, topical, intradermal, transdermal, subcutaneous, transcutaneous, enteral or parenteral administration, which forms another aspects of the present invention. Other routes are known in the art that could also be employed such as by way of chirurgical inlets. Thus, a device may be used for administration, such as conventional needles and syringes, micro needles, patches (e.g. as in WO 98/20734), needle free injection systems (e.g. as in WO 1999027961 A1), spray devices and the like, depending on the dose form and administration route. The device may be pre-filled or coated with the inventive compound or pharmaceutical composition.

The term "topical administration" is used in its broadest sense to include administration to a surface on the body that is generally open to the surroundings. This includes not only the skin but also the nasal and oral passages and the genitalia. Thus, topical administration can include application to the skin, application to the nasal passages, application to the oral cavity (including the upper throat), and application to the genitalia. Topical formulations have been available in a variety of forms, including creams, ointments, solutions, lotions, suspensions, pastes, emulsions, foams and the like. Water miscible creams have generally been employed for moist or weeping lesions, whereas ointments have been generally chosen for dry, lichenified or scaly lesions or where a more occlusive effect has been required. Lotions have generally been useful when minimal application to a large or hair-bearing area has been required or for the treatment of exudative lesions. The term "local administration" is used herein to refer to topical administration as well as administration to the eyes.

The inventive compounds of formula I can be prepared according to the reaction scheme 1 and scheme 2. These schemes represent the synthesis of generic compounds of formula I and forms part of the present invention.

Thus, a process for preparing compounds of formula I involves synthesis of sulfonamide intermediate III, which is prepared from commercially available 5-chlorosulfonyl-2-ethoxybenzoic acid SM2 and amines II in aprotic solvents and excess of tertiary amines. Intermediate compounds IV are obtained under standard peptide formation conditions using commercially available 3-amino-1-methyl-4-propyl-pyrrole SM1 (described in WO2001/060825) and condensation agents like TBTU/DIPEA in polar solvents like DMF. Condensation under basic conditions using potassium hydroxide or similar bases under heating leads to pyrrolopyrimidin compounds V. This intermediate is directly converted to compounds of formula I by nitration using the in situ generated acetonitrile in solvents like acetonitrile. Intermediate V can also be hydroxyethylated in position 6 of the heterocycle with paraformaldehyde under acidic conditions leading to compounds with the general structure VI. Selective oxidation using $MnO_2/KMnO_4$ leads to aldehyde intermediates VII, which can be converted to the nitrate esters I using the described nitration conditions with acetonitrile (Scheme 1).

Compounds of formula I, with an ethyl substituent on position 5 of the pyrrolo-pyrimidin heterocycle can easily be obtained starting from mirodenafil (WO2001/060825) as outlined in Scheme 2. Acidic hydrolysis leads to the intermediate sulfonic acid X. Formation of the chlorosulfonic acid derivative XI and treatment with amines II leads to the sulfonamides XII. Nitration using acetonitrile leads to compounds I. Direct nitration of mirodenafil or the intermediates IX leads also to dual pharmacology compounds I.

Scheme 1

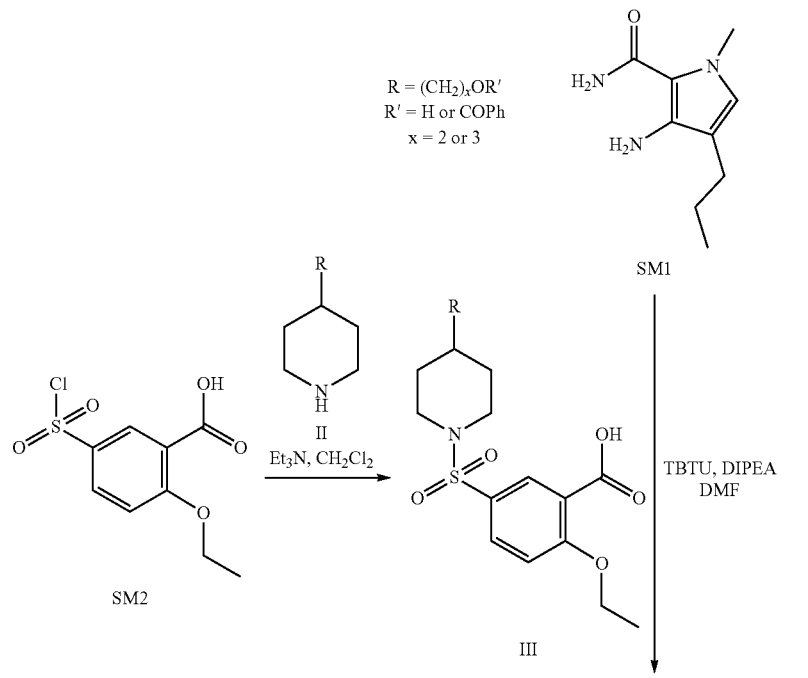

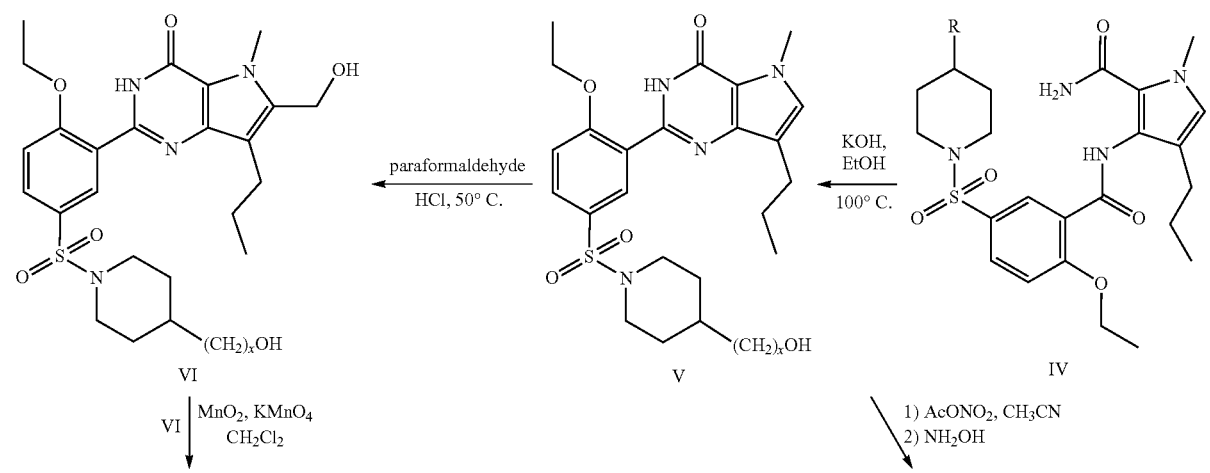

51
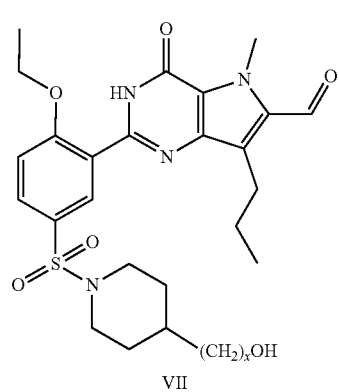
VII
1) AcONO$_2$, CH$_3$CN
2) NH$_2$OH
-continued
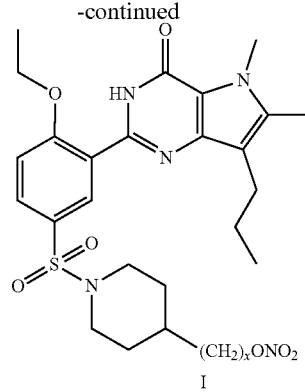
I
52
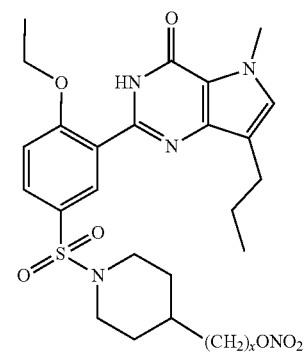
Scheme 2
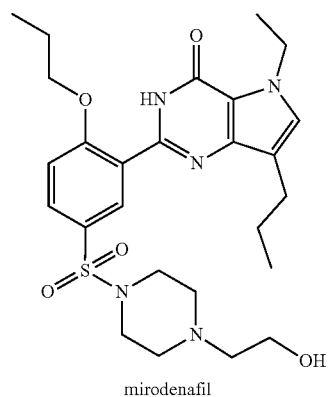
mirodenafil
1) Paraformaldehyde HCl
2) DMP, CH$_2$Cl$_2$
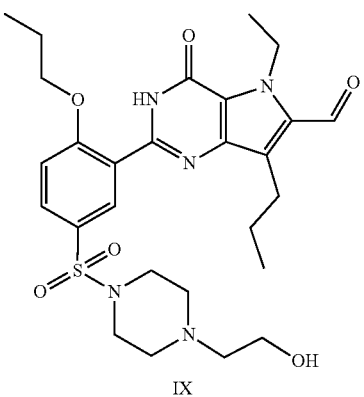
IX
H$_2$SO$_4$, H$_2$O
100° C.
AcONO$_2$, ACN
1) AcONO$_2$, ACN
2) NH$_2$OH, EtOH
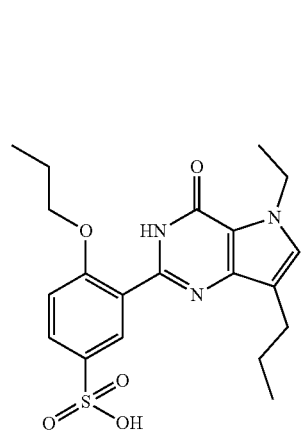
X
(COCl)$_2$, CH$_2$Cl$_2$
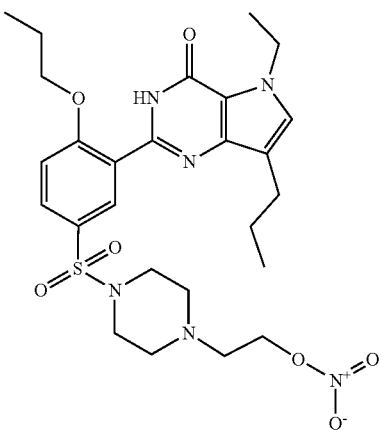
I
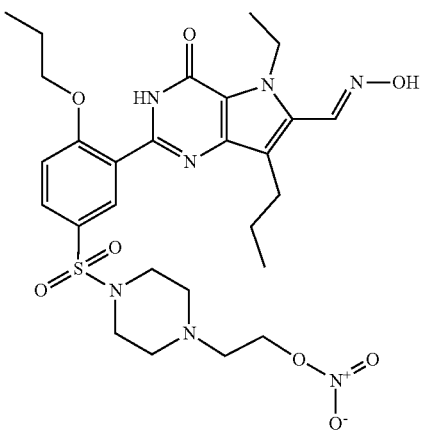
I

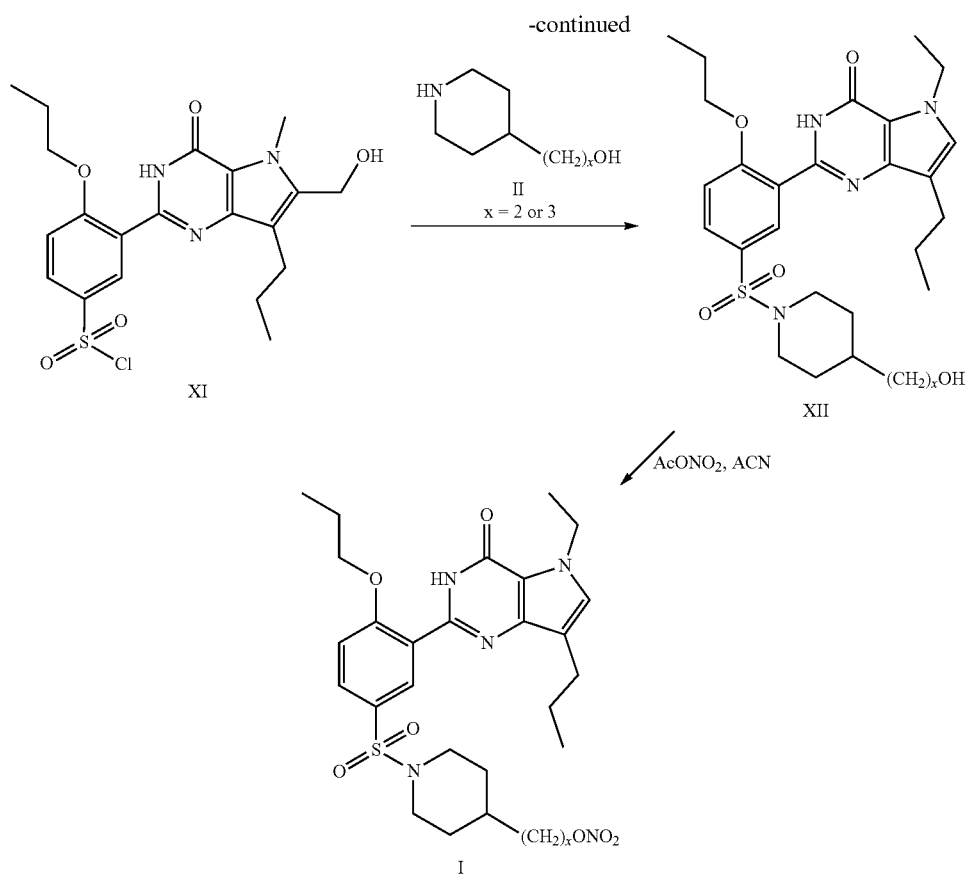
EXAMPLES
The synthesis of preferred compounds of formula I are exemplified below, typically preceded by a reaction scheme. The following examples further illustrate the present invention, but should not be construed in any way as to limit its scope.
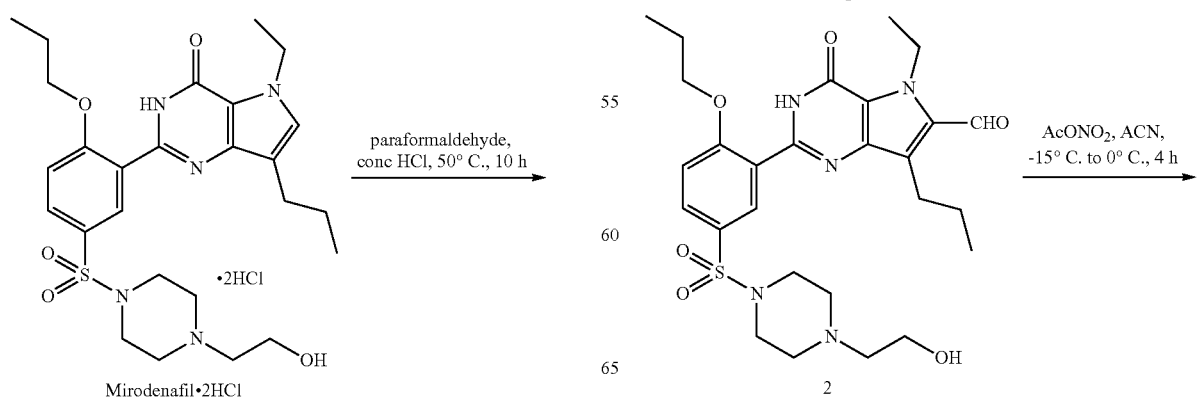

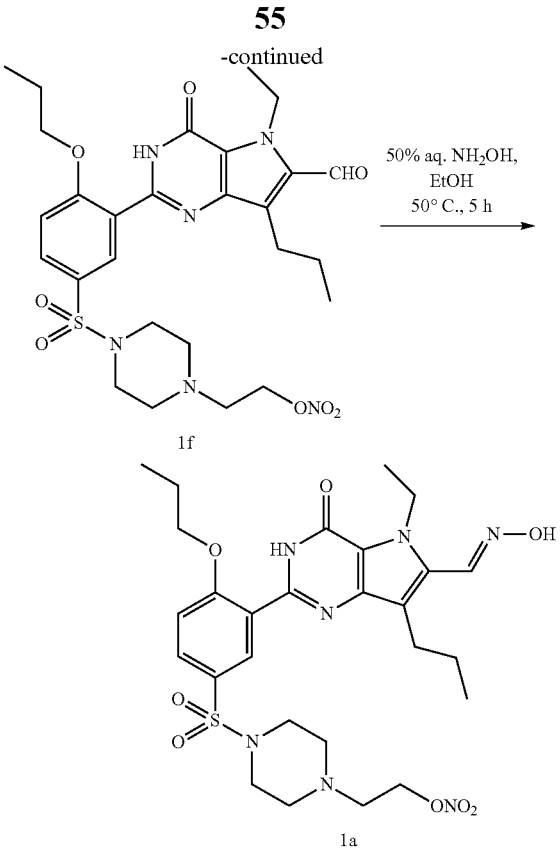

Example 1

5-ethyl-2-(5-((4-(2-hydroxyethyl)piperazin-1-yl)
sulfonyl)-2-propoxyphenyl)-6-(hydroxymethyl)-7-
propyl-3,5-dihydro-4H-pyrrolo[3,2-d]pyrimidin-4-
one (1)

To a stirred solution of 5-ethyl-2-(5-((4-(2-hydroxyethyl) piperazin-1-yl)sulfonyl)-2-propoxyphenyl)-7-propyl-3,5-dihydro-4H-pyrrolo[3,2-d]pyrimidin-4-one dihydrochloride salt (Mirodenafil·2HCl; WO01/60825) (2.0 g, 3.31 mmol) in concentrated HCl solution (20 mL) was added paraformaldehyde (1.0 g, 0.5 w/w) at room temperature. The reaction was heated at 50° C. for 10 h. The reaction was monitored by TLC (using 10% MeOH in CH$_2$C$_2$) and LCMS analysis. After completion of reaction, the reaction mixture was cooled to room temperature, diluted with water (20 mL) and pH was adjusted to ~8 using saturated NaHCO$_3$ solution (300 mL). The resultant solution was extracted with 10% methanol in dichloromethane (6×300 mL). The combined organic extracts were dried over anhydrous Na$_2$SO$_4$ and concentrated under reduced pressure. The obtained crude product was purified by reverse phase column chromatography (C18 column; Grace System) by eluting with 25-35% gradient acetonitrile with water. The pure fractions were concentrated under reduced pressure until acetonitrile was completely removed. The resultant aqueous solution was extracted with 10% methanol in dichloromethane (8×500 mL). The combined organic extracts were concentrated under reduced pressure to afford 1 (1.5 g; 79% yield) as an off-white solid. $^1$H NMR (400 MHz, DMSO-d$_6$) δ ppm 11.63 (br s, 1H), 7.90 (br s, 1H), 7.80 (br d, J=8.8 Hz, 1H), 7.38 (br d, J=8.8 Hz, 1H), 5.19 (t, J=5.1 Hz, 1H), 4.57 (d, J=5.1 Hz, 2H), 4.47 (q, J=7.0 Hz, 2H), 4.33 (br s, 1H), 4.13 (t, J=6.4 Hz, 2H), 3.42-3.40 (m, 2H), 2.91-2.88 (m, 4H), 2.61-2.58 (m, 2H), 2.46-2.49 (m, 4H), 2.38-2.35 (m, 2H), 1.79-1.71 (m, 2H), 1.64-1.52 (m, 2H), 1.34 (t, J=7.1 Hz, 3H), 0.96 (t, J=7.3 Hz, 3H), 0.88 (t, J=7.3 Hz, 3H); LCMS (ESI): m/z 562.5 [M+H]$^+$; purity~97.6%.

Example 2

5-ethyl-2-(5-((4-(2-hydroxyethyl)piperazin-1-yl)
sulfonyl)-2-propoxyphenyl)-4-oxo-7-propyl-4,5-
dihydro-3H-pyrrolo[3,2-d]pyrimidine-6-carbaldehyde (2)

To a stirred solution of 5-ethyl-2-(5-((4-(2-hydroxyethyl) piperazin-1-yl)sulfonyl)-2-propoxyphenyl)-6-(hydroxymethyl)-7-propyl-3,5-dihydro-4H-pyrrolo[3,2-d]pyrimidin-4-one 1 (2.0 g, 3.56 mmol) in CH$_2$Cl$_2$ (40 mL) was added Dess-Martin periodinane (2.3 g, 5.34 mmol) at 0° C. in portion wise for 20 min under argon atmosphere. The reaction mixture was stirred at same temperature for 3 h. After completion of reaction (monitored by TLC), the reaction was quenched with 10% aqueous sodium thiosulphate solution (20 mL) and stirred for 30 min. The organic layer was separated and was washed with saturated NaHCO$_3$ solution (20 mL), brine (20 mL), dried over anhydrous Na$_2$SO$_4$ and concentrated under reduced pressure. The crude product purified by silica gel column chromatography (using Grace System) by eluting with 4-30% gradient methanol in dichloromethane to afford 2 (900 mg, 41% yield) as a pale yellow solid. $^1$H NMR (300 MHz, DMSO-d$_6$) δ ppm 12.15 (br s, 1H), 10.14 (s, 1H), 7.90-7.78 (m, 2H), 7.39 (d, J=8.8 Hz, 1H), 4.85 (q, J=6.7 Hz, 2H) 4.38 (t, J=5.3 Hz, 1H), 4.13 (br t, J=6.4 Hz, 2H), 3.42 (q, J=6.0 Hz, 2H). 3.03-2.80 (m, 6H), 2.49-2.46 (m, 2H), 2.48-2.44 (m, 2H), 2.38-2.32 (m, 2H), 1.80-1.58 (m, 4H), 1.15 (t, J=7.1 Hz, 3H), 0.98-0.93 (m, 6H); LCMS (ESI): m/z 560.6 [M+H]$^+$; purity~91%.

Example 3

2-(4-((3-(5-ethyl-6-formyl-4-oxo-7-propyl-4,5-di-
hydro-3H-pyrrolo[3,2-d]pyrimidin-2-yl)-4-propoxy-
phenyl)sulfonyl)piperazin-1-yl)ethyl nitrate (1f)

To a stirred solution of 5-ethyl-2-(5-((4-(2-hydroxyethyl) piperazin-1-yl)sulfonyl)-2-propoxyphenyl)-4-oxo-7-propyl-4,5-dihydro-3H-pyrrolo[3,2-d]pyrimidine-6-carbaldehyde 2 (500 mg, 0.90 mmol) in acetonitrile (15 mL) was added a solution of freshly prepared acetyl nitrate (0.4 mL; 4.5 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised above 0° C.))] drop wise at −15° C. for 30 min under argon atmosphere. The reaction was maintained at −15° C. to −5° C. for 4 h. After completion of reaction (monitored by TLC), the reaction was quenched with saturated NaHCO$_3$ solution (15 mL) at 0° C. and extracted with EtOAc (3×25 mL). The combined organic layer was washed with brine (25 mL), dried over anhydrous Na$_2$SO$_4$ and concentrated under reduced pressure to afford the crude product 1f (500 mg) as a brown semi solid, which was directly taken for next reaction without further purification. LCMS (ESI): m/z 605.5 [M+H]$^+$; purity~56%.

Example 4

(E)-2-(4-((3-(5-ethyl-6-((hydroxyimino)methyl)-4-oxo-7-propyl-4,5-dihydro-3H-pyrrolo[3,2-d]pyrimidin-2-yl)-4-propoxyphenyl)sulfonyl)piperazin-1-yl)ethyl nitrate (1a)

To a stirred solution of 2-(4-((3-(5-ethyl-6-formyl-4-oxo-7-propyl-4,5-dihydro-3H-pyrrolo[3,2-d]pyrimidin-2-yl)-4-propoxyphenyl)sulfonyl)piperazin-1-yl)ethyl nitrate if (500 mg) in EtOH (60 mL) was added 50% aqueous hydroxylamine solution (10 mL) at room temperature. The reaction was stirred at 50° C. for 5 h under argon atmosphere. After completion of reaction (monitored by TLC and LCMS), the reaction was cooled to room temperature and concentrated under reduced pressure. The resultant residue was diluted in ethyl acetate (25 mL), washed with water (15 mL), brine (15 mL), dried over anhydrous $Na_2SO_4$ and concentrated under reduced pressure. The crude product was purified by silica gel column chromatography (Grace system) using 50-60% gradient ethyl acetate in petroleum ether followed by re-crystallization from iso-propanol (3 mL) and dried under vacuum to afford 1a (130 mg; ~22% overall yield in two steps from 2) as an off-white solid. $^1$H NMR (400 MHz, DMSO-$d_6$) δ ppm 11.77 (br s, 1H; $D_2O$ exchangeable), 11.59 (s, 1H; $D_2O$ exchangeable), 8.34 (s, 1H) 7.89 (d, J=2.4 Hz, 1H), 7.81 (dd, J=8.8, 2.4 Hz, 1H), 7.38 (d, J=8.8 Hz, 1H), 4.72 (q, J=6.8 Hz, 2H), 4.56 (t, J=5.1 Hz, 2H), 4.14 (t, J=6.4 Hz, 2H), 2.92-2.89 (m, 4H), 2.76-2.73 (m, 2H), 2.67-2.64 (m, 2H), 2.57-2.51 (m, 4H), 1.77-1.74 (m, 2H), 1.59-1.56 (m, 2H), 1.28 (t, J=7.1 Hz, 3H), 0.96 (t, J=7.3 Hz, 3H), 0.88 (t, J=7.3 Hz, 3H); LCMS (ES): m/z 620.5 [M+H$^+$]; purity~95%.

Scheme 4

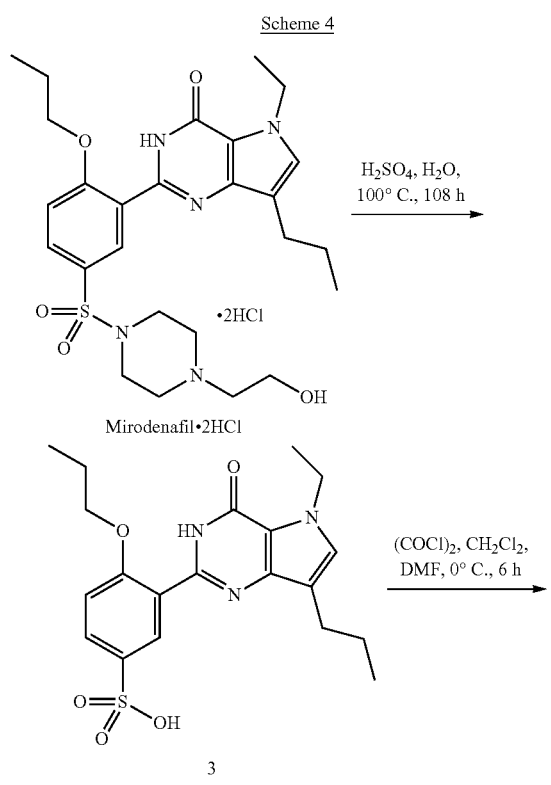

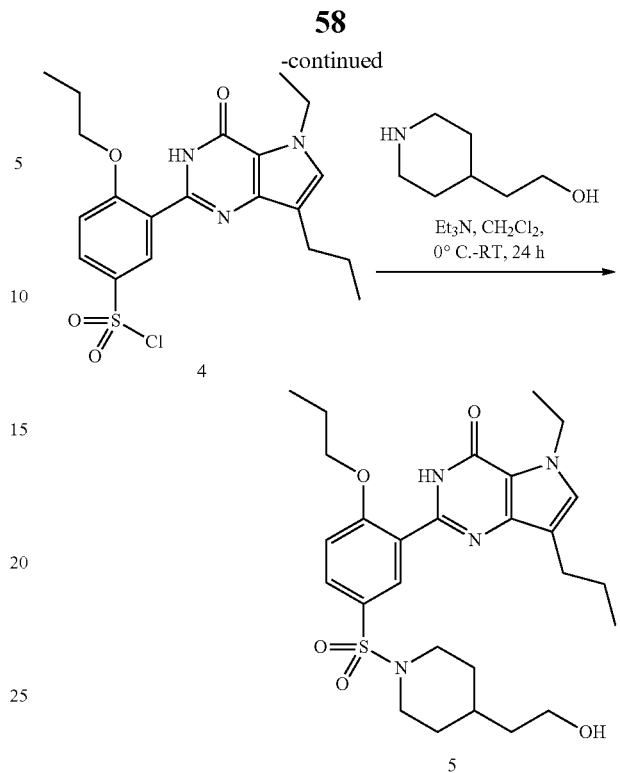

Example 5

3-(5-ethyl-4-oxo-7-propyl-4,5-dihydro-3H-pyrrolo[3,2-d]pyrimidin-2-yl)-4-propoxybenzene sulfonic acid (3)

To a stirred solution of 5-ethyl-2-(5-((4-(2-hydroxyethyl)piperazin-1-yl)sulfonyl)-2-propoxyphenyl)-7-propyl-3,5-dihydro-4H-pyrrolo[3,2-d]pyrimidin-4-one dihydrochloride (Mirodinafil·2HCl; WO01/60825) (5.0 g, 8.27 mmol) in water (105 mL), was added concentrated sulphuric acid (80 mL) drop wise at room temperature under inert atmosphere for 1 h. After addition, the reaction was heated to 100° C. for 108 h (4.5 days). After completion of reaction (monitored by TLC and LCMS), the reaction mixture was cooled to ~10° C. and neutralized with 25% aqueous NaOH solution (360 mL). The resultant heterogeneous mixture was concentrated under reduced pressure until the water removed completely. The residue obtained was treated with 20% methanol in dichloromethane (6×500 ml) and filtered. The combined organic filtrates were dried over anhydrous $Na_2SO_4$ and concentrated under reduced pressure. The crude product was co-distilled with toluene (2×100 mL), then triturated with diethyl ether (100 mL), filtered and dried under vacuum to afford the title compound 3 (3.2 g, 92% yield) as an off-white solid. $^1$H NMR (300 MHz, DMSO-$d_6$) δ ppm 11.50 (br s, 1H), 7.96 (d, J=2.2 Hz, 1H), 7.65 (dd, J=8.4, 2.2 Hz, 1H), 7.29 (s, 1H), 7.08 (d, J=8.8 Hz, 1H), 4.37 (q, J=7.0 Hz, 2H), 4.06 (t, J=6.42 Hz, 2H), 2.64-2.55 (m, 2H), 1.82-1.57 (m, 4H), 1.36 (t, J=7.1 Hz, 3H), 0.98 (t, J=7.4 Hz, 3H), 0.95 (t, J=7.4 Hz, 3H); LCMS (ESI): m/z 420.4 [M+H$^+$]; purity~95.4%.

Example 6

5-ethyl-2-(5-((4-(2-hydroxyethyl)piperidin-1-yl)sulfonyl)-2-propoxyphenyl)-7-propyl-3,5-dihydro-4H-pyrrolo[3,2-d]pyrimidin-4-one (5)

To a stirred solution of 3-(5-ethyl-4-oxo-7-propyl-4,5-dihydro-3H-pyrrolo[3,2-d]pyrimidin-2-yl)-4-propoxybenzenesulfonic acid (3) (1.6 g, 3.63 mmol) in CH$_2$Cl$_2$ (96 mL) and DMF (0.8 mL) mixture, was added oxalyl chloride (1 mL, 10.89 mmol) at 0° C. drop wise under argon atmosphere for 20 min. After addition, the reaction mixture was stirred at same temperature for 6 h. After completion of reaction (monitored by TLC), the reaction was concentrated at below 20° C. under reduced pressure and the vacuum was back-filled with argon atmosphere to afford the crude 2 as a pale yellow liquid, which was directly taken for next reaction without any purification.

To a stirred solution of crude material 2 in CH$_2$Cl$_2$ (96 mL) was added triethylamine (7.6 mL, 54.45 mmol) drop wise at 0° C., followed by a solution of 2-(piperidin-4-yl)ethan-1-ol (590 mg, 4.54 mmol) in CH$_2$Cl$_2$ (15 mL) at same temperature under inert atmosphere. The reaction was allowed to stir at room temperature for 24 h. After completion of reaction (monitored by LCMS), the reaction mixture was concentrated under reduced pressure. The residue obtained was diluted with EtOAc (200 mL), washed with water (50 mL), brine (50 mL), dried over anhydrous Na$_2$SO$_4$ and concentrated under reduced pressure to obtain the crude (1 g) as a semi solid. Note: The reaction was repeated on 1.5 g scale and both the crude materials were combined and purified by silica gel column chromatography by eluting with 1-3% gradient methanol in CH$_2$Cl$_2$ to afford the title compound 5 (1.6 g, 40% yield) as an off-white solid. $^1$H NMR (300 MHz, DMSO-d$_6$) δ ppm 11.62 (br s, 1H), 7.92 (d, J=2.2 Hz, 1H), 7.79 (dd, J=8.8, 2.2 Hz, 1H), 7.36 (d, J=8.8 Hz, 1H), 7.30 (s, 1H), 4.37-4.28 (m, 3H), 4.13 (t, J=6.4 Hz, 2H), 3.62-3.59 (m, 2H), 3.39-3.36 (m, 2H), 2.58-2.55 (m, 2H), 2.30-2.17 (m, 2H), 1.83-1.54 (m, 6H), 1.45-1.24 (m, 6H), 1.23-1.16 (m, 2H), 0.97 (t, J=7.3 Hz, 3H), 0.96 (t, J=7.3 Hz, 3H); LCMS (ESI): m/z 531.5 [M+H]$^+$; purity~94.2%.

Scheme 5

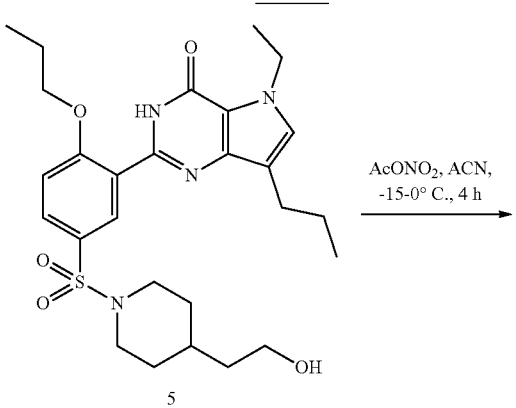

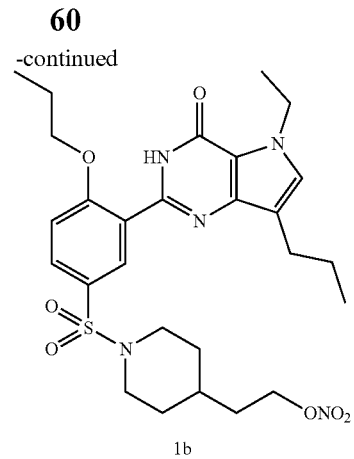

Example 7

2-(1-((3-(5-ethyl-4-oxo-7-propyl-4,5-dihydro-3H-pyrrolo[3,2-d]pyrimidin-2-yl)-4-propoxy phenyl)sulfonyl)piperidin-4-yl)ethyl nitrate (1b)

To a stirred solution of 5-ethyl-2-(5-((4-(2-hydroxyethyl)piperidin-1-yl)sulfonyl)-2-propoxyphenyl)-7-propyl-3,5-dihydro-4H-pyrrolo[3,2-d]pyrimidin-4-one 5 (90 mg, 0.17 mmol) in acetonitrile (2.7 mL) was added a solution of freshly prepared acetyl nitrate (0.08 mL; 0.85 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised above 0° C.))] drop wise at −15° C. for 30 min under argon atmosphere. The reaction was stirred at −15-0° C. for 4 h. After completion of reaction (monitored by TLC), the reaction was quenched with saturated NaHCO$_3$ solution (6 mL) at 0° C. and extracted with EtOAc (3×10 mL). The combined organic layer was washed with brine (10 mL), dried over anhydrous Na$_2$SO$_4$ and concentrated under reduced pressure. The obtained crude product was purified by reverse phase column chromatography (C-18 column; Grace System) by eluting with 60-65% gradient acetonitrile with water. The pure fractions were lyophilized to afford the title compound 1b (19 mg; 19% yield) as a white solid. $^1$H NMR (400 MHz, DMSO-d$_6$) δ ppm 11.61 (s, 1H; D$_2$O exchangeable), 7.93 (d, J=2.2 Hz, 1H), 7.80 (dd, J=8.8, 2.2 Hz, 1H), 7.36 (d, J=8.8 Hz, 1H), 7.30 (s, 1H), 4.51 (t, J=6.6 Hz, 2H), 4.37 (q, J=7.0 Hz, 2H), 4.13 (t, J=6.4 Hz, 2H), 3.64-3.61 (m, 2H), 2.58-2.55 (m, 2H), 2.28-2.24 (m, 2H), 1.82-1.69 (m, 4H), 1.68-1.53 (m, 4H), 1.37-1.35 (m, 4H), 1.28-1.17 (m, 2H), 1.03-0.85 (m, 6H); LCMS (ES): m/z 576.4 [M+H$^+$]; purity~99%.

Scheme 6

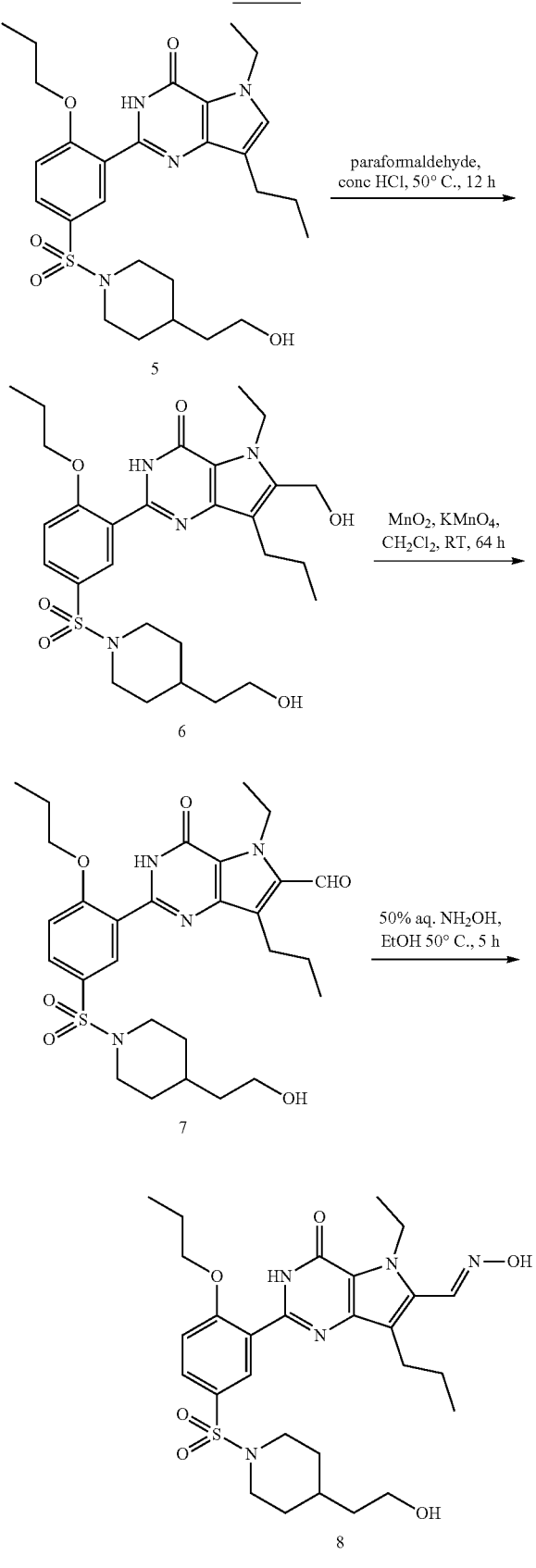

Example 8

5-ethyl-2-(5-((4-(2-hydroxyethyl)piperidin-1-yl)sulfonyl)-2-propoxyphenyl)-6-(hydroxymethyl)-7-propyl-3,5-dihydro-4H-pyrrolo[3,2-d]pyrimidin-4-one (6)

To a stirred solution of 5-ethyl-2-(5-((4-(2-hydroxyethyl)piperidin-1-yl)sulfonyl)-2-propoxyphenyl)-7-propyl-3,5-dihydro-4H-pyrrolo[3,2-d]pyrimidin-4-one 5 (650 mg, 1.23 mmol) in concentrated HCl solution (6.5 mL) was added paraformaldehyde (325 mg, 0.5 w/w) at room temperature under inert atmosphere. The reaction was heated to 50° C. for 12 h. Reaction was monitored by TLC and LCMS analysis. After 12 h, the reaction mixture was cooled to room temperature, pH was adjusted to 7-8 with saturated $NaHCO_3$ solution (100 mL). The resultant solution was extracted with 10% methanol in dichloromethane (3×100 mL). The combined organic extracts were dried over anhydrous $Na_2SO_4$ and concentrated under reduced pressure to afford the crude product. Note: the same reaction was performed on 50 mg and 100 mg scales earlier. All the batches were combined and purified by reverse phase chromatography (C18 column; Grace System) by eluting with 40-50% gradient acetonitrile with water to afford the titled compound 6 (380 mg; 54% yield based on the recovery of 5) as an off-white solid and unreacted 5 (200 mg; ~69% purity).

$^1$H NMR (300 MHz, DMSO-$d_6$) δ ppm 11.64 (br s, 1H; $D_2O$ exchangeable), 7.91 (br d, J=1.8 Hz, 1H), 7.80 (dd, J=8.8, 1.8 Hz, 1H), 7.36 (d, J=8.8 Hz, 1H), 5.22 (br s, 1H; $D_2O$ exchangeable), 4.58-4.56 (m, 2H), 4.48-4.44 (m, 2H), 4.32 (br t, J=4.8 Hz, 1H; $D_2O$ exchangeable), 4.13-4.11 (m, 2H), 3.61-3.57 (m, 2H), 3.39-3.36 (m, 2H), 2.64-2.56 (m, 2H), 2.28-2.22 (m, 2H), 1.80-1.65 (m, 4H), 1.59-1.56 (m, 2H), 1.40-1.27 (m, 6H), 1.21-1.16 (m, 2H), 0.97 (t, J=7.3 Hz, 3H), 0.88 (t, J=7.3 Hz, 3H); LCMS (ESI): m/z 561.5 [M+H$^+$]; purity~98.9%.

Example 9

5-ethyl-2-(5-((4-(2-hydroxyethyl)piperidin-1-yl)sulfonyl)-2-propoxyphenyl)-4-oxo-7-propyl-4,5-dihydro-3H-pyrrolo[3,2-d]pyrimidine-6-carbaldehyde (7)

To a stirred solution of 5-ethyl-2-(5-((4-(2-hydroxyethyl)piperidin-1-yl)sulfonyl)-2-propoxyphenyl)-6-(hydroxymethyl)-7-propyl-3,5-dihydro-4H-pyrrolo[3,2-d]pyrimidin-4-one 6 (400 mg, 0.71 mmol) in $CH_2Cl_2$ (80 mL) was added activated $MnO_2$ (1.08 g, 12.33 mmol) and $KMnO_4$ (360 mg, 2.28 mmol) at room temperature. After 24 h stirring, the reaction mixture was filtered through Celite pad and washed with $CH_2Cl_2$ (200 mL). The filtrate was concentrated until to its ⅓ of its volume and added activated $MnO_2$ (1.08 g, 12.33 mmol) and $KMnO_4$ (360 mg, 2.28 mmol) again at room temperature and stirred for 40 h. After complete consumption of starting material (monitored by TLC), the reaction mixture was filtered through Celite pad and washed with $CH_2Cl_2$ (200 mL). The filtrate was evaporated and the obtained crude product was purified by silica gel column chromatography (Grace System) by eluting with 4% of 30% methanol in dichloromethane solution with dichloromethane to afford 7 (215 mg, 52% yield) as an off-white solid. $^1$H NMR (300 MHz, DMSO-$d_6$) δ ppm 12.09 (s, 1H), 10.14 (s, 1H), 7.89 (d, J=2.20 Hz, 1H), 7.82 (dd, J=8.8, 2.2 Hz, 1H), 7.37 (d, J=8.8 Hz, 1H), 4.85 (q, J=6.6 Hz, 2H), 4.31 (t, J=5.1 Hz, 1H), 4.12 (t, J=6.4 Hz, 2H), 3.62-3.59 (m, 2H), 3.40-

3.35 (m, 2H), 2.97-2.94 (m, 2H), 2.26-2.21 (m, 2H), 1.80-1.61 (m, 6H), 1.34-1.29 (m, 6H), 1.18-1.14 (m, 2H), 1.01-0.85 (m, 6H); LCMS (ESI): m/z 559.5 [M+H]⁺; purity~96%.

Example 10

(E)-5-ethyl-2-(5-((4-(2-hydroxyethyl)piperidin-1-yl)sulfonyl)-2-propoxyphenyl)-4-oxo-7-propyl-4,5-dihydro-3H-pyrrolo[3,2-d]pyrimidine-6-carbaldehyde oxime (8)

To a stirred solution of 5-ethyl-2-(5-((4-(2-hydroxyethyl)piperidin-1-yl)sulfonyl)-2-propoxyphenyl)-4-oxo-7-propyl-4,5-dihydro-3H-pyrrolo[3,2-d]pyrimidine-6-carbaldehyde 7 (75 mg, 0.13 mmol) in EtOH (9 mL) was added 50% aqueous hydroxylamine solution (1.5 mL) at room temperature. The reaction was heated to 50° C. and stirred under argon atmosphere for 5 h. After completion of reaction (monitored by TLC), the reaction was concentrated under reduced pressure. The resultant residue was diluted in ethyl acetate (20 mL), washed with water (5 mL), brine (5 mL), dried over anhydrous Na₂SO₄ and concentrated under reduced pressure. The obtained crude product was purified by re-crystallization from iso-propanol (2 mL) and dried under vacuum to afford the title compound 8 (41 mg; 52% yield) as an off-white solid. ¹H NMR (400 MHz, DMSO-d₆) δ ppm 11.75 (s, 1H; D₂O exchangeable), 11.59 (s, 1H; D₂O exchangeable), 8.34 (s, 1H), 7.93 (d, J=2.4 Hz, 1H), 7.80 (dd, J=8.8, 2.4 Hz, 1H), 7.37 (d, J=8.8 Hz, 1H), 4.73-4.71 (m, 2H), 4.29 (t, J=4.9 Hz, 1H; D₂O exchangeable), 4.13 (t, J=6.4 Hz, 2H), 3.62-3.58 (m, 2H), 3.40-3.36 (m, 2H), 2.76-2.73 (m, 2H), 2.27-2.23 (m, 2H), 1.88-1.69 (m, 4H), 1.63-1.49 (m, 2H), 1.42-1.21 (m, 6H), 1.18-1.14 (m, 2H), 0.97 (t, J=7.3 Hz, 3H), 0.88 (t, J=7.3 Hz, 3H); LCMS (ES): m/z 574.6 [M+H⁺]; purity~97.6%.

Scheme 7

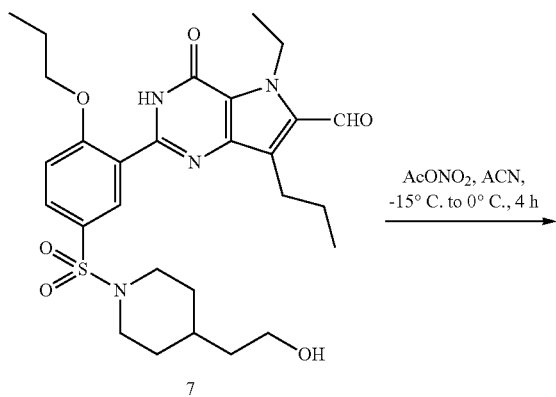

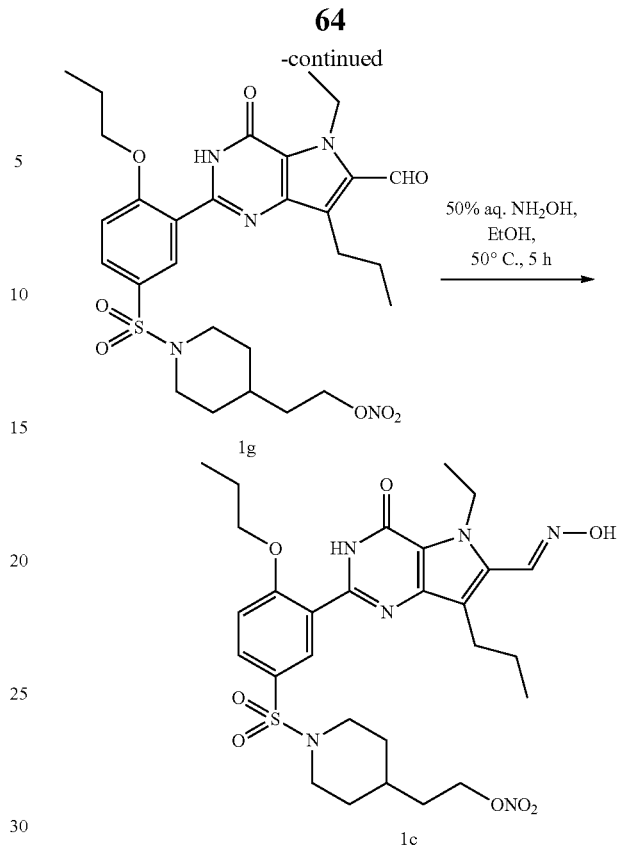

Example 11

2-(1-((3-(5-ethyl-6-formyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (1g)

To a stirred solution of 5-ethyl-2-(5-((4-(2-hydroxyethyl)piperidin-1-yl)sulfonyl)-2-propoxyphenyl)-4-oxo-7-propyl-4,5-dihydro-3H-pyrrolo[3,2-d]pyrimidine-6-carbaldehyde 7 (215 mg, 0.42 mmol) in acetonitrile (6.5 mL) was added a solution of freshly prepared acetyl nitrate (0.19 mL; 2.1 mmol) [(acetyl nitrate was prepared separately by addition of fuming HNO₃ (2.15 mL, 51 mmol) drop wise in to acetic anhydride (5.0 mL, 53.0 mmol) slowly at −15° C. for 30 min under argon atmosphere (Note: temperature should not be raised to 0° C.))] drop wise at −15° C. for 30 min under argon atmosphere. The reaction was stirred at −15-0° C. for 4 h. After completion of reaction (monitored by TLC), the reaction was quenched with saturated NaHCO₃ solution (10 mL) and extracted with EtOAc (3×20 mL). The combined organic layer was washed with brine (10 mL), dried over anhydrous Na₂SO₄ and concentrated under reduced pressure to afford the crude product 1g (190 mg) as brown semi solid, which was directly taken for next reaction without further purification. LCMS (ESI): m/z 604.5 [M+H]⁺; purity~64%.

Example 12

(E)-2-(1-((3-(5-ethyl-6-((hydroxyimino)methyl)-4-oxo-7-propyl-4,5-dihydro-3H-pyrrolo[3,2-d]pyrimidin-2-yl)-4-propoxyphenyl)sulfonyl)piperidin-4-yl)ethyl nitrate (1c)

To a stirred solution of 2-(1-((3-(5-ethyl-6-formyl-4-oxo-7-propyl-4,5-dihydro-3H-pyrrolo[3,2-d]pyrimidin-2-yl)-4- propoxyphenyl)sulfonyl)piperidin-4-yl)ethyl nitrate 1g (190 mg) in EtOH (24 mL) was added 50% hydroxylamine in aqueous solution (4 mL) at room temperature. The reaction was heated to 50° C. and stirred for 5 h under argon atmosphere. After completion of reaction (monitored by TLC), the reaction was concentrated under reduced pressure. The resultant residue was diluted in water (5 mL) and extracted with EtOAc (3×20 mL). The combined organic layer was washed with brine (10 mL), dried over anhydrous $Na_2SO_4$ and concentrated under reduced pressure. Obtained crude product was purified by silica gel column chromatography (Grace system) by eluting with 45-50% gradient EtOAc in petroleum ether to afford (110 mg; ~91% LCMS purity), which was further purified by trituration with isopropanol (7.5 mL) at 80° C. for 30 min and then stirred at room temperature for 2 h. The solid was filtered and dried under vacuum to afford 1c (80 mg; 39% yield) as an off-white solid. $^1$H NMR (400 MHz, DMSO-$d_6$) δ ppm 11.80 (br s, 1H; $D_2O$ exchangeable), 11.63 (br s, 1H; $D_2O$ exchangeable), 8.35 (s, 1H), 7.91 (d, J=2.2 Hz, 1H), 7.81 (dd, J=8.8, 2.2 Hz, 1H), 7.37 (d, J=8.8 Hz, 1H), 4.72 (q, J=6.8 Hz, 2H), 4.51 (t, J=6.4 Hz, 2H), 4.13 (t, J=6.1 Hz, 2H), 3.63-3.61 (m, 2H), 2.75-2.72 (m, 2H), 2.26-2.21 (m, 2H), 1.83-1.67 (m, 4H), 1.65-1.50 (m, 4H), 1.43-1.12 (m, 6H), 0.97 (t, J=7.3 Hz, 3H), 0.88 (t, J=7.3 Hz, 3H); LCMS (ES): m/z 619.5 [M+H$^+$]; purity~95.7%.

mmol) drop wise at 0° C. followed by added 3-(piperidin-4-yl)propan-1-ol (811 mg, 5.66 mmol) in $CH_2Cl_2$ (20 mL) solution in drop wise at 0° C. The reaction mixture was allowed to stir at room temperature for 16 h. After completion of reaction (monitored by LCMS), the reaction mixture was concentrated under reduced pressure. The residue was dissolved in EtOAc (30 mL), washed with water (30 mL), dried over anhydrous $Na_2SO_4$ and concentrated under reduced pressure. The obtained crude product was purified by silica gel column chromatography by eluting with 60-70% gradient EtOAc in petroleum ether to afford 15 (650 mg, 27% yield) as a white solid. 1H NMR (300 MHz, DMSO-$d_6$) δ ppm 11.66 (br s, 1H), 7.91 (d, J=2.0 Hz, 1H), 7.78 (dd, J=8.8, 2.0 Hz, 1H), 7.35 (d, J=8.8 Hz, 1H), 7.29 (s, 1H), 4.38-4.31 (m, 3H), 4.12 (t, J=6.4 Hz, 2H), 3.62-3.60 (m, 2H), 3.35-3.31 (m, 2H), 2.58-2.56 (m, 2H), 2.25-2.22 (m, 2H), 1.81-1.59 (m, 6H), 1.37-1.33 (m, 5H), 1.23-1.10 (m, 5H), 1.02-0.88 (m, 6H); LCMS (ESI): m/z 545.5 [M+H]$^+$; purity~97.1%.

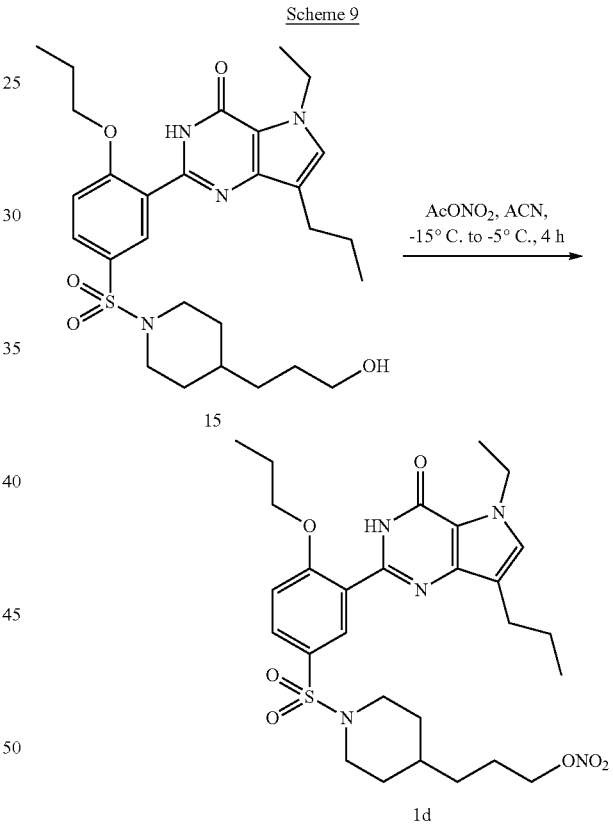

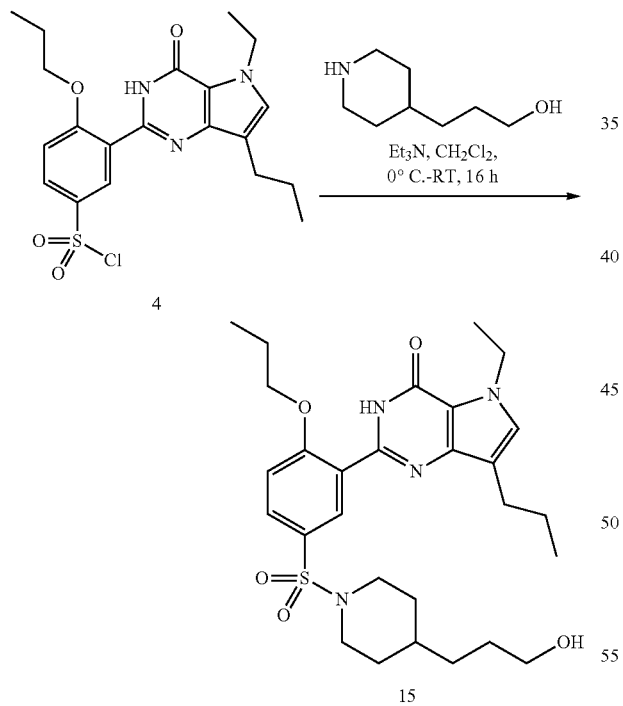

Example 13

5-ethyl-2-(5-((4-(3-hydroxypropyl)piperidin-1-yl) sulfonyl)-2-propoxyphenyl)-7-propyl-3,5-dihydro-4H-pyrrolo[3,2-d]pyrimidin-4-one (15)

To a stirred solution of above crude material 4 in in $CH_2Cl_2$ (60 mL) and added triethylamine (9.5 mL, 65.66

Example 14

3-(1-((3-(5-ethyl-4-oxo-7-propyl-4,5-dihydro-3H-pyrrolo[3,2-d]pyrimidin-2-yl)-4-propoxy phenyl) sulfonyl)piperidin-4-yl)propyl nitrate (1d)

To a stirred solution of 5-ethyl-2-(5-((4-(3-hydroxypropyl)piperidin-1-yl)sulfonyl)-2-propoxyphenyl)-7-propyl-3,5-dihydro-4H-pyrrolo[3,2-d]pyrimidin-4-one 15 (160 mg, 0.29 mmol) in acetonitrile (5.0 mL) was added a solution of freshly prepared acetyl nitrate (0.13 mL; 1.47 mmol) [(acetyl nitrate was prepared separately by addition of fuming HNO₃ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −15° C. for 30 min under argon atmosphere. The reaction was stirred at −15° C. to −5° C. for 4 h. After completion of reaction (monitored by TLC), the reaction was quenched with saturated NaHCO₃ solution (15 mL) at 0° C. and extracted with EtOAc (3×25 mL). The combined organic layer was washed with brine (10 mL), dried over anhydrous Na₂SO₄ and concentrated under reduced pressure. The obtained crude product was purified reverse phase column chromatography (C-18 column, Grace System) by eluting with 60-65% gradient acetonitrile with water. The pure fractions were lyophilized to afford the title compound 1d (45 mg; ~25% yield) as an off-white solid. ¹H NMR (400 MHz, DMSO-d₆) δ ppm 11.62 (br s, 1H; D₂O exchangeable), 7.93 (d, J=2.4 Hz, 1H), 7.79 (dd, J=8.8, 2.4 Hz, 1H), 7.36 (d, J=8.8 Hz, 1H), 7.30 (s, 1H), 4.46 (t, J=6.6 Hz, 2H), 4.37 (q, J=7.3 Hz, 2H), 4.13 (t, J=6.4 Hz, 2H), 3.64-3.62 (m, 2H), 2.58-2.56 (m, 2H), 2.26-2.22 (m, 2H), 1.81-1.56 (m, 8H), 1.36 (t, J=7.3 Hz, 3H), 1.29-1.10 (m, 5H), 1.01-0.87 (m, 6H); LCMS (ESI): m/z 590.5 [M+H⁺]; purity~98.9%.

Scheme 10

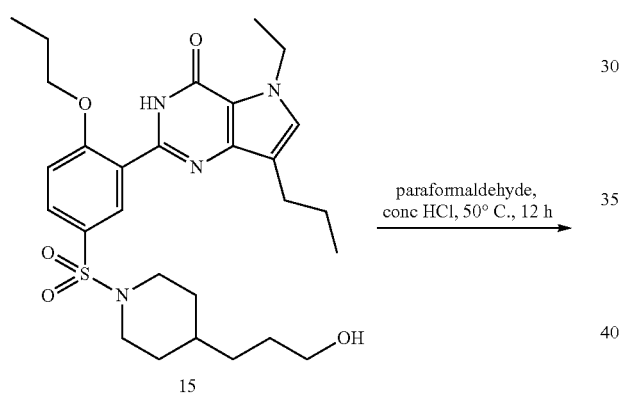

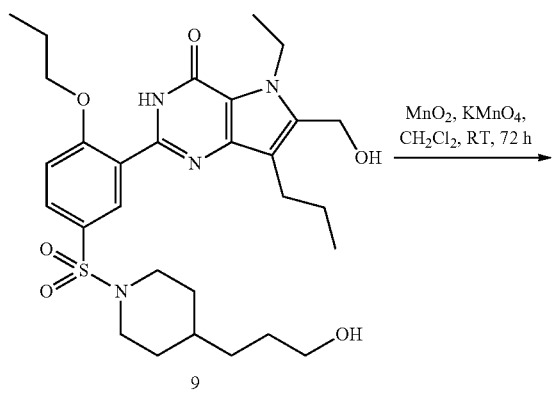

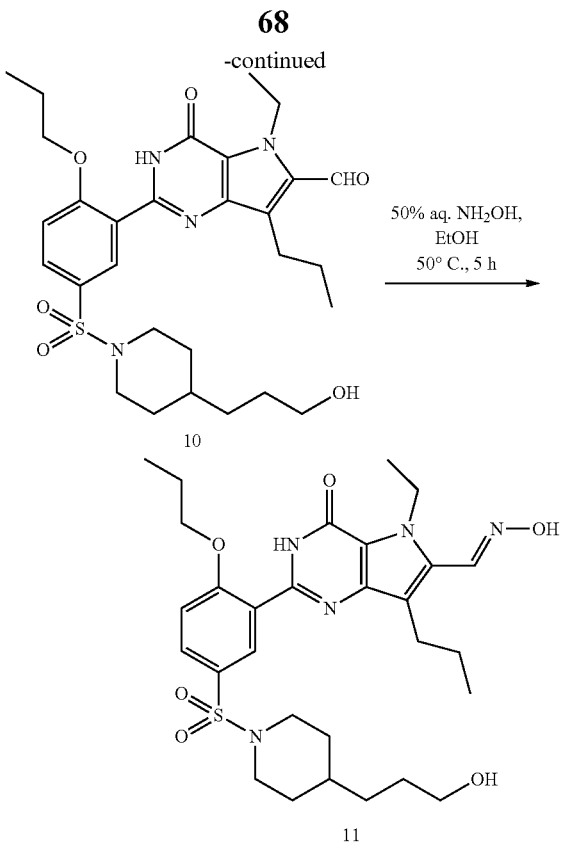

Example 15

5-ethyl-6-(hydroxymethyl)-2-(5-((4-(3-hydroxypropyl)piperidin-1-yl)sulfonyl)-2-propoxy phenyl)-7-propyl-3,5-dihydro-4H-pyrrolo[3,2-d]pyrimidin-4-one (9)

To a stirred solution of 5-ethyl-2-(5-((4-(3-hydroxypropyl)piperidin-1-yl)sulfonyl)-2-propoxyphenyl)-7-propyl-3,5-dihydro-4H-pyrrolo[3,2-d]pyrimidin-4-one 15 (900 mg, 1.65 mmol) in concentrated HCl solution (9 mL), was added paraformaldehyde (450 mg, 0.5 w/w) at room temperature and heated to 50° C. under inert atmosphere. Reaction was monitored by LCMS analysis. After 12 h stirring, the reaction mixture was cooled to room temperature and neutralized with saturated NaHCO₃ solution (150 mL). The resultant solution was extracted with 10% methanol in dichloromethane (3×100 mL). The combined the organic extracts were dried over anhydrous Na₂SO₄ and concentrated under reduced pressure. The obtained crude product was purified by reverse phase column chromatography (C-18 column; Grace System) by eluting with 40-50% gradient acetonitrile with water to afford the titled compound 9 (240 mg; 46% yield based on recovery of 8) as an off-white solid and 420 mg of unreacted 8.

¹H NMR (300 MHz, DMSO-d₆) δ ppm 11.66 (s, 1H), 7.90 (d, J=2.5 Hz, 1H), 7.79 (dd, J=8.8, 2.5 Hz, 1H), 7.36 (d, J=8.80 Hz, 1H), 5.26-5.21 (m, 1H), 4.57 (d, J=4.4 Hz, 2H), 4.46 (q, J=7.0 Hz, 2H), 4.35 (br s, 1H), 4.13-4.11 (m, 2H), 3.63-3.61 (m, 2H), 3.42-3.35 (m, 2H), 2.61-2.55 (m, 2H), 2.26-2.18 (m, 2H), 1.78-1.66 (m, 4H), 1.60-1.54 (m, 2H), 1.39-1.33 (m, 5H), 1.18-1.11 (m, 5H), 0.96 (t, J=7.3 Hz, 3H), 0.88 (t, J=7.3 Hz, 3H); LCMS (ESI): m/z 575.4 [M+H⁺]; purity~97.6%.

Example 16

5-ethyl-2-(5-((4-(3-hydroxypropyl)piperidin-1-yl)sulfonyl)-2-propoxyphenyl)-4-oxo-7-propyl-4,5-dihydro-3H-pyrrolo[3,2-d]pyrimidine-6-carbaldehyde (10)

To a stirred solution of 5-ethyl-6-(hydroxymethyl)-2-(5-((4-(3-hydroxypropyl)piperidin-1-yl)sulfonyl)-2-propoxyphenyl)-7-propyl-3,5-dihydro-4H-pyrrolo[3,2-d]pyrimidin-4-one 9 (240 mg, 0.42 mmol) in CH$_2$Cl$_2$ (48 mL) was added activated MnO$_2$ (632 mg, 7.3 mmol) and KMnO$_4$ (213 mg, 1.35 mmol) at room temperature and stirred for 24 h. Reaction was monitored by TLC and LCMS analysis. After 24 h, the reaction mixture was filtered through Celite pad and washed with CH$_2$Cl$_2$ (100 mL). The filtrate was concentrated up to 50 mL solution and added activated MnO$_2$ (632 mg, 7.3 mmol) and KMnO$_4$ (213 mg, 1.35 mmol) again at room temperature and stirred for 24 h. The same was repeated again and stirred for additional 24 h for completion conversion of starting material. The reaction mixture was then filtered through a Celite pad and washed with CH$_2$Cl$_2$ (200 mL). The filtrate was concentrated to afford the title compound 10 (150 mg, 57% yield) as an off-white solid. 1H NMR (300 MHz, DMSO-d$_6$) δ ppm 12.10 (s, 1H), 10.14 (s, 1H), 7.89 (d, J=2.2 Hz, 1H), 7.82 (dd, J=8.8, 2.2 Hz, 1H), 7.37 (d, J=8.8 Hz, 1H), 4.85 (q, J=7.0 Hz, 2H), 4.33 (t, J=5.1 Hz, 1H), 4.13-4.11 (m, 2H), 3.63-3.61 (m, 2H), 3.35-3.33 (m, 2H), 2.97-2.94 (m, 2H), 2.26-2.20 (m, 2H), 1.78-1.61 (m, 6H), 1.41-1.27 (m, 5H) 1.19-1.12 (m, 5H), 1.01-0.84 (m, 6H); LCMS (ESI): m/z 573.5 [M+H]$^+$; purity~92.10%.

Example 17

(E)-5-ethyl-2-(5-((4-(3-hydroxypropyl)piperidin-1-yl)sulfonyl)-2-propoxyphenyl)-4-oxo-7-propyl-4,5-dihydro-3H-pyrrolo[3,2-d]pyrimidine-6-carbaldehyde oxime (11)

To a stirred solution of 5-ethyl-2-(5-((4-(3-hydroxypropyl)piperidin-1-yl)sulfonyl)-2-propoxyphenyl)-4-oxo-7-propyl-4,5-dihydro-3H-pyrrolo[3,2-d]pyrimidine-6-carbaldehyde 10 (150 mg, 0.26 mmol) in EtOH (18 mL) was added 50% hydroxylamine in aqueous solution (3 mL) at room temperature. Reaction was heated to 50° C. for 5 h under argon atmosphere. After completion of reaction (monitored by TLC), the reaction was concentrated under reduced pressure. The resultant residue was diluted in ethyl acetate (25 mL), washed with water (10 mL), brine (10 mL), dried over anhydrous Na$_2$SO$_4$ and concentrated under reduced pressure. The obtained crude product was purified by silica gel column chromatography (Grace System) by eluting with 4% of 30% methanol in dichloromethane solution with dichloromethane to afford the product with 94% purity, which was further purified by re-crystallization from isopropanol (2 mL) to afford the title compound 11 (65 mg; 42% yield) as a white solid. $^1$H NMR (400 MHz, DMSO-d$_6$) δ ppm 11.78 (br s, 1H; D$_2$O exchangeable), 11.61 (s, 1H; D$_2$O exchangeable), 8.35 (s, 1H), 7.92 (d, J=2.4 Hz, 1H), 7.80 (dd, J=8.8, 2.4 Hz, 1H), 7.37 (d, J=8.8 Hz, 1H), 4.76-4.68 (m, 2H), 4.32 (t, J=5.4 Hz, 1H; D$_2$O exchangeable), 4.14-4.12 (m, 2H), 3.63-3.61 (m, 2H), 3.36-3.33 (m, 2H), 2.75-2.73 (m, 2H), 2.24-2.21 (m, 2H), 1.81-1.66 (m, 4H), 1.63-1.53 (m, 2H), 1.41-1.33 (m, 2H), 1.28 (t, J=7.1 Hz, 3H), 1.22-1.09 (m, 5H), 0.97 (t, J=7.3 Hz, 3H), 0.88 (t, J=7.3 Hz, 3H); LCMS (ESI): m/z 588.5 [M+H$^+$]; purity~99.4%.

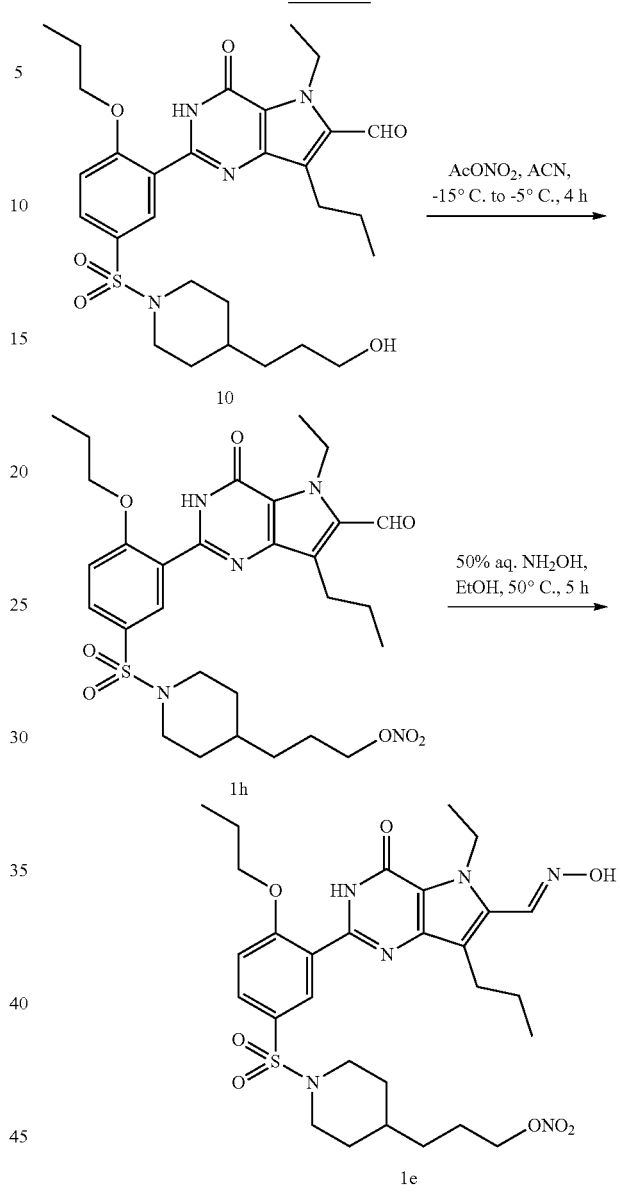

Scheme 11

Example 18

3-(1-((3-(5-ethyl-6-formyl-4-oxo-7-propyl-4,5-dihydro-3H-pyrrolo[3,2-d]pyrimidin-2-yl)-4-propoxyphenyl)sulfonyl)piperidin-4-yl)propyl nitrate (1h)

To a stirred solution of 5-ethyl-2-(5-((4-(3-hydroxypropyl)piperidin-1-yl)sulfonyl)-2-propoxyphenyl)-4-oxo-7-propyl-4,5-dihydro-3H-pyrrolo[3,2-d]pyrimidine-6-carbaldehyde 10 (150 mg, 0.26 mmol) in acetonitrile (6.5 mL) was added a solution of freshly prepared acetyl nitrate (0.12 mL; 1.31 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised above 0° C.))] drop wise at −15° C. for 30 min under argon atmosphere. The reaction was stirred at −15° C. to −5° C. for 4 h. After completion of reaction

71

(monitored by TLC), the reaction was quenched with saturated NaHCO₃ solution (10 mL) at 0° C. and extracted with EtOAc (3×20 mL). The combined organic layer was washed with brine (10 mL), dried over anhydrous Na₂SO₄ and concentrated under reduced pressure to afford the crude product 1h (100 mg) as brown semi solid, which was directly taken for next reaction without further purification. LCMS (ESI): m/z 618.7 [M+H⁺]; purity~59%.

Example 19

(E)-3-(1-((3-(5-ethyl-6-((hydroxyimino)methyl)-4-oxo-7-propyl-4,5-dihydro-3H-pyrrolo[3,2-d]pyrimidin-2-yl)-4-propoxyphenyl)sulfonyl)piperidin-4-yl) propyl nitrate (e)

To a stirred solution of 3-(1-((3-(5-ethyl-6-formyl-4-oxo-7-propyl-4,5-dihydro-3H-pyrrolo[3,2-d]pyrimidin-2-yl)-4-propoxyphenyl)sulfonyl)piperidin-4-yl)propyl nitrate 1h (100 mg) in EtOH (12 mL) was added 50% hydroxylamine in aqueous solution (2 mL) at room temperature and stirred at 50° C. for 5 h under argon atmosphere. After completion of reaction (monitored by TLC), the reaction was concentrated under reduced pressure. The resultant residue was diluted in water (5 mL) and extracted with EtOAc (3×20 mL). The combined organic layer was washed with brine (10 mL), dried over anhydrous Na₂SO₄ and concentrated under reduced pressure. The crude product was purified by silica gel column chromatography (Grace System) by eluting with 45-50% gradient EtOAc in petroleum ether to afford 110 mg of title compound with ~91% purity, which was further purified by re-crystallization in hot iso-propanol (7.5 mL) to afford the title compound 1e (40 mg) as an off-white solid. ¹H NMR (400 MHz, DMSO-d₆) δ ppm 11.75 (br s, 1H; D₂O exchangeable), 11.59 (s, 1H; D₂O exchangeable), 8.34 (s, 1H), 7.93 (d, J=2.4 Hz, 1H), 7.81 (dd, J=8.8, 2.4 Hz, 1H), 7.37 (d, J=8.8 Hz, 1H), 4.72 (q, J=6.8 Hz, 2H), 4.46 (t, J=6.6 Hz, 2H), 4.13 (t, J=6.4 Hz, 2H) 3.64-3.62 (m, 2H), 2.75-2.73 (m, 2H), 2.27-2.23 (m, 2H), 1.81-1.67 (m, 4H), 1.67-1.53 (m, 4H), 1.33-1.08 (m, 8H), 0.97 (t, J=7.6 Hz, 3H), 0.88 (t, J=7.3 Hz, 3H); LCMS (ESI): m/z 633.5 [M+H⁺]; purity~98.7%.

Scheme 12

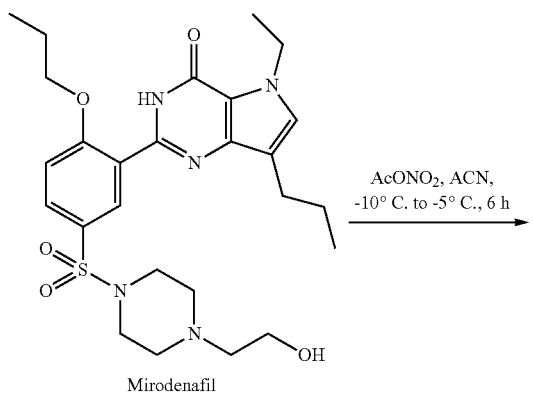

Mirodenafil

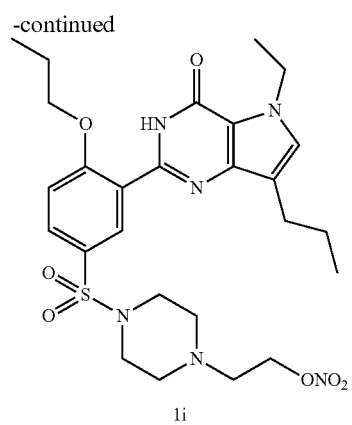

1i

Example 20

2-(4-((3-(5-ethyl-4-oxo-7-propyl-4,5-dihydro-3H-pyrrolo[3,2-d]pyrimidin-2-yl)-4-propoxyphenyl) sulfonyl)piperazin-1-yl)ethyl nitrate (1i)

To a stirred solution of 5-ethyl-2-(5-((4-(2-hydroxyethyl) piperazin-1-yl)sulfonyl)-2-propoxyphenyl)-7-propyl-3,5-dihydro-4H-pyrrolo[3,2-d]pyrimidin-4-one (Mirodenafil) (300 mg, 0.56 mmol) in acetonitrile (12 mL) was added a freshly prepared acetyl nitrate (0.25 mL; 2.82 mmol) [(acetyl nitrate was prepared separately by addition of fuming HNO₃ (1.1 mL, 25.5 mmol) drop wise in to acetic anhydride (2.5 mL, 26.5 mmol) slowly at −15° C. for 30 min under argon atmosphere (Note: temperature should not be raised above 0° C.))] drop wise at −10° C. under argon atmosphere. The reaction was maintained at −10° C. to −5° C. and monitored by LCMS analysis. After 4 h, an additional 2 equivalents of acetyl nitrate (0.1 mL) was added at −10° C. and stirring was continued at −10° C. to −5° C. for 2 h. The reaction was then quenched with saturated NaHCO₃ solution (15 mL) at 0° C. and stirred at room temperature for 16 h. The resultant solution was extracted with EtOAc (2×30 mL). The combined organic layer was washed with brine (20 mL), dried over anhydrous Na₂SO₄ and concentrated under reduced pressure. The crude product was purified by silica gel column chromatography (Grace System) by eluting with 4% of 30% methanol in CH₂Cl₂ with CH₂Cl₂ to afford 180 mg of product as a sticky solid, which was further purified by reverse phase column chromatography (C18 column; Grace System) by eluting with 45% acetonitrile with water to afford the pure title compound 1i (25 mg; 95% purity) as a pale yellow solid and its mixture (80 mg, 78% purity). ¹H NMR (400 MHz, DMSO-d₆) δ ppm 11.64 (br s, 1H; D₂O exchangeable), 7.89 (d, J=2.4 Hz, 1H), 7.80 (dd, J=8.8, 2.4 Hz, 1H), 7.38 (d, J=8.8 Hz, 1H), 7.31 (s, 1H), 4.56 (t, J=5.1 Hz, 2H), 4.37 (q, J=7.3 Hz, 2H), 4.13 (t, J=6.4 Hz, 2H), 2.90-2.87 (m, 4H), 2.66-2.63 (m, 4H), 2.58-2.55 (m, 2H), 2.54-2.51 (m, 4H), 1.76-1.72 (m, 2H), 1.67-1.58 (m, 2H), 1.36 (t, J=7.3 Hz, 3H), 0.96 (t, J=7.4 Hz, 3H), 0.92 (t, J=7.3 Hz, 3H); LCMS (ESI): m/z 577.2 [M+H⁺]; purity~95.1%.

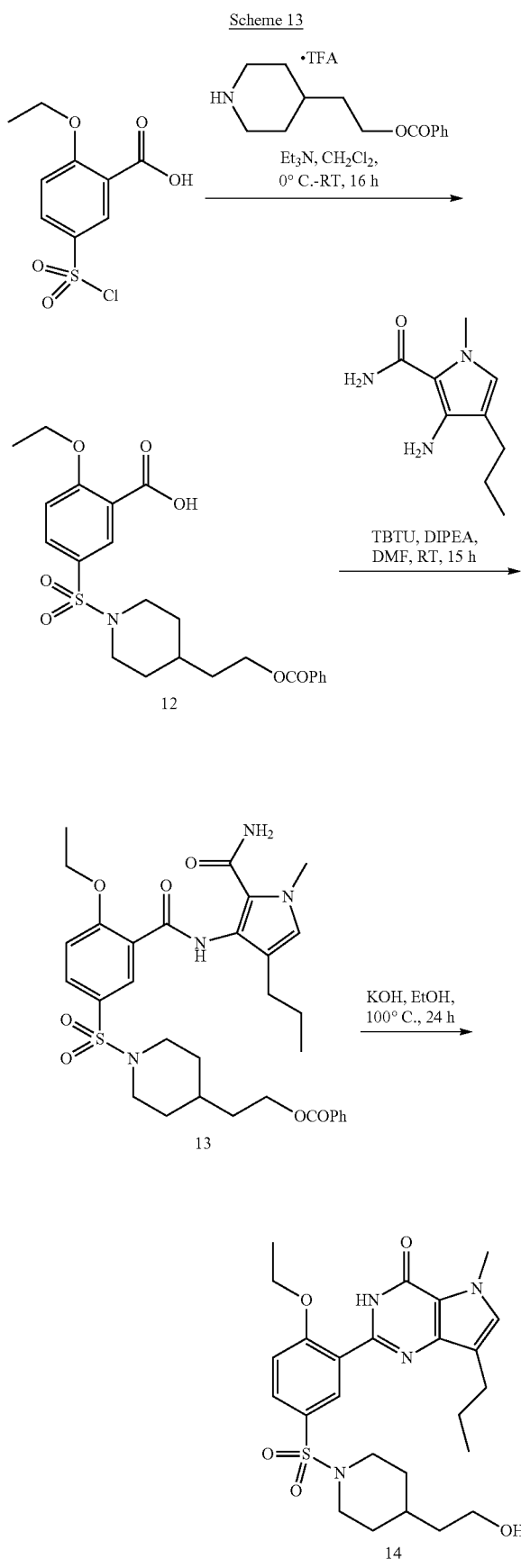

Scheme 13

Example 21

5-((4-(2-(benzoyloxy)ethyl)piperidin-1-yl)sulfonyl)-2-ethoxybenzoic acid (12)

To a stirred solution of 2-(piperidin-4-yl)ethyl benzoate as a TFA salt (980 mg, 2.83 mmol) in CH$_2$Cl$_2$ (5 mL) was added triethylamine (1.96 mL, 14.1 mmol) at 0° C. under inert atmosphere. To this, a solution of 5-(chlorosulfonyl)-2-ethoxybenzoic acid (750 mg, 2.83 mmol) in CH$_2$Cl$_2$ (10 mL) was added drop wise at 0° C. under inert atmosphere. The reaction mixture was allowed to stir at room temperature for 16 h. After completion of reaction (monitored by TLC & LCMS), the reaction mixture was diluted in CH$_2$Cl$_2$ (50 mL), washed with chilled water (10 mL), chilled 10% aqueous citric acid solution (2×10 mL), brine (10 mL), dried over Na$_2$SO$_4$ and concentrated under reduced pressure to afford the title compound 12 (710 mg, 52% yield) as a white solid. 1H NMR (300 MHz, CDCl$_3$) δ ppm 8.49 (d, J=2.2 Hz, 1H), 8.08-7.83 (m, 3H), 7.59-7.51 (m, 1H), 7.47-7.38 (m, 2H), 7.14 (d, J=8.8 Hz, 1H), 4.49-4.25 (m, 4H), 3.83-3.80 (m, 2H), 2.30-2.26 (m, 2H), 1.84-1.82 (m, 2H), 1.73-1.71 (m, 2H), 1.60 (t, J=7.1 Hz, 3H), 1.45-1.33 (m, 3H); LCMS (ESI): m/z 462.4 [M+H$^+$]; purity~96.4%.

Example 22

2-(1-((3-((2-carbamoyl-1-methyl-4-propyl-1H-pyrrol-3-yl)carbamoyl)-4-ethoxyphenyl)sulfonyl) piperidin-4-yl)ethyl benzoate (13)

To a stirred solution of 5-((4-(2-(benzoyloxy)ethyl)piperidin-1-yl)sulfonyl)-2-ethoxybenzoic acid 12 (250 mg, 0.54 mmol) in DMF (2.5 mL) was added diisopropyl ethylamine (210 mg, 1.62 mmol) and TBTU (347 mg, 1.08 mmol) at room temperature and stirred for 30 min. To this, 3-amino-1-methyl-4-propyl-1H-pyrrole-2-carboxamide (98 mg, 0.541 mmol) was added at room temperature and stirred for 15 h under inert atmosphere. After completion of reaction (monitored by TLC & LCMS), reaction was quenched with chilled water (25 mL) and extracted with EtOAc (2×25 mL). The combined organic layer was washed with brine (2×15 mL), dried over anhydrous Na$_2$SO$_4$ and concentrated under reduced pressure. The obtained crude product was purified by reverse phase column chromatography (C-18 column, Grace System) by eluting with 50% acetonitrile with water. The fractions were concentrated to afford the solid, which was triturated with diethyl ether (5 mL), filtered and dried to afford the title compound 13 (85 mg; ~23% yield) as an off white solid. $^1$H NMR (400 MHz, CDCl$_3$) δ ppm 9.17 (s, 1H), 8.64 (d, J=2.4 Hz, 1H), 8.03-7.96 (m, 2H), 7.91 (dd, J=8.8, 2.4 Hz, 1H), 7.60-7.52 (m, 1H), 7.47-7.38 (m, 2H), 7.15 (d, J=8.8 Hz, 1H), 6.53 (s, 1H), 4.43-4.29 (m, 4H), 3.85-3.83 (m, 5H), 2.39-2.24 (m, 4H), 1.84-1.82 (m, 2H), 1.73-1.71 (m, 2H), 1.56-1.43 (m, 5H), 1.43-1.39 (m, 3H), 0.92 (t, J=7.3 Hz, 3H); LCMS (ESI): m/z 625.5 [M+H$^+$]; purity~93%.

Example 23

2-(2-ethoxy-5-((4-(2-hydroxyethyl)piperidin-1-yl)sulfonyl)phenyl)-5-methyl-7-propyl-3,5-dihydro-4H-pyrrolo[3,2-d]pyrimidin-4-one (14)

A sealed tube was charged with 2-(1-((3-((2-carbamoyl-1-methyl-4-propyl-1H-pyrrol-3-yl)carbamoyl)-4-ethoxyphenyl)sulfonyl) piperidin-4-yl)ethyl benzoate 13 (85 mg, 0.14 mmol), ethanol (1.3 mL), followed by 1M aqueous KOH solution (1.2 mL) at room temperature. The tube was capped and stirred the reaction mixture at 100° C. for 24 h. After completion of reaction (monitored by TLC & LCMS), the reaction was cooled to room temperature and concentrated under reduced pressure. The resultant residue was diluted in water (5 mL) and extracted with dichloromethane (3×20 mL). The combined organic layer was washed with brine (10 mL), dried over anhydrous Na$_2$SO$_4$ and concentrated under reduced pressure. The obtained crude product was purified by reverse phase column chromatography (C-18 column; Grace System) by eluting with 40-43% gradient acetonitrile with water. The pure fractions were lyophilized to afford the title compound 14 (34.5 mg, 50% yield) as a white solid. 1H NMR (400 MHz, DMSO-d$_6$) δ ppm 11.67 (br s, 1H; D$_2$O exchangeable), 7.89 (d, J=2.4 Hz, 1H), 7.79 (dd, J=8.8, 2.4 Hz, 1H), 7.34 (d, J=8.80 Hz, 1H), 7.20 (s, 1H), 4.31 (br s, 1H; D$_2$O exchangeable), 4.21 (q, J=6.9 Hz, 2H), 3.98 (s, 3H), 3.61-3.59 (m, 2H), 3.39-3.37 (m, 2H), 2.57-2.55 (m, 2H), 2.31-2.17 (m, 2H), 1.77-1.56 (m, 4H), 1.43-1.26 (m, 6H), 1.23-1.09 (m, 2H), 0.92 (t, J=7.6 Hz, 3H); LCMS (ESI): m/z 503.4 [M+H$^+$]; purity~99.2%.

nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.)] drop wise at −10° C. for 10 min under argon atmosphere. The reaction was stirred at −10° C. to −5° C. for 4 h. After completion of reaction (monitored by TLC), the reaction was quenched with saturated NaHCO$_3$ solution (10 mL) at 0° C. and extracted with EtOAc (3×20 mL). The combined organic layer was washed with brine (10 mL), dried over anhydrous Na$_2$SO$_4$ and concentrated under reduced pressure. The obtained crude product was purified reverse phase column chromatography (C-18 column, Grace System) by eluting with 55-60% gradient acetonitrile with water. The pure fractions were lyophilized to afford the title compound 2c (42 mg; ~26% yield) as a pale yellow solid. 1H NMR (400 MHz, DMSO-d$_6$) δ ppm 11.64 (br s, 1H; D$_2$O exchangeable), 7.91 (d, J=2.4 Hz, 1H), 7.80 (dd, J=8.8, 2.4 Hz, 1H), 7.35 (d, J=8.8 Hz, 1H), 7.21 (s, 1H), 4.51 (t, J=6.6 Hz, 2H), 4.22 (q, J=6.9 Hz, 2H), 3.98 (s, 3H), 3.64-3.59 (m, 2H), 2.58-2.56 (m, 2H), 2.30-2.26 (m, 2H), 1.76-1.72 (m, 2H), 1.66-1.58 (m, 4H), 1.40-1.35 (m, 4H), 1.22-1.06 (m, 2H), 0.92 (t, J=7.3 Hz, 3H); LCMS (ESI): m/z 548.5 [M+H$^+$]; purity~97%.

Scheme 14

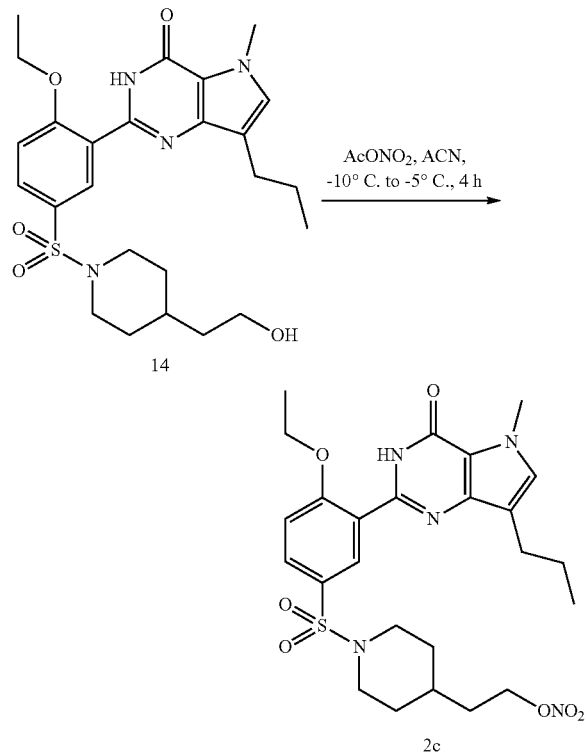

Example 24

2-(1-((4-ethoxy-3-(5-methyl-4-oxo-7-propyl-4,5-dihydro-3H-pyrrolo[3,2-d]pyrimidin-2-yl)phenyl)sulfonyl)piperidin-4-yl)ethyl nitrate (2c)

To a stirred solution of 2-(2-ethoxy-5-((4-(2-hydroxyethyl)piperidin-1-yl)sulfonyl)phenyl)-5-methyl-7-propyl-3,5-dihydro-4H-pyrrolo[3,2-d]pyrimidin-4-one 14 (150 mg, 0.30 mmol) in acetonitrile (4.5 mL) was added a solution of freshly prepared acetyl nitrate (0.13 mL; 1.5 mmol) [(acetyl Scheme 15

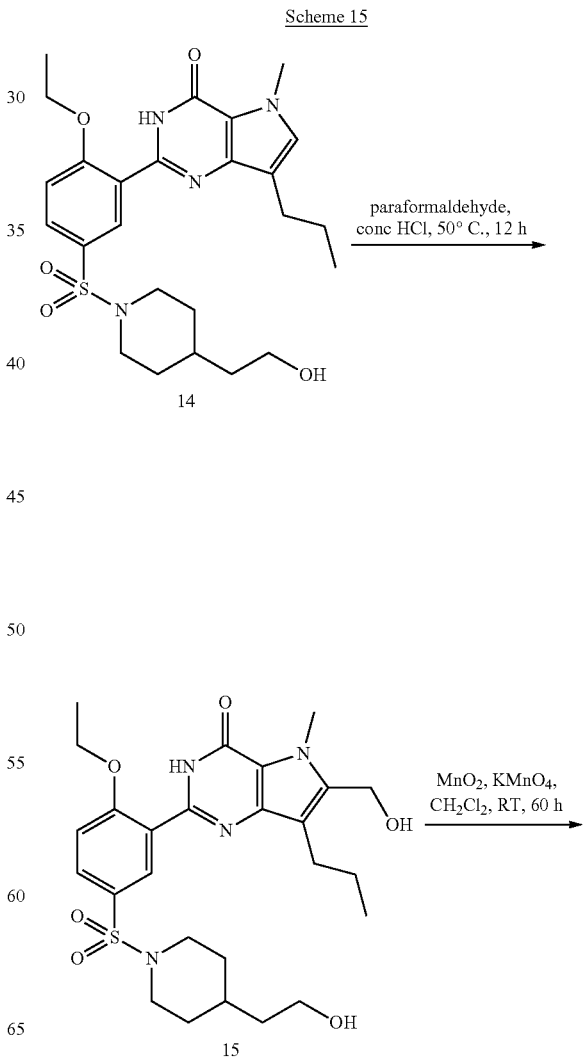

-continued

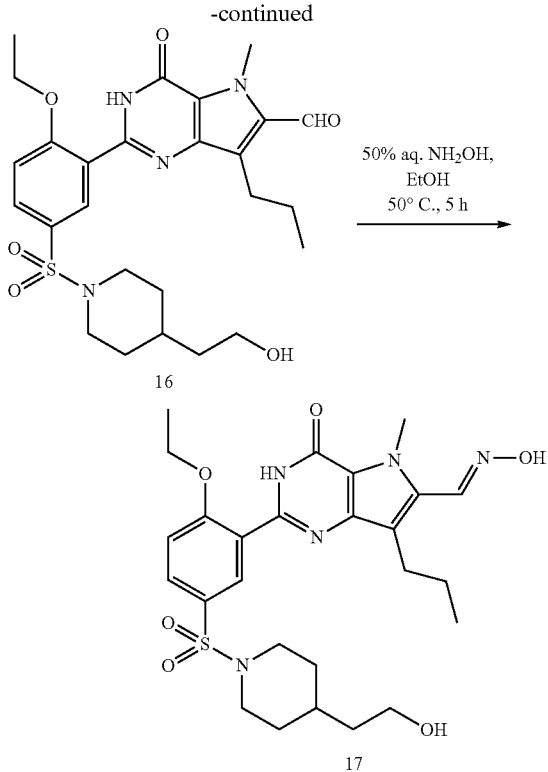

Example 25

2-(2-ethoxy-5-((4-(2-hydroxyethyl)piperidin-1-yl)sulfonyl)phenyl)-6-(hydroxymethyl)-5-methyl-7-propyl-3,5-dihydro-4H-pyrrolo[3,2-d]pyrimidin-4-one (5)

To a stirred solution of 2-(2-ethoxy-5-((4-(2-hydroxyethyl)piperidin-1-yl)sulfonyl)phenyl)-5-methyl-7-propyl-3,5-dihydro-4H-pyrrolo[3,2-d]pyrimidin-4-one 14 (450 mg, 0.9 mmol) in concentrated HCl solution (4.5 mL), was added paraformaldehyde (225 mg, 0.5 w/w) at room temperature and heated to 50° C. under inert atmosphere. Reaction was monitored by LCMS analysis. After 12 h stirring, the reaction mixture was cooled to room temperature and neutralized with saturated NaHCO₃ solution (100 mL). The resultant solution was extracted with 10% methanol in dichloromethane (3×100 mL). The combined organic extracts were dried over anhydrous Na₂SO₄ and concentrated under reduced pressure. The obtained crude product was purified by reverse phase column chromatography (C-18 column; Grace System) by eluting with 35-40% gradient acetonitrile with water to afford the titled compound 15 (380 mg; 76% yield) as an off-white solid. $^1$H NMR (300 MHz, DMSO-d₆) δ ppm 11.67 (br s, 1H), 7.91 (d, J=2.4 Hz, 1H), 7.79 (dd, J=8.8, 2.4 Hz, 1H), 7.35 (d, J=8.8 Hz, 1H), 5.17 (t, J=5.1 Hz, 1H), 4.56 (d, J=5.1 Hz, 2H), 4.32 (t, J=5.0 Hz, 1H), 4.21 (q, J=6.7 Hz, 2H), 4.05 (s, 3H), 3.63-3.59 (m, 2H), 3.42-3.38 (m, 2H), 2.61-2.58 (m, 2H), 2.26-2.22 (m, 2H), 1.74-1.51 (m, 4H), 1.38-1.26 (m, 6H), 1.21-1.15 (m, 2H), 0.88 (t, J=7.3 Hz, 3H); LCMS (ESI): m/z 533.5 [M+H]⁺; purity~95%.

Example 26

2-(2-ethoxy-5-((4-(2-hydroxyethyl)piperidin-1-yl)sulfonyl)phenyl)-5-methyl-4-oxo-7-propyl-4,5-dihydro-3H-pyrrolo[3,2-d]pyrimidine-6-carbaldehyde (16)

To a stirred solution of 2-(2-ethoxy-5-((4-(2-hydroxyethyl)piperidin-1-yl)sulfonyl)phenyl)-6-(hydroxymethyl)-5-methyl-7-propyl-3,5-dihydro-4H-pyrrolo[3,2-d]pyrimidin-4-one 15 (330 mg, 0.62 mmol) in CH₂Cl₂ (80 mL) was added activated MnO₂ (58% min Mn) (933 mg, 10.73 mmol) and KMnO₄ (314 mg, 2.0 mmol) at room temperature and stirred for 60 h. Reaction was monitored by TLC. After 60 h, the reaction mixture was then filtered through a Celite pad and washed with CH₂Cl₂ (200 mL). The filtrate was concentrated to afford the title compound 16 (220 mg) as an off-white solid, which was directly taken for next reaction without further purification. $^1$H NMR (300 MHz, DMSO-d₆) δ ppm 12.11 (br s, 1H), 10.15 (s, 1H), 7.88 (d, J=2.4 Hz, 1H), 7.82 (dd, J=8.8, 2.4 Hz, 1H), 7.36 (d, J=8.8 Hz, 1H), 4.29-4.25 (m, 4H), 4.21 (q, J=7.0 Hz, 2H), 3.63-3.59 (m, 2H), 3.41-3.38 (m, 2H), 2.96-2.93 (m, 2H), 2.28-2.21 (m, 2H), 1.74-1.67 (m, 4H), 1.34-1.26 (m, 6H), 1.24-1.12 (m, 2H), 0.91 (t, J=7.3 Hz, 3H); LCMS (ESI): m/z 531.5 [M+H]⁺; purity~88.6%.

Example 27

(E)-2-(2-ethoxy-5-((4-(2-hydroxyethyl)piperidin-1-yl)sulfonyl)phenyl)-5-methyl-4-oxo-7-propyl-4,5-dihydro-3H-pyrrolo[3,2-d]pyrimidine-6-carbaldehyde oxime (17)

To a stirred solution of 2-(2-ethoxy-5-((4-(2-hydroxyethyl)piperidin-1-yl)sulfonyl)phenyl)-5-methyl-4-oxo-7-propyl-4,5-dihydro-3H-pyrrolo[3,2-d]pyrimidine-6-carbaldehyde 16 (80 mg, 0.15 mmol) in ethanol (9.6 mL) was added 50% hydroxylamine in aqueous solution (1.6 mL) at room temperature. Reaction was heated to 50° C. for 5 h under argon atmosphere. After completion of reaction (monitored by TLC), the reaction was concentrated under reduced pressure. The resultant residue was diluted in water (4 mL), and extracted with ethyl acetate (3×10 mL). The combined organic layers were washed with brine (10 mL), dried over anhydrous Na₂SO₄ and concentrated under reduced pressure. The obtained crude product was purified by reverse phase column chromatography (C-18 column; Grace System) by eluting with 35% gradient acetonitrile with water. The pure fractions were lyophilized to afford the title compound 17 (16.7 mg) as a white solid. $^1$H NMR (400 MHz, DMSO-d₆) δ ppm 11.78 (br s, 1H; D₂O exchangeable), 11.59 (s, 1H, D₂O exchangeable), 8.34 (s, 1H), 7.92 (d, J=2.4 Hz, 1H), 7.80 (dd, J=8.8, 2.4 Hz, 1H), 7.35 (d, J=8.8 Hz, 1H), 4.28 (t, J=5.1 Hz, 1H; D₂O exchangeable), 4.22 (q, J=6.9 Hz, 2H), 4.17 (s, 3H), 3.64-3.59 (m, 2H), 3.42-3.38 (m, 2H), 2.79-2.75 (m, 2H), 2.26-2.20 (m, 2H), 1.74-1.70 (m, 2H), 1.63-1.56 (m, 2H), 1.40-1.29 (m, 6H), 1.14-1.09 (m, 2H), 0.88 (t, J=7.3 Hz, 3H); LCMS (ESI): m/z 546.6 [M+H]⁺; purity~97.7%.

79

Scheme 16

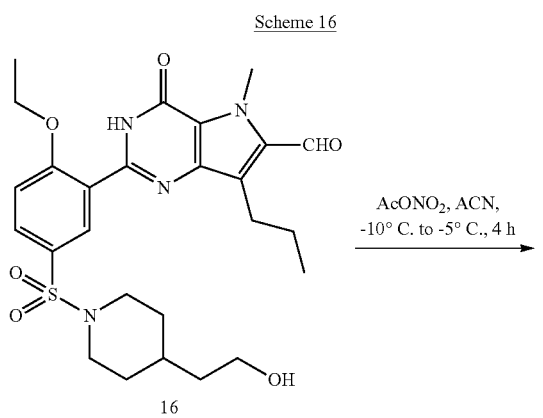

Example 28

2-(1-((4-ethoxy-3-(6-formyl-5-methyl-4-oxo-7-propyl-4,5-dihydro-3H-pyrrolo[3,2-d]pyrimidin-2-yl)phenyl)sulfonyl)piperidin-4-yl)ethyl nitrate (2e)

To a stirred solution of 2-(2-ethoxy-5-((4-(2-hydroxyethyl)piperidin-1-yl)sulfonyl)phenyl)-5-methyl-4-oxo-7-propyl-4,5-dihydro-3H-pyrrolo[3,2-d]pyrimidine-6-carbaldehyde 2 (140 mg, 0.26 mmol) in acetonitrile (5.6 mL) was added a solution of freshly prepared acetyl nitrate (0.12 mL; 1.32 mmol) [(acetyl nitrate was prepared separately by addition of fuming $HNO_3$ (1.1 mL, 25.5 mmol) drop wise in to acetic anhydride (2.5 mL, 26.5 mmol) slowly at −15° C. for 30 min under argon atmosphere (Note: temperature should not be raised above 0° C.))] drop wise at −10° C. for 10 min under argon atmosphere. The reaction was stirred at −5° C. for 4 h. After completion of reaction (monitored by TLC), the reaction was quenched with saturated $NaHCO_3$ solution (10 mL) at 0° C. and extracted with EtOAc (2×25 mL). The combined organic layer was washed with brine (20 mL), dried over anhydrous $Na_2SO_4$ and concentrated under reduced pressure to afford the crude product 3 (140 mg) as a brown semi solid, which was directly taken for next reaction without further purification. LCMS (ESI): m/z 576.6 [M+H$^+$]; purity~75.5%.

Example 29

(E)-2-(1-((4-ethoxy-3-(6-((hydroxyimino)methyl)-5-methyl-4-oxo-7-propyl-4,5-dihydro-3H-pyrrolo[3,2-d]pyrimidin-2-yl)phenyl)sulfonyl)piperidin-4-yl) ethyl nitrate (2a)

To a stirred solution of 2-(1-((4-ethoxy-3-(6-formyl-5-methyl-4-oxo-7-propyl-4,5-dihydro-3H-pyrrolo[3,2-d]pyrimidin-2-yl)phenyl)sulfonyl)piperidin-4-yl)ethyl nitrate 2e (140 mg) in ethanol (17 mL) was added 50% hydroxylamine in aqueous solution (2.8 mL) at room temperature and stirred at 50° C. for 5 h under argon atmosphere. After completion of reaction (monitored by LCMS analysis), the reaction was concentrated under reduced pressure. The resultant residue was diluted in water (5 mL) and extracted with EtOAc (2×20 mL). The combined organic layer was washed with brine (20 mL), dried over anhydrous $Na_2SO_4$ and concentrated under reduced pressure. The crude product was purified by silica gel column chromatography (Grace System) by eluting with 45-50% gradient EtOAc in petroleum ether to afford 70 mg of title compound with ~93% purity, which was further purified by re-crystallization in hot iso-propanol (2.5 mL) to afford the title compound 2a (38 mg) as an off-white solid. $^1$H NMR (400 MHz, DMSO-d$_6$) δ ppm 11.77 (br s, 1H; D$_2$O exchangeable), 11.59 (s, 1H; D$_2$O exchangeable), 8.34 (s, 1H), 7.92 (d, J=2.4 Hz, 1H), 7.81 (dd, J=8.8, 2.4 Hz, 1H), 7.36 (d, J=8.8 Hz, 1H), 4.51 (t, J=6.4 Hz, 2H), 4.22 (q, J=6.8 Hz, 2H), 4.17 (s, 3H), 3.64-3.59 (m, 2H), 2.79-2.75 (m, 2H), 2.27-2.22 (m, 2H), 1.78-1.74 (m, 2H), 1.63-1.56 (m, 4H), 1.38-1.33 (m, 4H), 1.22-1.17 (m, 2H), 0.88 (t, J=7.3 Hz, 3H); LCMS (ESI): m/z 591.1 [M+H$^+$]; purity~99.1%.

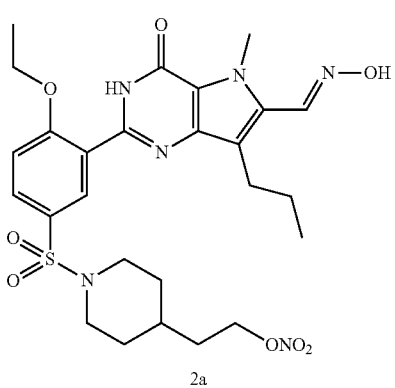

Scheme 17

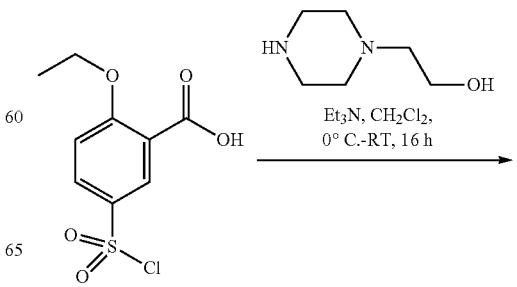

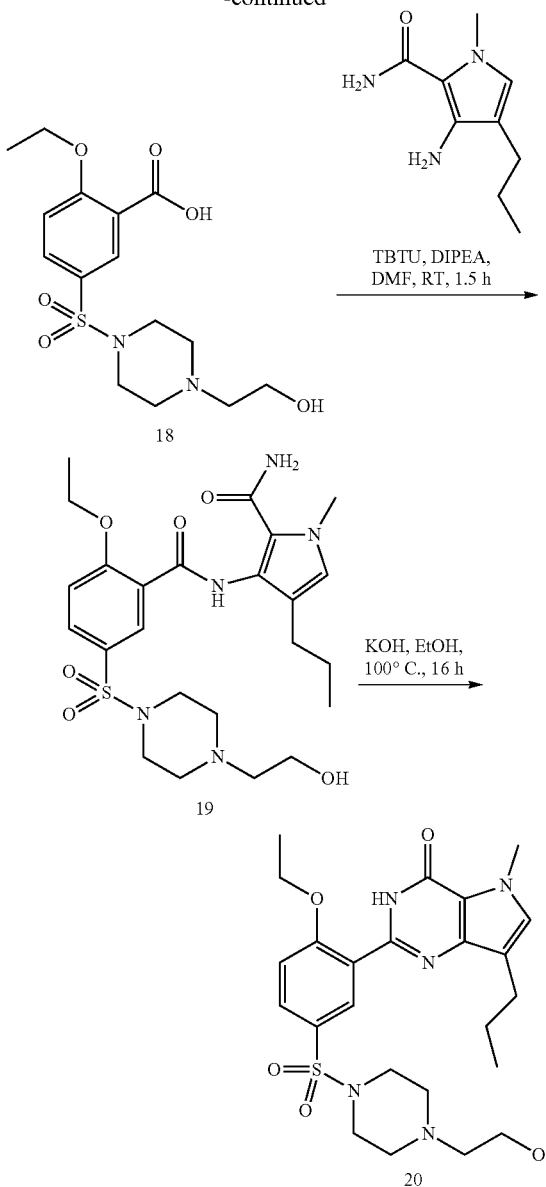

J=8.4 Hz, 1H), 4.16 (q, J=6.9 Hz, 2H), 3.44-3.29 (m, 3H), 2.83-2.78 (m, 4H), 2.51-2.47 (m, 4H), 2.36-2.33 (m, 2H), 1.34 (t, J=6.9 Hz, 3H); LCMS (ESI): m/z 359.0 [M+H]$^+$; purity~95.9%.

Example 31

3-(2-ethoxy-5-((4-(2-hydroxyethyl)piperazin-1-yl)sulfonyl)benzamido)-1-methyl-4-propyl-1H-pyrrole-2-carboxamide (19)

To a stirred solution of 2-ethoxy-5-((4-(2-hydroxyethyl)piperazin-1-yl)sulfonyl)benzoic acid 18 (8.0 g, 22.32 mmol) in DMF (40 mL) was added diisopropyl ethylamine (19.5 mL, 111.64 mmol) drop wise, followed by TBTU (14.5 g, 45.16 mmol) at 15° C. and stirred for 20 min. To this, 3-amino-1-methyl-4-propyl-1H-pyrrole-2-carboxamide (4.0 g, 22.32 mmol) was added lots wise at 15° C. under inert atmosphere. The reaction was allowed to stir at room temperature for 1.5 h. After completion of reaction (monitored by TLC & LCMS analysis), reaction was quenched ice-water (400 mL) and extracted with EtOAc (4×200 mL). The combined organic layer was washed with brine (4×100 mL), dried over anhydrous Na$_2$SO$_4$ and concentrated under reduced pressure. The obtained crude product was purified by trituration with dichloromethane (50 mL) and n-hexane (200 mL) and filtered. The solid was washed with diethyl ether (50 mL) and dried under vacuum to afford the title compound 19 (7.5 g, ~59% yield) as a pale brown solid. $^1$H NMR (300 MHz, DMSO-d$_6$) δ ppm 9.57 (br s, 1H), 7.83-7.78 (m, 2H), 7.41 (d, J=8.4 Hz, 1H), 7.24 (br s, 1H), 6.93 (br s, 1H), 6.72 (s, 1H), 4.37 (t, J=5.3 Hz, 1H), 4.29 (q, J=6.7 Hz, 2H), 3.75 (s, 3H), 3.43-3.39 (m, 2H), 2.87-2.84 (m, 4H), 2.57-2.54 (m, 4H), 2.37-2.34 (m, 2H), 2.28-2.26 (m, 2H), 1.54-1.38 (m, 5H), 0.88 (t, J=7.1 Hz, 3H); LCMS (ESI): m/z 522.2 [M+H$^+$]; purity~91.5%.

Example 32

2-(2-ethoxy-5-((4-(2-hydroxyethyl)piperazin-1-yl)sulfonyl)phenyl)-5-methyl-7-propyl-3,5-dihydro-4H-pyrrolo[3,2-d]pyrimidin-4-one (20)

A seal tube was charged with 3-(2-ethoxy-5-((4-(2-hydroxyethyl)piperazin-1-yl)sulfonyl)benzamido)-1-methyl-4-propyl-1H-pyrrole-2-carboxamide 19 (190 mg, 0.364 mmol), ethanol (3.0 mL), followed by 1M aqueous KOH solution (2.7 mL) at room temperature. The tube was capped and stirred the reaction mixture at 100° C. for 16 h. After completion of reaction (monitored by TLC & LCMS analysis), the reaction was cooled to room temperature and concentrated under reduced pressure. The resultant residue was diluted in water (5 mL) and extracted with ethyl acetate (2×25 mL). The combined organic layer was washed with brine (20 mL), dried over anhydrous Na$_2$SO$_4$ and concentrated under reduced pressure. The obtained crude product was purified by silica gel column chromatography (Grace System) by eluting with 12% of 30% methanol in CH$_2$Cl$_2$: CH$_2$Cl$_2$. The pure fractions were lyophilized and the solid obtained was triturated with n-pentane (4×10 mL) to afford the title compound 20 (35 mg) as a white solid. $^1$H NMR (400 MHz, DMSO-d$_6$) δ ppm 11.67 (br s, 1H; D$_2$O exchangeable), 7.88 (d, J=2.0 Hz, 1H), 7.80 (dd, J=8.8, 2.0 Hz, 1H), 7.36 (d, J=8.8 Hz, 1H), 7.21 (s, 1H), 4.33 (t, J=5.4 Hz, 1H; D$_2$O exchangeable), 4.22 (q, J=6.8 Hz, 2H), 3.98 (s, 3H), 3.43-3.41 (m, 2H), 2.90-2.87 (m, 4H), 2.60-2.57 (m, 2H), 2.52-2.48 (m, 4H), 2.39-2.36 (m, 2H), 1.67-1.60 (m,

Example 30

2-ethoxy-5-((4-(2-hydroxyethyl)piperazin-1-yl)sulfonyl)benzoic acid (18)

To a stirred solution of 2-(piperazin-1-yl)ethan-1-ol (740 mg, 5.67 mmol) in CH$_2$Cl$_2$ (9 mL) was added triethylamine (4 mL, 28.35 mmol) at 0° C. under inert atmosphere. To this, a solution of 5-(chlorosulfonyl)-2-ethoxybenzoic acid (1.5 g, 5.67 mmol) in CH$_2$Cl$_2$ (9 mL) was added drop wise at 0° C. under inert atmosphere. The reaction mixture was allowed to stir at room temperature for 16 h. After completion of reaction (monitored by LCMS analysis), the reaction mixture was purified by (without work-up) reverse phase column chromatography (C-18 column, Grace System) by eluting with 0-15% acetonitrile with water to afford the title compound 18 (2.0 g) as an off-white semi solid. 1H NMR (300 MHz, DMSO-d$_6$) δ ppm 7.72-7.63 (m, 2H), 7.24 (d, 2H), 1.36 (t, J=6.8 Hz, 3H), 0.92 (t, J=7.3 Hz, 3H); LCMS (ESI): m/z 504.1 [M+H$^+$]; purity~99%.

Scheme 18

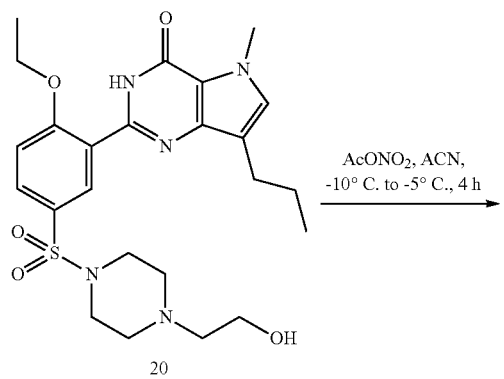

Example 33

2-(4-((4-ethoxy-3-(5-methyl-4-oxo-7-propyl-4,5-dihydro-3H-pyrrolo[3,2-d]pyrimidin-2-yl)phenyl)sulfonyl)piperazin-1-yl)ethyl nitrate (2d)

To a stirred solution of 2-(2-ethoxy-5-((4-(2-hydroxyethyl)piperazin-1-yl)sulfonyl)phenyl)-5-methyl-7-propyl-3,5-dihydro-4H-pyrrolo[3,2-d]pyrimidin-4-one 20 (100 mg, 0.20 mmol) in acetonitrile (4 mL) was added a solution of freshly prepared acetyl nitrate (0.12 mL; 1.4 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 10 min under argon atmosphere. The reaction was stirred at −10° C. to −5° C. for 4 h. After completion of reaction (monitored by TLC), the reaction was quenched with saturated NaHCO$_3$ solution (10 mL) at 0° C. and extracted with EtOAc (3×20 mL). The combined organic layer was washed with brine (20 mL), dried over anhydrous Na$_2$SO$_4$ and concentrated under reduced pressure. The obtained crude product was purified reverse phase column chromatography (C-18 column, Grace System) by eluting with 40% acetonitrile with water to afford 38 mg of title compound with ~$_{93}$% purity, which was further purified by re-crystallization in hot iso-propanol (2.5 mL) to afford the title compound 2d (22 mg) as a pale yellow solid. $^1$H NMR (400 MHz, DMSO-d$_6$) δ ppm 11.66 (s, 1H; D$_2$O exchangeable), 7.88 (d, J=2.2 Hz, 1H), 7.80 (dd, J=8.8, 2.2 Hz, 1H), 7.36 (d, J=8.8 Hz, 1H), 7.21 (s, 1H), 4.56 (t, J=5.1 Hz, 2H), 4.22 (q, J=6.8 Hz, 2H), 3.98 (s, 3H), 2.90-2.87 (m, 4H), 2.64-2.61 (m, 2H), 2.59-2.54 (m, 2H), 2.52-2.49 (m, 4H), 1.68-1.59 (m, 2H), 1.35 (t, J=6.8 Hz, 3H), 0.92 (t, J=7.34 Hz, 3H); LCMS (ESI): m/z 549.1 [M+H$^+$]; purity~96.7%.

Scheme 19

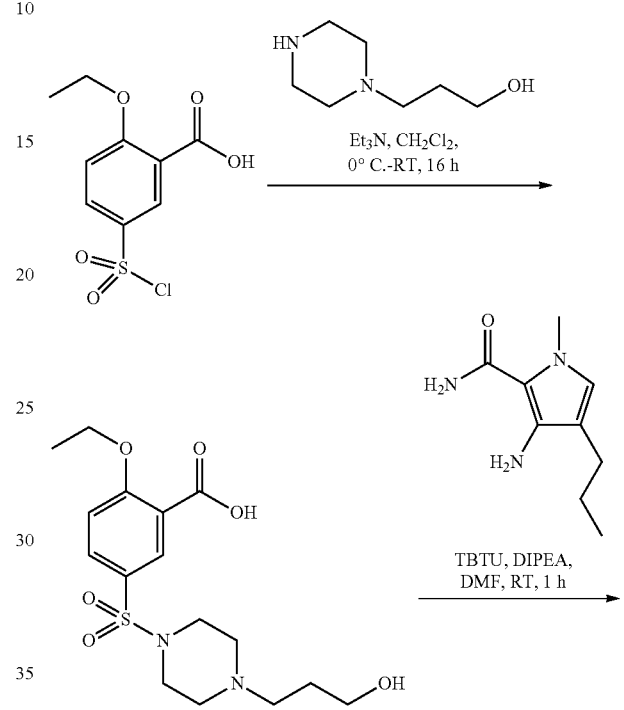

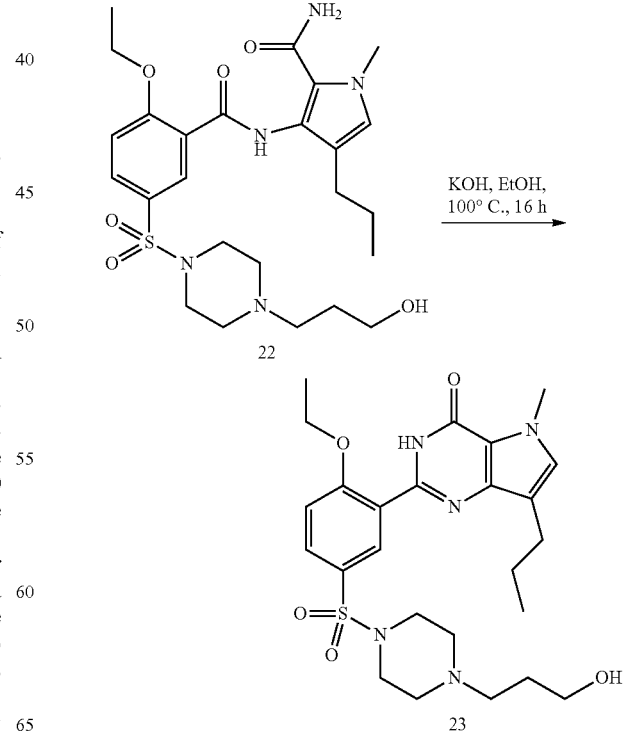

Example 34

2-ethoxy-5-((4-(3-hydroxypropyl)piperazin-1-yl) sulfonyl)benzoic acid (21)

To a stirred solution of 2-(piperazin-1-yl)propane-1-ol (1.0 g, 6.8 mmol) in $CH_2Cl_2$ (11 mL) was added triethylamine (4.6 mL, 34 mmol) at 0° C. under inert atmosphere. To this, a solution of 5-(chlorosulfonyl)-2-ethoxybenzoic acid (1.8 g, 6.8 mmol) in $CH_2Cl_2$ (11 mL) was added drop wise at 0° C. under inert atmosphere. The reaction mixture was allowed to stir at room temperature for 16 h. After completion of reaction (monitored by LCMS analysis), the reaction mixture was directly purified by (without work-up) reverse phase column chromatography (C-18 column, Grace System) by eluting with 0-15% acetonitrile with water to afford the title compound 21 (2.6 g) as an off-white semi solid, which was directly taken for next reaction without further purification. $^1H$ NMR (300 MHz, DMSO-$d_6$) δ ppm 7.74-7.68 (m, 2H), 7.26 (d, J=8.80 Hz, 1H), 4.17 (q, J=6.9 Hz, 2H), 3.36-3.34 (m, 3H), 2.85-2.80 (m, 4H), 2.42-2.39 (m, 4H), 2.32-2.29 (m, 2H), 1.54-1.49 (m, 2H), 1.34 (t, J=6.9 Hz, 3H); LCMS (ESI): m/z 373.08 [M+H$^+$]; purity~87%.

Example 35

3-(2-ethoxy-5-((4-(3-hydroxypropyl)piperazin-1-yl) sulfonyl)benzamido)-1-methyl-4-propyl-1H-pyrrole-2-carboxamide (22)

To a stirred solution of 2-ethoxy-5-((4-(3-hydroxypropyl) piperazin-1-yl)sulfonyl)benzoic acid 21 (2.6 g) in DMF (10 mL) was added diisopropyl ethylamine (6.1 mL, 35.0 mmol) drop wise, followed by TBTU (4.5 g, 14.0 mmol) at 15° C. and stirred for 20 min. To this, 3-amino-1-methyl-4-propyl-1H-pyrrole-2-carboxamide (1.27 g, 7.0 mmol) in DMF (3 mL) solution was added at 15° C. and stirred for 1 h at room temperature under inert atmosphere. After completion of reaction (monitored by TLC & LCMS), reaction was quenched in ice-cold water (130 g) and extracted with EtOAc (4×50 mL). The combined organic layer was washed with brine (4×50 mL), dried over anhydrous $Na_2SO_4$ and concentrated under reduced pressure. The obtained crude product was purified by silica gel column chromatography (Grace System) by eluting with 10-15% gradient 30% methanol in $CH_2Cl_2$:$CH_2Cl_2$ to afford the title compound 22 (2.4 g; ~66% yield in two steps) as pale brown solid. LCMS (ESI): m/z 536.2 [M+H$^+$]; purity~95%.

Example 36

2-(2-ethoxy-5-((4-(3-hydroxypropyl)piperazin-1-yl) sulfonyl)phenyl)-5-methyl-7-propyl-3,5-dihydro-4H-pyrrolo[3,2-d]pyrimidin-4-one (23)

A seal tube was charged with 3-(2-ethoxy-5-((4-(3-hydroxypropyl)piperazin-1-yl)sulfonyl)benzamido)-1-methyl-4-propyl-1H-pyrrole-2-carboxamide 22 (170 mg, 0.32 mmol), ethanol (2.7 mL), followed by 1M aqueous KOH solution (2.4 mL) at room temperature. The tube was capped and stirred the reaction mixture at 100° C. for 16 h. After completion of reaction (monitored by TLC & LCMS), the reaction was cooled to room temperature and concentrated under reduced pressure. The resultant residue was diluted in water (5 mL) and extracted with ethyl acetate (2×25 mL). The combined organic layer was washed with brine (20 mL), dried over anhydrous $Na_2SO_4$ and concentrated under reduced pressure. The obtained crude product was purified by silica gel column chromatography (Grace System) by eluting with 14% of 30% MeOH in $CH_2Cl_2$:$CH_2Cl_2$. The pure fractions were lyophilized and trituration with n-pentane (4×10 mL) to afford the title compound 23 (32 mg) as a white solid. 1H NMR (400 MHz, DMSO-$d_6$) δ ppm 11.67 (s, 1H; $D_2O$ exchangeable), 7.88 (d, J=2.2 Hz, 1H), 7.80 (dd, J=8.8, 2.2 Hz, 1H), 7.36 (d, J=8.8 Hz, 1H), 7.21 (s, 1H), 4.31 (br t, J=5.1 Hz, 1H; $D_2O$ exchangeable), 4.22 (q, J=6.9 Hz, 2H), 3.98 (s, 3H), 3.39-3.33 (m, 2H), 2.90-2.87 (m, 4H), 2.59-2.56 (m, 2H), 2.43-2.39 (m, 4H), 2.34-2.29 (m, 2H), 1.67-1.59 (m, 2H), 1.53-1.45 (m, 2H), 1.35 (t, J=6.9 Hz, 3H), 0.92 (t, J=7.3 Hz, 3H); LCMS (ESI): m/z 518.2 [M+H$^+$]; purity~99.7%.

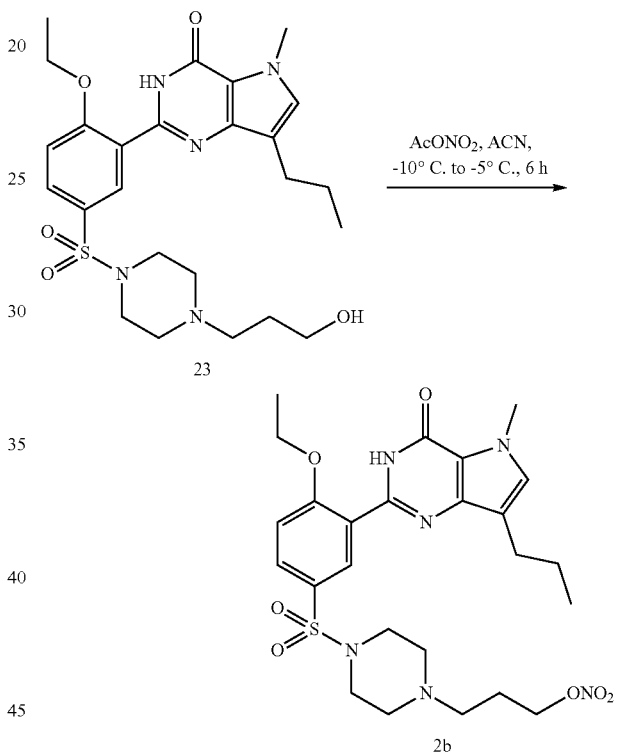

Scheme 20

Example 37

3-(4-((4-ethoxy-3-(5-methyl-4-oxo-7-propyl-4,5-dihydro-3H-pyrrolo[3,2-d]pyrimidin-2-yl)phenyl) sulfonyl)piperazin-1-yl)propyl nitrate (2b)

To a stirred solution of 2-(2-ethoxy-5-((4-(3-hydroxypropyl)piperazin-1-yl)sulfonyl)phenyl)-5-methyl-7-propyl-3,5-dihydro-4H-pyrrolo[3,2-d]pyrimidin-4-one 23 (150 mg, 0.29 mmol) in acetonitrile (6.0 mL) was added a solution of freshly prepared acetyl nitrate (0.13 mL; 1.5 mmol) [(acetyl nitrate was prepared separately by addition of fuming $HNO_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.)] drop wise at −10° C. for 10 min under argon atmosphere. The reaction was stirred at −10° C. to −5° C. for 4 h. Reaction was monitored by TLC. After 4 h, the reaction was cooled to −15° C. and added acetyl nitrate (0.05 mL; 0.6 mmol). The reaction was stirred at −10° C. to −5° C. for additional 2 h. After completion of reaction (monitored by TLC), the reaction was quenched with saturated NaHCO$_3$ solution (10 mL) at 0° C. and extracted with EtOAc (3×20 mL). The combined organic layer was washed with brine (20 mL), dried over anhydrous Na$_2$SO$_4$ and concentrated under reduced pressure. The obtained crude product was purified reverse phase column chromatography (C-18 column, Grace System) by eluting with 45% gradient acetonitrile with water. The obtained solid was triturated with diethyl ether (3 mL) to afford the title compound 2b (43.4 mg; ~26% yield) as a pale yellow solid. $^1$H NMR (400 MHz, DMSO-d$_6$) δ ppm 11.67 (s, 1H; D$_2$O exchangeable), 7.89 (d, J=2.4 Hz, 1H), 7.80 (dd, J=8.8, 2.4 Hz, 1H), 7.36 (d, J=8.8 Hz, 1H), 7.21 (s, 1H), 4.48 (t, J=6.6 Hz, 2H), 4.22 (q, J=6.8 Hz, 2H), 3.98 (s, 3H), 2.93-2.89 (m, 4H), 2.58-2.55 (m, 2H), 2.45-2.42 (m, 4H), 2.36-2.32 (m, 2H), 1.81-1.77 (m, 2H), 1.67-1.59 (m, 2H), 1.35 (t, J=6.8 Hz, 3H), 0.92 (t, J=7.3 Hz, 3H); LCMS (ESI): m/z 563.1 [M+H$^+$]; purity~97.5%.

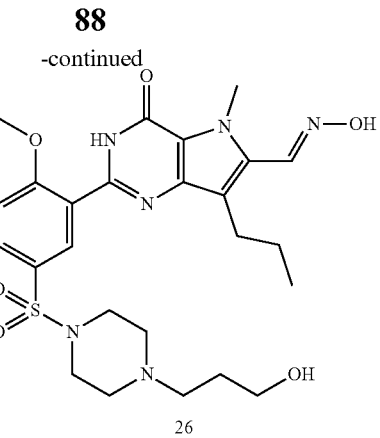

26

Example 38

2-(2-ethoxy-5-((4-(3-hydroxypropyl)piperazin-1-yl) sulfonyl)phenyl)-6-(hydroxymethyl)-5-methyl-7-propyl-3,5-dihydro-4H-pyrrolo[3,2-d]pyrimidin-4-one (24)

To a stirred solution of 2-(2-ethoxy-5-((4-(3-hydroxypropyl)piperazin-1-yl)sulfonyl)phenyl)-5-methyl-7-propyl-3,5-dihydro-4H-pyrrolo[3,2-d]pyrimidin-4-one 23 (1.55 g, 3.0 mmol) in concentrated HCl solution (15.5 mL), was added paraformaldehyde (780 mg, 0.5 w/w) at room temperature and heated to 50° C. under inert atmosphere. Reaction was monitored by LCMS analysis. After 12 h stirring, the reaction mixture was cooled to room temperature and neutralized with saturated NaHCO$_3$ solution (200 mL). The resultant solution was extracted with 10% methanol in dichloromethane (3×150 mL). The combined organic extracts were dried over anhydrous Na$_2$SO$_4$ and concentrated under reduced pressure. The obtained crude product was purified by reverse phase column chromatography (C-18 column; Grace System) by eluting with 45% acetonitrile with water to afford the titled compound 24 (1.12 g; 68% yield) as an off-white solid. $^1$H NMR (300 MHz, DMSO-d$_6$) δ ppm 11.70 (br s, 1H), 7.87 (d, J=2.2 Hz, 1H), 7.80 (dd, J=8.8, 2.2 Hz, 1H), 7.36 (d, J=8.8 Hz, 1H), 5.16 (br s, 1H), 4.56 (br d, J=4.4 Hz, 2H), 4.35 (t, J=5.0 Hz, 2H), 4.22 (q, J=6.8 Hz, 2H), 4.05 (s, 3H), 3.42-3.35 (m, 2H), 2.90-2.86 (m, 4H), 2.62-2.59 (m, 2H), 2.42-2.39 (m, 4H), 2.33-2.29 (m, 2H), 1.64-1.45 (m, 4H), 1.34 (t, J=6.8 Hz, 3H), 0.88 (t, J=7.3 Hz, 3H); LCMS (ESI): m/z 548.6 [M+H$^+$]; purity~94%.

Example 39

2-(2-ethoxy-5-((4-(3-hydroxypropyl)piperazin-1-yl) sulfonyl)phenyl)-5-methyl-4-oxo-7-propyl-4,5-dihydro-3H-pyrrolo[3,2-d]pyrimidine-6-carbaldehyde (25)

To a stirred solution of 2-(2-ethoxy-5-((4-(3-hydroxypropyl)piperazin-1-yl)sulfonyl)phenyl)-6-(hydroxymethyl)-5-methyl-7-propyl-3,5-dihydro-4H-pyrrolo[3,2-d]pyrimidin-4-one 24 (920 mg, 1.68 mmol) in CH$_2$Cl$_2$ (230 mL) was added activated MnO$_2$ (58% min Mn) (2.53 g, 29.1 mmol) and KMnO$_4$ (850 mg, 5.38 mmol) at room temperature and stirred for 48 h. Reaction was monitored by TLC (~30% of unreacted starting material present after 48 h). The reaction mixture was filtered through a Celite pad and washed with Scheme 21

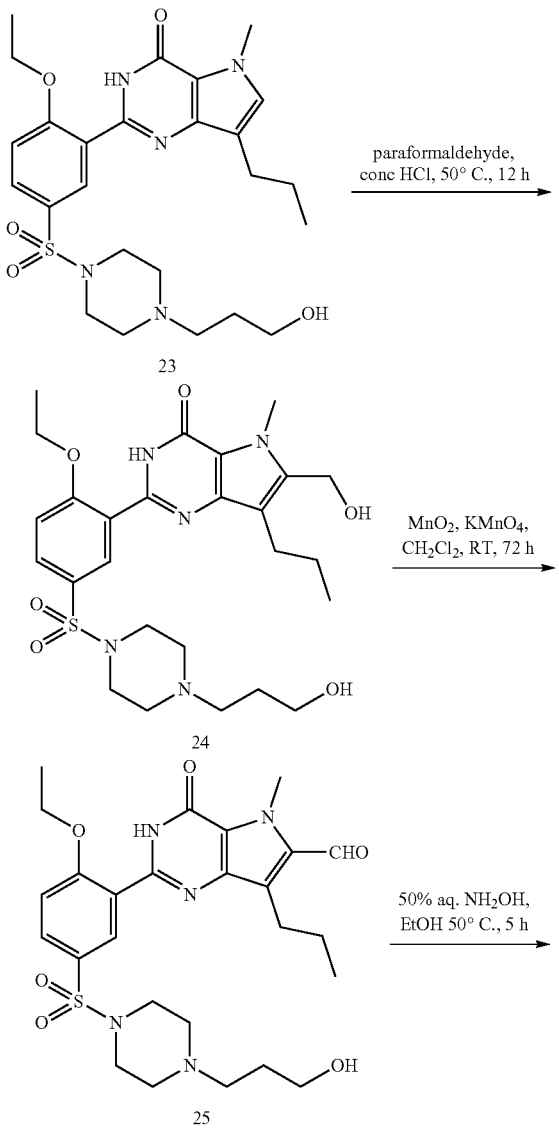

CH₂Cl₂ (50 mL). An additional quantity of activated MnO₂ (1.82 g, 21.0 mmol) was added to the filtrate in a RB flask and stirred at room temperature for 24 h. After complete consumption of starting material, the reaction mixture was filtered through a Celite pad and washed with CH₂Cl₂ (250 mL). The filtrate was concentrated to afford the title compound 25 (750 mg, ~86% pure) as a pale yellow solid, which was directly taken for next reaction without further purification. ¹H NMR (300 MHz, DMSO-d₆) δ ppm 12.15 (br s, 1H), 10.15 (s, 1H), 7.86-7.78 (m, 2H), 7.39 (d, J=8.8 Hz, 1H), 4.39-4.34 (m, 3H+OH), 4.22 (q, J=6.8 Hz, 2H), 3.38-3.34 (m, 2H), 2.99-2.84 (m, 6H), 2.41-2.38 (m, 4H), 2.31-2.29 (m, 2H), 1.71-1.62 (m, 2H), 1.49-1.42 (m, 2H), 1.34 (t, J=6.8 Hz, 3H), 0.91 (t, J=7.3 Hz, 3H); LCMS (ESI): m/z 546.5 [M+H]⁺; purity~86.0%.

Example 40

(E)-2-(2-ethoxy-5-((4-(3-hydroxypropyl)piperazin-1-yl)sulfonyl)phenyl)-5-methyl-4-oxo-7-propyl-4,5-dihydro-3H-pyrrolo[3,2-d]pyrimidine-6-carbaldehyde oxime (26)

To a stirred solution of 2-(2-ethoxy-5-((4-(3-hydroxypropyl)piperazin-1-yl)sulfonyl)phenyl)-5-methyl-4-oxo-7-propyl-4,5-dihydro-3H-pyrrolo[3,2-d]pyrimidine-6-carbaldehyde 25 (150 mg) in ethanol (18 mL) was added 50% hydroxylamine in aqueous solution (3 mL) at room temperature. Reaction was heated to 50° C. for 5 h under argon atmosphere. After completion of reaction (monitored by TLC), the reaction was concentrated under reduced pressure. The resultant residue was diluted in water (10 mL), and extracted with ethyl acetate (5×25 mL). The combined organic layers were washed with brine (20 mL), dried over anhydrous Na₂SO₄ and concentrated under reduced pressure. The obtained crude product was purified by reverse phase column chromatography (C-18 column; Grace System) by eluting with 35% acetonitrile with water. The pure fractions were lyophilized to afford the title compound 26 (52.7 mg) as an off-white solid. ¹H NMR (400 MHz, DMSO-d₆) δ ppm 11.82 (br s, 1H; D₂O exchangeable), 11.60 (s, 1H), 8.34 (s, 1H), 7.88 (d, J=2.2 Hz, 1H), 7.81 (dd, J=8.8, 2.2 Hz, 1H), 7.37 (d, J=8.8 Hz, 1H), 4.33 (t, J=5.1 Hz, 1H; D₂O exchangeable), 4.22 (q, J=6.8 Hz, 2H), 4.17 (s, 3H), 3.37-3.35 (m, 2H), 2.91-2.88 (m, 4H), 2.76-2.73 (m, 2H), 2.43-2.40 (m, 4H), 2.32-2.28 (m, 2H), 1.61-1.57 (m, 2H), 1.51-1.47 (m, 2H), 1.35 (t, J=6.8 Hz, 3H), 0.88 (t, J=7.3 Hz, 3H); LCMS (ESI): m/z 559.4 [M−H]⁻; purity~95.8%.

Scheme 22

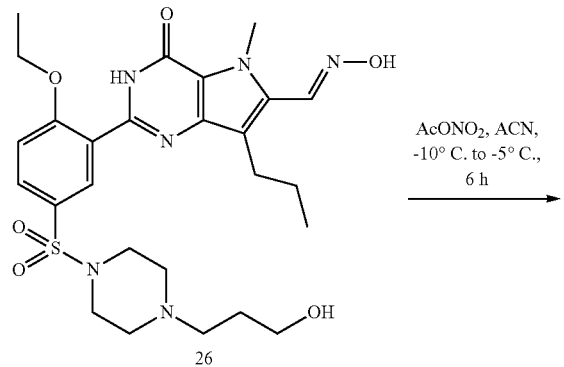

AcONO₂, ACN,
−10° C. to −5° C.,
6 h

26

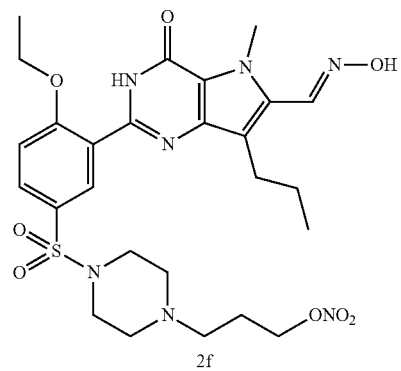

2f

Example 41

(E)-3-(4-((4-ethoxy-3-(6-((hydroxyimino)methyl)-5-methyl-4-oxo-7-propyl-4,5-dihydro-3H-pyrrolo[3,2-d]pyrimidin-2-yl)phenyl)sulfonyl)piperazin-1-yl) propyl nitrate (2f)

In analogy to 2a (Example 29) and 2b (Example 37), to a stirred solution of (E)-2-(2-ethoxy-5-((4-(3-hydroxypropyl)piperazin-1-yl)sulfonyl)phenyl)-5-methyl-4-oxo-7-propyl-4,5-dihydro-3H-pyrrolo[3,2-d]pyrimidine-6-carbaldehyde oxime 26 (150 mg, 0.29 mmol) in acetonitrile (6.0 mL) is added a solution of freshly prepared acetyl nitrate (0.13 mL; 1.5 mmol) [(acetyl nitrate is prepared separately by addition of fuming HNO₃ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 10 min under argon atmosphere. The reaction is stirred at −10° C. to −5° C. for 4 h. Reaction is monitored by TLC. After 4 h, the reaction is cooled to −15° C. and added acetyl nitrate (0.05 mL; 0.6 mmol). The reaction is stirred at −10° C. to −5° C. for additional 2 h. After completion of reaction (monitored by TLC), the reaction is quenched with saturated NaHCO₃ solution (10 mL) at 0° C. and extracted with EtOAc (3×20 mL). The combined organic layer is washed with brine (20 mL), dried over anhydrous Na₂SO₄ and concentrated under reduced pressure. The obtained crude product is purified reverse phase column chromatography (C-18 column, Grace System) by eluting with 45% gradient acetonitrile with water. The obtained solid is triturated with diethyl ether (3 mL) to afford the title compound 2f Scheme 23

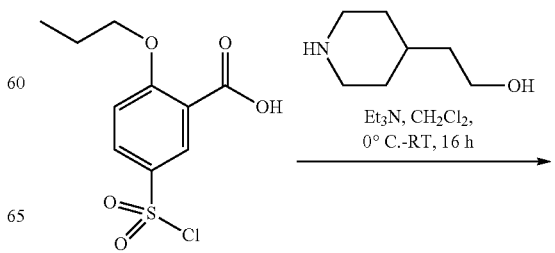

Et₃N, CH₂Cl₂,
0° C.-RT, 16 h

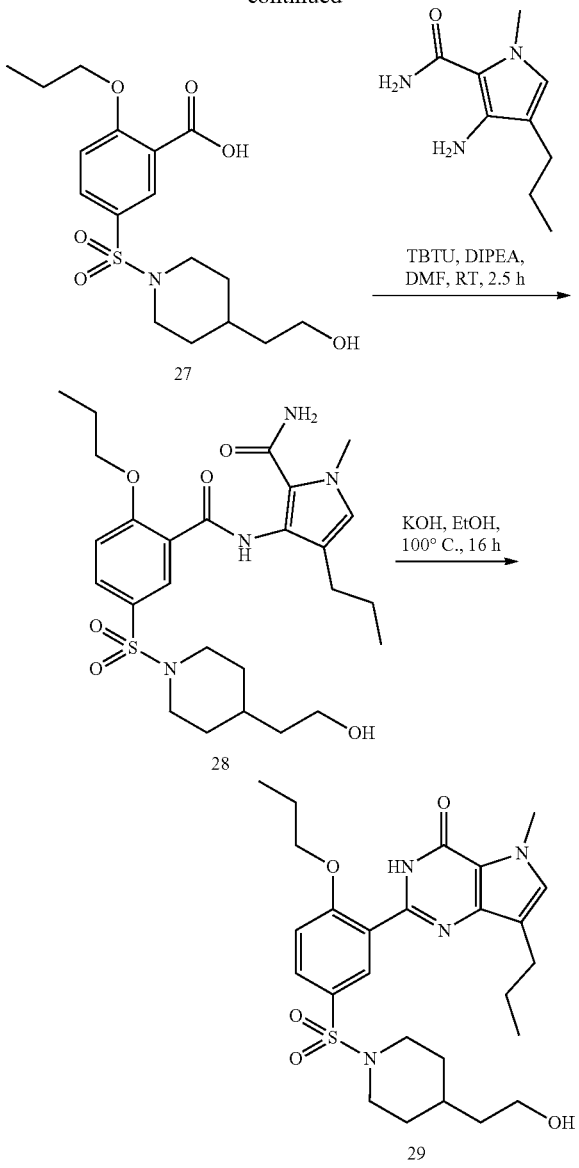

Example 42

5-((4-(2-hydroxyethyl)piperidin-1-yl)sulfonyl)-2-propoxybenzoic acid (27)

To a stirred solution of 2-(piperidin-4-yl)ethan-1-ol (231 mg, 1.79 mmol) in CH$_2$Cl$_2$ (3 mL) was added triethylamine (1.26 mL, 8.96 mmol) at 0° C. under inert atmosphere. To this, a solution of 5-(chlorosulfonyl)-2-propoxybenzoic acid (500 mg, 1.79 mmol) in CH$_2$Cl$_2$ (3 mL) was added drop wise at 0° C. under inert atmosphere. The reaction mixture was allowed to stir at room temperature for 16 h. After completion of reaction (monitored by TLC & LCMS), the reaction mixture was diluted in CH$_2$Cl$_2$ (40 mL), washed with chilled water (10 mL), chilled 10% aqueous citric acid solution (2×10 mL), brine (10 mL), dried over anhydrous Na$_2$SO$_4$ and concentrated under reduced pressure to afford the title compound 27 (410 mg, ~57% yield) as a white solid. $^1$H NMR (300 MHz, DMSO-d$_6$) δ ppm 13.05 (br s, 1H), 7.90 (d, J=2.2 Hz, 1H), 7.81 (dd, J=8.8, 2.2 Hz, 1H), 7.33 (d, J=8.8 Hz, 1H), 4.30 (br t, J=4.9 Hz, 1H), 4.10 (t, J=6.21 Hz, 2H), 3.60-3.56 (m, 2H), 3.41-3.34 (m, 2H), 2.19-2.15 (m, 2H), 1.82-1.64 (m, 4 H), 1.25-1.20 (m, 3H), 1.16-1.08 (m, 2H), 1.00 (t, J=7.3 Hz, 3H); LCMS (ESI): m/z 372.4 [M+H$^+$]; purity~92%.

Example 43

3-(5-((4-(2-hydroxyethyl)piperidin-1-yl)sulfonyl)-2-propoxybenzamido)-1-methyl-4-propyl-1H-pyrrole-2-carboxamide (28)

To a stirred solution of 5-((4-(2-hydroxyethyl)piperidin-1-yl)sulfonyl)-2-propoxybenzoic acid 27 (400 mg, 1.07 mmol) in DMF (3 mL), were added diisopropylethylamine (418 mg, 3.23 mmol) and TBTU (692 mg, 2.15 mmol) at ~15° C. and stirred for 20 min. To this, a solution of 3-amino-1-methyl-4-propyl-1H-pyrrole-2-carboxamide (196 mg, 1.07 mmol) in DMF (1 mL) was added under inert atmosphere. The reaction was allowed to stir at room temperature for 2.5 h. After completion of reaction (monitored by TLC & LCMS), the reaction was quenched with chilled water (50 mL) and extracted with EtOAc (2×50 mL). The combined organic layer was washed with brine (50 mL), dried over anhydrous Na$_2$SO$_4$ and concentrated under reduced pressure. The obtained crude product was purified by silica gel column chromatography (Grace System) by eluting with 2-8% gradient 30% MeOH in CH$_2$Cl$_2$:CH$_2$Cl$_2$ to afford the title compound 28 (210 mg; ~34% yield) as an off-white solid. $^1$H NMR (300 MHz, DMSO-d$_6$) δ ppm 9.52 (br s, 1H), 7.84-7.77 (m, 2H), 7.40 (d, J=8.8 Hz, 1H), 7.22 (br s, 1H), 6.91 (br s, 1H), 6.72 (s, 1H), 4.32 (t, J=5.1 Hz, 1H), 4.18 (t, J=6.6 Hz, 2H), 3.74 (s, 3H), 3.62-3.58 (m, 2H), 3.41-3.36 (m, 2H), 2.33-2.28 (m, 2H), 2.24-2.18 (m, 2H), 1.87-1.77 (m, 2H), 1.73-1.69 (m, 2H), 1.55-1.43 (m, 2H), 1.28-1.19 (m, 3H), 1.19-1.12 (m, 2H), 0.98 (t, J=7.3 Hz, 3H), 0.88 (t, J=7.3 Hz, 3H); LCMS (ESI): m/z 535.1 [M+H$^+$]; purity~94.7%.

Example 44

2-(5-((4-(2-hydroxyethyl)piperidin-1-yl)sulfonyl)-2-propoxyphenyl)-5-methyl-7-propyl-3,5-dihydro-4H-pyrrolo[3,2-d]pyrimidin-4-one (29)

A seal tube was charged with 3-(5-((4-(2-hydroxyethyl)piperidin-1-yl)sulfonyl)-2-propoxybenzamido)-1-methyl-4-propyl-1H-pyrrole-2-carboxamide 28 (200 mg, 0.37 mmol), ethanol (3.2 mL), followed by 1M aqueous KOH solution (2.8 mL) at room temperature. The tube was capped and stirred the reaction mixture at 100° C. for 16 h. After completion of reaction (monitored by TLC & LCMS), the reaction was cooled to room temperature and concentrated under reduced pressure. The resultant residue was diluted in water (20 mL) and extracted with dichloromethane (3×50 mL). The combined organic layer was washed with brine (50 mL), dried over anhydrous Na$_2$SO$_4$ and concentrated under reduced pressure. The obtained crude product was purified by silica gel column chromatography (Grace System) by eluting with 2-8% gradient 30% methanol in CH$_2$Cl$_2$:CH$_2$Cl$_2$. The pure fractions were concentrated to afford the title compound 29 (130 mg, 67% yield) as a white solid. $^1$H NMR (400 MHz, DMSO-d$_6$) δ ppm 11.63 (br s, 1H; D$_2$O exchangeable), 7.90 (d, J=2.2 Hz, 1H), 7.79 (dd, J=8.8, 2.2 Hz, 1H), 7.35 (d, J=8.8 Hz, 1H), 7.21 (s, 1H), 4.31 (t, J=5.1 Hz, 1H; D$_2$O exchangeable), 4.12 (t, J=6.4 Hz, 2H), 3.98 (s, 3H), 3.62-3.59 (m, 2H), 3.42-3.36 (m, 2H), 2.60-2.56 (m, 2H), 2.24-2.19 (m, 2H), 1.81-1.59 (m, 6H), 1.33-1.31 (m, 3H), 1.20-1.15 (m, 2H), 1.00-0.92 (m, 6H); LCMS (ESI): m/z 517.6 [M+H$^+$]; purity~98.1%.

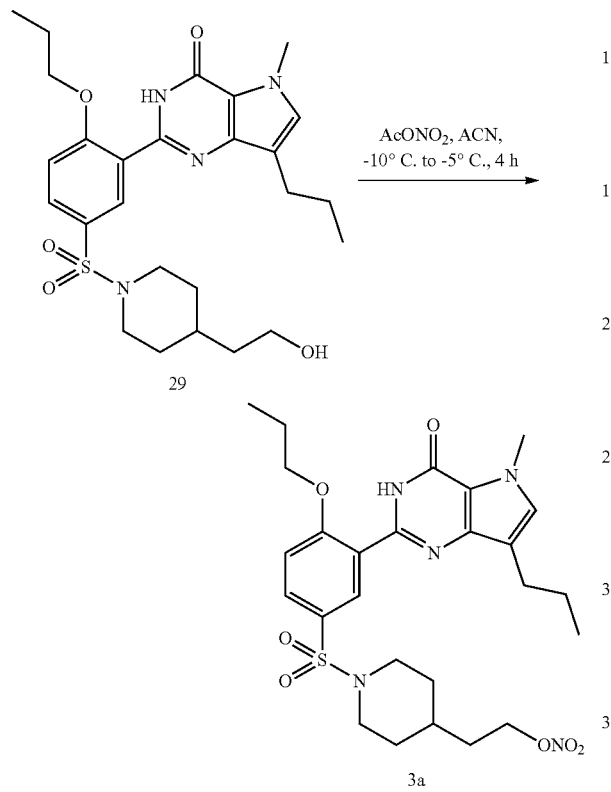

Example 45

2-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (3a)

To a 2-(5-((4-(2-hydroxyethyl)piperidin-1-yl)sulfonyl)-2-propoxyphenyl)-5-methyl-7-propyl-3,5-dihydro-4H-pyrrolo[3,2-d]pyrimidin-4-one 29 (150 mg, 0.29 mmol) in acetonitrile (4.5 mL) was added a solution of freshly prepared acetyl nitrate (0.12 mL; 1.45 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 10 min under argon atmosphere. The reaction was stirred at −10° C. to −5° C. for 4 h. After completion of reaction (monitored by TLC), the reaction was quenched with saturated NaHCO$_3$ solution (10 mL) at 0° C. and extracted with EtOAc (3×20 mL). The combined organic layer was washed with brine (10 mL), dried over anhydrous Na$_2$SO$_4$ and concentrated under reduced pressure. The obtained crude product was purified reverse phase column chromatography (C-18 column, Grace System) by eluting with 60-70% gradient acetonitrile with water. The pure fractions were lyophilized to afford the title compound 3a (33 mg; ~20% yield) as a white solid. 1H NMR (400 MHz, DMSO-d$_6$) δ ppm 11.60 (br s, 1H; D$_2$O exchangeable), 7.92 (d, J=2.4 Hz, 1H), 7.80 (dd, J=8.8, 2.4 Hz, 1H), 7.36 (d, J=8.8 Hz, 1H), 7.21 (s, 1H), 4.51 (t, J=6.6 Hz, 2H), 4.12 (t, J=6.4 Hz, 2H), 3.98 (s, 3H), 3.63-3.61 (m, 2H), 2.59-2.56 (m, 2H), 2.28-2.23 (m, 2H), 1.79-1.71 (m, 4H), 1.67-1.58 (m, 4H), 1.35-1.31 (m, 1H), 1.26-1.18 (m, 2H), 0.97 (t, J=7.3 Hz, 3H), 0.92 (t, J=7.3 Hz, 3H); LCMS (ESI): m/z 562.1 [M+H$^+$]; purity~97%.

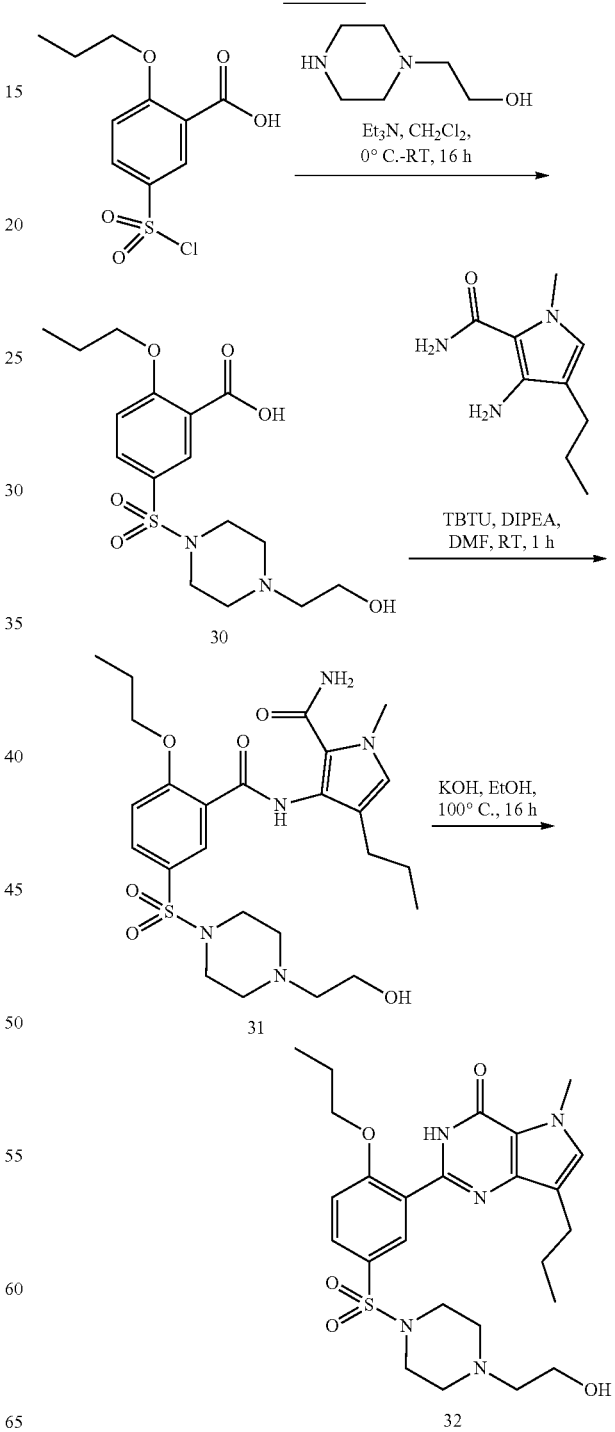

Example 46

5-((4-(2-hydroxyethyl)piperazin-1-yl)sulfonyl)-2-propoxybenzoic acid (30)

To a stirred solution of 2-(piperazin-1-yl)ethan-1-ol (233 mg, 1.79 mmol) in $CH_2Cl_2$ (3 mL) was added triethylamine (1.24 mL, 8.97 mmol) at 0° C. under inert atmosphere. To this, a solution of 5-(chlorosulfonyl)-2-propoxybenzoic acid (500 mg, 1.79 mmol) in $CH_2Cl_2$ (3 mL) was added drop wise at 0° C. under inert atmosphere. The reaction mixture was allowed to stir at room temperature for 16 h. After completion of reaction (monitored by LCMS), the reaction mixture was purified by reverse phase column chromatography (C-18 column; Grace System) by eluting with 30-40% gradient acetonitrile with water. The product fractions were concentrated under reduced pressure. The obtained sticky solid was triturated with $CH_2Cl_2$ (0.5 mL) and hexane (6 mL) to afford the title compound 30 (510 mg) as a white solid, which was directly taken for next reaction without further purification. LCMS (ESI): m/z 373.5 [M+H$^+$]; purity~85%.

Example 47

3-(5-((4-(2-hydroxyethyl)piperazin-1-yl)sulfonyl)-2-propoxybenzamido)-1-methyl-4-propyl-1H-pyrrole-2-carboxamide (31)

To a stirred solution of 5-((4-(2-hydroxyethyl)piperidin-1-yl)sulfonyl)-2-propoxybenzoic acid 30 (500 mg) in DMF (3 mL), were added diisopropyl ethylamine (0.7 mL, 4.03 mmol) and TBTU (862 mg, 2.68 mmol) at ~15° C. and stirred for 30 min. To this, a solution of 3-amino-1-methyl-4-propyl-1H-pyrrole-2-carboxamide (243.6 mg, 1.34 mmol) in DMF (2 mL) was added drop wise at ~15° C. under inert atmosphere. The reaction was allowed to stir at room temperature for 1 h. After completion of reaction (monitored by TLC and LCMS), reaction was quenched with chilled water (50 mL) and extracted with EtOAc (2×50 mL). The combined organic layer was washed with brine (50 mL), dried over anhydrous $Na_2SO_4$ and concentrated under reduced pressure. The obtained crude product was purified by silica gel column chromatography (Grace System) by eluting with 10-15% gradient 30% methanol in $CH_2Cl_2$: $CH_2Cl_2$. The product fractions were concentrated under reduced pressure to afford the title compound 31 (260 mg; ~27% overall yield in two steps) as a pale yellow solid. $^1$H NMR (300 MHz, DMSO-d$_6$) δ ppm 9.54 (br s, 1H), 7.82-7.79 (m, 2H), 7.41 (d, J=8.4 Hz, 1H), 7.24 (br s, 1H), 6.92 (br s, 1H), 6.72 (s, 1H), 4.37 (br t, J=5.3 Hz, 1H), 4.19 (t, J=6.6 Hz, 2H), 3.74 (s, 3H), 3.42-3.39 (m, 2H), 2.83-2.78 (m, 4H), 2.53-2.49 (m, 4H), 2.38-2.35 (m, 2H), 2.28-2.25 (m, 2H), 1.83-1.79 (m, 2H), 1.52-1.44 (m, 2H), 0.98 (t, J=7.3 Hz, 3H), 0.88 (t, J=7.3 Hz, 3H); LCMS (ESI): m/z 536.2 [M+H$^+$]; purity~90%.

Example 48

2-(5-((4-(2-hydroxyethyl)piperazin-1-yl)sulfonyl)-2-propoxyphenyl)-5-methyl-7-propyl-3,5-dihydro-4H-pyrrolo[3,2-d]pyrimidin-4-one (32)

A seal tube was charged with 3-(5-((4-(2-hydroxyethyl)piperazin-1-yl)sulfonyl)-2-propoxybenzamido)-1-methyl-4-propyl-1H-pyrrole-2-carboxamide 31 (260 mg, 0.48 mmol), ethanol (4.2 mL), followed by 1M aqueous KOH solution (3.6 mL) at room temperature. The tube was capped and stirred the reaction mixture at 100° C. for 16 h. After completion of reaction (monitored by TLC & LCMS), the reaction was cooled to room temperature and concentrated under reduced pressure. The resultant residue was diluted in water (20 mL) and extracted with ethyl acetate (3×20 mL). The combined organic layer was washed with brine (50 mL), dried over anhydrous $Na_2SO_4$ and concentrated under reduced pressure. The obtained crude product was purified by reverse phase column chromatography (C-18 column; Grace System) by eluting with 60-70% gradient acetonitrile with water. The pure fractions were lyophilized to afford the title compound 32 (130 mg, 51% yield) as a white solid. $^1$H NMR (400 MHz, DMSO-d$_6$) δ ppm 11.64 (br s, 1H; D$_2$O exchangeable), 7.88 (d, J=2.0 Hz, 1H), 7.79 (dd, J=8.8, 2.0 Hz, 1H), 7.37 (d, J=8.8 Hz, 1H), 7.21 (s, 1H), 4.33 (t, J=5.4 Hz, 1H; D$_2$O exchangeable), 4.12 (t, J=6.4 Hz, 2H), 3.98 (s, 3H), 3.43-3.41 (m, 2H), 2.89-2.87 (m, 4H), 2.58-2.55 (m, 2H), 2.51-2.48 (m, 4H), 2.37-2.35 (m, 2H), 1.78-1.71 (m, 2H), 1.67-1.59 (m, 2H), 0.96 (t, J=7.3 Hz, 3H), 0.92 (t, J=7.3 Hz, 3H); LCMS (ESI): m/z 518.2 [M+H$^+$]; purity~99.4%.

Scheme 26

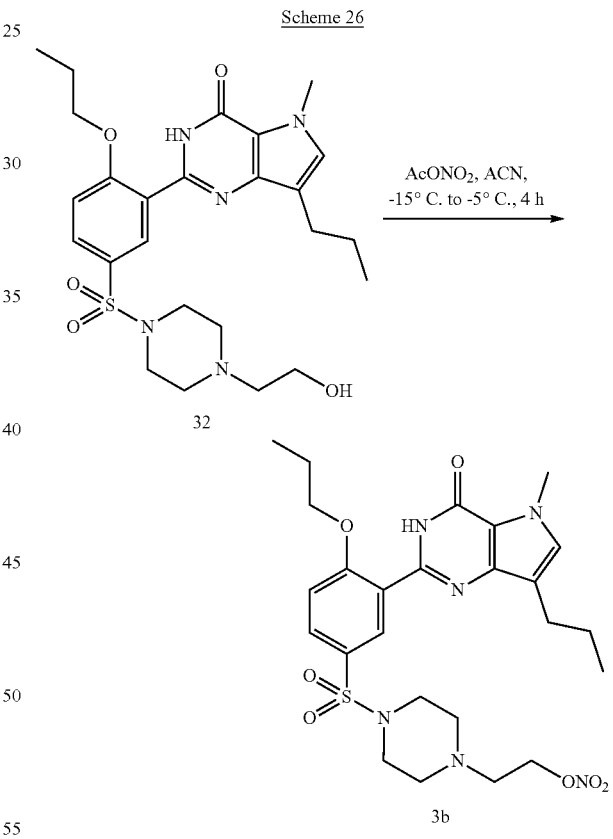

Example 49

2-(4-((3-(5-methyl-4-oxo-7-propyl-4,5-dihydro-3H-pyrrolo[3,2-d]pyrimidin-2-yl)-4-propoxyphenyl)sulfonyl)piperazin-1-yl)ethyl nitrate (3b)

To a stirred solution of 2-(5-((4-(2-hydroxyethyl)piperazin-1-yl)sulfonyl)-2-propoxyphenyl)-5-methyl-7-propyl-3,5-dihydro-4H-pyrrolo[3,2-d]pyrimidin-4-one 32 (100 mg, 0.19 mmol) in acetonitrile (3 mL) was added a solution of freshly prepared acetyl nitrate (0.13 mL) [(acetyl nitrate was prepared separately by addition of fuming $HNO_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −15° C. for 15 min under argon atmosphere. The reaction was stirred at −15° C. to −5° C. for 4 h. After completion of reaction (monitored by TLC), the reaction was quenched with saturated $NaHCO_3$ solution (10 mL) at 0° C. and extracted with EtOAc (3×20 mL). The combined organic layer was washed with brine (20 mL), dried over anhydrous $Na_2SO_4$ and concentrated under reduced pressure. The obtained crude product was purified reverse phase column chromatography (C-18 column, Grace System) by eluting with 60-70% gradient acetonitrile with water. The pure fractions were lyophilized to afford the title compound 3b (40 mg; ~36% yield) as a white solid. 1H NMR (400 MHz, DMSO-$d_6$) δ ppm 11.62 (s, 1H; $D_2O$ exchangeable), 7.88 (d, J=2.4 Hz, 1H), 7.80 (dd, J=8.8, 2.4 Hz, 1H), 7.37 (d, J=8.8 Hz, 1H), 7.21 (s, 1H), 4.56 (t, J=5.1 Hz, 2H), 4.13 (t, J=6.4 Hz, 2H), 3.98 (s, 3H), 2.90-2.87 (m, 4H), 2.66 (t, J=5.1 Hz, 2H), 2.59-2.55 (m, 2H), 2.53-2.50 (m, 4H), 1.78-1.71 (m, 2H), 1.66-1.59 (m, 2H), 0.96 (t, J=7.3 Hz, 3H), 0.92 (t, J=7.3 Hz, 3H); LCMS (ESI): m/z 563.1 [M+H$^+$]; purity~96.5%.

Scheme 27

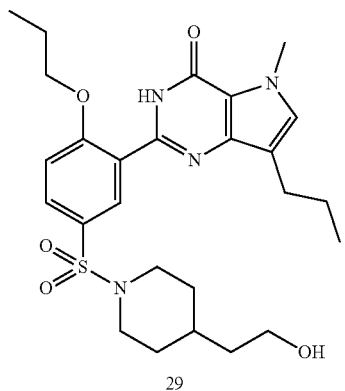

29

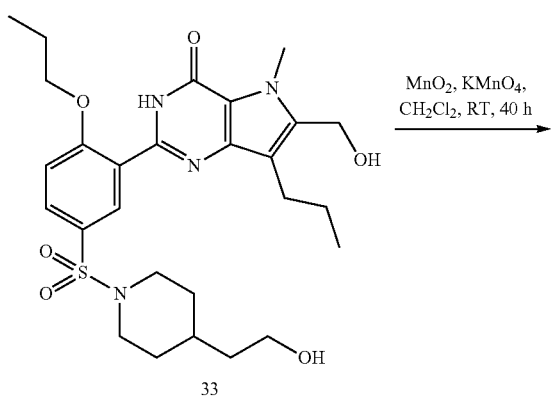

33

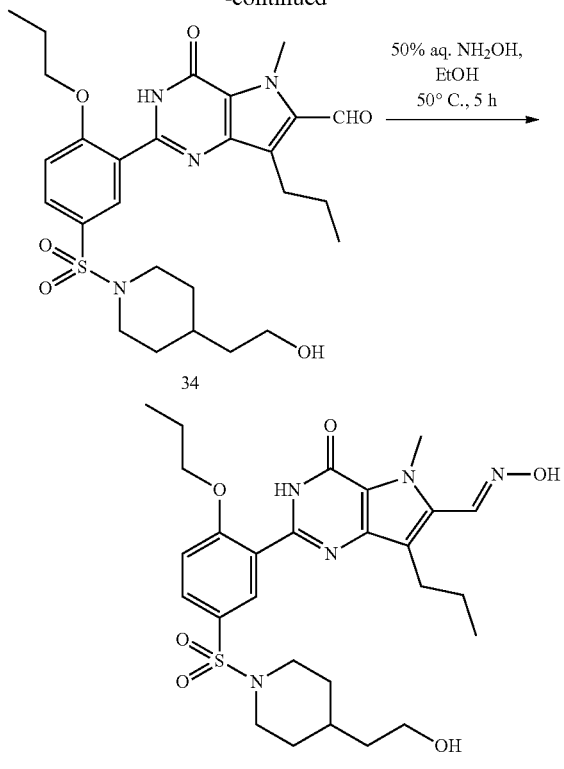

34

35

Example 50

2-(5-((4-(2-hydroxyethyl)piperidin-1-yl)sulfonyl)-2-propoxyphenyl)-6-(hydroxymethyl)-5-methyl-7-propyl-3,5-dihydro-4H-pyrrolo[3,2-d]pyrimidin-4-one (33)

To a stirred solution of 2-(5-((4-(2-hydroxyethyl)piperidin-1-yl)sulfonyl)-2-propoxyphenyl)-5-methyl-7-propyl-3,5-dihydro-4H-pyrrolo[3,2-d]pyrimidin-4-one 29 (430 mg, 0.83 mmol) in concentrated HCl solution (4.3 mL), was added paraformaldehyde (215 mg, 0.5 w/w) at room temperature and heated to 50° C. for 15 h. Reaction was monitored by LCMS analysis. The reaction mixture was cooled to room temperature and neutralized with saturated $NaHCO_3$ solution (100 mL). The resultant solution was extracted with 10% methanol in dichloromethane (3×100 mL). The combined the organic extracts were dried over anhydrous $Na_2SO_4$ and concentrated under reduced pressure. The obtained crude product was purified by reverse phase column chromatography (C-18 column; Grace System) by eluting with 60-70% gradient acetonitrile with water to afford the titled compound 33 (270 mg; ~56% yield) as a white solid. 1H NMR (300 MHz, DMSO-$d_6$) δ ppm 10.42 (br s, 1H), 7.87 (d, J=2.2 Hz, 1H), 7.80 (dd, J=8.8, 2.2 Hz, 1H), 7.37 (d, J=8.8 Hz, 1H), 5.16 (br s, 1H), 4.56 (s, 2H), 4.35 (br s, 1H), 4.13-4.10 (m, 2H), 4.05 (s, 3H), 3.43-3.39 (m, 2H), 2.91-2.86 (m, 4H), 2.61-2.57 (m, 2H), 2.47-2.43 (m, 4H), 2.37-2.33 (m, 2H), 1.79-1.69 (m, 2H), 1.62-1.52 (m, 2H), 0.97 (t, J=7.3 Hz, 3H), 0.88 (t, J=7.3 Hz, 3H); LCMS (ESI): m/z 548.6 [M+H$^+$]; purity~95.3%.

Example 51

2-(5-((4-(2-hydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde (34)

To a stirred solution of 2-(5-((4-(2-hydroxyethyl)piperidin-1-yl)sulfonyl)-2-propoxyphenyl)-6-(hydroxymethyl)-5-methyl-7-propyl-3,5-dihydro-4H-pyrrolo[3,2-d]pyrimidin-4-one 33 (260 mg, 0.47 mmol) in CH$_2$Cl$_2$ (78 mL) was added activated MnO$_2$ (58% min Mn) (704 mg, 8.10 mmol) and KMnO$_4$ (240 mg, 1.52 mmol) at room temperature and stirred for 40 h.

Reaction was monitored by TLC. The reaction mixture was then filtered through a Celite pad and washed with CH$_2$Cl$_2$ (100 mL). The filtrate was concentrated and the obtained crude product was purified by silica gel column chromatography (Grace System) by eluting with 2-5% gradient methanol in dichloromethane to afford the title compound 34 (190 mg) as a white solid, which was directly taken for next reaction without further purification. $^1$H NMR (300 MHz, DMSO-d$_6$) δ ppm 12.13 (br s, 1H), 10.14 (s, 1H), 7.90-7.77 (m, 2H), 7.39 (d, J=8.4 Hz, 1H), 4.38 (t, J=5.3 Hz, 1H), 4.32 (s, 3H), 4.12 (t, J=6.2 Hz, 2H), 3.44-3.40 (m, 2H), 3.01-2.78 (m, 6H), 2.48-2.45 (m, 4H), 2.38-2.35 (m, 2H), 1.78-1.61 (m, 4H), 0.97-0.84 (m, 6H); LCMS (ESI): m/z 546.3 [M+H$^+$]; purity~98.9%.

Example 52

(E)-2-(5-((4-(2-hydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde oxime (35)

To a stirred solution of 2-(5-((4-(2-hydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde 34 (190 mg, 0.34 mmol) in ethanol (22.8 mL) was added 50% hydroxylamine in aqueous solution (3.8 mL) at room temperature. Reaction was heated to 50° C. for 5 h under argon atmosphere. After completion of reaction (monitored by TLC), the reaction was concentrated under reduced pressure. The resultant residue was diluted in water (10 mL) and extracted with ethyl acetate (3×25 mL). The combined organic layer was washed with brine (25 mL), dried over anhydrous Na$_2$SO$_4$ and concentrated under reduced pressure. The obtained crude product was purified by reverse phase column chromatography (C-18 column; Grace System) by eluting with 40-50% gradient acetonitrile with water. The pure fractions were lyophilized to afford the title compound 35 (60 mg; ~22% yield in two steps) as a white solid. $^1$H NMR (400 MHz, DMSO-d$_6$) δ ppm 11.77 (br s, 1H; D$_2$O exchangeable), 11.58 (br s, 1H; D$_2$O exchangeable), 8.33 (s, 1H), 7.88 (d, J=2.0 Hz, 1H), 7.80 (dd, J=8.8, 2.0 Hz, 1H), 7.37 (d, J=8.8 Hz, 1H), 4.34 (d, J=5.1 Hz, 1H; D$_2$O exchangeable), 4.17 (s, 3H), 4.13-4.04 (m, 2H), 3.44-3.39 (m, 2H), 2.91-2.87 (m, 4H), 2.76-2.72 (m, 2H), 2.51-2.47 (m, 4H), 2.38-2.35 (m, 2H), 1.78-1.70 (m, 2H), 1.63-1.54 (m, 2H), 0.96 (t, J=7.3 Hz, 3H), 0.88 (t, J=7.3 Hz, 3H); LCMS (ESI): m/z 561.6 [M+H$^+$]; purity~95.3%.

Scheme 28

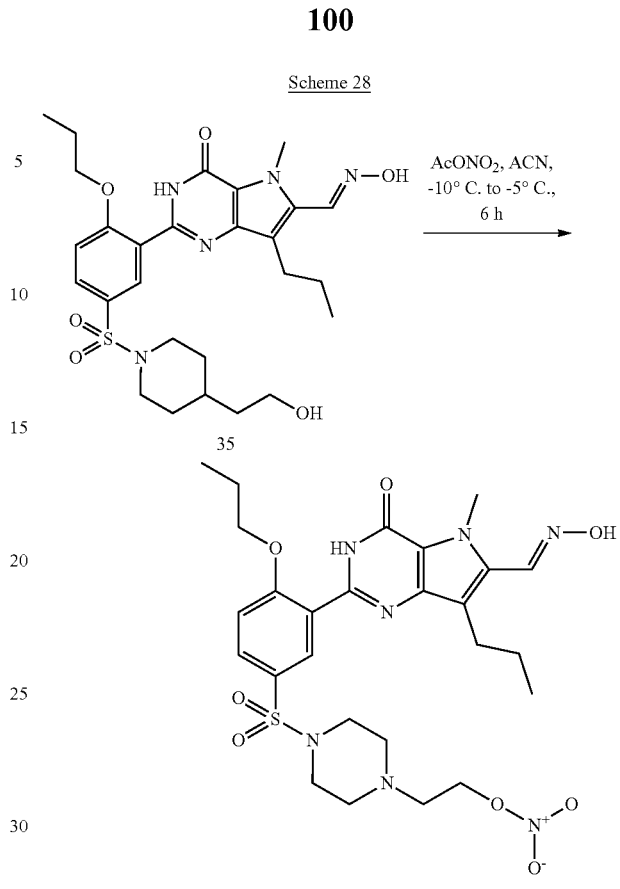

Example 53

(E)-2-(1-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (3c)

In analogy to 2a (Example 29) and 2b (Example 37), to a stirred solution of (E)-2-(5-((4-(2-hydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde oxime 35 (150 mg, 0.29 mmol) in acetonitrile (6.0 mL) is added a solution of freshly prepared acetyl nitrate (0.13 mL; 1.5 mmol) [(acetyl nitrate is prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 10 min under argon atmosphere. The reaction is stirred at −10° C. to −5° C. for 4 h. Reaction is monitored by TLC. After 4 h, the reaction is cooled to −15° C. and added acetyl nitrate (0.05 mL; 0.6 mmol). The reaction is stirred at −10° C. to −5° C. for additional 2 h. After completion of reaction (monitored by TLC), the reaction is quenched with saturated NaHCO$_3$ solution (10 mL) at 0° C. and extracted with EtOAc (3×20 mL). The combined organic layer is washed with brine (20 mL), dried over anhydrous Na$_2$SO$_4$ and concentrated under reduced pressure. The obtained crude product is purified reverse phase column chromatography (C-18 column, Grace System) by eluting with 45% gradient acetonitrile with water. The obtained solid is triturated with diethyl ether (3 mL) to afford the title compound 3c. $^1$H NMR (400 MHz, DMSO-$d_6$) δ ppm 11.81 (s, 1H; $D_2O$ exchangeable), 11.63 (s, 1H; $D_2O$ exchangeable), 8.34 (s, 1H), 7.87 (d, J=2.0 Hz, 1H), 7.81 (dd, J=8.8, 2.0 Hz, 1H), 7.38 (d, J=8.8 Hz, 1H), 4.57-4.55 (m, 2H), 4.17 (s, 3H), 4.12 (t, J=6.1 Hz, 2H), 2.91-2.88 (m, 4H), 2.76-2.73 (m, 2H), 2.67-2.64 (m, 2H), 2.54-2.51 (m, 4H), 1.78-1.69 (m, 2H), 1.62-1.53 (m, 2H), 0.96 (t, J=7.6 Hz, 3H), 0.87 (t, J=7.3 Hz, 3H); LCMS (ESI): m/z 606.5 [M+H$^+$]; purity~96.5%.

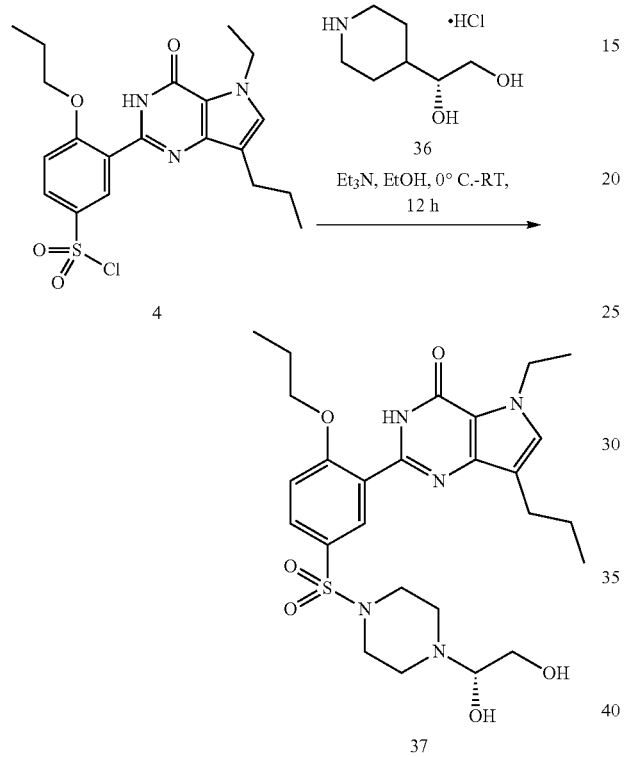

Example 54

(R)-2-(5-((4-(1,2-dihydroxyethyl)piperidin-1-yl)sulfonyl)-2-propoxyphenyl)-5-ethyl-7-propyl-3,5-dihydro-4H-pyrrolo[3,2-d]pyrimidin-4-one (37)

To a stirred solution of 3-(5-ethyl-4-oxo-7-propyl-4,5-dihydro-3H-pyrrolo[3,2-d]pyrimidin-2-yl)-4-propoxybenzenesulfonic acid (3) (500 mg, 1.13 mmol) in a solution of $CH_2Cl_2$ (30 mL) and DMF (0.5 mL), was added oxalyl chloride (0.5 mL, 5.67 mmol) at 0° C. drop wise under argon atmosphere for 15 min. After addition, the reaction mixture was stirred at same temperature for 6 h. After completion of reaction (monitored by TLC & LCMS), the reaction mixture was concentrated at below 20° C. under reduced pressure and the vacuum was back-filled with argon atmosphere. The obtained residue was co-distilled with $CH_2Cl_2$ (2×6 mL) to afford the crude product 4 as a pale yellow liquid.

To a stirred solution of above crude material 4 in ethanol (20 mL) was added triethylamine (2.4 mL, 17 mmol) drop wise at 0° C., followed by a solution of (R)-1-(piperidin-4-yl)ethane-1,2-diol·HCl salt (36 preparation WO2005026145 A1) (186 mg, 0.56 mmol) in ethanol (10 mL) at same temperature under inert atmosphere. The reaction was allowed to stir at room temperature for 12 h. After completion of reaction (monitored by LCMS), the reaction mixture was concentrated under reduced pressure to afford the residue, which was purified by reverse phase column chromatography (C-18 column; Grace System) by eluting with 50-55% gradient acetonitrile with water to afford the title compound 37 (37 mg) as an off-white solid. $^1$H NMR (400 MHz, DMSO-$d_6$) δ ppm 11.61 (br s, 1H; $D_2O$ exchangeable), 7.92 (d, J=2.4 Hz, 1H), 7.79 (dd, J=8.8, 2.4 Hz, 1H), 7.36 (d, J=9.3 Hz, 1H), 7.30 (s, 1H), 4.27-4.49 (m, 2H+(2-OH; $D_2O$ exchangeable)), 4.13 (t, J=6.1 Hz, 2H), 3.67-3.64 (m, 2H), 3.27-3.12 (m, 3H), 2.59-2.55 (m, 2H), 2.25-2.11 (m, 2H), 1.78-1.72 (m, 3H), 1.69-1.54 (m, 3H), 1.45-1.18 (m, 6H), 0.97 (t, J=7.3 Hz, 3H), 0.92 (t, J=7.3 Hz, 3H); LCMS (ESI): m/z 547.49 [M+H]$^+$; purity~98.5%.

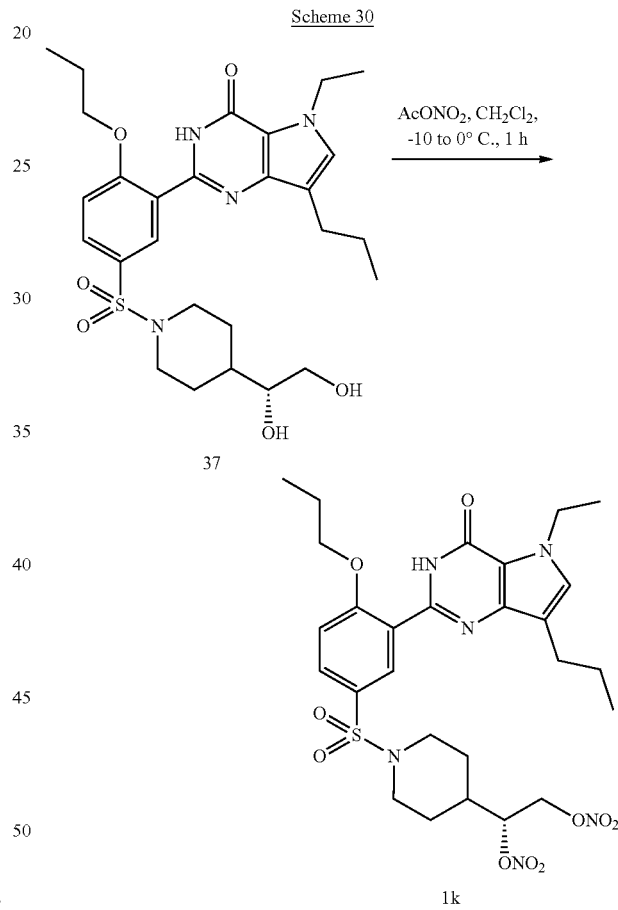

Example 55

(R)-1-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (1k)

To a stirred solution of (R)-2-(5-((4-(1,2-dihydroxyethyl)piperidin-1-yl)sulfonyl)-2-propoxyphenyl)-5-ethyl-7-propyl-3,5-dihydro-4H-pyrrolo[3,2-d]pyrimidin-4-one 37 (140 mg, 0.25 mmol) in $CH_2C_2$ (2.1 mL) was added a solution of freshly prepared acetyl nitrate (0.24 mL) [(acetyl nitrate was prepared separately by addition of fuming $HNO_3$ (0.04 mL;

6.0 eq) drop wise in to acetic anhydride (0.2 mL, 1:5 of HNO₃)) slowly at −10° C. under argon atmosphere (Note: temperature should not be raised above 0° C.))] drop wise at −10° C. under argon atmosphere. The reaction mixture was stirred at 0° C. for 1 h. After completion of reaction (monitored by TLC), the reaction mixture was quenched with saturated NaHCO₃ solution (15 mL) and extracted with CH₂Cl₂ (2×25 mL). The combined organic layer was washed with brine (25 mL) and dried over anhydrous Na₂SO₄ and concentrated under reduced pressure. The obtained crude product purified by preparative HPLC (XBridge C18 column; 35-100% gradient acetonitrile with water). The pure fractions were lyophilized to afford the title compound 1k (50 mg; 31% yield) as a white solid. ¹H NMR (400 MHz, DMSO-d₆) δ ppm 11.61 (s, 1H; D₂O exchangeable), 7.94 (d, J=2.4 Hz, 1H), 7.80 (dd, J=8.8, 2.4 Hz, 1H), 7.37 (d, J=8.8 Hz, 1H), 7.31 (s, 1H), 5.33-5.29 (m, 1H), 4.94 (dd, J=12.7, 2.4 Hz, 1H), 4.71 (dd, J=12.7, 6.1 Hz, 1H), 4.37 (q, J=7.3 Hz, 2H), 4.13 (t, J=6.4 Hz, 2H), 3.76-3.64 (m, 2H), 2.59-2.55 (m, 2H), 2.29-2.23 (m, 2H), 1.87-1.70 (m, 5H), 1.66-1.61 (m, 2H), 1.46-1.42 (m, 2H), 1.36 (t, J=7.1 Hz, 3H), 0.97 (t, J=7.3 Hz, 3H), 0.92 (t, J=7.3 Hz, 3H); LCMS (ESI): m/z 637.31 [M+H]⁺; purity~99.7%.

Scheme 31

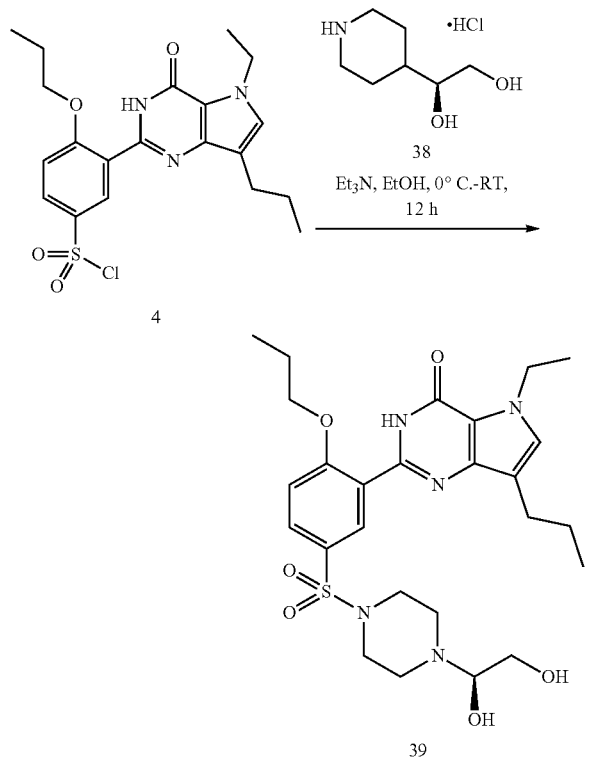

Example 56

(S)-2-(5-((4-(1,2-dihydroxyethyl)piperidin-1-yl)sulfonyl)-2-propoxyphenyl)-5-ethyl-7-propyl-3,5-dihydro-4H-pyrrolo[3,2-d]pyrimidin-4-one (39)

To a stirred solution of 3-(5-ethyl-4-oxo-7-propyl-4,5-dihydro-3H-pyrrolo[3,2-d]pyrimidin-2-yl)-4-propoxybenzenesulfonic acid 3 (250 mg, 0.56 mmol) in a solution of CH₂Cl₂ (15 mL) and DMF (0.25 mL), was added oxalyl chloride (0.29 mL, 3.39 mmol) at 0° C. drop wise under argon atmosphere for 15 min. After addition, the reaction mixture was stirred at same temperature for 6 h. After completion of reaction (monitored by LCMS), the reaction was concentrated at below 20° C. under reduced pressure and the vacuum was backfilled with argon atmosphere. The residue obtained was co-distilled with CH₂Cl₂ (2×5 mL) to afford the crude product 4 as a pale yellow liquid.

To a stirred solution of above crude material 4 in ethanol (5 mL) was added triethylamine (1.17 mL, 8.49 mmol) drop wise at 0° C., followed by a solution of (S)-1-(piperidin-4-yl)ethane-1,2-diol·HCl salt (38 preparation WO2005026145 A1) (154 mg, 0.84 mmol) in ethanol (10 mL) at same temperature under inert atmosphere. The reaction was allowed to stir at room temperature for 12 h. After completion of reaction (monitored by LCMS), the reaction mixture was concentrated under reduced pressure to afford the residue, which was purified by reverse phase column chromatography (C-18 column; Grace System) by eluting with 50% acetonitrile with water to afford the title compound 39 (36 mg) as a white solid. 1H NMR (400 MHz, DMSO-d₆) δ ppm 11.61 (br s, 1H; D₂O exchangeable), 7.92 (d, J=2.4 Hz, 1H), 7.79 (dd, J=8.8, 2.4 Hz, 1H), 7.36 (d, J=9.3 Hz, 1H), 7.30 (s, 1H), 4.27-4.49 (m, 2H+(2-OH; D₂O exchangeable)), 4.13 (t, J=6.1 Hz, 2H), 3.67-3.64 (m, 2H), 3.27-3.12 (m, 3H), 2.59-2.55 (m, 2H), 2.25-2.11 (m, 2H), 1.78-1.72 (m, 3H), 1.69-1.54 (m, 3H), 1.45-1.18 (m, 6H), 0.97 (t, J=7.3 Hz, 3H), 0.92 (t, J=7.3 Hz, 3H); LCMS(ESI): m/z 547.46 [M+H]⁺; purity~98.74%.

Scheme 32

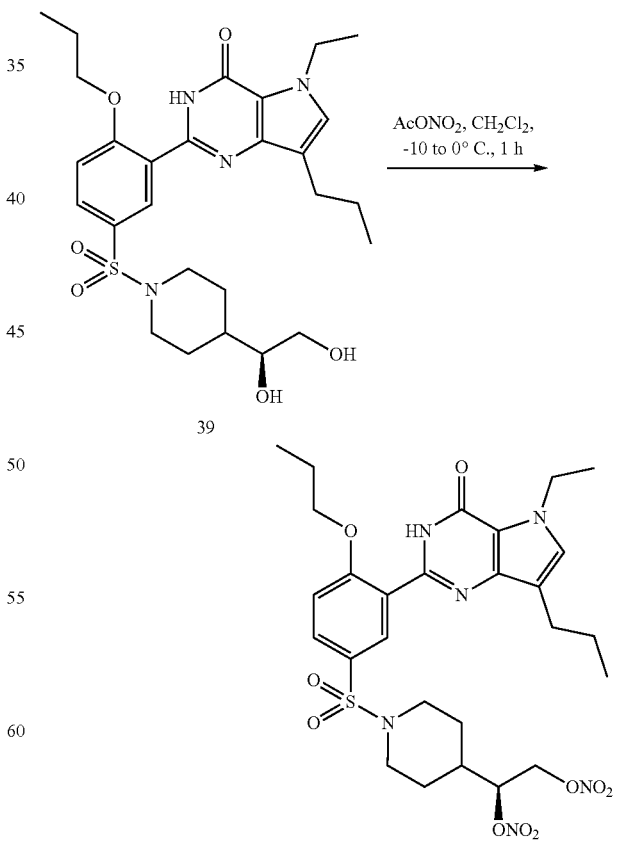

Example 57

(S)-1-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (11)

To a stirred solution of (S)-2-(5-((4-(1,2-dihydroxyethyl)piperidin-1-yl)sulfonyl)-2-propoxyphenyl)-5-ethyl-7-propyl-3,5-dihydro-4H-pyrrolo[3,2-d]pyrimidin-4-one 39 (140 mg, 0.25 mmol) in CH$_2$Cl$_2$ (2.1 mL) was added a solution of freshly prepared acetyl nitrate (0.24 mL) [(acetyl nitrate was prepared separately by addition of fuming HNO$_3$ (0.04 mL; 6.0 eq) drop wise in to acetic anhydride (0.2 mL, 1:5 of HNO$_3$)) slowly at −10° C. under argon atmosphere (Note: temperature should not be raised above 0° C.))] drop wise at −10° C. under argon atmosphere. The reaction mixture was stirred at 0° C. for 1 h. After completion of reaction (monitored by TLC), the reaction mixture was quenched with saturated NaHCO$_3$ solution (20 mL) and extracted with 10% methanol in CH$_2$Cl$_2$ (3×10 mL). The combined organic layer was washed with brine (25 mL) and dried over anhydrous Na$_2$SO$_4$ and concentrated under reduced pressure. The obtained crude product purified by preparative HPLC (XBridge C18 column; 35-100% gradient acetonitrile with water). The pure appropriate pure fractions were lyophilized to afford the title compound 11 (13.5 mg) as a white solid. $^1$H NMR (400 MHz, DMSO-d$_6$) δ ppm 11.61 (s, 1H; D$_2$O exchangeable), 7.94 (d, J=2.4 Hz, 1H), 7.80 (dd, J=8.8, 2.4 Hz, 1H), 7.37 (d, J=8.8 Hz, 1H), 7.31 (s, 1H), 5.33-5.29 (m, 1H), 4.94 (dd, J=12.7, 2.4 Hz, 1H), 4.71 (dd, J=12.7, 6.1 Hz, 1H), 4.37 (q, J=7.3 Hz, 2H), 4.13 (t, J=6.4 Hz, 2H), 3.76-3.64 (m, 2H), 2.59-2.55 (m, 2H), 2.29-2.23 (m, 2H), 1.87-1.70 (m, 5H), 1.66-1.61 (m, 2H), 1.46-1.42 (m, 2H), 1.36 (t, J=7.1 Hz, 3H), 0.97 (t, J=7.3 Hz, 3H), 0.92 (t, J=7.3 Hz, 3H); LCMS(ESI): m/z 637.29 [M+H]$^+$; purity~98.2%.

Scheme 32

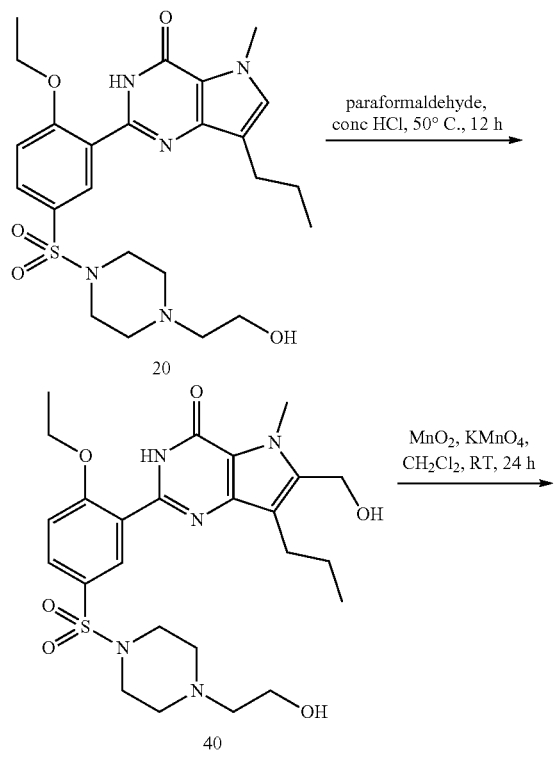

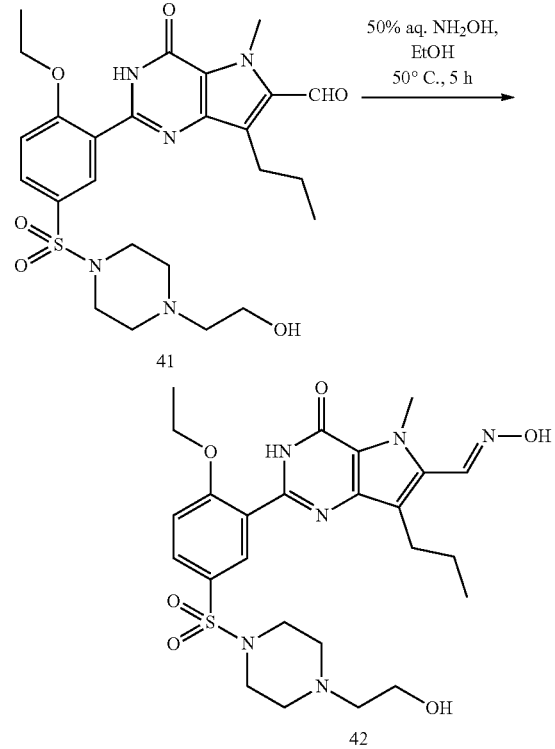

Example 58

2-(2-ethoxy-5-((4-(2-hydroxyethyl)piperazin-1-yl)sulfonyl)phenyl)-6-(hydroxymethyl)-5-methyl-7-propyl-3,5-dihydro-4H-pyrrolo[3,2-d]pyrimidin-4-one (40)

To a stirred solution of 2-(2-ethoxy-5-((4-(2-hydroxyethyl)piperazin-1-yl)sulfonyl)phenyl)-5-methyl-7-propyl-3,5-dihydro-4H-pyrrolo[3,2-d]pyrimidin-4-one 20 (2.5 g, 4.96 mmol) in concentrated HCl solution (25 mL), was added paraformaldehyde (1.25 g, 0.5 w/w) at room temperature and heated to 50° C. under inert atmosphere for 12 h. After completion of reaction (monitored by TLC), the reaction mixture was cooled to room temperature and neutralized with saturated NaHCO$_3$ solution (250 mL). The resultant solution was extracted with 10% methanol in dichloromethane (3×200 mL). The combined organic layer was dried over anhydrous Na$_2$SO$_4$ and concentrated under reduced pressure. The obtained crude product was purified by reverse phase column chromatography (C18 column; Grace System) by eluting with 20-35% gradient acetonitrile with water to afford the titled compound 40 (1.5 g; ~86% purity) as an off-white solid, which was directly taken for next reaction without further purification. $^1$H NMR (300 MHz, DMSO-d$_6$) δ ppm 11.73 (br s, 1H), 7.96-7.81 (m, 2H), 7.39 (d, J=8.4 Hz, 1H), 5.18 (t, J=4.9 Hz, 1H), 4.56 (d, J=4.9 Hz, 2H), 4.23 (q, J=6.8 Hz, 2H), 4.05 (s, 3H), 3.82-3.682 (m, 4H), 3.22-3.11 (m, 2H), 2.91-2.79 (m, 4H), 2.63-2.58 (m, 2H), 2.48-2.32 (m, 3H), 1.63-1.52 (m, 2H), 1.35 (t, J=6.8 Hz, 3H), 0.88 (t, J=7.3 Hz, 3H); LCMS (ESI): m/z 534.1 [M+H$^+$]; purity~86%.

Example 59

2-(2-ethoxy-5-((4-(2-hydroxyethyl)piperazin-1-yl)sulfonyl)phenyl)-5-methyl-4-oxo-7-propyl-4,5-dihydro-3H-pyrrolo[3,2-d]pyrimidine-6-carbaldehyde (41)

To a stirred solution of 2-(2-ethoxy-5-((4-(2-hydroxyethyl)piperazin-1-yl)sulfonyl)phenyl)-6-(hydroxymethyl)-5-methyl-7-propyl-3,5-dihydro-4H-pyrrolo[3,2-d]pyrimidin-4-one 40 (800 mg) in dichloromethane (320 mL) was added activated 58% MnO$_2$ (2.26 g, 26 mmol) and KMnO$_4$ (760 mg, 4.8 mmol) at room temperature and stirred for 24 h. Reaction was monitored by TLC. The reaction mixture was filtered through a Celite pad and washed with dichloromethane (250 mL). The filtrate was concentrated and the obtained crude product was purified by silica gel column chromatography (Grace System) by eluting with 6-8% gradient 30% methanol in dichloromethane with dichloromethane to afford the title compound 41 (180 mg) as a white solid; followed by eluting further with 15-20% gradient 30% methanol in dichloromethane with dichloromethane obtained the unreacted 40 (400 mg) as an off-white solid. $^1$H NMR (300 MHz, DMSO-d$_6$) δ ppm 12.14 (br s, 1H), 10.15 (s, 1H), 7.86 (d, J=2.1 Hz, 1H), 7.84 (dd, J=8.4, 2.1 Hz, 1H), 7.38 (d, J=8.4 Hz, 1H), 4.36 (t, J=5.3 Hz, 1H), 4.32 (s, 3H), 4.22 (q, J=6.8 Hz, 2H), 3.44-3.38 (m, 2H), 2.97-2.86 (m, 6H), 2.49-2.43 (m, 4H), 2.38-2.34 (m, 2H), 1.72-1.60 (m, 2H), 1.34 (t, J=6.8 Hz, 3H), 0.91 (t, J=7.3 Hz, 3H); LCMS (ESI): m/z 532.3 [M+H]$^+$; purity~96.7%.

Example 60

(E)-2-(2-ethoxy-5-((4-(2-hydroxyethyl)piperazin-1-yl)sulfonyl)phenyl)-5-methyl-4-oxo-7-propyl-4,5-dihydro-3H-pyrrolo[3,2-d]pyrimidine-6-carbaldehyde oxime (42)

To a stirred solution of 2-(2-ethoxy-5-((4-(2-hydroxyethyl)piperazin-1-yl)sulfonyl)phenyl)-5-methyl-4-oxo-7-propyl-4,5-dihydro-3H-pyrrolo[3,2-d]pyrimidine-6-carbaldehyde 41 (80 mg, 0.15 mmol) in ethanol (9.6 mL) was added 50% aqueous hydroxylamine solution (1.6 mL) at room temperature and heated to 50° C. for 5 h. After completion of reaction (monitored by TLC), the reaction was concentrated under reduced pressure. The resultant residue was diluted in water (10 mL), and extracted with 10% methanol in dichloromethane (3×20 mL). The combined organic layer was washed with brine (20 mL), dried over anhydrous Na$_2$SO$_4$ and concentrated under reduced pressure. The crude product was dissolved in iso-propanol (3.0 mL) at 80° C. and allowed to cool to room temperature. The solid precipitated was filtered and dried to afford the title compound 42 (24.5 mg, 30% yield) as a pale yellow solid. $^1$H NMR (400 MHz, DMSO-d$_6$) δ ppm 11.81 (s, 1H; D$_2$O exchangeable), 11.59 (s, 1H; D$_2$O exchangeable), 8.34 (s, 1H), 7.89 (d, J=2.2 Hz, 1H), 7.81 (dd, J=8.8, 2.2 Hz, 1H), 7.37 (d, J=8.8 Hz, 1H), 4.33 (t, J=5.4 Hz, 1H; D$_2$O exchangeable), 4.23 (q, J=6.8 Hz, 2H), 4.17 (s, 3H), 3.44-3.40 (m, 2H), 2.91-2.87 (m, 4H), 2.76-2.74 (m, 2H), 2.49-2.44 (m, 4H), 2.38-2.34 (m, 2H), 1.62-1.56 (m, 2H), 1.35 (t, J=6.8 Hz, 3H), 0.88 (t, J=7.3 Hz, 3H); LCMS (ESI): m/z 547.6 [M+H]$^+$; purity~95.9%.

Scheme 33

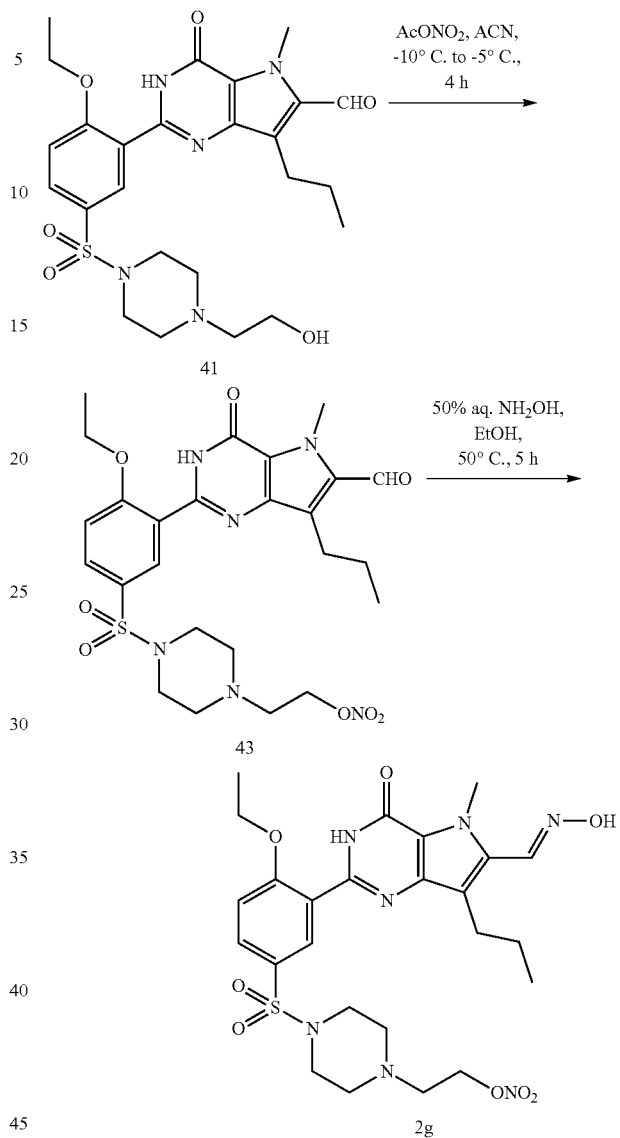

Example 61

2-(4-((4-ethoxy-3-(6-formyl-5-methyl-4-oxo-7-propyl-4,5-dihydro-3H-pyrrolo[3,2-d]pyrimidin-2-yl)phenyl)sulfonyl)piperazin-1-yl)ethyl nitrate (43)

To a stirred solution of 2-(2-ethoxy-5-((4-(2-hydroxyethyl)piperazin-1-yl)sulfonyl)phenyl)-5-methyl-4-oxo-7-propyl-4,5-dihydro-3H-pyrrolo[3,2-d]pyrimidine-6-carbaldehyde 41 (230 mg, 0.43 mmol) in acetonitrile (9.2 mL) was added a solution of freshly prepared acetyl nitrate (0.4 mL; 4.6 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised above 0° C.)] drop wise at −10° C. for 10 min under argon atmosphere. The reaction was stirred at −5° C. for 4 h. After completion of reaction (monitored by TLC), the reaction was quenched with saturated NaHCO$_3$ solution (20 mL) at 0° C. and extracted with ethyl acetate (3×20 mL). The combined organic layer was washed with brine (20 mL), dried over anhydrous Na$_2$SO$_4$ and concentrated under reduced pressure to afford the crude product 43 (250 mg) as a brown semi solid, which was directly taken for next reaction without purification. LCMS (ESI): m/z 577.6 [M+H$^+$]; purity~74%.

Example 62

(E)-2-(4-((4-ethoxy-3-(6-((hydroxyimino)methyl)-5-methyl-4-oxo-7-propyl-4,5-dihydro-3H-pyrrolo[3,2-d]pyrimidin-2-yl)phenyl)sulfonyl)piperazin-1-yl) ethyl nitrate (2g)

To a stirred solution of 2-(4-((4-ethoxy-3-(6-formyl-5-methyl-4-oxo-7-propyl-4,5-dihydro-3H-pyrrolo[3,2-d]pyrimidin-2-yl)phenyl)sulfonyl)piperazin-1-yl)ethyl nitrate 43 (250 mg, ~74% pure) in ethanol (30 mL) was added 50% aqueous hydroxylamine solution (5 mL) at room temperature. The reaction was heated to 50° C. for 5 h. After completion of reaction (monitored by LCMS analysis), the reaction was cooled to room temperature and concentrated under reduced pressure. The resultant residue was diluted in water (15 mL) and extracted with ethyl acetate (3×25 mL). The combined organic layer was washed with brine (20 mL), dried over anhydrous Na$_2$SO$_4$ and concentrated under reduced pressure. The crude product was purified by silica gel column chromatography (Grace System) by eluting with 6% of 30% methanol in dichloromethane with dichloromethane followed by re-crystallization from hot iso-propanol (3 mL) to afford the title compound 2g (29.3 mg) as pale yellow solid. $^1$H NMR (400 MHz, DMSO-d$_6$) δ ppm 11.80 (s, 1H; D$_2$O exchangeable), 11.59 (s, 1H; D$_2$O exchangeable), 8.34 (s, 1H), 7.89 (d, J=2.4 Hz, 1H), 7.81 (dd, J=8.8, 2.4 Hz, 1H), 7.37 (d, J=8.8 Hz, 1H), 4.56 (t, J=5.1 Hz, 2H), 4.23 (q, J=6.8 Hz, 2H), 4.17 (s, 3H), 2.91-2.89 (m, 4H), 2.77-2.74 (m, 2H), 2.67-2.65 (m, 2H), 2.54-2.51 (m, 4H), 1.63-1.54 (m, 2H), 1.35 (t, J=6.8 Hz, 3H), 0.88 (t, J=7.3 Hz, 3H); LCMS (ESI): m/z 590.4 [M−H]$^−$; purity~96.6%.

Scheme 34

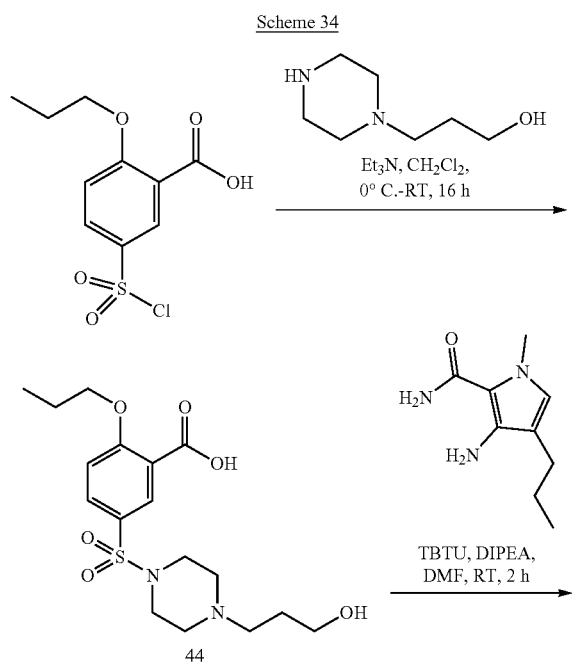

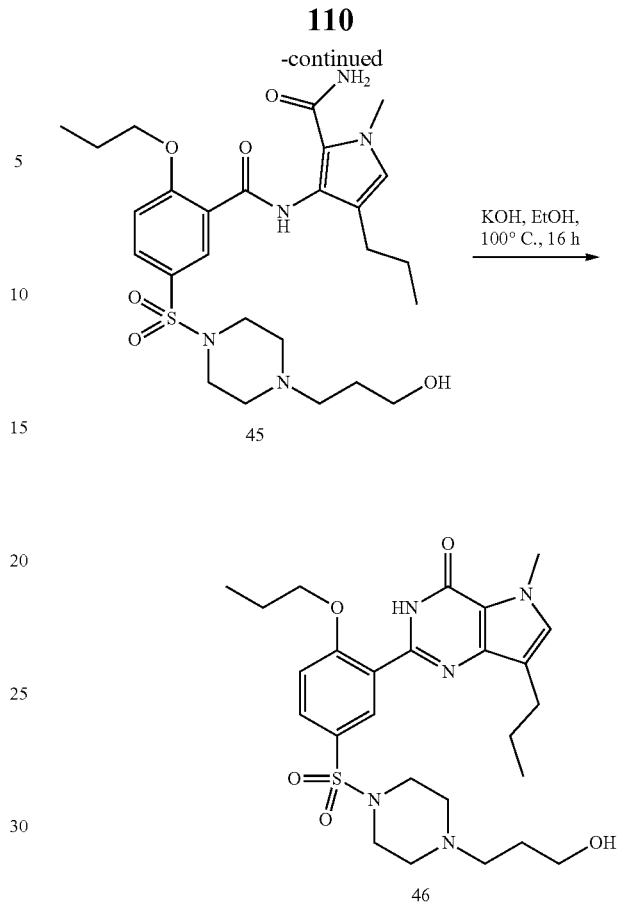

Example 63

5-((4-(3-hydroxypropyl)piperazin-1-yl)sulfonyl)-2-propoxybenzoic acid (44)

To a stirred solution of 2-(piperazin-1-yl)propane-1-ol (3.1 g, 21.52 mmol) in dichloromethane (36 mL) was added triethylamine (14.9 mL, 107.64 mmol) at 0° C. under inert atmosphere. To this, a solution of 5-(chlorosulfonyl)-2-propoxybenzoic acid (6.0 g, 21.52 mmol) in dichloromethane (36 mL) was added drop wise at 0° C. under inert atmosphere. The reaction mixture was allowed to stir at room temperature for 16 h. After completion of reaction (by LCMS analysis), the reaction mixture was directly purified (without work-up) by reverse phase column chromatography (C18 column, Grace System) by eluting with 5-20% gradient acetonitrile with water to afford 12 g of compound 44, having triethylamine hydrochloride salts as impurity. The obtained product was dissolved in CH$_2$Cl$_2$ (30 mL) and then diluted with n-hexane (200 mL). The resultant mixture was stirred at room temperature for 2 h and filtered. The filtrate was concentrated under reduced pressure to afford the title compound 2 (8.3 g) as a white gum. $^1$H NMR (400 MHz, CDCl$_3$) δ ppm 11.8 (br s, 1H), 8.24 (d, J=2.4 Hz, 1H), 7.76 (dd, J=8.4, 2.4 Hz, 1H), 7.05 (d, J=8.4 Hz, 1H), 4.18-4.15 (m, 2H), 3.72-3.70 (m, 2H), 3.06-3.03 (m, 5H), 2.61-2.58 (m, 6H), 1.94-1.89 (m, 2H), 1.70-1.67 (m, 2H), 1.09 (t, J=7.2 Hz, 3H); LCMS (ESI): m/z 387.5 [M+H$^+$]; purity~95.4%.

Example 64

3-(5-((4-(3-hydroxypropyl)piperazin-1-yl)sulfonyl)-2-propoxybenzamido)-1-methyl-4-propyl-1H-pyrrole-2-carboxamide (45)

To a stirred solution of 5-((4-(3-hydroxypropyl)piperazin-1-yl)sulfonyl)-2-propoxybenzoic acid 44 (8.3 g) in DMF (49.8 mL) was added diisopropyl ethylamine (11.2 mL, 64.5 mmol) followed by TBTU (13.8 g, 43.0 mmol) at 15-20° C. and stirred for 20 min. To this, 3-amino-1-methyl-4-propyl-1H-pyrrole-2-carboxamide (WO2001060825 A1) (3.89 g, 21.50 mmol) was added portion wise at same temperature for 30 min. The reaction was allowed to stir at room temperature for 2 h under inert atmosphere. After completion of reaction (monitored by TLC and LCMS analysis), reaction was quenched in ice-cold water (500 mL) and extracted with ethyl acetate (3×100 mL). The combined organic layer was washed with brine (150 mL), dried over anhydrous Na$_2$SO$_4$ and concentrated under reduced pressure. The obtained crude product was purified by silica gel column chromatography (Grace System) by eluting with 10-15% gradient 30% methanol in dichloromethane with dichloromethane to afford the title compound 45 (2.1 g) as a white solid. $^1$H NMR (300 MHz, DMSO-d$_6$) δ ppm 9.49 (s, 1H), 7.82-7.79 (m, 2H), 7.41 (d, J=8.8 Hz, 1H), 7.24 (br s, 1H), 6.92 (br s, 1H), 6.71 (s, 1H), 4.34 (br t, J=4.8 Hz, 1H), 4.21-4.16 (m, 2H), 3.74 (s, 3H), 3.38-3.31 (m, 2H), 2.89-2.84 (m, 4H), 2.45-2.39 (m, 4H), 2.33-2.24 (m, 4H), 1.85-1.75 (m, 2H), 1.51-1.42 (m, 4H), 0.98 (t, J=7.2 Hz, 3H), 0.88 (t, J=7.2 Hz, 3H).

Example 65

2-(5-((4-(3-hydroxypropyl)piperazin-1-yl)sulfonyl)-2-propoxyphenyl)-5-methyl-7-propyl-3,5-dihydro-4H-pyrrolo[3,2-d]pyrimidin-4-one (46)

To a stirred solution of 3-(5-((4-(3-hydroxypropyl)piperazin-1-yl)sulfonyl)-2-propoxybenzamido)-1-methyl-4-propyl-1H-pyrrole-2-carboxamide 45 (2.1 g, 3.82 mmol) in ethanol (33.6 mL) was added 1M aqueous KOH solution (29.4 mL) at room temperature. The reaction mixture was heated at 100° C. for 16 h. After completion of reaction (monitored by TLC), the reaction was cooled to room temperature and concentrated under reduced pressure. The resultant residue was diluted with water (110 mL) and extracted with ethyl acetate (3×50 mL). The combined organic layer was washed with brine (50 mL), dried over anhydrous Na$_2$SO$_4$ and concentrated under reduced pressure to afford the title compound 46 (1.55 g, 73% yield) as a white solid. $^1$H NMR (400 MHz, DMSO-d$_6$) δ ppm 11.64 (br s, 1H; D$_2$O exchangeable), 7.88 (d, J=2.4 Hz, 1H), 7.79 (dd, J=8.8, 2.4 Hz, 1H), 7.37 (d, J=8.8 Hz, 1H), 7.21 (s, 1H), 4.32 (br t, J=5.1 Hz, 1H; D$_2$O exchangeable), 4.13 (t, J=6.4 Hz, 2H), 3.98 (s, 3H), 3.41-3.32 (m, 2H), 2.92-2.86 (m, 4H), 2.58-2.55 (m, 2H), 2.44-2.38 (m, 4H), 2.32-2.29 (m, 2H), 1.78-1.70 (m, 2H), 1.68-1.59 (m, 2H), 1.53-1.48 (m, 2H), 0.96 (t, J=7.3 Hz, 3H), 0.92 (t, J=7.3 Hz, 3H); LCMS (ESI): m/z 532.6 [M+H$^+$]; purity~97.5%.

Scheme 35

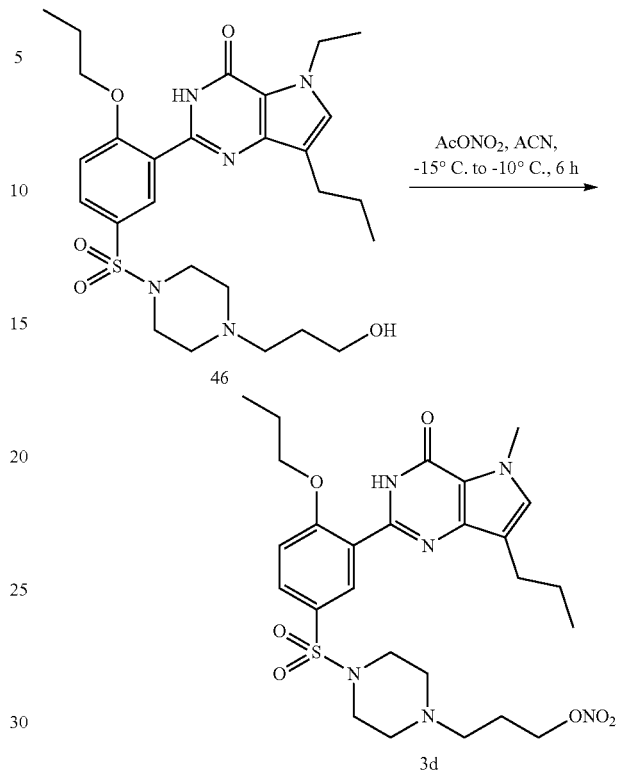

Example 65

3-(4-((3-(5-methyl-4-oxo-7-propyl-4,5-dihydro-3H-pyrrolo[3,2-d]pyrimidin-2-yl)-4-propoxyphenyl)sulfonyl)piperazin-1-yl)propyl nitrate (3d)

To a stirred solution of 2-(5-((4-(3-hydroxypropyl)piperazin-1-yl)sulfonyl)-2-propoxyphenyl)-5-methyl-7-propyl-3,5-dihydro-4H-pyrrolo[3,2-d]pyrimidin-4-one 46 (200 mg, 0.37 mmol) in acetonitrile (6.0 mL) was added a solution of freshly prepared acetyl nitrate (0.13 mL; 1.88 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 10 min under argon atmosphere. The reaction was stirred at −15° C. to −10° C. for 4 h. Reaction was monitored by TLC and LCMS analysis. The reaction was quenched with saturated NaHCO$_3$ solution (14 mL) at 0° C. and extracted with ethyl acetate (3×20 mL). The combined organic layer was washed with brine (30 mL), dried over anhydrous Na$_2$SO$_4$ and concentrated under reduced pressure. The obtained crude product was purified reverse phase column chromatography (C18 column, Grace System) by eluting with 35-40% gradient acetonitrile with water. Pure fractions were lyophilized to afford the title compound 3d (32 mg) as a white solid. $^1$H NMR (400 MHz, DMSO-d$_6$) δ ppm 11.63 (s, 1H; D$_2$O exchangeable), 7.89 (d, J=2.4 Hz, 1H), 7.80 (dd, J=8.8, 2.4 Hz, 1H), 7.37 (d, J=8.8 Hz, 1H), 7.21 (s, 1H), 4.48 (t, J=6.6 Hz, 2H), 4.13 (t, J=6.1 Hz, 2H), 3.98 (s, 3H), 2.95-2.89 (m, 4H), 2.58-2.55 (m, 2H), 2.48-2.42 (m, 4H), 2.38-2.34 (m, 2H), 1.80-1.70 (m, 4H), 1.68-1.58 (m, 2H), 0.97 (t, J=7.4 Hz, 3H), 0.92 (t, J=7.4 Hz, 3H); LCMS(ESI): m/z 577.6 [M+H⁺]; purity~95.2%.

Scheme 36

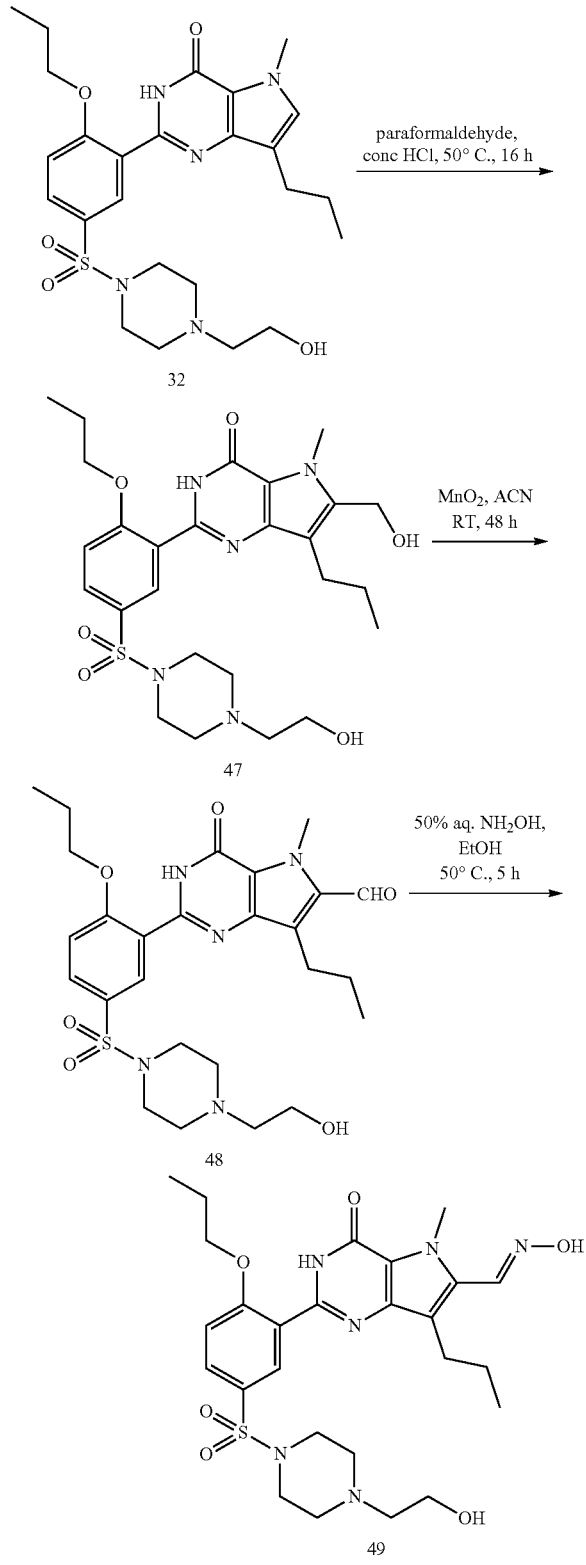

Example 66

2-(5-((4-(2-hydroxyethyl)piperazin-1-yl)sulfonyl)-2-propoxyphenyl)-6-(hydroxymethyl)-5-methyl-7-propyl-3,5-dihydro-4H-pyrrolo[3,2-d]pyrimidin-4-one (47)

To a stirred solution of 2-(5-((4-(2-hydroxyethyl)piperazin-1-yl)sulfonyl)-2-propoxyphenyl)-5-methyl-7-propyl-3,5-dihydro-4H-pyrrolo[3,2-d]pyrimidin-4-one 32 (550 mg, 1.06 mmol) in concentrated HCl solution (5.5 mL), was added paraformaldehyde (275 mg, 0.5 w/w) at room temperature and heated to 50° C. under inert atmosphere. Reaction was monitored by LCMS analysis. After 16 h, the reaction was cooled to room temperature, diluted with water (30 mL) and neutralized with saturated NaHCO₃ solution (150 mL). The resultant solution was extracted with 10% methanol in dichloromethane (3×100 mL). The combined the organic layer was dried over anhydrous Na₂SO₄ and concentrated under reduced pressure. The crude product was purified by reverse phase column chromatography (C-18 column; Grace System) by eluting with 35-40% gradient acetonitrile with water to afford the title compound 47 (230 mg; 37% yield) as a white solid. ¹H NMR (300 MHz, DMSO-d₆) δ ppm 10.42 (br s, 1H), 7.87 (d, J=2.2 Hz, 1H), 7.80 (dd, J=8.8, 2.2 Hz, 1H), 7.37 (d, J=8.8 Hz, 1H), 5.16 (br s, 1H), 4.56 (s, 2H), 4.35 (br s, 1H), 4.13-4.10 (m, 2H), 4.05 (s, 3H), 3.43-3.39 (m, 2H), 2.91-2.86 (m, 4H), 2.61-2.57 (m, 2H), 2.47-2.43 (m, 4H), 2.37-2.33 (m, 2H), 1.79-1.69 (m, 2H), 1.62-1.52 (m, 2H), 0.97 (t, J=7.3 Hz, 3H), 0.88 (t, J=7.3 Hz, 3H); LCMS (ESI): m/z 548.6 [M+H⁺]; purity~95.3%.

Example 67

2-(5-((4-(2-hydroxyethyl)piperazin-1-yl)sulfonyl)-2-propoxyphenyl)-5-methyl-4-oxo-7-propyl-4,5-dihydro-3H-pyrrolo[3,2-d]pyrimidine-6-carbaldehyde (48)

To a stirred solution of 2-(5-((4-(2-hydroxyethyl)piperazin-1-yl)sulfonyl)-2-propoxyphenyl)-6-(hydroxymethyl)-5-methyl-7-propyl-3,5-dihydro-4H-pyrrolo[3,2-d]pyrimidin-4-one 47 (700 mg, 1.28 mmol) in acetonitrile (350 mL) was added activated 58% activated MnO₂ (1.89 g, 21.79 mmol) at room temperature and stirred for 24 h. Reaction was monitored by TLC and LCMS analysis. Reaction mixture was filtered through a Celite pad. 58% activated MnO₂ (1.89 g, 21.79 mmol) was added to the filtrate at room temperature and stirred for additional 24 h. The reaction mixture was filtered through a Celite pad and washed with acetonitrile (100 mL). The resultant filtrate was concentrated under reduced pressure. The crude product was purified by silica gel column chromatography (Grace system) by eluting with 4-8% gradient of 30% methanol in dichloromethane with dichloromethane to afford the title compound 48 (220 mg, 31% yield) as a white solid. 1H NMR (300 MHz, DMSO-d₆) δ ppm 12.13 (br s, 1H), 10.14 (s, 1H), 7.90-7.77 (m, 2H), 7.39 (d, J=8.4 Hz, 1H), 4.38 (t, J=5.3 Hz, 1H), 4.32 (s, 3H), 4.12 (t, J=6.2 Hz, 2H), 3.44-3.40 (m, 2H), 3.01-2.78 (m, 6H), 2.48-2.45 (m, 4H), 2.38-2.35 (m, 2H), 1.78-1.61 (m, 4H), 0.97-0.84 (m, 6H); LCMS (ESI): m/z 546.3 [M+H⁺]; purity~98.9%.

Example 68

(E)-2-(5-((4-(2-hydroxyethyl)piperazin-1-yl)sulfonyl)-2-propoxyphenyl)-5-methyl-4-oxo-7-propyl-4,5-dihydro-3H-pyrrolo[3,2-d]pyrimidine-6-carbaldehyde oxime (49)

To a stirred solution of 2-(5-((4-(2-hydroxyethyl)piperazin-1-yl)sulfonyl)-2-propoxyphenyl)-5-methyl-4-oxo-7-propyl-4,5-dihydro-3H-pyrrolo[3,2-d]pyrimidine-6-carbaldehyde 48 (80 mg, 0.15 mmol) in ethanol (9.6 mL) was added 50% aqueous hydroxylamine solution (1.6 mL) at room temperature. Reaction was heated to 50° C. for 5 h under argon atmosphere. After completion of reaction (monitored by TLC), the reaction was concentrated under reduced pressure. The resultant residue was diluted in water (10 mL) and extracted with ethyl acetate (3×10 mL). The combined organic layer washed with brine (10 mL), dried over anhydrous $Na_2SO_4$ and concentrated under reduced pressure. The crude product was purified by reverse phase column chromatography (C18 column; Grace System) by eluting with 35-40% gradient acetonitrile with water. Pure fractions were lyophilized to afford the title compound 49 (13.3 mg) as a white solid. $^1$H NMR (400 MHz, DMSO-$d_6$) δ ppm 11.77 (br s, 1H; $D_2O$ exchangeable), 11.58 (br s, 1H; $D_2O$ exchangeable), 8.33 (s, 1H), 7.88 (d, J=2.0 Hz, 1H), 7.80 (dd, J=8.8, 2.0 Hz, 1H), 7.37 (d, J=8.8 Hz, 1H), 4.34 (d, J=5.1 Hz, 1H; $D_2O$ exchangeable), 4.17 (s, 3H), 4.13-4.04 (m, 2H), 3.44-3.39 (m, 2H), 2.91-2.87 (m, 4H), 2.76-2.72 (m, 2H), 2.51-2.47 (m, 4H), 2.38-2.35 (m, 2H), 1.78-1.70 (m, 2H), 1.63-1.54 (m, 2H), 0.96 (t, J=7.3 Hz, 3H), 0.88 (t, J=7.3 Hz, 3H); LCMS (ESI): m/z 561.6 [M+H$^+$]; purity~95.3%.

Scheme 37

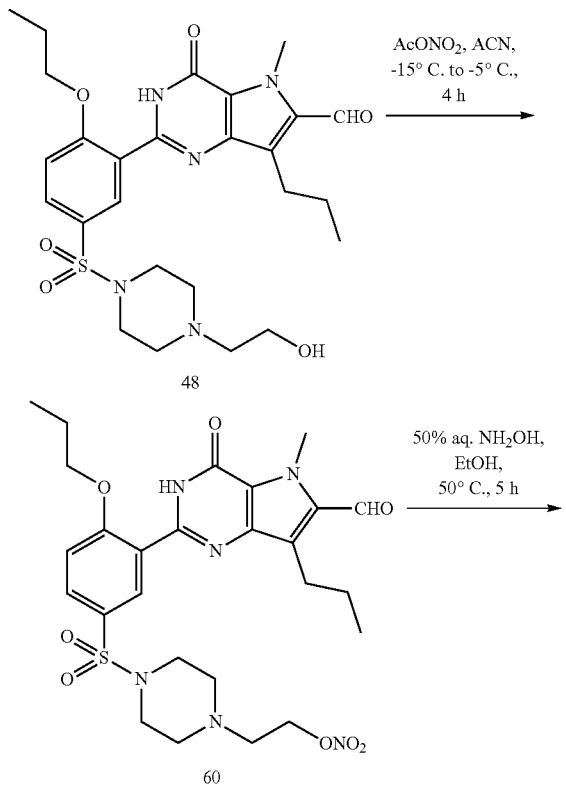

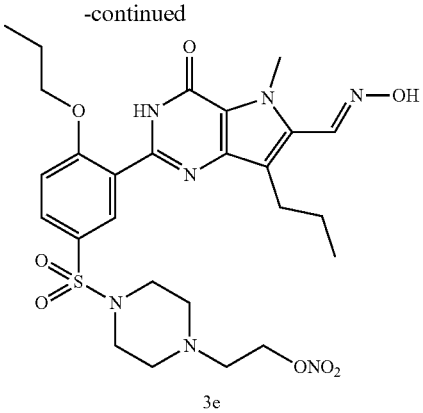

3e

Example 68

2-(4-((3-(6-formyl-5-methyl-4-oxo-7-propyl-4,5-dihydro-3H-pyrrolo[3,2-d]pyrimidin-2-yl)-4-propoxyphenyl)sulfonyl)piperazin-1-yl)ethyl nitrate (50)

To a stirred solution of 2-(5-((4-(2-hydroxyethyl)piperazin-1-yl)sulfonyl)-2-propoxyphenyl)-5-methyl-4-oxo-7-propyl-4,5-dihydro-3H-pyrrolo[3,2-d]pyrimidine-6-carbaldehyde 48 (220 mg, 0.40 mmol) in acetonitrile (6.6 mL) was added a solution of freshly prepared acetyl nitrate (0.2 mL; 2.82 mmol) [(acetyl nitrate was prepared separately by addition of fuming $HNO_3$ (1.1 mL, 25.5 mmol) drop wise in to acetic anhydride (2.5 mL, 26.5 mmol) slowly at −15° C. for 30 min under argon atmosphere (Note: temperature should not be raised above 0° C.))] drop wise at −15° C. for 30 min under argon atmosphere. The reaction was stirred at −10° C. to −5° C. for 4 h. After completion of reaction (monitored by TLC), the reaction was quenched with saturated $NaHCO_3$ solution (15 mL) at 0° C. and extracted with ethyl acetate (3×20 mL). The combined organic layer was washed with brine (20 mL), dried over anhydrous $Na_2SO_4$ and concentrated under reduced pressure to afford the crude product 50 (200 mg) as yellow solid, which was directly taken for next reaction. LCMS (ESI): m/z 591.3 [M+H$^+$]; purity~94.6%.

Example 69

(E)-2-(4-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperazin-1-yl)ethyl nitrate (3e)

To a stirred solution of 2-(4-((3-(6-formyl-5-methyl-4-oxo-7-propyl-4,5-dihydro-3H-pyrrolo[3,2-d]pyrimidin-2-yl)-4-propoxyphenyl)sulfonyl)piperazin-1-yl)ethyl nitrate 50 (200 mg, 0.34 mmol) in ethanol (24 mL) was added 50% aqueous hydroxylamine solution (3 mL) at room temperature. Reaction was heated to 50° C. for 5 h. After completion of reaction (monitored by TLC), the reaction mixture was concentrated under reduced pressure. The resultant residue was diluted with water (10 mL) and extracted with ethyl acetate (3×30 mL). The combined organic layer was washed with brine (30 mL), dried over anhydrous $Na_2SO_4$ and concentrated under reduced pressure. The crude product was purified by silica gel column chromatography (Grace System) by eluting with 10% of 30% methanol in dichloromethane with dichloromethane to afford the title compound 3e (43.8 mg) as an off-white solid. 1H NMR (400 MHz, DMSO-$d_6$) δ ppm 11.81 (s, 1H; $D_2O$ exchangeable), 11.63 (s, 1H; $D_2O$ exchangeable), 8.34 (s, 1H), 7.87 (d, J=2.0 Hz, 1H), 7.81 (dd, J=8.8, 2.0 Hz, 1H), 7.38 (d, J=8.8 Hz, 1H), 4.57-4.55 (m, 2H), 4.17 (s, 3H), 4.12 (t, J=6.1 Hz, 2H), 2.91-2.88 (m, 4H), 2.76-2.73 (m, 2H), 2.67-2.64 (m, 2H), 2.54-2.51 (m, 4H), 1.78-1.69 (m, 2H), 1.62-1.53 (m, 2H), 0.96 (t, J=7.6 Hz, 3H), 0.87 (t, J=7.3 Hz, 3H); LCMS (ESI): m/z 606.5 [M+H$^+$]; purity~96.5%.

Scheme 38

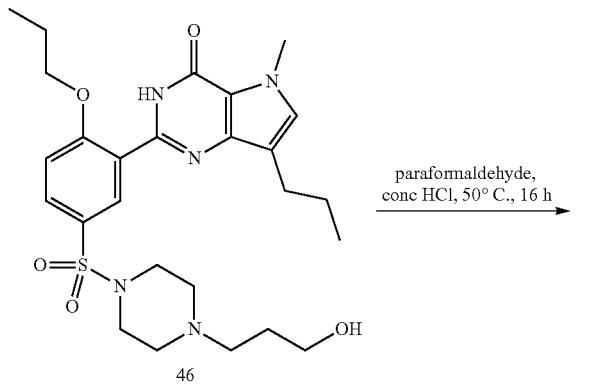

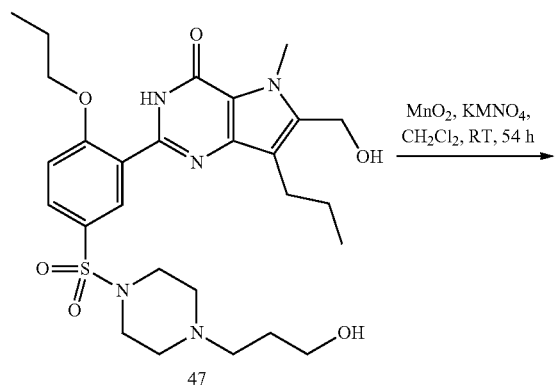

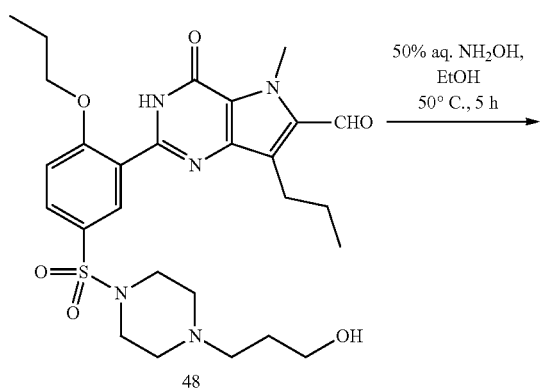

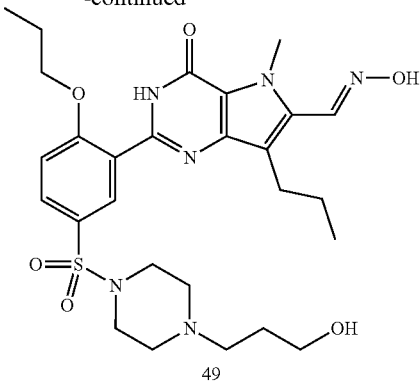

Example 70

6-(hydroxymethyl)-2-(5-((4-(3-hydroxypropyl)piperazin-1-yl)sulfonyl)-2-propoxyphenyl)-5-methyl-7-propyl-3,5-dihydro-4H-pyrrolo[3,2-d]pyrimidin-4-one (47)

To a stirred solution of 2-(5-((4-(3-hydroxypropyl)piperazin-1-yl)sulfonyl)-2-propoxyphenyl)-5-methyl-7-propyl-3,5-dihydro-4H-pyrrolo[3,2-d]pyrimidin-4-one 46 (1.0 g, 1.88 mmol) in concentrated HCl solution (10 mL), was added paraformaldehyde (500 mg, 0.5 w/w) at room temperature and heated to 50° C. for 16 h. After completion of reaction (monitored by TLC and LCMS analysis), the reaction mixture was cooled to room temperature, diluted with ice-cold water (50 mL) and neutralized with saturated NaHCO$_3$ solution (200 mL). The resultant solution was extracted with 10% methanol in dichloromethane (3×150 mL). The combined organic layer was dried over anhydrous Na$_2$SO$_4$ and concentrated under reduced pressure. The crude product was purified by reverse phase column chromatography (C18 column; Grace System) by eluting with 25-35% gradient acetonitrile with water to afford the title compound 47 (560 mg; 51% yield) as a white solid. $^1$H NMR (300 MHz, DMSO-$d_6$) δ ppm 11.69 (br s, 1H), 7.88 (s, 1H), 7.82 (d, J=8.8 Hz, 1H), 7.38 (d, J=8.8 Hz, 1H), 5.18 (br t, J=5.1 Hz, 1H), 4.56 (br d, J=5.1 Hz, 2H), 4.36 (br s, 1H), 4.13 (t, J=6.2 Hz, 2H), 4.05 (s, 3H), 3.39-3.34 (m, 2H), 2.91-2.86 (m, 4H), 2.63-2.58 (m, 4H), 2.50-2.21 (m, 4H), 1.80-1.68 (m, 2H), 1.64-1.62 (m, 4H), 0.96 (t, J=7.3 Hz, 3H), 0.88 (t, J=7.3 Hz, 3H); LCMS (ESI): m/z 562.4 [M+H$^+$]; purity~82.4%.

Example 71

2-(5-((4-(3-hydroxypropyl)piperazin-1-yl)sulfonyl)-2-propoxyphenyl)-5-methyl-4-oxo-7-propyl-4,5-dihydro-3H-pyrrolo[3,2-d]pyrimidine-6-carbaldehyde (48)

To a stirred solution of 6-(hydroxymethyl)-2-(5-((4-(3-hydroxypropyl)piperazin-1-yl)sulfonyl)-2-propoxyphenyl)-5-methyl-7-propyl-3,5-dihydro-4H-pyrrolo[3,2-d]pyrimidin-4-one 47 (450 mg) in dichloromethane (225 mL) was added activated 58% MnO$_2$ (1.18 g, 13.66 mmol) and KMnO$_4$ (405 mg, 2.56 mmol) at room temperature and stirred for 30 h. The reaction mixture was then filtered through a Celite pad. To the filtrate, activated 58% MnO$_2$ (1.18 g, 21.79 mmol) and KMnO$_4$ (405 mg, 2.56 mmol) were added again at room temperature and stirred for 24 h.

Reaction was monitored by TLC and LCMS analysis. The reaction mixture was filtered through a Celite pad and washed with dichloromethane (200 mL). The filtrate was concentrated under reduced pressure and the obtained crude product was purified by Silica gel column chromatography (Grace System) by eluting with 6-8% gradient 30% methanol in dichloromethane with dichloromethane to afford the title compound 48 (220 mg, 35% yield) as a white solid. $^1$H NMR (300 MHz, DMSO-$d_6$) δ ppm 12.13 (br s, 1H), 10.14 (s, 1H), 7.85-7.80 (m, 2H), 7.39 (d, J=8.8 Hz, 1H), 4.37 (t, J=5.3 Hz, 1H), 4.32 (s, 3H), 4.12 (t, J=6.2 Hz, 2H), 3.30-3.24 (m, 2H), 3.01-2.83 (m, 6H), 2.46-2.38 (m, 4H), 2.33-2.28 (m, 2H), 1.78-1.61 (m, 4H), 1.54-1.45 (m, 2H), 0.97-0.88 (m, 6H); LCMS (ESI): m/z 560.6 [M+H$^+$]; purity~88.3%.

Example 72

(E)-2-(5-((4-(3-hydroxypropyl)piperazin-1-yl)sulfonyl)-2-propoxyphenyl)-5-methyl-4-oxo-7-propyl-4, 5-dihydro-3H-pyrrolo[3,2-d]pyrimidine-6-carbaldehyde oxime (49)

To a stirred solution of 2-(5-((4-(3-hydroxypropyl)piperazin-1-yl)sulfonyl)-2-propoxyphenyl)-5-methyl-4-oxo-7-propyl-4,5-dihydro-3H-pyrrolo[3,2-d]pyrimidine-6-carbaldehyde 48 (80 mg, 0.14 mmol) in ethanol (9.6 mL) was added 50% aqueous hydroxylamine solution (1.6 mL) at room temperature and heated to 50° C. for 5 h. After completion of reaction (monitored by TLC and LCMS analysis), the reaction mixture was concentrated under reduced pressure. The resultant residue was diluted in water (10 mL), and extracted with ethyl acetate (2×10 mL). The combined organic layer was washed with brine (10 mL), dried over anhydrous Na$_2$SO$_4$ and concentrated under reduced pressure. The crude product was purified by reverse phase column chromatography (C18 column; Grace System) by eluting with 30-35% gradient acetonitrile with water and the pure fractions were lyophilized to afford the title compound 49 (17.4 mg) as a white solid. $^1$H NMR (400 MHz, DMSO-$d_6$) δ ppm 11.77 (br s, 1H; D$_2$O exchangeable), 11.59 (s, 1H; D$_2$O exchangeable), 8.34 (s, 1H), 7.88 (d, J=2.0 Hz, 1H), 7.80 (dd, J=8.8, 2.0 Hz, 1H), 7.38 (d, J=8.8 Hz, 1H), 4.32 (t, J=5.1 Hz, 1H; D$_2$O exchangeable), 4.17 (s, 3H), 4.13 (t, J=6.4 Hz, 2H), 3.38-3.33 (m, 2H), 2.92-2.88 (m, 4H), 2.76-2.73 (m, 2H), 2.44-2.39 (m, 4H), 2.33-2.29 (m, 2H), 1.77-1.71 (m, 2H), 1.61-1.55 (m, 2H), 1.53-1.46 (m, 2H), 0.96 (t, J=7.3 Hz, 3H), 0.88 (t, J=7.3 Hz, 3H); LCMS (ESI): m/z 575.2 [M+H$^+$]; purity~95.8%.

Scheme 39

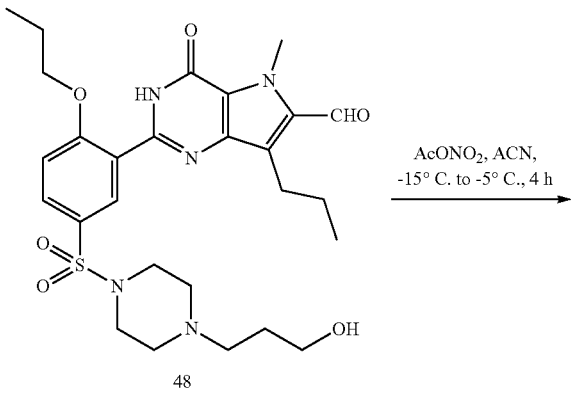

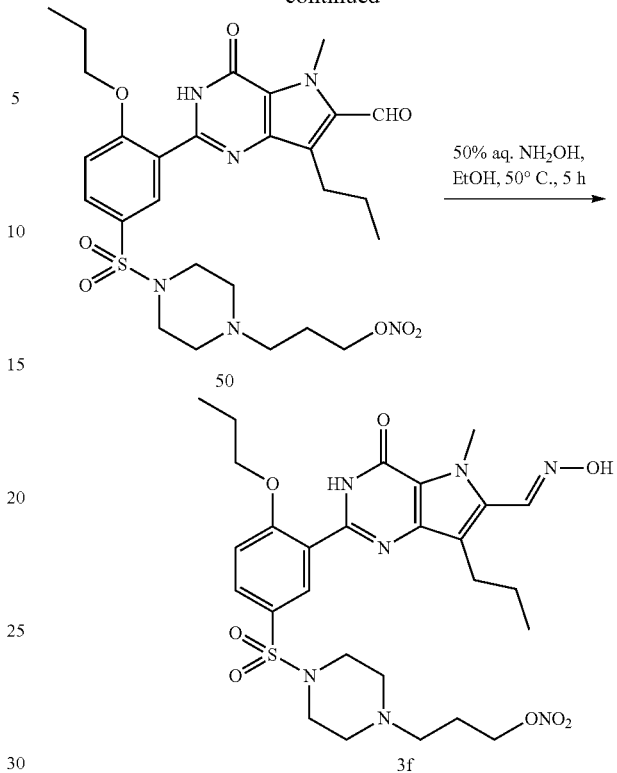

Example 73

3-(4-((3-(6-formyl-5-methyl-4-oxo-7-propyl-4,5-dihydro-3H-pyrrolo[3,2-d]pyrimidin-2-yl)-4-propoxyphenyl)sulfonyl)piperazin-1-yl)propyl nitrate (50)

To a stirred solution of 2-(5-((4-(3-hydroxypropyl)piperazin-1-yl)sulfonyl)-2-propoxyphenyl)-5-methyl-4-oxo-7-propyl-4,5-dihydro-3H-pyrrolo[3,2-d]pyrimidine-6-carbaldehyde 48 (140 mg, 0.25 mmol) in acetonitrile (4.2 mL) was added a solution of freshly prepared acetyl nitrate (0.09 mL; 1.25 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised above 0° C.))] drop wise at −15° C. for 30 min under argon atmosphere. The reaction was stirred at −10° C. to −5° C. for 4 h. After completion of reaction (monitored by TLC), the reaction was quenched with saturated NaHCO$_3$ solution (10 mL) at 0° C. and extracted with ethyl acetate (3×20 mL). The combined organic layer was washed with brine (10 mL), dried over anhydrous Na$_2$SO$_4$ and concentrated under reduced pressure to afford the crude product 50 (130 mg) as a light brown solid, which was directly taken for next reaction without further purification. LCMS (ESI): m/z 605.2 [M+H$^+$]; purity~75.1%.

Example 74

(E)-3-(4-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperazin-1-yl) propyl nitrate (3f)

To a stirred solution of crude 3-(4-((3-(6-formyl-5-methyl-4-oxo-7-propyl-4,5-dihydro-3H-pyrrolo[3,2-d]pyrimidin-2-yl)-4-propoxyphenyl)sulfonyl)piperazin-1-yl)
propyl nitrate 50 (130 mg) in ethanol (15.6 mL) was added
50% aqueous hydroxylamine solution (2.6 mL) at room
temperature and heated to 50° C. for 5 h. After completion
of reaction (monitored by TLC), the reaction was concentrated under reduced pressure. The resultant residue was
diluted in water (10 mL) and extracted with ethyl acetate
(3×10 mL). The combined organic layer was washed with
brine (20 mL), dried over anhydrous Na$_2$SO$_4$ and concentrated under reduced pressure. The crude product was purified by preparative HPLC (XBrige C18 column, 50-100%
gradient acetonitrile in water) and the pure fractions were
lyophilized to afford the title compound 3f (13.6 mg) as a
white solid. $^1$H NMR (400 MHz, DMSO-d$_6$) δ ppm 11.81
(br s, 1H; D$_2$O exchangeable), 11.63 (s, 1H; D$_2$O exchangeable), 8.30 (s, 1H), 7.88 (s, 1H), 7.83 (d, J=8.8 Hz, 1H), 7.39
(d, J=8.8 Hz, 1H), 4.48 (t, J=6.6 Hz, 2H), 4.18 (s, 3H),
4.10-4.04 (m, 2H), 2.94-2.89 (m, 4H), 2.73-2.68 (m, 2H),
2.47-2.41 (m, 4H), 2.38-2.35 (m, 2H), 1.81-1.72 (m, 4H),
1.61-1.55 (m, 2H), 0.97 (t, J=7.4 Hz, 3H), 0.92 (t, J=7.4 Hz,
3H); LCMS (ESI): m/z 618.1 [M+H$^+$]; purity~97.2%.

Scheme 40

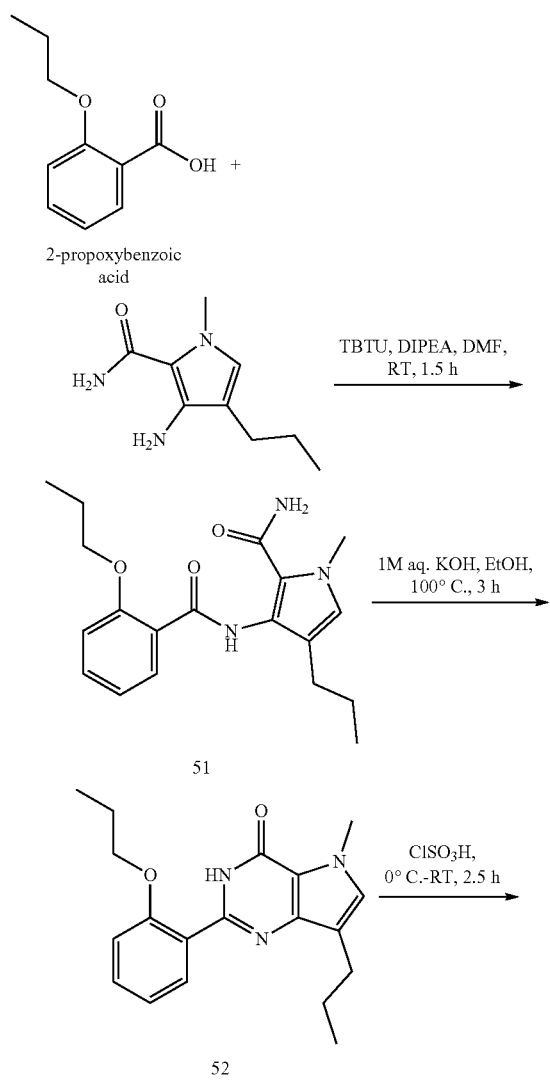

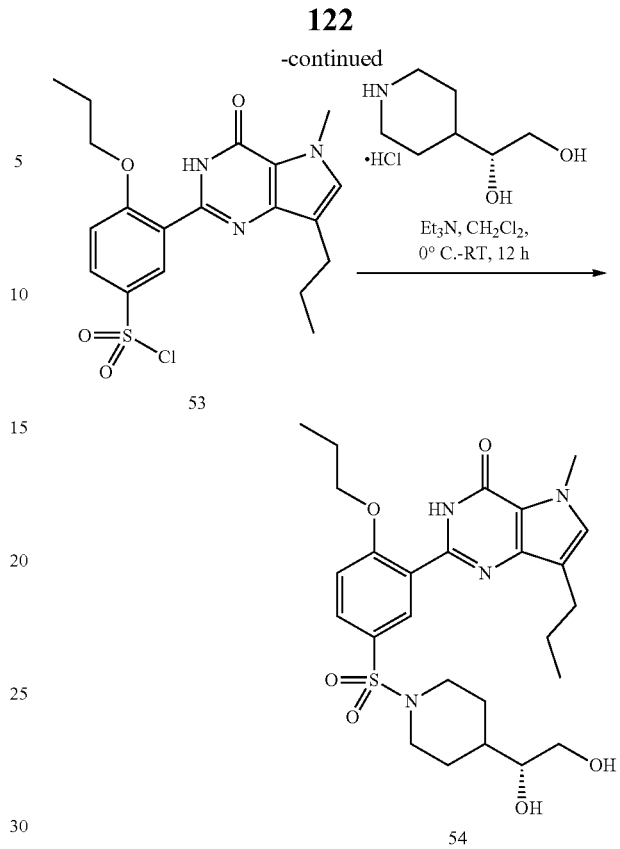

Example 75

1-methyl-3-(2-propoxybenzamido)-4-propyl-1H-pyrrole-2-carboxamide (51)

To a stirred solution of 2-propoxybenzoic acid (5.0 g,
27.75 mmol) in DMF (25 mL) was added diisopropyl
ethylamine (24 mL, 138.7 mmol) and TBTU (17.9 g, 55.5
mmol) at cooled temperature (~15° C.). Reaction was stirred
at same temperature for 30 min and 3-amino-1-methyl-4-propyl-1H-pyrrole-2-carboxamide (WO2001060825 A1)
(5.03 g, 27.7 mmol) was added in portions wise for 5 min.
The reaction was allowed to stir at room temperature for 1.5
h. After completion of reaction (monitored by TLC), the
reaction was quenched with chilled water (250 mL) and
extracted with ethyl acetate (3×100 mL). The combined
organic layer was washed with brine (3×100 mL), dried over
anhydrous Na$_2$SO$_4$ and concentrated under reduced pressure. The crude product was triturated with methyl tert-butyl
ether (90 mL) at room temperature for 1 h. The solid was
filtered, washed with n-hexane (30 mL) and dried under
vacuum to afford the title compound 51 (7.3 g; 76% yield)
as an off-white solid. 1H NMR (300 MHz, DMSO-d$_6$) δ ppm
9.39 (br s, 1H), 7.60 (dd, J=7.5, 1.7 Hz, 1H), 7.53-7.42 (m,
1H), 7.28-6.90 (m, 4H), 6.70 (s, 1H), 4.09 (t, J=6.6 Hz, 2H),
3.74 (s, 3H), 2.26 (t, J=7.7 Hz, 2H), 1.85-1.73 (m, 2H),
1.54-1.42 (m, 2H), 0.97 (t, J=7.3 Hz, 3H), 0.87 (t, J=7.3 Hz,
3H); LCMS (ESI): m/z 344.3 [M+H$^+$]; purity~99%.

Example 76

5-methyl-2-(2-propoxyphenyl)-7-propyl-3,5-di-hydro-4H-pyrrolo[3,2-d]pyrimidin-4-one (52)

To a stirred solution of 1-methyl-3-(2-propoxyben-zamido)-4-propyl-1H-pyrrole-2-carboxamide 51 (7.3 g, 21.26 mmol) in ethanol (117 mL) was added 1M aqueous KOH solution (102 mL) at room temperature. The reaction vessel was capped and heated to 100° C. for 3 h. After completion of reaction (monitored by TLC), the reaction was cooled to room temperature and concentrated under reduced pressure. The resultant residue was diluted in water (50 mL) and extracted with ethyl acetate (3×100 mL). The combined organic layer was washed with brine (100 mL), dried over anhydrous $Na_2SO_4$ and concentrated under reduced pressure. The crude product was triturated with n-hexane (70 mL) at room temperature for 1 h, filtered the solid and dried under vacuum to afford the title compound 52 (5.5 g, 78% yield) as an off-white solid. $^1$H NMR (300 MHz, DMSO-$d_6$) δ ppm 11.45 (br s, 1H), 7.75 (dd, J=7.7, 1.5 Hz, 1H), 7.54-7.38 (m, 1H), 7.20 (s, 1H), 7.15 (d, J=8.4 Hz, 1H), 7.06 (t, J=7.5 Hz, 1H), 4.05 (t, J=6.2 Hz, 2H), 3.97 (s, 3H), 2.59-2.54 (m, 2H), 1.82-1.56 (m, 4H), 0.98 (t, J=7.5 Hz, 3H), 0.92 (t, J=7.3 Hz, 3H); LCMS (ESI): m/z 326.3 [M+H$^+$]; purity~98.1%.

Example 77

3-(5-methyl-4-oxo-7-propyl-4,5-dihydro-3H-pyrrolo[3,2-d]pyrimidin-2-yl)-4-propoxybenzene sulfonyl chloride (53)

To a stirred and cooled chlorosulfonic acid (6.2 mL) in an ice bath (0-5° C.) under nitrogen atmosphere was added portion wise 5-methyl-2-(2-propoxyphenyl)-7-propyl-3,5-dihydro-4H-pyrrolo[3,2-d]pyrimidin-4-one 52 (1.5 g, 4.61 mmol), and the reaction mixture was stirred at same temperature for 1 h. The reaction was warmed to room temperature gradually and stirring was continued for additional 1.5 h. Resulting mixture was transferred drop wise to the well stirred mixture of chloroform (50 mL) and ice (50 g), and was extracted with 5% methanol in chloroform (2×100 mL). The combined organic layer was dried over anhydrous $Na_2SO_4$ and concentrated under reduced pressure at below 30° C. under inert atmosphere to afford the crude product as a pale yellow semi solid. The crude product was solidified by dissolving in chloroform (20 mL) followed by diluting with diethyl ether (30 mL) and n-hexane (110 mL). The solid precipitated was filtered under inert atmosphere and dried under vacuum to afford the title compound 53 (1.7 g, 79% yield) as an off-white solid. $^1$H NMR (300 MHz, DMSO-$d_6$) δ ppm 13.44 (br s, 1H), 7.94 (d, J=1.8 Hz, 1H), 7.85-7.81 (m, 1H), 7.53-7.44 (m, 1H), 7.23-7.18 (m, 1H), 4.14-3.94 (m, 5H), 2.63-2.58 (m, 2H), 1.77-1.49 (m, 4H), 0.96-0.87 (m, 6H); LCMS (ESI): m/z 424.3 [M+H$^+$]; purity~90.9%.

Example 78

(R)-2-(5-((4-(1,2-dihydroxyethyl)piperidin-1-yl)sulfonyl)-2-propoxyphenyl)-5-methyl-7-propyl-3,5-dihydro-4H-pyrrolo[3,2-d]pyrimidin-4-one (54)

To a stirred solution of 3-(5-methyl-4-oxo-7-propyl-4,5-dihydro-3H-pyrrolo[3,2-d]pyrimidin-2-yl)-4-propoxybenzenesulfonyl chloride 53 (500 mg, 1.2 mmol) and (R)-1-(piperidin-4-yl)ethane-1,2-diol hydrochloride (WO2005026145 A1) (262 mg, 1.44 mmol) in dichloromethane (40 mL) was added triethylamine (0.9 mL, 6.0 mmol) drop wise at 0° C. under argon atmosphere. The reaction mixture was allowed to stir at room temperature for 12 h. After completion of reaction (monitored by TLC & LCMS analysis), the reaction mixture was washed with water (20 mL) and brine (20 mL). The organic layer was dried over anhydrous $Na_2SO_4$ and concentrated under reduced pressure. The obtained crude product was purified by silica gel column chromatography (Grace System) by eluting with 15% of 30% methanol in dichloromethane and dichloromethane to afford the title compound 54 (380 mg, purity~93%) as an off-white solid. Analytically pure compound was obtained by trituration of 80 mg material in diethyl ether (3 mL) for 1 h. The solid was filtered and dried under vacuum to afford 60 mg of the title compound with >99% purity as a white solid. $^1$H NMR (400 MHz, DMSO-$d_6$) δ ppm 11.64 (s, 1H; $D_2O$ exchangeable), 7.89 (d, J=2.4 Hz, 1H), 7.79 (dd, J=8.8, 2.4 Hz, 1H), 7.36 (d, J=8.8 Hz, 1H), 7.22 (s, 1H), 4.43 (d, J=4.9 Hz, 1H; $D_2O$ exchangeable), 4.39 (t, J=5.6 Hz, 1H; $D_2O$ exchangeable), 4.12 (t, J=6.1 Hz, 2H), 3.98 (s, 3H), 3.68-3.63 (m, 2H), 3.31-3.23 (m, 2H), 3.22-3.16 (m, 1H), 2.58-2.54 (m, 2H), 2.23-2.10 (m, 2H), 1.80-1.69 (m, 3H), 1.68-1.56 (m, 3H), 1.42-1.25 (m, 3H), 0.96 (t, J=7.6 Hz, 3H), 0.92 (t, J=7.3 Hz, 3H); LCMS (ESI): m/z 533.5 [M+H$^+$]; purity~99.3%; SOR: −1.2° (c=0.5% in methanol); ee=59.84% by chiral SFC.

Scheme 41

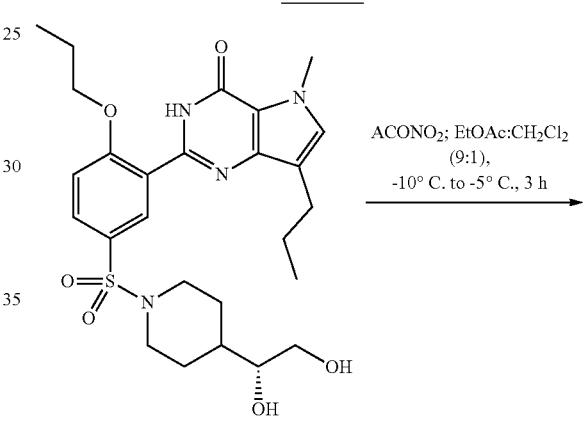

ACONO$_2$; EtOAc:CH$_2$Cl$_2$ (9:1), −10° C. to −5° C., 3 h

54

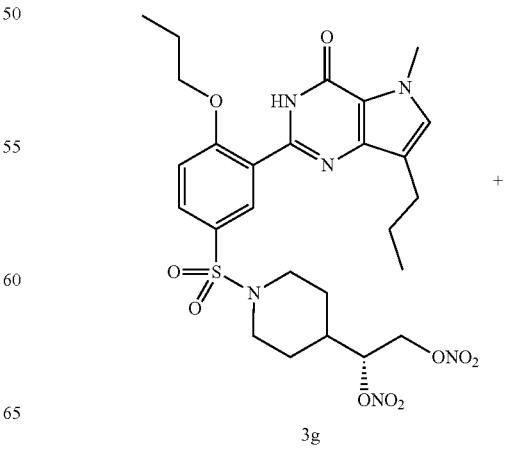

3g

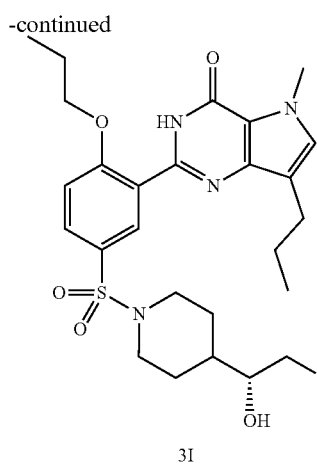

Example 79

(R)-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (3g) and (R)-2-hydroxy-2-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (3l)

To a stirred solution of (R)-2-(5-((4-(1,2-dihydroxyethyl)piperidin-1-yl)sulfonyl)-2-propoxyphenyl)-5-methyl-7-propyl-3,5-dihydro-4H-pyrrolo[3,2-d]pyrimidin-4-one 54 (350 mg, 0.66 mmol) in ethyl acetate (16.0 mL) and dichloromethane (1.8 mL) was added freshly prepared solution of acetyl nitrate (0.84 mL; 9.9 mmol) [(acetyl nitrate was prepared separately by addition of fuming HNO₃ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 10 min under argon atmosphere. The reaction was stirred at −5° C. for 3 h. After completion of reaction (monitored by TLC), the reaction mixture was quenched with saturated NaHCO₃ solution (100 mL) at 0° C. and extracted with ethyl acetate (3×25 mL). The combined organic layer was washed with brine (40 mL), dried over anhydrous Na₂SO₄ and concentrated under reduced pressure. The crude mixture was purified by reverse phase column chromatography (C18 column, Grace system) by eluting with 60-65% gradient acetonitrile with water to afford the title compound 3g (31.6 mg) as pale yellow solid and mono-nitrate 3l (25.2 mg) as a pale yellow solid.

3g:
¹H NMR (400 MHz, DMSO-d₆) δ ppm 11.60 (s, 1H; D₂O exchangeable), 7.93 (d, J=2.2 Hz, 1H), 7.80 (dd, J=8.8, 2.2 Hz, 1H), 7.36 (d, J=8.8 Hz, 1H), 7.21 (s, 1H), 5.33-5.30 (m, 1H), 4.95-4.92 (m, 1H), 4.73-4.68 (m, 1H), 4.12 (t, J=6.1 Hz, 2H), 3.98 (s, 3H), 3.73-3.67 (m, 2H), 2.58-2.55 (m, 2H), 2.31-2.19 (m, 2H), 1.84-1.71 (m, 5H), 1.68-1.59 (m, 2H), 1.49-1.35 (m, 2H), 0.97 (t, J=7.3 Hz, 3H), 0.92 (t, J=7.3 Hz, 3H); LCMS (ESI): m/z 623.3 [M+H⁺]; purity~96.9%.

3l:
¹H NMR (400 MHz, DMSO-d₆) δ ppm 11.60 (s, 1H; D₂O exchangeable), 7.92 (d, J=2.4 Hz, 1H), 7.79 (dd, J=8.8, 2.4 Hz, 1H), 7.36 (d, J=8.8 Hz, 1H), 7.21 (s, 1H), 5.20 (d, J=5.4 Hz, 1H; D₂O exchangeable), 4.52 (dd, J=11.0, 3.2 Hz, 1H), 4.37 (dd, J=11.0, 7.1 Hz, 1H), 4.12 (t, J=6.4 Hz, 2H), 3.98 (s, 3H), 3.69-3.64 (m, 2H), 3.55-3.50 (m, 1H), 2.58-2.55 (m, 2H), 2.24-2.18 (m, 2H), 1.80-1.72 (m, 3H), 1.66-1.61 (m, 3H), 1.39-1.31 (m, 3H), 0.97 (t, J=7.3 Hz, 3H), 0.92 (t, J=7.3 Hz, 3H); LCMS (ESI): m/z 578.3 [M+H⁺]; purity~95.8%.

Scheme 42

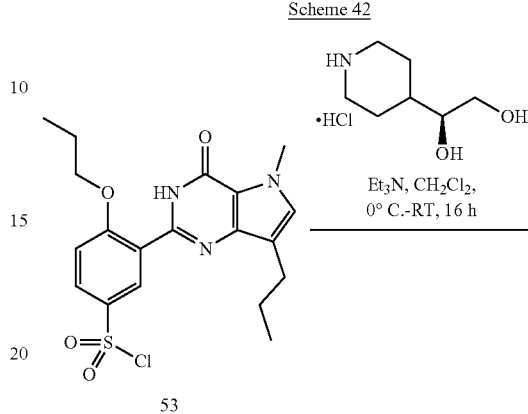

Example 80

(S)-2-(5-((4-(1,2-dihydroxyethyl)piperidin-1-yl)sulfonyl)-2-propoxyphenyl)-5-methyl-7-propyl-3,5-dihydro-4H-pyrrolo[3,2-d]pyrimidin-4-one (55)

To a stirred solution of 3-(5-methyl-4-oxo-7-propyl-4,5-dihydro-3H-pyrrolo[3,2-d]pyrimidin-2-yl)-4-propoxybenzenesulfonyl chloride 53 (500 mg, 1.18 mmol) and (S)-1-(piperidin-4-yl)ethane-1,2-diol hydrochloride (WO2005026145 A1) (321 mg, 1.76 mmol) in dichloromethane (40 mL) was added triethylamine (0.84 mL, 5.89 mmol) drop wise at 0° C. under argon atmosphere. The reaction mixture was allowed to stir at room temperature for 16 h. After completion of reaction (monitored by TLC & LCMS analysis), the reaction mixture was washed with water (30 mL). The aqueous layer was extracted with dichloromethane (25 mL). The combined organic layer was dried over anhydrous Na₂SO₄ and concentrated under reduced pressure. The obtained crude product was purified by reverse phase column chromatography (Grace System) by eluting with 40-50% gradient acetonitrile with water. The pure fractions were concentrated under vacuum to afford the title compound 55 (44.2 mg) as a white solid. ¹H NMR (400 MHz, DMSO-d₆) δ ppm 11.60 (s, 1H; D₂O exchangeable), 7.89 (d, J=2.4 Hz, 1H), 7.79 (dd, J=8.8, 2.4 Hz, 1H), 7.36 (d, J=8.8 Hz, 1H), 7.22 (s, 1H), 4.40 (d, J=4.9 Hz, 1H; D$_2$O exchangeable), 4.36 (t, J=5.6 Hz, 1H; D$_2$O exchangeable), 4.12 (t, J=6.3 Hz, 2H), 3.98 (s, 3H), 3.68-3.63 (m, 2H), 3.31-3.23 (m, 2H), 3.22-3.16 (m, 1H), 2.58-2.54 (m, 2H), 2.22-2.11 (m, 2H), 1.80-1.69 (m, 3H), 1.68-1.56 (m, 3H), 1.42-1.25 (m, 3H), 0.96 (t, J=7.6 Hz, 3H), 0.92 (t, J=7.3 Hz, 3H); LCMS (ESI): m/z 533.3 [M+H$^+$]; purity~99.1%; ee=50.25% by chiral SFC.

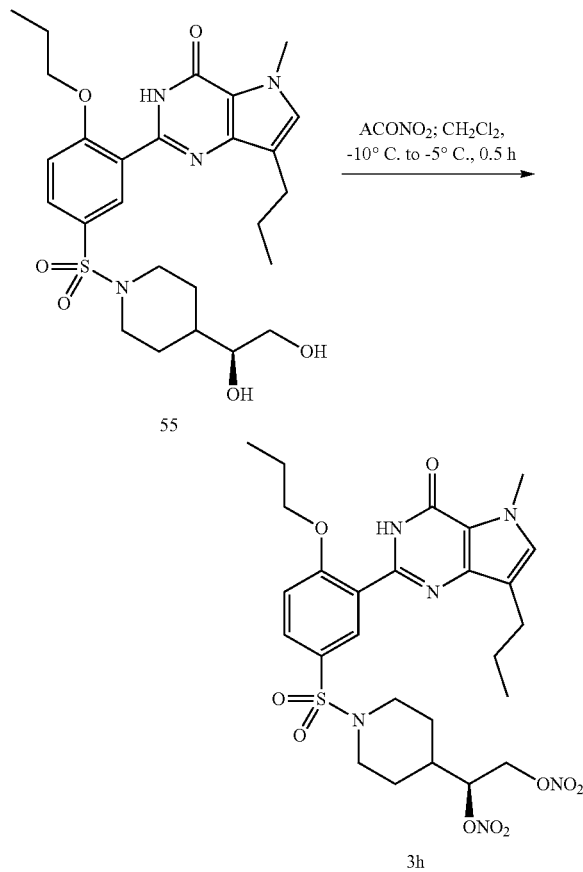

Example 81

(S)-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (3h)

To a stirred solution of (S)-2-(5-((4-(1,2-dihydroxyethyl)piperidin-1-yl)sulfonyl)-2-propoxyphenyl)-5-methyl-7-propyl-3,5-dihydro-4H-pyrrolo[3,2-d]pyrimidin-4-one 55 (160 mg, 0.30 mmol) in dichloromethane (8.0 mL) was added freshly prepared solution of acetyl nitrate (0.38 mL; 4.50 mmol) [(acetyl nitrate was prepared separately by addition of fuming HNO$_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 10 min under argon atmosphere. The reaction was stirred at −5° C. for 30 min. After completion of reaction (monitored by TLC and LCMS analysis), the reaction mixture was quenched with saturated NaHCO$_3$ solution (20 mL) at 0° C. and stirred for 1 h. The resultant solution was extracted with dichloromethane (3×20 mL). The combined organic layer was washed with brine (40 mL), dried over anhydrous Na$_2$SO$_4$ and concentrated under reduced pressure. The crude product was purified by reverse phase column chromatography (C18 column, Grace System) by eluting with 60-70% gradient acetonitrile with water. The pure fractions were lyophilized to afford the title compound 3h (40 mg, 21% yield) as a white solid. $^1$H NMR (300 MHz, DMSO-d$_6$) δ ppm 11.64 (s, 1H; D$_2$O exchangeable), 7.92 (d, J=2.2 Hz, 1H), 7.80 (dd, J=8.8, 2.2 Hz, 1H), 7.36 (d, J=8.8 Hz, 1H), 7.21 (s, 1H), 5.33-5.30 (m, 1H), 4.97-4.92 (m, 1H), 4.73-4.68 (m, 1H), 4.12 (t, J=6.2 Hz, 2H), 3.98 (s, 3H), 3.73-3.67 (m, 2H), 2.58-2.55 (m, 2H), 2.30-2.19 (m, 2H), 1.82-1.70 (m, 5H), 1.68-1.59 (m, 2H), 1.49-1.35 (m, 2H), 0.97 (t, J=7.3 Hz, 3H), 0.92 (t, J=7.3 Hz, 3H); LCMS (ESI): m/z 623.4 [M+H$^+$]; purity~98.5%.

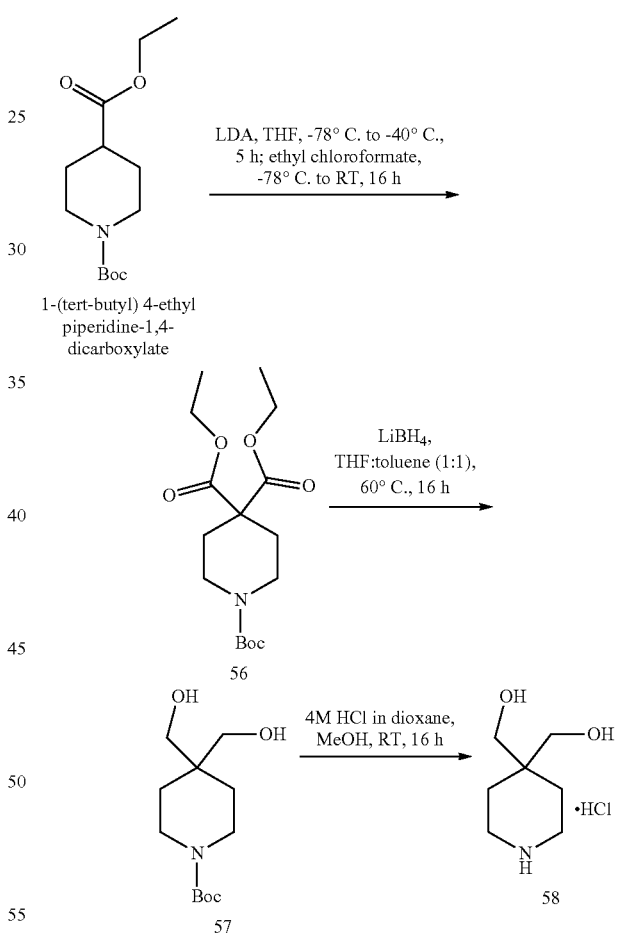

Example 82

1-(tert-butyl) 4,4-diethyl piperidine-1,4,4-tricarboxylate (56)

To a stirred solution of 1-(tert-butyl) 4-ethyl piperidine-1,4-dicarboxylate (5.0 g, 19.45 mmol) in THF (50 mL) was added lithium diisopropylamide (2M solution in THF; 28.66 mL, 57.32 mmol) drop wise at −78° C. under inert atmosphere for 30 min. The reaction was stirred at −78° C. for 2 h then at −40° C. for 3 h. The solution was cooled back to −78° C. and a solution of ethyl chloroformate (6.5 mL, 68.28 mmol) in THF (40 mL) was added. The resultant solution was allowed to warm to room temperature for 16 h. The reaction was quenched with 10% aqueous ammonium chloride solution (100 mL) and the resulting solution was extracted with ethyl acetate (3×100 mL). The combined the organic layers and dried over anhydrous Na$_2$SO$_4$ and concentrated under reduced pressure to afford crude title compound 56 (10.1 g) as a brown liquid, which was directly taken for next reaction without purification. GC-FID: m/z 329.2 [M$^+$]; purity~55%.

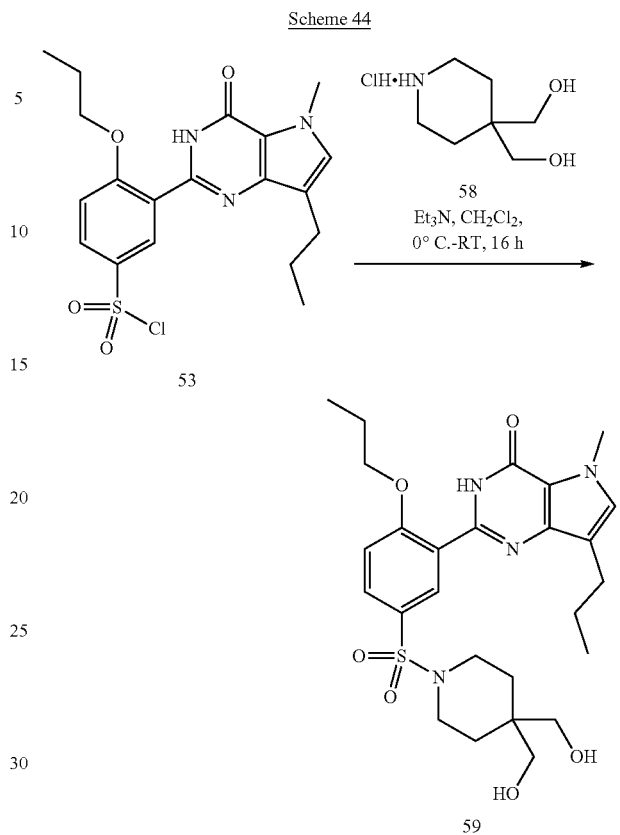

Scheme 44

Example 83 tert-butyl 4,4-bis(hydroxymethyl)piperidine-1-carboxylate (57): In analogy as described in WO2005026145 A1, to a stirred solution of crude 1-(tert-butyl) 4,4-diethyl piperidine-1,4,4-tricarboxylate 56 (10.0 g) in toluene:THF (1:1; 200 mL) was added lithium borohydride (2.27 g, 104.4 mmol) at room temperature under inert atmosphere. The reaction was heated to 60° C. for 16 h. The reaction was cooled to 0° C. and quenched with saturated ammonium chloride solution (200 mL). The resultant solution was adjusted to pH~12 with saturated NaHCO$_3$ solution (100 mL) and layers were separated. The aqueous layer was extracted into ethyl acetate (3×200 mL). The combined organic layer was washed with water (500 mL), dried over anhydrous Na$_2$SO$_4$ and concentrated under reduced pressure. The crude product was purified by trituration with pentane (200 mL) at room temperature for 1 h. The solid formed was filtered and washed with n-pentane (200 mL) and dried under vacuum to afford 57 (2.8 g, 59% in two steps) as a white solid. $^1$H NMR (300 MHz, CDCl$_3$) δ ppm 3.66 (s, 4H), 3.44-3.37 (m, 4H), 2.40 (br s, 2H), 1.47-1.45 (m, 13H).

Example 84

Piperidine-4,4-diyldimethanol hydrochloride (58)

In analogy as described in WO2006043490 A1, to a stirred solution of tert-butyl 4,4-bis(hydroxymethyl)piperidine-1-carboxylate 57 (1.0 g; 4.08 mmol) in methanol (4 mL) was added 4M HCl in 1,4-dioxane solution (4 mL) at 0° C. The reaction was allowed to stir at room temperature for 16 h. After completion of reaction (checked by $^1$H NMR analysis), the reaction mixture was concentrated under reduced pressure. The crude product was purified by trituration with n-pentane (20 mL) at room temperature for 1 h and filtered the solid, washed again with n-pentane (10 mL) and dried under vacuum to afford 58 (0.6 g, quantitative) as a white solid. 1H NMR (300 MHz, DMSO-d$_6$) δ ppm 8.67 (br s, 2H), 4.39 (br s, 2H), 3.43-3.32 (m, 4H), 3.03-2.97 (m, 4H), 1.54-1.52 (m, 4H); MS (ESI): m/z 146.3 [M+H$^+$].

Example 85

2-(5-((4,4-bis(hydroxymethyl)piperidin-1-yl)sulfonyl)-2-propoxyphenyl)-5-methyl-7-propyl-3,5-dihydro-4H-pyrrolo[3,2-d]pyrimidin-4-one (59)

To a stirred solution of piperidine-4,4-diyldimethanol hydrochloride 58 (206 mg, 1.41 mmol) in dichloromethane (10 mL), was added a solution of 3-(5-methyl-4-oxo-7-propyl-4,5-dihydro-3H-pyrrolo[3,2-d]pyrimidin-2-yl)-4-propoxybenzenesulfonyl chloride 53 (500 mg, 1.18 mmol) in dichloromethane (10 mL) at 0° C. To this, triethylamine (0.81 mL, 5.90 mmol) was added drop wise at 0° C. under argon atmosphere. The reaction was allowed to stir at room temperature for 16 h. After completion of reaction (monitored by TLC & LCMS analysis), the reaction mixture was diluted with dichloromethane (20 mL) and washed with water (20 mL), brine (20 mL), dried over anhydrous Na$_2$SO$_4$ and concentrated under reduced pressure. The obtained crude product was purified by silica gel column chromatography (Grace System) by eluting with 5-10% gradient 10% methanol in dichloromethane and dichloromethane to afford the title compound 59 (335 mg, 49% yield) as a white solid. 1H NMR (400 MHz, DMSO-d$_6$) δ ppm 11.67 (s, 1H; D$_2$O exchangeable), 7.91 (d, J=2.4 Hz, 1H), 7.80 (dd, J=8.8, 2.4 Hz, 1H), 7.36 (d, J=8.8 Hz, 1H), 7.22 (s, 1H), 4.39 (t, J=5.4 Hz, 2H; D$_2$O exchangeable), 4.12 (t, J=6.4 Hz, 2H), 3.98 (s, 3H), 3.16 (d, J=5.4 Hz, 4H), 2.93-2.89 (m, 4H), 2.58-2.54 (m, 2H), 1.79-1.70 (m, 2H), 1.68-1.58 (m, 2H), 1.46-1.41 (m, 4H), 0.97 (t, J=7.3 Hz, 3H), 0.92 (t, J=7.3 Hz, 3H); LCMS(ESI): m/z 533.2 [M+H]$^+$; purity~92.4%.

Scheme 45

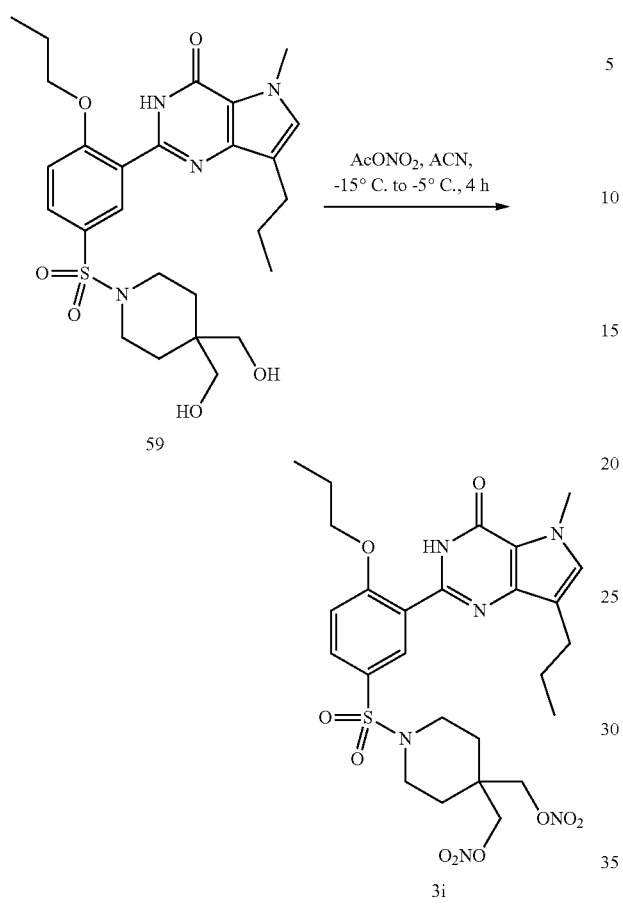

Example 86

(1-((3-(5-methyl-4-oxo-7-propyl-4,5-dihydro-3H-pyrrolo[3,2-d]pyrimidin-2-yl)-4-propoxyphenyl)sulfonyl)piperidine-4,4-diyl)bis(methylene) dinitrate (3i)

To a stirred solution of 2-(5-((4,4-bis(hydroxymethyl)piperidin-1-yl)sulfonyl)-2-propoxyphenyl)-5-methyl-7-propyl-3,5-dihydro-4H-pyrrolo[3,2-d]pyrimidin-4-one 59 (200 mg, 0.37 mmol) in acetonitrile (6 mL) was added a solution of freshly prepared acetyl nitrate (0.31 mL; 3.75 mmol) [(acetyl nitrate was prepared separately by addition of fuming $HNO_3$ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −15° C. for 30 min under argon atmosphere. The reaction was stirred at −10° C. to −5° C. for 4 h. After completion of reaction (monitored by TLC), the reaction was quenched with saturated $NaHCO_3$ solution (10 mL) at 0° C. and extracted with ethyl acetate (3×30 mL). The combined organic layer was washed with brine (30 mL), dried over anhydrous $Na_2SO_4$ and concentrated under reduced pressure. The crude product was silica gel column chromatography (Grace System) by eluting with 2-8% gradient 10% methanol in dichloromethane and dichloromethane to afford the title compound 3i (53 mg; 21% yield) as a pale yellow solid. 1H NMR (400 MHz, DMSO-$d_6$) δ ppm 11.63 (s, 1H; $D_2O$ exchangeable), 7.96 (d, J=2.0 Hz, 1H), 7.82 (dd, J=8.8, 2.0 Hz, 1H), 7.36 (d, J=8.8 Hz, 1H), 7.22 (s, 1H), 4.43 (s, 4H), 4.13 (t, J=6.4 Hz, 2H), 3.98 (s, 3H), 3.10-3.06 (m, 4H), 2.59-2.45 (m, 2H), 1.80-1.71 (m, 2H), 1.69-1.58 (m, 6H), 0.97 (t, J=7.3 Hz, 3H), 0.92 (t, J=7.3 Hz, 3H); LCMS (ESI): m/z 623.2 [M+H$^+$]; purity~97.5%.

Scheme 46

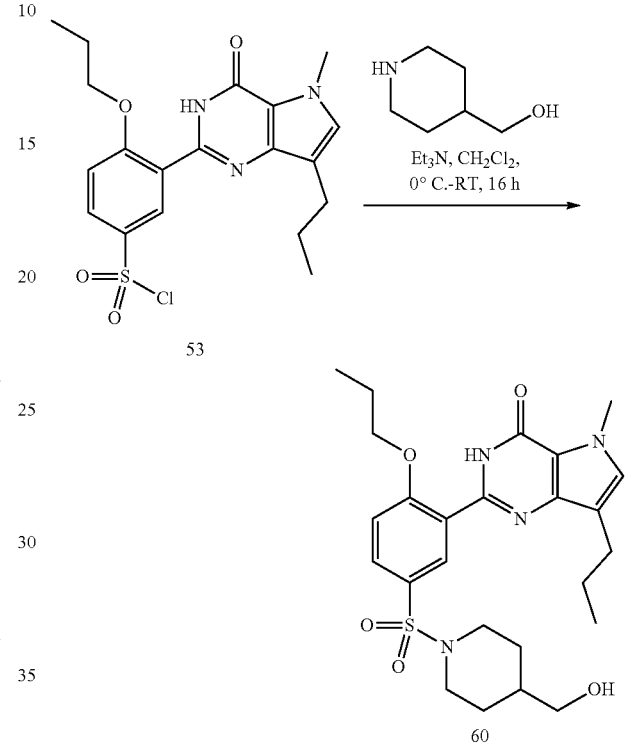

Example 87

2-(5-((4-(hydroxymethyl)piperidin-1-yl)sulfonyl)-2-propoxyphenyl)-5-methyl-7-propyl-3,5-dihydro-4H-pyrrolo[3,2-d]pyrimidin-4-one (60)

To a stirred solution of 3-(5-methyl-4-oxo-7-propyl-4,5-dihydro-3H-pyrrolo[3,2-d]pyrimidin-2-yl)-4-propoxybenzene-1-sulfonyl chloride 53 (100 mg, 0.23 mmol) and piperidin-4-ylmethanol (32.6 mg, 0.28 mmol) in dichloromethane (10 mL) was added triethylamine (0.164 mL, 1.18 mmol) at 0° C. in drop wise under argon atmosphere. The reaction mixture was stirred at room temperature for 16 h. After completion of reaction (monitored by TLC), the reaction mixture was diluted with dichloromethane (5 mL) and washed with water (2×10 mL). The organic layer was dried over anhydrous $Na_2SO_4$ and evaporated. The crude product was purified by silica gel column chromatography (Grace System) by eluting with 10-15% gradient 10% methanol in dichloromethane and dichloromethane to afford the title compound 60 (35.2 mg, 28% yield) as a white solid. $^1$H NMR (400 MHz, DMSO-$d_6$) δ ppm 11.66 (s, 1H; $D_2O$ exchangeable), 7.90 (d, J=2.0 Hz, 1H), 7.80 (dd, J=8.8, 2.0 Hz, 1H), 7.36 (d, J=8.8 Hz, 1H), 7.22 (s, 1H), 4.49 (t, J=5.1 Hz, 1H; $D_2O$ exchangeable), 4.12 (t, J=6.4 Hz, 2H), 3.98 (s, 3H), 3.67-3.62 (m, 2H), 3.23-3.19 (m, 2H), 2.58-2.54 (m, 2H), 2.27-2.19 (m, 2H), 1.78-1.58 (m, 6H), 1.36-1.23 (m, 1H), 1.21-1.10 (m, 2H), 0.97 (t, J=7.3 Hz, 3H), 0.92 (t, J=7.3 Hz, 3H); LCMS (ESI): m/z 503.3 [M+H]⁺; purity~97.7%.

Scheme 47

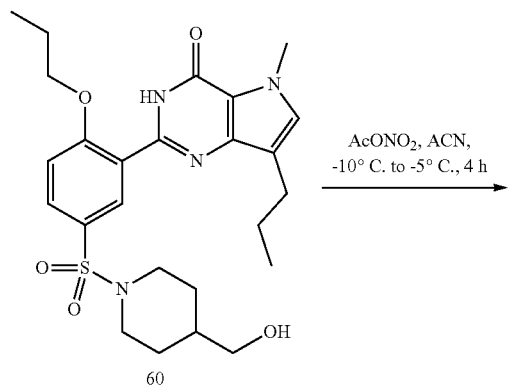

Example 88

(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)methyl nitrate (3k)

To a stirred solution of 2-(5-((4-(hydroxymethyl)piperidin-1-yl)sulfonyl)-2-propoxyphenyl)-5-methyl-7-propyl-3,5-dihydro-4H-pyrrolo[3,2-d]pyrimidin-4-one 60 (200 mg, 0.39 mmol) in acetonitrile (6 mL) was added a solution of freshly prepared acetyl nitrate (0.23 mL; 2.78 mmol) [(acetyl nitrate was prepared separately by addition of fuming HNO₃ (1.1 mL, 25.5 mmol) drop wise in to acetic anhydride (2.5 mL, 26.5 mmol) slowly at −15° C. for 30 min under argon atmosphere (Note: temperature should not be raised to 0° C.))] drop wise at −10° C. for 30 min under argon atmosphere. The reaction was stirred at −10° C. to −5° C. for 4 h. After completion of reaction (monitored by TLC), the reaction was quenched with saturated NaHCO₃ solution (10 mL) at 0° C. and extracted with ethyl acetate (3×30 mL). The combined organic layer was washed with brine (30 mL), dried over anhydrous Na₂SO₄ and concentrated under reduced pressure. The crude product was purified by reverse phase column chromatography (C18 column; Grace System) by eluting with 50-60% gradient acetonitrile with water. Pure fractions were lyophilized to afford the title compound 3k (19.5 mg) as a white solid. 1H NMR (400 MHz, DMSO-d₆) δ ppm 11.61 (s, 1H; D₂O exchangeable), 7.93 (d, J=2.4 Hz, 1H), 7.80 (dd, J=8.8, 2.4 Hz, 1H), 7.36 (d, J=8.8 Hz, 1H), 7.21 (s, 1H), 4.38 (d, J=6.4 Hz, 2H), 4.12 (t, J=6.1 Hz, 2H), 3.98 (s, 3H), 3.69-3.64 (m, 2H), 2.58-2.54 (m, 2H), 2.32-2.27 (m, 2H), 1.79-1.71 (m, 5H), 1.68-1.59 (m, 2H), 1.37-1.26 (m, 2H), 0.97 (t, J=7.3 Hz, 3H), 0.92 (t, J=7.3 Hz, 3H); LCMS (ESI): m/z 548.5 [M+H⁺]; purity~99.7%.

Scheme 48

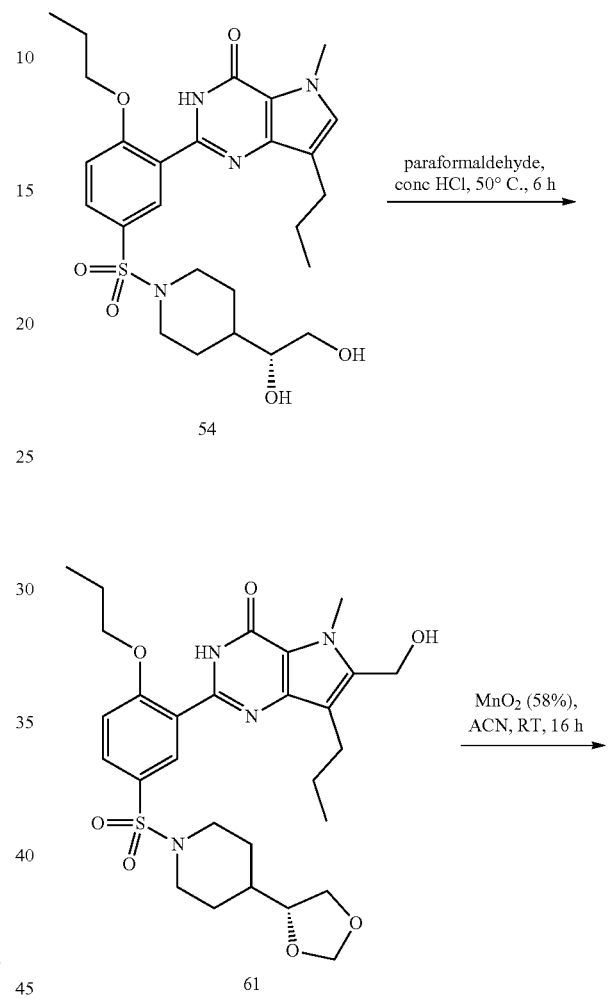

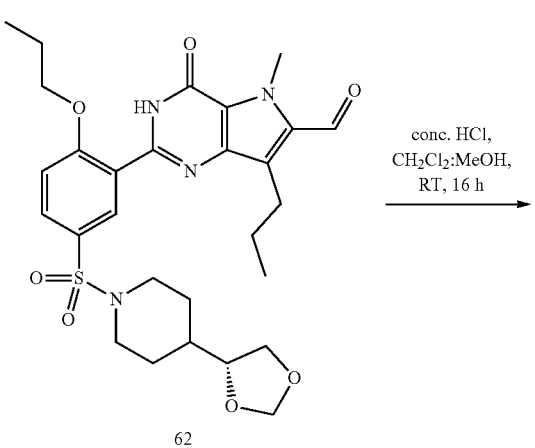

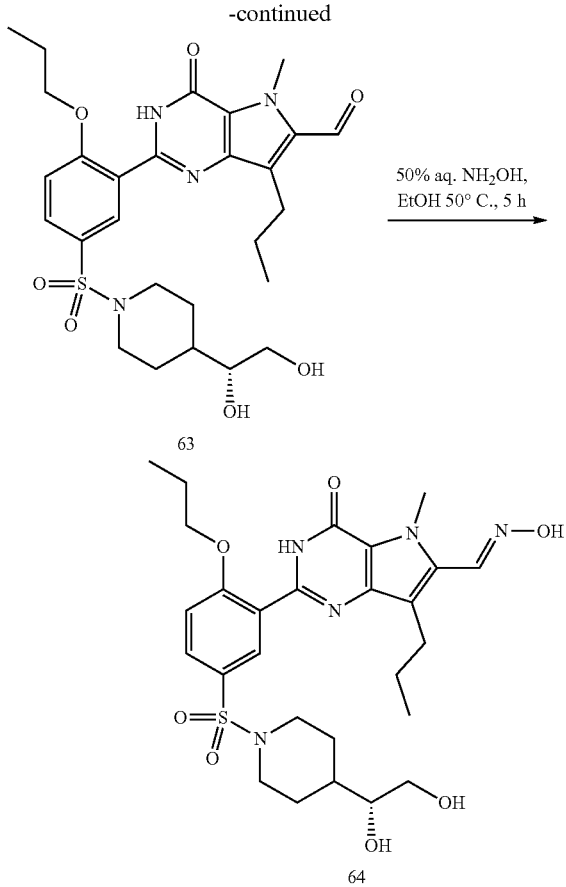

3.45 (m, 1H), 2.63-2.57 (m, 2H), 2.27-2.20 (m, 2H), 1.87-1.83 (m, 1H), 1.77-1.70 (m, 2H), 1.61-1.54 (m, 3H), 1.36-1.22 (m, 3H), 0.96 (t, J=6.9 Hz, 3H), 0.88 (t, J=6.9 Hz, 3H); LCMS (ESI): m/z 575.40 [M+H$^+$]; purity~87.7%.

Example 90

(R)-2-(5-((4-(1,3-dioxolan-4-yl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde (62)

To a stirred solution of (R)-2-(5-((4-(1,3-dioxolan-4-yl)piperidin-1-yl)sulfonyl)-2-propoxyphenyl)-6-(hydroxymethyl)-5-methyl-7-propyl-3,5-dihydro-4H-pyrrolo[3,2-d]pyrimidin-4-one (61) (230 mg, 0.40 mmol) in CH$_3$CN (115 mL) was added activated MnO$_2$ (58% Mn; 1.05 g, 12 mmol) at room temperature and stirred for 16 h. After completion of reaction (monitored by LCMS), the reaction mixture was filtered through a Celite pad and washed with CH$_2$Cl$_2$ (300 mL). The filtrate was concentrated to afford the crude product. Note: Same reaction was repeated on 170 mg scale and both the crude products were combined and purified by silica gel column chromatography (100-200 mesh) by eluting with 1% of MeOH:CH$_2$Cl$_2$ to afford the title compound 62 (250 mg, ~58% yield) as a white solid. $^1$H NMR (300 MHz, DMSO-d$_6$) δ ppm 12.13 (s, 1H), 10.15 (s, 1H), 7.90-7.81 (m, 2H), 7.37 (d, J=8.8 Hz, 1H), 4.86 (s, 1H), 4.72 (s, 1H), 4.32 (s, 3H), 4.13-4.09 (m, 2H), 3.86-3.82 (m, 1H), 3.71-3.63 (m, 3H), 3.50-3.46 (m, 1H), 2.96-2.92 (m, 2H), 2.28-2.20 (m, 2H), 1.86-1.82 (m, 1H), 1.76-1.62 (m, 4H), 1.41-1.24 (m, 4H), 0.97-0.87 (m, 6H); LCMS (ESI): m/z 573.42 [M+H$^+$]; purity~92.6%.

Example 91

(R)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde (63)

To a stirred solution of (R)-2-(5-((4-(1,3-dioxolan-4-yl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde 62 (120 mg, 0.21 mmol) in MeOH:CH$_2$Cl$_2$ (1:2, 3.0 mL) was added concentrated HCl solution (35% aq.; 1.0 mL) at room temperature and stirred for 16 h. After completion of reaction (monitored by TLC), the reaction mixture was neutralized (pH~7-8) with saturated NaHCO$_3$ aqueous solution (20 mL). The resultant solution was extracted with CH$_2$Cl$_2$ (2×20 mL). The combined organic layer was dried over anhydrous Na$_2$SO$_4$ and concentrated under reduced pressure to afford the crude 63 (110 mg) as a semi solid, which was directly taken for next reaction without further purification. LCMS (ESI): m/z 561.47 [M+H$^+$]; purity~68%.

Example 92

(R,E)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde oxime (64)

To a stirred solution of (R)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carb- Example 89

(R)-2-(5-((4-(1,3-dioxolan-4-yl)piperidin-1-yl)sulfonyl)-2-propoxyphenyl)-6-(hydroxymethyl)-5-methyl-7-propyl-3,5-dihydro-4H-pyrrolo[3,2-d]pyrimidin-4-one (61)

To a stirred solution of (R)-2-(5-((4-(1,2-dihydroxyethyl)piperidin-1-yl)sulfonyl)-2-propoxyphenyl)-5-methyl-7-propyl-3,5-dihydro-4H-pyrrolo[3,2-d]pyrimidin-4-one (54) (500 mg, 0.94 mmol) in concentrated HCl solution (35% aq.; 5.0 mL), was added paraformaldehyde (250 mg, 0.5 w/w) at room temperature under inert atmosphere. Reaction mixture was heated to 50° C. and stirred for 6 h. After completion of reaction (monitored by LCMS), the reaction mixture was cooled to room temperature and pH was adjusted to 7.0-8.0 with saturated NaHCO$_3$ aqueous solution (100 mL). The resultant solution was extracted with 10% methanol in dichloromethane (3×100 mL). The combined the organic extracts were dried over anhydrous Na$_2$SO$_4$ and concentrated under reduced pressure. The crude product was purified by reverse phase column chromatography (C-18 column; Grace System) by eluting with 45-50% gradient acetonitrile with water to afford the title compound 61 (230 mg; 38% yield) as a white solid. $^1$H NMR (300 MHz, DMSO-d$_6$) δ ppm 11.72 (br s, 1H; D$_2$O exchangeable), 7.91 (d, J=2.1 Hz, 1H), 7.81 (dd, J=8.8, 2.1 Hz, 1H), 7.36 (d, J=8.8 Hz, 1H), 4.86 (s, 1H), 4.72 (s, 1H), 4.56 (s, 2H), 4.14-4.09 (m, 2H), 4.05 (s, 3H), 3.87 (br s, 1H; D$_2$O exchangeable), 3.86-3.81 (m, 1H), 3.71-3.64 (m, 3H), 3.49- aldehyde 63 (110 mg, ~68% pure) in ethanol (13.2 mL) was added 50% hydroxylamine in aqueous solution (1.7 mL) at room temperature under inert atmosphere. Reaction was heated to 50° C. and stirred for 5 h. After completion of reaction (monitored by LCMS), the reaction mixture was concentrated under reduced pressure. The resultant residue was diluted in ethyl acetate (30 mL), washed with water (10 mL), brine (10 mL) and dried over anhydrous Na₂SO₄ and concentrated under reduced pressure. The crude product was purified by reverse phase column chromatography (C-18 column; Grace System) by eluting with 30-35% gradient acetonitrile with water. The pure fractions were lyophilized to afford the title compound 64 (18.5 mg; 15% yield in two steps) as a white solid. $^1$H NMR (400 MHz, DMSO-d$_6$) δ ppm 11.77 (br s, 1H; D₂O exchangeable), 11.58 (br s, 1H; D₂O exchangeable), 8.33 (s, 1H), 7.88 (d, J=2.0 Hz, 1H), 7.80 (dd, J=8.8, 2.0 Hz, 1H), 7.34 (d, J=8.8 Hz, 1H), 4.43-4.36 (m, 2H; D₂O exchangeable), 4.17 (s, 3H), 4.13-4.09 (m, 2H), 3.65-3.62 (m, 2H), 3.27-3.18 (m, 3H), 2.75-2.71 (m, 2H), 2.22-2.14 (m, 2H), 1.77-1.69 (m, 3H), 1.61-1.53 (m, 3H), 1.41-1.27 (m, 3H), 0.96 (t, J=7.2 Hz, 3H), 0.88 (t, J=7.2 Hz, 3H); LCMS (ESI): m/z 576.48 [M+H⁺]; purity~98.5%.

Scheme 49

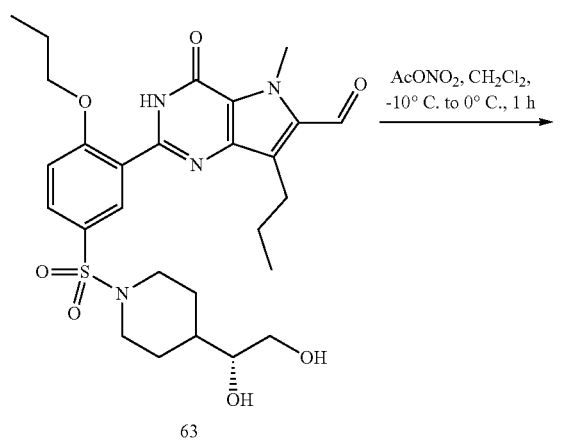

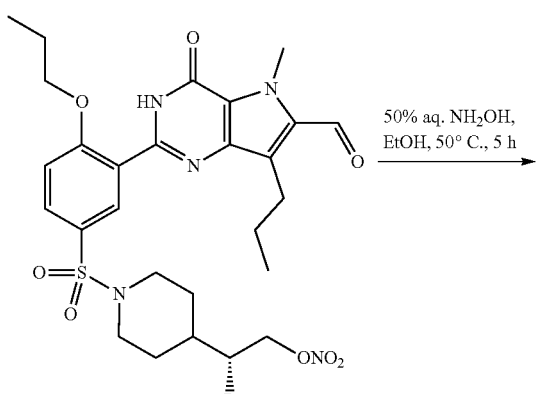

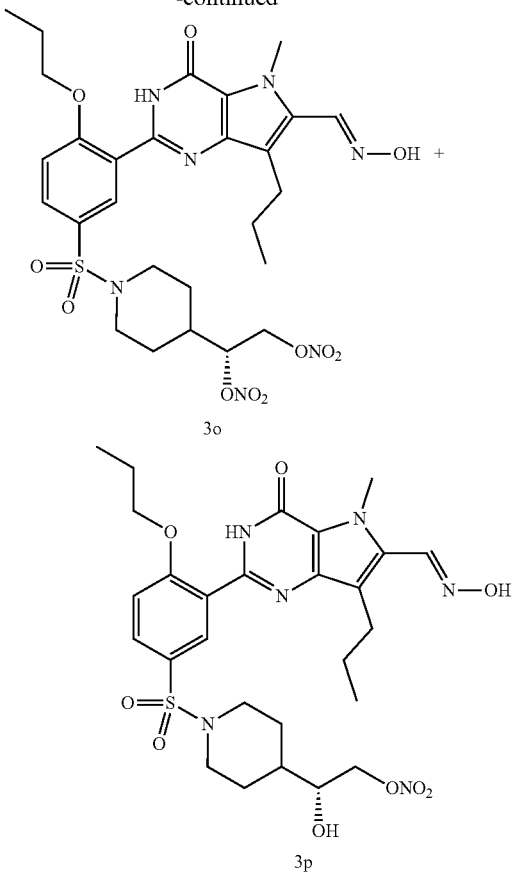

Example 93

(R)-1-(1-((3-(6-formyl-5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (64)

To a stirred solution of (R)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde 63 (240 mg, 0.43 mmol) in CH₂Cl₂ (3.6 mL) was added a solution of freshly prepared acetyl nitrate (0.36 mL) [(acetyl nitrate was prepared separately by addition of fuming HNO₃ (0.06 mL; 6.0 eq) drop wise in to acetic anhydride (0.3 mL, 1:5 of HNO₃)) slowly at −10° C. under argon atmosphere (Note: temperature should not be raised above 0° C.))] drop wise at −10° C. under argon atmosphere. The reaction mixture was stirred at −10° C. to 0° C. for 1 h. After completion of reaction (monitored by TLC), the reaction mixture pH was adjusted to 7.0-8.0 with saturated NaHCO₃ solution (~25 mL) at 0° C. The resultant solution was extracted with CH₂Cl₂ (2×30 mL). The combined organic layer was washed with brine (25 mL) and dried over anhydrous Na₂SO₄ and concentrated under reduced pressure to afford the crude product 64 (250 mg) containing mixture of desired di-nitrate (55%) along with mono-nitrate (21%); which was directly taken for next reaction without further purification. LCMS (ESI): m/z 651.47 [M+H⁺]; purity~55% & m/z 606.47 [M+H⁺]; purity~21%.

Example 94

(R,E)-1-(1-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (3o) and (R,E)-2-hydroxy-2-(1-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate (3q)

To a stirred solution of above crude mixture 64 (250 mg) in ethanol (30 mL) was added 50% hydroxylamine in aqueous solution (3.8 mL) at room temperature and stirred at 50° C. for 5 h under argon atmosphere. After completion of reaction (monitored by LCMS), the reaction mixture was concentrated under reduced pressure. The resultant residue was diluted in water (10 mL) and extracted with EtOAc (2×30 mL). The combined organic layer was washed with brine (25 mL), dried over anhydrous $Na_2SO_4$ and concentrated under reduced pressure. The crude product purified by preparative HPLC (Column: XBridge C18 (19*150) mm; 5 g) by eluting with 35-100% gradient acetonitrile with water. The pure fractions were lyophilized to afford the title compound 3o (52 mg) as a white solid and 3q (21.6 mg) as a white solid.

3o: $^1$H NMR (400 MHz, DMSO-$d_6$) δ ppm 11.74 (br s, 1H; $D_2O$ exchangeable), 11.60 (s, 1H; $D_2O$ exchangeable), 8.34 (s, 1H), 7.93 (d, J=2.4 Hz, 1H), 7.81 (dd, J=8.8, 2.4 Hz, 1H), 7.37 (d, J=8.8 Hz, 1H), 5.32-5.30 (m, 1H), 4.93 (dd, J=12.4, 2.4 Hz, 1H), 4.71 (dd, J=12.4, 6.0 Hz, 1H), 4.17 (s, 3H), 4.14-4.11 (m, 2H), 3.72-3.68 (m, 2H), 2.77-2.72 (m, 2H), 2.31-2.23 (m, 2H), 1.83-1.72 (m, 5H), 1.63-1.56 (m, 2H), 1.51-1.36 (m, 2H), 0.97 (t, J=7.3 Hz, 3H), 0.88 (t, J=7.6 Hz, 3H); LCMS (ESI): m/z 666.28 [M+H$^+$]; purity~96.54%.

3q: $^1$H NMR (400 MHz, DMSO-$d_6$) δ ppm 11.79 (br s, 1H; $D_2O$ exchangeable), 11.61 (s, 1H; $D_2O$ exchangeable), 8.34 (s, 1H), 7.91 (d, J=2.4 Hz, 1H), 7.81 (dd, J=8.8, 2.4 Hz, 1H), 7.37 (d, J=8.8 Hz, 1H), 5.22 (d, J=5.6 Hz, 1H; $D_2O$ exchangeable), 4.52 (dd, J=11.6, 3.2 Hz, 1H), 4.37 (dd, J=11.6, 7.6 Hz, 1H), 4.17 (s, 3H), 4.14-4.11 (m, 2H), 3.71-3.63 (m, 2H), 3.55-3.51 (m, 1H), 2.77-2.72 (m, 2H), 2.25-2.17 (m, 2H), 1.81-1.70 (m, 3H), 1.63-1.55 (m, 3H), 1.41-1.29 (m, 3H), 0.96 (t, J=7.2 Hz, 3H), 0.88 (t, J=7.2 Hz, 3H); LCMS (ESI): m/z 621.30 [M+H$^+$]; purity~97.79%.

Scheme 50

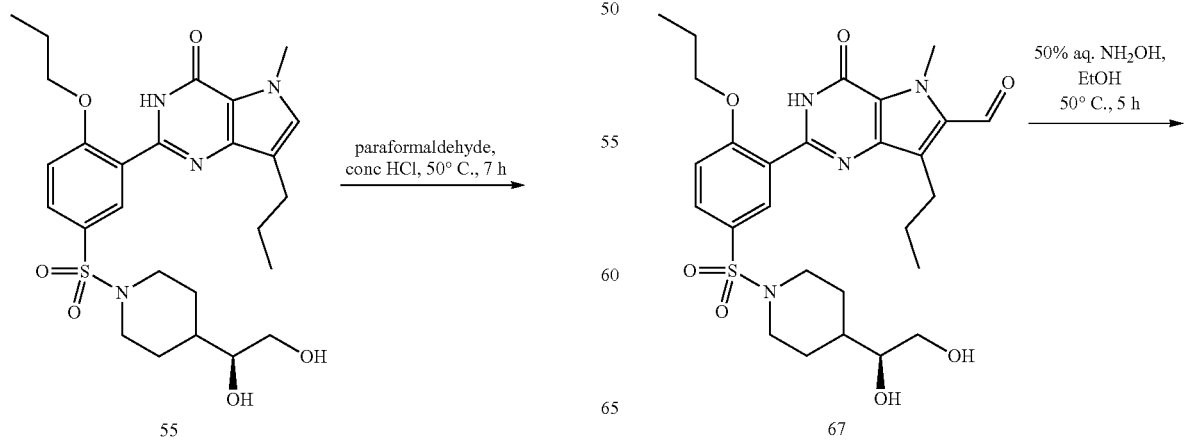

-continued

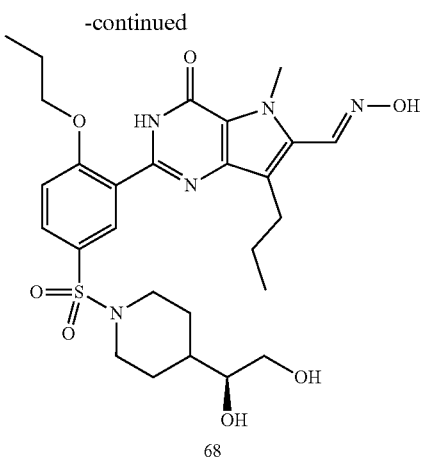

68

Example 95

(S)-2-(5-((4-(1,3-dioxolan-4-yl)piperidin-1-yl)sulfonyl)-2-propoxyphenyl)-6-(hydroxymethyl)-5-methyl-7-propyl-3,5-dihydro-4H-pyrrolo[3,2-d]pyrimidin-4-one (65)

To a stirred solution of (S)-2-(5-((4-(1,2-dihydroxyethyl)piperidin-1-yl)sulfonyl)-2-propoxyphenyl)-5-methyl-7-propyl-3,5-dihydro-4H-pyrrolo[3,2-d]pyrimidin-4-one 55 (500 mg, 0.94 mmol) in concentrated HCl solution (35% aq.; 5.0 mL), was added paraformaldehyde (250 mg, 0.5 w/w) at room temperature. Reaction was heated to 50° C. and stirred for 7 h. After completion of reaction (monitored by LCMS analysis), the reaction mixture was cooled to room temperature diluted with water (50 mL) and neutralized with saturated NaHCO$_3$ solution (200 mL). The resultant solution was extracted with 10% methanol in dichloromethane (3×100 mL). The combined the organic extracts were dried over anhydrous Na$_2$SO$_4$ and concentrated under reduced pressure. The obtained crude product was purified by reverse phase column chromatography (C-18 column; Grace System) by eluting with 45-60% gradient acetonitrile with water to afford the title compound 65 (250 mg; 43% yield) as a white solid. $^1$H NMR (300 MHz, DMSO-d$_6$) δ ppm 11.72 (br s, 1H), 7.91 (d, J=2.1 Hz, 1H), 7.81 (dd, J=8.8, 2.1 Hz, 1H), 7.36 (d, J=8.8 Hz, 1H), 5.16 (br s, 1H), 4.86 (s, 1H), 4.72 (s, 1H), 4.56 (s, 2H), 4.14-4.09 (m, 2H), 4.05 (s, 3H), 3.86-3.81 (m, 1H), 3.71-3.64 (m, 3H), 3.49-3.45 (m, 1H), 2.63-2.57 (m, 2H), 2.27-2.20 (m, 2H), 1.87-1.83 (m, 1H), 1.77-1.70 (m, 2H), 1.61-1.54 (m, 3H), 1.38-1.23 (m, 3H), 0.96 (t, J=6.9 Hz, 3H), 0.88 (t, J=6.9 Hz, 3H); LCMS (ESI): m/z 575.47 [M+H$^+$]; purity~94.1%.

Example 96

(S)-2-(5-((4-(1,3-dioxolan-4-yl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde (66)

To a stirred solution of (S)-2-(5-((4-(1,3-dioxolan-4-yl)piperidin-1-yl)sulfonyl)-2-propoxyphenyl)-6-(hydroxymethyl)-5-methyl-7-propyl-3,5-dihydro-4H-pyrrolo[3,2-d]pyrimidin-4-one 1 (250 mg, 0.435 mmol) in ACN (125 mL) was added activated MnO$_2$ (58% Mn; 757 mg, 8.702 mmol) at room temperature and stirred for 16 h. After completion of reaction (monitored by LCMS), the reaction mixture was then filtered through a Celite pad and washed with ACN (50 mL). The filtrate was concentrated to afford the title compound 66 (250 mg, 90% yield), as a white solid. $^1$H NMR (300 MHz, DMSO-d$_6$) δ ppm 12.11 (s, 1H), 10.16 (s, 1H), 7.90-7.81 (m, 2H), 7.38 (d, J=8.8 Hz, 1H), 4.86 (s, 1H), 4.72 (s, 1H), 4.32 (s, 3H), 4.13-4.09 (m, 2H), 3.86-3.82 (m, 1H), 3.71-3.63 (m, 3H), 3.50-3.46 (m, 1H), 2.96-2.92 (m, 2H), 2.28-2.20 (m, 2H), 1.86-1.82 (m, 1H), 1.76-1.62 (m, 4H), 1.41-1.24 (m, 4H), 0.97-0.87 (m, 6H); LCMS (ESI): m/z 573.45 [M+H$^+$]; purity~94.9%.

Example 97

(S)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde (67)

To a stirred solution of (S)-2-(5-((4-(1,3-dioxolan-4-yl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde 66 (250 mg, 0.43 mmol) in MeOH:CH$_2$Cl$_2$ (1:1; 5 mL) was added concentrated HCl solution (35% aq.; 2.5 mL) at room temperature and stirred for 24 h. After completion of reaction (monitored by LCMS), the reaction mixture was diluted with water (10 mL) and neutralized with saturated NaHCO$_3$ solution (100 mL). The resultant solution was extracted with 10% methanol in dichloromethane (2×50 mL). The combined organic layer was washed with brine (50 mL), dried over anhydrous Na$_2$SO$_4$ and concentrated under reduced pressure to afford the title compound 67 (210 mg; 76% yield) as an off-white solid. $^1$H NMR (400 MHz, DMSO-d) δ ppm 12.09 (br s, 1H; D$_2$O exchangeable), 10.17 (br s, 1H), 7.87 (d, J=2.4 Hz, 1H), 7.81 (dd, J=8.8, 2.4 Hz, 1H), 7.37 (d, J=8.8 Hz, 1H), 4.43-4.36 (m, 2H; D$_2$O exchangeable), 4.32 (s, 3H), 4.13-4.09 (m, 2H), 3.68-3.62 (m, 2H), 3.29-3.24 (m, 2H), 3.23-3.17 (m, 1H), 2.97-2.91 (m, 2H), 2.22-2.13 (m, 2H), 1.78-1.62 (m, 6H), 1.43-1.28 (m, 3H), 0.97-0.85 (m, 6H); LCMS (ESI): m/z 561.47 [M+H$^+$]; purity~89.5%.

Example 98

(S,E)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde oxime (68)

To a stirred solution of (S)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde 67 (50 mg, 0.089 mmol) in ethanol (6 mL) was added 50% hydroxylamine in aqueous solution (0.75 mL) at room temperature. Reaction was heated to 50° C. and stirred for 5 h. After completion of reaction (monitored by TLC), the reaction mixture was concentrated under reduced pressure. The resultant residue was diluted in water (5 mL) and extracted with ethyl acetate (3×10 mL). The combined organic extracts were washed with brine (10 mL), dried over anhydrous Na$_2$SO$_4$ and concentrated under reduced pressure. The crude product was purified by reverse phase column chromatography (C-18 column; Grace System) by eluting with 35-40% gradient acetonitrile with water to afford the title compound 68 (9.4 mg; ~17% yield) as a white solid. $^1$H NMR (400 MHz, DMSO-d$_6$) δ ppm 11.77 (br s, 1H; D$_2$O exchangeable), 11.58 (br s, 1H; D$_2$O exchangeable), 8.33 (s, 1H), 7.86 (d, J=2.0 Hz, 1H), 7.78 (dd, J=8.8, 2.0 Hz, 1H), 7.33 (d, J=8.8 Hz, 1H), 4.43-4.36 (m, 2H; D₂O exchangeable), 4.17 (s, 3H), 4.12-4.07 (m, 2H), 3.65-3.62 (m, 2H), 3.27-3.18 (m, 3H), 2.75-2.71 (m, 2H), 2.22-2.14 (m, 2H), 1.77-1.69 (m, 3H), 1.61-1.53 (m, 3H), 1.41-1.27 (m, 3H), 0.96 (t, J=7.2 Hz, 3H), 0.88 (t, J=7.2 Hz, 3H); LCMS (ESI): m/z 576.64 [M+H]⁺; purity~96.07%.

Scheme 51

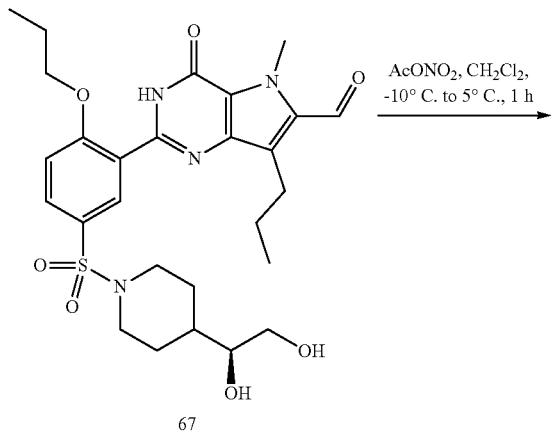

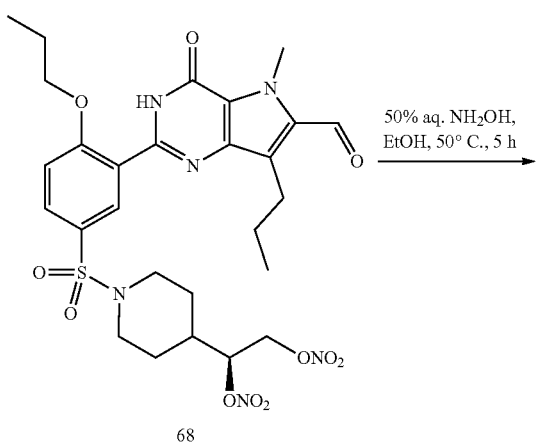

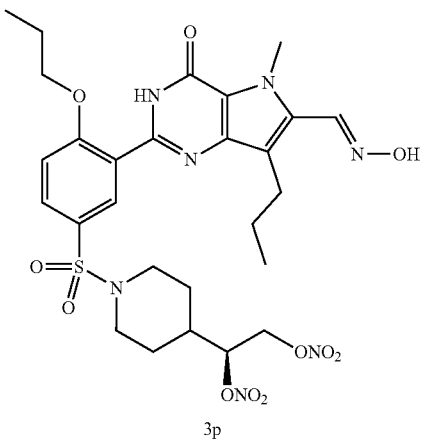

Example 99

(S)-1-(1-((3-(6-formyl-5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (68)

To a stirred solution of (S)-2-(5-((4-(1,2-dihydroxyethyl)piperidin-1-yl)sulfonyl)-2-propoxyphenyl)-5-methyl-4-oxo-7-propyl-4,5-dihydro-3H-pyrrolo[3,2-d]pyrimidine-6-carbaldehyde 67 (200 mg, 0.35 mmol) in CH₂Cl₂ (2.1 mL) was added a solution of freshly prepared acetyl nitrate (0.45 mL) [(acetyl nitrate was prepared separately by addition of fuming HNO₃ (0.075 mL) drop wise in to acetic anhydride (0.375 mL)) slowly at −15° C. for 30 min under argon atmosphere (Note: temperature should not be raised above 0° C.))] drop wise at −10° C. under argon atmosphere. The reaction was stirred at −10° C. to −5° C. for 1 h. After completion of reaction (monitored by TLC), the reaction was quenched with saturated NaHCO₃ solution (20 mL) at 0° C. The resultant solution was extracted with 10% methanol in dichloromethane (3×30 mL). The combined organic layer was washed with brine (40 mL), dried over anhydrous Na₂SO₄ and concentrated under reduced pressure to afford the crude product 68 (200 mg) as a yellow solid, which was directly taken for next reaction without further purification. LCMS (ESI): m/z 651.4 [M+H]⁺; purity~71.1%.

Example 100

(S,E)-1-(1-((3-(6-((hydroxyimino)methyl)-5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate (3p)

To a stirred solution of (S)-1-(1-((3-(6-formyl-5-methyl-4-oxo-7-propyl-4,5-dihydro-3H-pyrrolo[3,2-d]pyrimidin-2-yl)-4-propoxyphenyl)sulfonyl)piperidin-4-yl)ethane-1,2-diyl dinitrate 68 (200 mg; ~71% pure) in ethanol (24 mL) was added 50% hydroxylamine in aqueous solution (3 mL) at room temperature and stirred at 50° C. for 5 h. After completion of reaction (monitored by TLC), the reaction was concentrated under reduced pressure. The resultant residue was diluted in water (10 mL) and extracted with ethyl acetate (3×30 mL). The combined organic layer was washed with brine (30 mL), dried over anhydrous Na₂SO₄ and concentrated under reduced pressure. The crude product was purified by preparative HPLC (Column: XBridge C18 (19*150 mm); 5 μm) by eluting with 50-100% gradient acetonitrile with water. The pure fractions were lyophilized to afford the title compound 3p (22 mg) as a white solid. ¹H NMR (400 MHz, DMSO-d₆) δ ppm 11.71 (br s, 1H; D₂O exchangeable), 11.50 (s, 1H; D₂O exchangeable), 8.32 (s, 1H), 7.90 (d, J=2.4 Hz, 1H), 7.77 (dd, J=8.8, 2.4 Hz, 1H), 7.34 (d, J=8.8 Hz, 1H), 5.32-5.30 (m, 1H), 4.93 (dd, J=12.4, 2.4 Hz, 1H), 4.71 (dd, J=12.4, 6.0 Hz, 1H), 4.17 (s, 3H), 4.14-4.11 (m, 2H), 3.72-3.68 (m, 2H), 2.76-2.72 (m, 2H), 2.31-2.23 (m, 2H), 1.83-1.72 (m, 5H), 1.61-1.55 (m, 2H), 1.50-1.37 (m, 2H), 0.96 (t, J=7.3 Hz, 3H), 0.88 (t, J=7.6 Hz, 3H); LCMS (ESI): m/z 666.33 [M+H]⁺; purity~98.62%.

Scheme 51

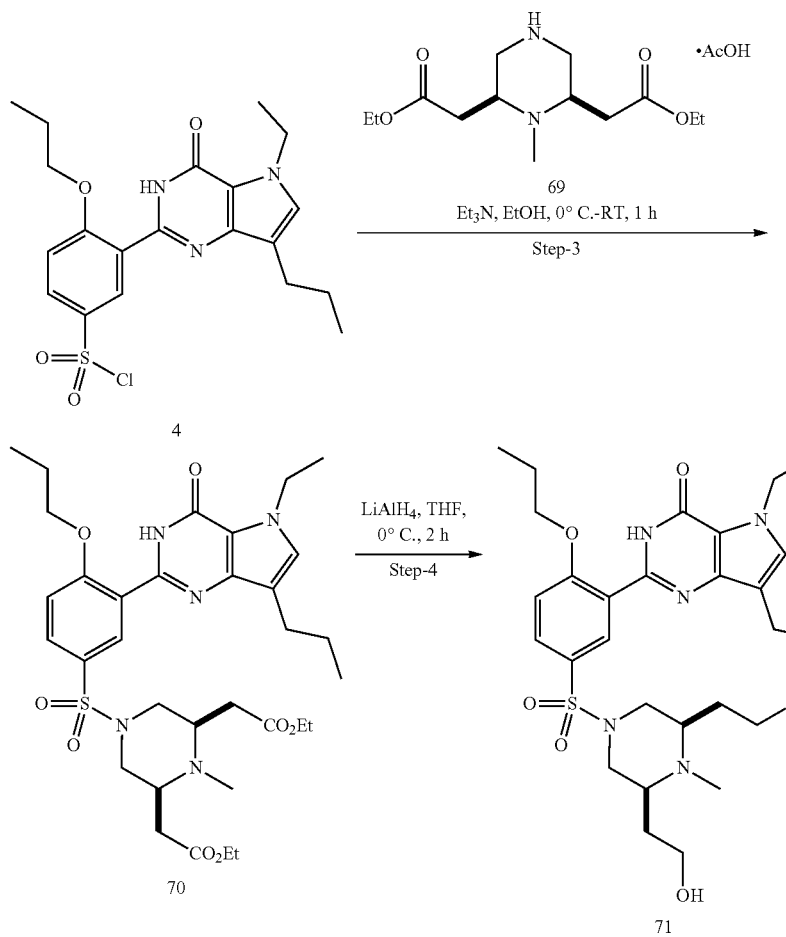

Example 101 diethyl 2,2'-((2S,6R)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)diacetate (70)

To a stirred solution of diethyl 2,2'-((2R,6S)-1-methylpiperazine-2,6-diyl)diacetate acetate 69 (see J. Med. Chem. 2009, 52, 3689-3702) (617 mg, 2.26 mmol) in ethanol (30 mL) was added Amberlyst A-21 basic resin (3.0 g) at room temperature and stirred for 2 h. The mixture was filtered and washed with ethanol (15 mL). To the filtrate, triethylamine (2.3 mL, 17.48 mmol) followed by a solution of 3-(5-ethyl-4-oxo-7-propyl-4,5-dihydro-3H-pyrrolo[3,2-d]pyrimidin-2-yl)-4-propoxybenzenesulfonyl chloride (4) (500 mg, 1.13 mmol) in dichloromethane (10 mL) were added at 0° C. under atmosphere. The reaction mixture was stirred at room temperature for 1 h. After completion (monitored by LCMS), the reaction mixture was directly taken for reverse phase column chromatography (without workup) (Reveleris® C18-40 g column; Grace System) by eluting with 30-65% gradient acetonitrile with water to afford the title compound 70 (90 mg) as an off-white solid. 1H NMR (300 MHz, DMSO-$d_6$) δ ppm 11.67 (br s, 1H), 7.90 (d, J=2.2 Hz, 1H), 7.79 (dd, J=8.8, 2.2 Hz, 1H), 7.39 (d, J=8.8 Hz, 1H), 7.31 (s, 1H), 4.37 (q, J=7.1 Hz, 2H), 4.13 (t, J=6.2 Hz, 2H), 4.03 (q, J=7.1 Hz, 4H), 3.44-3.37 (m, 2H), 2.77-2.71 (m, 2H), 2.63-2.52 (m, 4H), 2.39-2.28 (m, 4H), 2.08 (s, 3H), 1.78-1.66 (m, 2H), 1.64-1.38 (m, 2H), 1.34 (t, J=7.1 Hz, 3H), 1.13 (t, J=7.1 Hz, 6H), 0.97 (t, J=7.1 Hz, 3H), 0.91 (t, J=7.1 Hz, 3H); LCMS(ESI): m/z 674.62 [M+H]$^+$; purity~88.69%.

Example 102

2-(5-(((3S,5R)-3,5-bis(2-hydroxyethyl)-4-methylpiperazin-1-yl)sulfonyl)-2-propoxyphenyl)-5-ethyl-7-propyl-3,5-dihydro-4H-pyrrolo[3,2-d]pyrimidin-4-one (71)

To a stirred solution of diethyl 2,2'-((2S,6R)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)diacetate (70) (90 mg, 0.13 mmol) in THF (4.5 mL) was added 1M LiAlH$_4$ solution in THF (0.3 mL, 0.4 mmol) at 0° C. drop wise for 10 min under argon atmosphere. The reaction mixture was stirred at 0° C. for 2 h. After completion of reaction (monitored by TLC and LCMS analysis), the reaction was quenched with saturated ammonium chloride solution (4 mL) at 0° C. and extracted with ethyl acetate (3×30 mL). The combined organic layer was washed with brine (40 mL), dried over anhydrous Na$_2$SO$_4$ and concentrated under reduced pressure. The crude product was purified by reverse phase column chromatography (Reveleris® C18-12g column; Grace System) by eluting with 30-35% gradient acetonitrile with water and pure fractions were lyophilized to afford the title compound 71 (35 mg, yield: 33%) as a white solid. $^1$H NMR (400 MHz, DMSO-$d_6$) δ ppm 11.59 (br s, 1H; $D_2O$ exchangeable), 7.90 (d, J=2.0 Hz, 1H), 7.81 (dd, J=8.8, 2.0 Hz, 1H), 7.36 (d, J=8.8 Hz, 1H), 7.30 (s, 1H), 4.47 (br s, 2H; $D_2O$ exchangeable), 4.37 (d, J=7.1 Hz, 2H), 4.12 (t, J=6.4 Hz, 2H), 3.45-3.36 (m, 6H), 2.59-2.53 (m, 2H), 2.51-2.45 (m, 2H), 2.20-2.14 (m, 2H), 1.77 (s, 3H), 1.77-1.66 (m, 6H), 1.42-1.38 (m, 2H), 1.35 (t, J=7.1 Hz, 3H), 0.97 (t, J=7.1 Hz, 3H), 0.91 (t, J=7.1 Hz, 3H); LCMS(ESI): m/z 590.37 [M+H]$^+$; purity~99.59%.

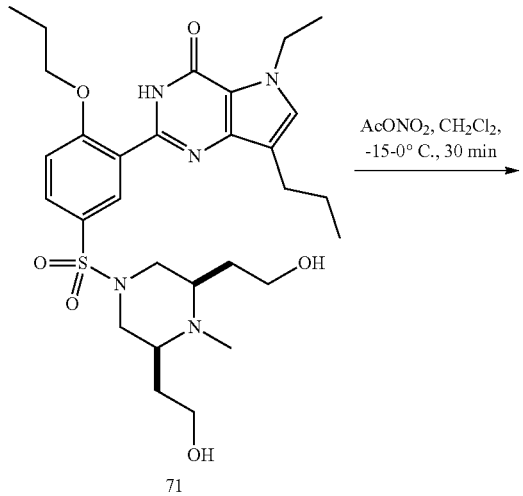

Example 103

((2S,6R)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)bis(ethane-2,1-diyl) dinitrate (1m)

To a stirred solution of 2-(5-(((3S,5R)-3,5-bis(2-hydroxyethyl)-4-methylpiperazin-1-yl)sulfonyl)-2-propoxyphenyl)-5-ethyl-7-propyl-3,5-dihydro-4H-pyrrolo[3,2-d]pyrimidin-4-one (71) (130 mg, 0.22 mmol) in dichloromethane (2 mL) was added a solution of freshly prepared acetyl nitrate (0.32 mL) [(acetyl nitrate was prepared separately by addition of fuming $HNO_3$ (0.05 mL, 2.64 mmol) drop wise in to acetic anhydride (0.27 mL) slowly at −15° C. for 30 min under argon atmosphere (Note: temperature should not be raised to 0° C.))] drop wise at −15° C. for 30 min under argon atmosphere. The reaction was stirred at −15° C. to −0° C. for 30 min. After completion of reaction (monitored by TLC), the reaction was quenched with saturated aq. $NaHCO_3$ solution (10 mL) at 0° C. and extracted with dichloromethane (3×20 mL). The combined organic layer was washed with brine (30 mL), dried over anhydrous $Na_2SO_4$ and concentrated under reduced pressure. The crude product was purified by preparative HPLC (column: KROMOSIL C18 (150*25) mm, 10 u; Mobile phase A: 100% water, B: Acetonitrile; Flow: 25 mL/min Solubility: ACN+water+ THF). The appropriate pure fractions were lyophilized to afford the title compound 1m (10 mg) as a white solid. 1H NMR (400 MHz, DMSO-$d_6$) δ ppm 11.68 (br s, 1H; $D_2O$ exchangeable), 7.93 (d, J=2.0 Hz, 1H), 7.84-7.81 (m, 1H), 7.36 (d, J=8.8 Hz, 1H), 7.31 (s, 1H), 4.52 (t, J=6.6 Hz, 4H), 4.37 (q, J=7.1 Hz, 2H), 4.13 (t, J=6.4 Hz, 2H), 3.38-3.31 (m, 2H), 2.65-2.59 (m, 2H), 2.58-2.53 (m, 2H), 2.33-2.27 (m, 2H), 2.04 (s, 3H), 1.88-1.70 (m, 6H), 1.66-1.59 (m, 2H), 1.35 (t, J=7.1 Hz, 3H), 0.97 (t, J=7.1 Hz, 3H), 0.91 (t, J=7.1 Hz, 3H); LCMS (ESI): m/z 678.43[M−H]$^-$; purity~95.48%.

In an analogous manner, ((2S,6S)-4-((3-(5-ethyl-4-oxo-7-propyl-4,5-dihydro-3H-pyrrolo[3,2-d]pyrimidin-2-yl)-4-propoxyphenyl)sulfonyl)-1-methylpiperazine-2,6-diyl)bis(ethane-2,1-diyl) dinitrate (1o) was synthesized by using diethyl 2,2'-((2S,6S)-1-methylpiperazine-2,6-diyl)diacetate acetate (see J. Med. Chem. 2009, 52, 3689-3702) instead of 69.

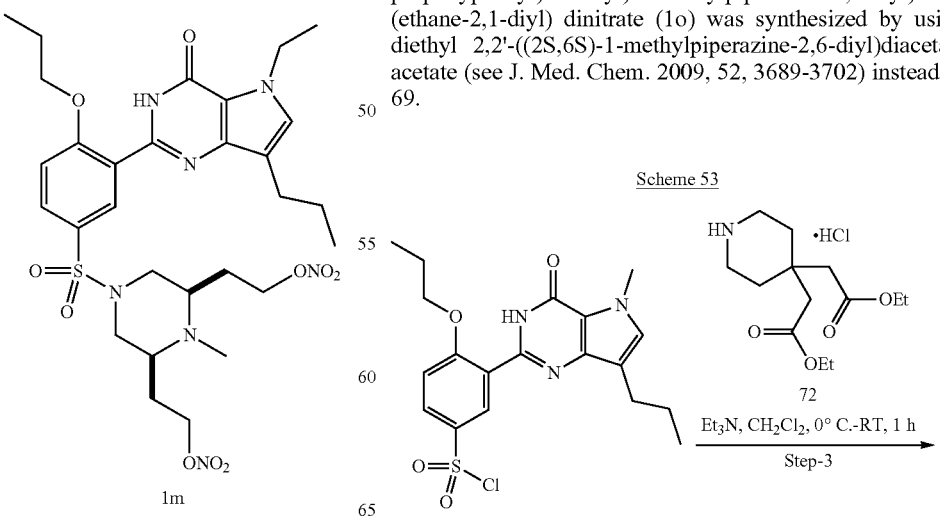

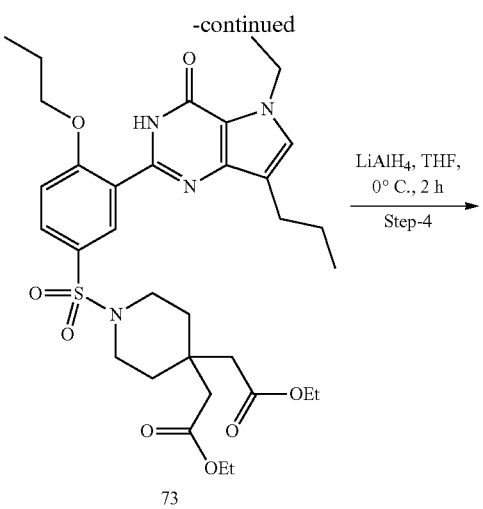

brine (20 mL), dried over anhydrous Na₂SO₄ and concentrated under reduced pressure to the title compound 73 (650 mg) as a brown liquid, which was taken for next reaction without purification. LCMS (ESI): m/z 659.80 [M+H]⁺; purity~83.75%.

Example 105

2-(5-((4,4-bis(2-hydroxyethyl)piperidin-1-yl)sulfonyl)-2-propoxyphenyl)-5-ethyl-7-propyl-3,5-dihydro-4H-pyrrolo[3,2-d]pyrimidin-4-one (74)

To a stirred solution of diethyl 2,2'-(1-((3-(5-ethyl-4-oxo-7-propyl-4,5-dihydro-3H-pyrrolo[3,2-d]pyrimidin-2-yl)-4-propoxyphenyl) sulfonyl)piperidine-4,4-diyl)diacetate 73 (600 mg, 0.91 mmol) in THF (12 mL) was added 1M LiAlH₄ solution in THF (1.8 mL) at 0° C. drop wise for 10 min under argon atmosphere. The reaction mixture was stirred at 0° C. for 2 h. After completion of reaction (monitored by TLC and LCMS analysis). The reaction was quenched with saturated ammonium chloride solution (25 mL) at 0° C. and extracted with ethyl acetate (3×50 mL). The combined organic layer was washed with brine (50 mL), dried over anhydrous Na₂SO₄ and concentrated under reduced pressure. The crude was purified by reverse phase column chromatography (Reveleris® C18-40 g column; Grace System) by eluting with 60-65% gradient acetonitrile with water and the pure fractions were lyophilized to afford the title compound 74 (150 mg, 28% yield) as a white solid. ¹H NMR (400 MHz, DMSO-d₆) δ ppm 11.69 (br s, 1H; D₂O exchangeable), 7.93 (d, J=2.0 Hz, 1H), 7.81 (dd, J=8.8, 2.0 Hz, 1H), 7.37 (d, J=8.8 Hz, 1H), 7.31 (s, 1H), 4.37 (q, J=7.3 Hz, 2H), 4.30 (t, J=4.9 Hz, 2H; D₂O exchangeable), 4.14-4.11 (m, 2H), 3.41-3.32 (m, 4H), 2.95-2.92 (m, 4H), 2.59-2.55 (m, 2H), 1.78-1.72 (m, 2H), 1.67-1.61 (m, 2H), 1.50-1.43 (m, 4H), 1.37-1.32 (m, 7H), 0.97 (t, J=7.3 Hz, 3H), 0.912 (t, J=7.1 Hz, 3H); LCMS(ESI): m/z 575.56 [M+H]⁺; purity~99.92%.

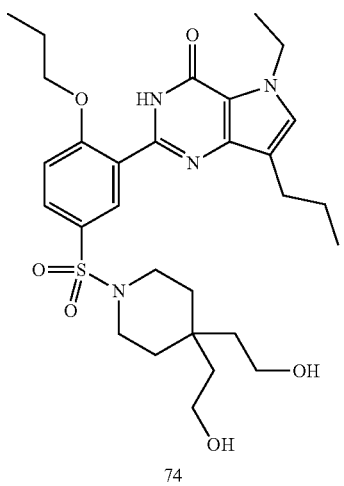

Example 104 diethyl 2,2'-(1-((3-(5-ethyl-4-oxo-7-propyl-4,5-dihydro-3H-pyrrolo[3,2-d]pyrimidin-2-yl)-4-propoxyphenyl)sulfonyl)piperidine-4,4-diyl)diacetate (73)

To a stirred solution of diethyl 2,2'-(piperidine-4,4-diyl) diacetate hydrochloride (72, see WO 02001096334) (882 mg, 3.42 mmol) in dichloromethane (30 mL) was added Amberlyst A-21 basic resin (3.0 g) at room temperature and stirred for 2 h. The mixture was filtered. To the filtrate, triethylamine (2.8 mL, 20.55 mmol) followed by a solution of 3-(5-ethyl-4-oxo-7-propyl-4,5-dihydro-3H-pyrrolo[3,2-d]pyrimidin-2-yl)-4-propoxybenzenesulfonyl chloride (4) (600 mg, 1.37 mmol) in dichloromethane (10 mL) were added at 0° C. under atmosphere. The reaction mixture was stirred at room temperature for 1 h. After completion (monitored by LCMS), the reaction mixture was diluted with dichloromethane (10 mL), washed with water (2×25 mL), Scheme 54

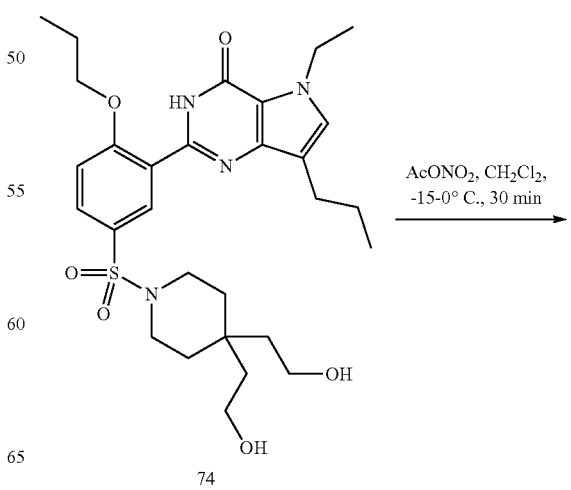

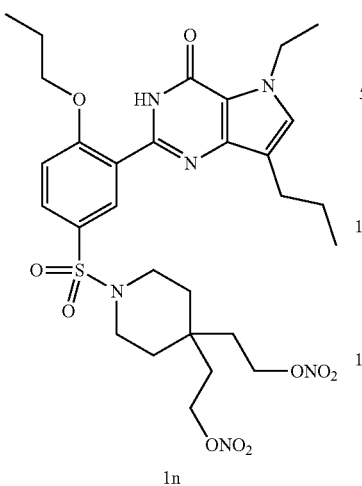

1n

Example 106

(1-((3-(5-ethyl-4-oxo-7-propyl-4,5-dihydro-3H-pyrrolo[3,2-d]pyrimidin-2-yl)-4-propoxyphenyl)sulfonyl) piperidine-4,4-diyl)bis(ethane-2,1-diyl) dinitrate (1n)

To a stirred solution of 2-(5-((4,4-bis(2-hydroxyethyl) piperidin-1-yl)sulfonyl)-2-propoxyphenyl)-5-ethyl-7-propyl-3,5-dihydro-4H-pyrrolo[3,2-d]pyrimidin-4-one (74) (125 mg, 0.217 mmol) in dichloromethane (1.8 mL) was added a solution of freshly prepared acetyl nitrate (0.32 mL) [(acetyl nitrate was prepared separately by addition of fuming HNO$_3$ (0.05 mL, 2.64 mmol) drop wise in to acetic anhydride (0.27 mL) slowly at −15° C. for 30 min under argon atmosphere (Note: temperature should not be raised to 0° C.)] drop wise at −15° C. for 30 min under argon atmosphere. The reaction was stirred at −15° C. to 0° C. for 30 min. After completion of reaction (monitored by TLC), the reaction was quenched with saturated NaHCO$_3$ solution (10 mL) at 0° C. and extracted with dichloromethane (3×20 mL). The combined organic layer was washed with brine (30 mL), dried over anhydrous Na$_2$SO$_4$ and concentrated under reduced pressure. The obtained crude product was purified by preparative HPLC (column: KROMASIL C18 (150*25) mm, 10 u; Mobile phase A: 10 mm Ammonium Bicarbonate (Aq); Mobile phase B: Acetonitrile Method T/% B=0/40, 1/40, 10/80, 10.5/100, 12/100, 12.5/40, 15/40; Flow: 25 mL/mL; Solubility: ACN+water+THF). The pure fractions were lyophilized to afford the title compound in (57 mg, 39% yield) as a white solid. $^1$H NMR (400 MHz, DMSO-d$_6$) δ ppm 11.68 (br s, 1H), 7.94 (d, J=2.0 Hz, 1H), 7.82 (dd, J=8.8, 2.0 Hz, 1H), 7.36 (d, J=8.8 Hz, 1H), 7.31 (s, 1H), 4.53 (t, J=7.3 Hz, 4H), 4.37 (q, J=6.9 Hz, 2H), 4.14-4.11 (m, 2H), 3.02-2.97 (m, 4H), 2.59-2.55 (m, 2H), 1.79-1.71 (m, 2H), 1.69-1.60 (m, 6H), 1.57-1.47 (m, 4H), 1.35 (t, J=6.9 Hz, 3H), 0.97 (t, J=7.3 Hz, 3H), 0.912 (t, J=7.1 Hz, 3H); LCMS (ESI): m/z 665.31 [M+H]$^+$; purity~98.81%.

Scheme 55

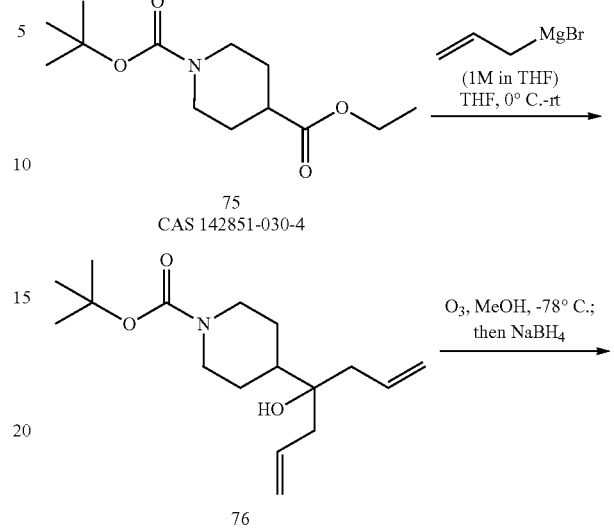

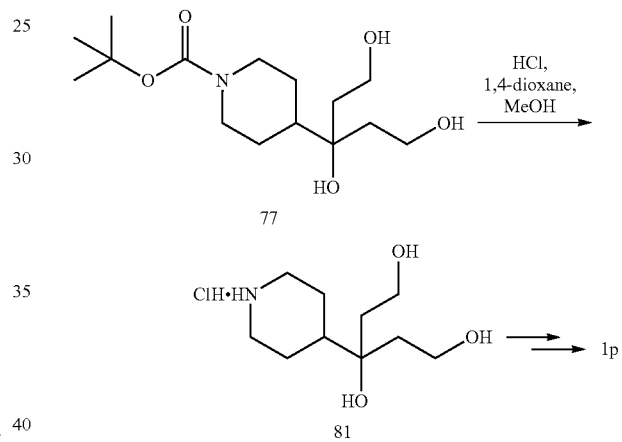

Scheme 56

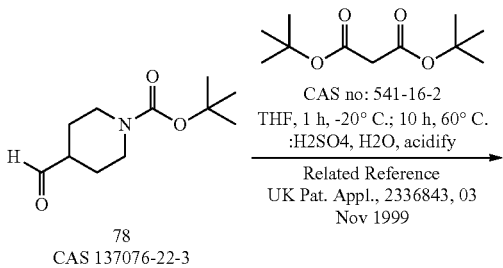

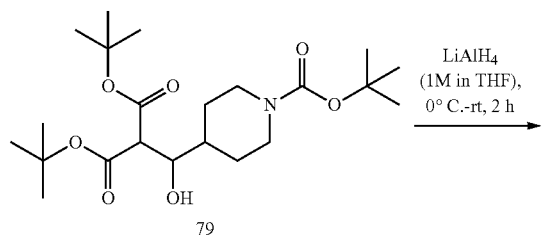

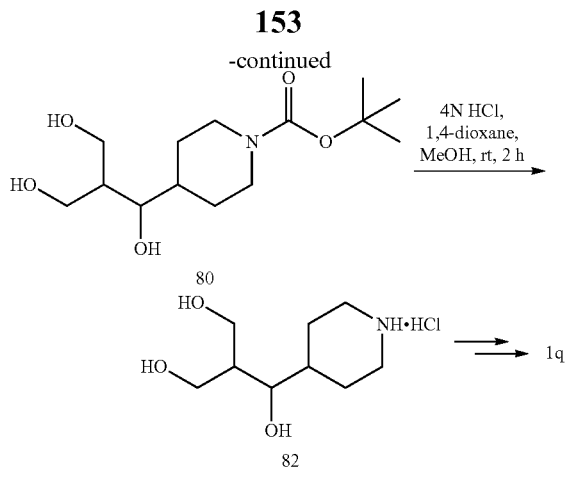

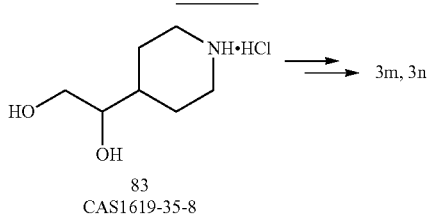

Example 107

General Procedures:

To a stirred solution of piperidine derivatives (81-83, Schemes 55-57) (3.5 mmol) in dichloromethane (30 mL) was added Amberlyst A-21 basic resin (3.0 g) at room temperature and stirred for 2 h. The mixture was filtered. To the filtrate, triethylamine (3 mL, 22 mmol) followed by a solution of 3-(5-ethyl-4-oxo-7-propyl-4,5-dihydro-3H-pyrrolo[3,2-d]pyrimidin-2-yl)-4-propoxybenzenesulfonyl chloride (4) (600 mg, 1.37 mmol) in dichloromethane (10 mL) were added at 0° C. under atmosphere. The reaction mixture was stirred at room temperature for 1h. After completion (monitored by LCMS), the reaction mixture was diluted with dichloromethane (10 mL), washed with water (2×25 mL), brine (20 mL), dried over anhydrous $Na_2SO_4$ and concentrated under reduced pressure.

The so obtained crude intermediate di- and triols were dissolved in dichloromethane (3 mL). To this solutions was added a solution of freshly prepared acetyl nitrate (0.32 mL) [(acetyl nitrate was prepared separately by addition of fuming $HNO_3$ (0.05 mL, 2.64 mmol) drop wise in to acetic anhydride (0.27 mL) slowly at −15° C. for 30 min under argon atmosphere (Note: temperature should not be raised to 0° C.))] drop wise at −15° C. for 30 min under argon atmosphere. The reaction was stirred at −15° C. to 0° C. for 30 min. After completion of reaction (monitored by TLC), the reaction was quenched with saturated $NaHCO_3$ solution (10 mL) at 0° C. and extracted with dichloromethane (3×20 mL). The combined organic layer was washed with brine (30 mL), dried over anhydrous $Na_2SO_4$ and concentrated under reduced pressure. The obtained crude products were purified by preparative HPLC (column: KROMASIL C18 (150*25) mm, 10 u; Mobile phase A: 10 mm Ammonium Bicarbonate (Aq); Mobile phase B: Acetonitrile Method T/% B=0/40, 1/40, 10/80, 10.5/100, 12/100, 12.5/40, 15/40; Flow: 25 mL/mL; Solubility: ACN+water+THF). The pure fractions were lyophilized to afford the following compounds:

3-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)-3-hydroxypentane-1,5-diyl dinitrate (1p)

And 2-(1-((3-(5-ethyl-4-oxo-7-propyl-4,5-dihydro-3H-pyrrolo[3,2-d]pyrimidin-2-yl)-4-propoxyphenyl)sulfonyl)piperidin-4-yl)-2-hydroxypropane-1,3-diyl dinitrate (1q)

Example 108

De-nitration of di-nitrate resulting from amine 83 and sulfonyl chloride 4 was achieved by partial hydrolysis using sodium iodide in acetone at room temperature. The two enantiomers can be separated on chiral HPLC column:

2-hydroxy-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate isomer a (3m)

And 2-hydroxy-1-(1-((3-(5-methyl-4-oxo-7-propyl-4,5-dihydro-3H-pyrrolo[3,2-d]pyrimidin-2-yl)-4-propoxyphenyl)sulfonyl)piperidin-4-yl)ethyl nitrate isomer b (3n)

Example 109

PDE5 Assay

Purpose: Evaluation of the effects of compounds of the present invention on the activity of the human phosphodiesterase-5 quantified by measuring the formation of 5'GMP from cGMP using PDE5 enzyme isolated from human platelets. The latter was effected in accordance with the method as described by Masaaki I, Nishikawa M, Fujioka M, Miyahara M, Isaka N, Shiku H, Nakano T, Cell Signal (1996), 8(8):575-581.

Experimental protocol: The test compound, i.e the compound of the present invention, reference compound or water (control) are added to a buffer containing 40 mM Tris/HCl (pH 7.8), 3 mM MgCl2, 1.4 mM DTT, 0.21% BSA, 200 mM NH4Cl, 1 μM cGMP and 0.1 μCi [3H]cGMP. Thereafter, the reaction is initiated by addition of the enzyme and the mixture is incubated for 60 min at 22° C.

For basal control measurements, the enzyme is omitted from the reaction mixture. Following incubation SPA beads are added. After 20 min at 22° C. under shaking, the amount of [3H]5'GMP is quantified with a scintillation counter (Topcount, Packard).

The results shown in Table 1 are expressed as a percent inhibition of the control enzyme activity. The standard inhibitory reference compound is dipyridamole, which is tested in each experiment at several concentrations to obtain an inhibition curve from which its IC50 value is calculated.

As shown in Table 1, the compounds of the present invention are potent and selective inhibitors of human cGMP-specific PDE5.

Example 110

Phosphodiesterase-5 Activity Assay

The inhibition of recombinant human (rh) PDE5A by test compounds is measured in a radiometric assay based on Scintillation Proximity Assay (SPA) technology. The substrate [3H]cGMP/cGMP is hydrolysed to [3H] 5'GMP/5'GMP contingent on the activity of rhPDE5A. The ensuing [3H] 5'GMP/5'GMP but not [3H] cGMP/cGMP binds to SPA yttrium silicate beads in the presence of $Zn^{++}$ stimulating the scintillant within the bead to emit light that is detected by a β-counter. The assay is performed in a 96 well format.

The assay is done in 20 mM Iris HCl pH 7.4, 5 mM $MgCl_2$, 0.5 µM cGMP/[3H] cGMP (about 60000 dpm/well) substrate with rhPDE5A1 (GST tagged, SIGMA E9034) added to an amount not exceeding 2000 cGMP hydrolysis within 20 min in Iris 20 mM pH 7.4 supplemented with 0.01% bovine serum albumin (BSA) in the presence of test compounds or vehicle (0.1% DMSO). The final assay volume amounts to 100 µl and the reaction is run for 20 min at 37° C.

The hydrolysis of [3H] cGMP/cGMP by rhPDE5A is terminated by adding SPA beads at 50 µl/well (Perkin Elmer, RPNQ0024), pre-diluted in water as per manufacturer's instructions and supplemented with 3-isobutyl-1-methyl-xanthine (1 mM). Beads are allowed to sediment for at least 30 min before measurement in a Wallac Microbeta 2 (Perkin Elmer).

In general, test compounds are added at seven different concentrations from 1 pM to 1 µM in log steps. Percent inhibition values compared to vehicle control (0.1% DMSO) are calculated and IC50 values calculated using GraphPad Prism 7.03 software. Results (IC50) are given as the mean from at least two independent experiments each performed in triplicate.

TABLE 1

| Compound | % inhibition at 5.0E−09 M | IC50 |
|---|---|---|
| sildenafil | 49.9 | $5.4 \times 10^{-9}$ M |
| mirodenafil | 64.9 | $3.4 \times 10^{-10}$ M |
| 1a | 20.7 | $1.2 \times 10^{-8}$ M |
| 1b | 12.4 | $>1.0 \times 10^{-8}$ M |
| 1d | 13.4 | $>1.0 \times 10^{-8}$ M |
| 1i | 60.0 | $2.0 \times 10^{-9}$ M |
| 1k |  | $3.5 \times 10^{-9}$ M* |
| 1l |  | $3.2 \times 10^{-9}$ M* |
| 1m |  | $8.6 \times 10^{-9}$ M* |
| 1n |  | $2.7 \times 10^{-9}$ M* |
| 1o |  | $7.1 \times 10^{-9}$ M* |
| 2a | 13.4 | $2.0 \times 10^{-9}$ M |
| 2b | 18.2 | $2.0 \times 10^{-9}$ M |
| 2d | 57.8 | $1.2 \times 10^{-9}$ M |
| 2g |  | $3.1 \times 10^{-8}$ M* |
| 3a | 6.5 |  |
| 3d |  | $9.0 \times 10^{-9}$ M* |
| 3e |  | $1.2 \times 10^{-8}$ M* |
| 3f |  | $4.2 \times 10^{-8}$ M* |
| 3g |  | $2.3 \times 10^{-8}$ M* |
| 3h |  | $3.7 \times 10^{-9}$ M* |
| 3i |  | $1.4 \times 10^{-8}$ M* |
| 3k |  | $1.5 \times 10^{-8}$ M* |
| 3l |  | $2.0 \times 10^{-9}$ M* |
| 3o |  | $1.3 \times 10^{-8}$ M* |
| 3p |  | $1.2 \times 10^{-8}$ M* |
| 3q |  | $3.3 \times 10^{-9}$ M* |
| 5 | 74.4 | $2.9 \times 10^{-10}$ M |
| 6 |  | $2.4 \times 10^{-9}$ M |
| 8 | 71.2 | $2.7 \times 10^{-9}$ M |
| 14 |  | $3.0 \times 10^{-10}$ M |
| 15 | 50.3 | $1.8 \times 10^{-9}$ M |
| 17 | 33.2 |  |
| 20 | 41.1 |  |
| 23 | 36.7 |  |
| 29 | 46.4 |  |
| 32 | 53.4 |  |

*IC50 values measured with assay described in Example 110, all other values determined by assay described in Example 109.

Example 111

Measurements of Human Plasma Protein Binding

An aliquot of 200 µL of human plasma containing test compound was spiked into donor well (red chamber) of the insert. 350 µL of PBS was spiked into receiver well (white chamber) of the insert.

The samples were matrix equilibrated with opposite matrix (25 µL of plasma/buffer sample was matched with 25 µL of blank buffer/plasma). Matrix matched samples were precipitated with 200 µL of acetonitrile containing internal standard. Samples were vortexed at 1000 rpm for 5 min and centrifuged at 4000 rpm for 10 min Supernatant was separated, diluted 2 fold with water and analysed in LC-MS/MS. TO control samples were processed immediately after the preparation of plasma working stock solutions. These samples serves as a measure for calculating the percentage recovery of test compounds.

TABLE 2

| Compound | % Unbound in Plasma | % Bound in Plasma | % Recovery |
|---|---|---|---|
| Sildenafil | 3.59 | 96.41 | 104.15 |
| Mirodenafil | 1.06 | 98.94 | 99.25 |
| 14 | 0.57 | 99.43 | 98.91 |
| 5 | 0.13 | 99.87 | 101.69 |
| 2c | 0.35 | 99.65 | 104.73 |
| 1b | 0.05 | 99.95 | 100.31 |
| Warfarin | 2.72 | 97.28 | 100.72 |

Example 112

Measurements of cGMP in Human Pulmonary Artery Smooth Muscle Cells (hPASMC)

Human Pulmonary Artery Smooth Muscle Cells (hPASMC) were purchased from Clonetics™ Lonza (Lonza, reference number CC-2581) and cultured in Clonetics™ smooth muscle growth medium (Clonetics™ SmGM™-2 with BulletKit™ growth factor supplements (Lonza, reference number CC-3182) at 37° C. in 5% $CO_2$. Culture medium was replaced each 48 hours. Cells were grown in 75 cm culture plates.

48 h before the experiments, cells were trypsinized (Trypsin kit One ReagentPack™ (CC-5034), Lonza) and plated in 96 well plates precoated with collagen I at 10000 cells per well. 24 h before the experiments culture medium was replaced by serum-reduced (0.5% FBS) medium. Immediately before the experiments, medium was exchanged and hPASMC incubated in presence of the inventive compounds 1b and 1i (in concentrations of $1 \times 10^{-13}$M (0.1 pM)-$1 \times 10^{-6}$M (1 uM)), or vehicle (0.1% DMSO) over 30 min.

Figure 3:
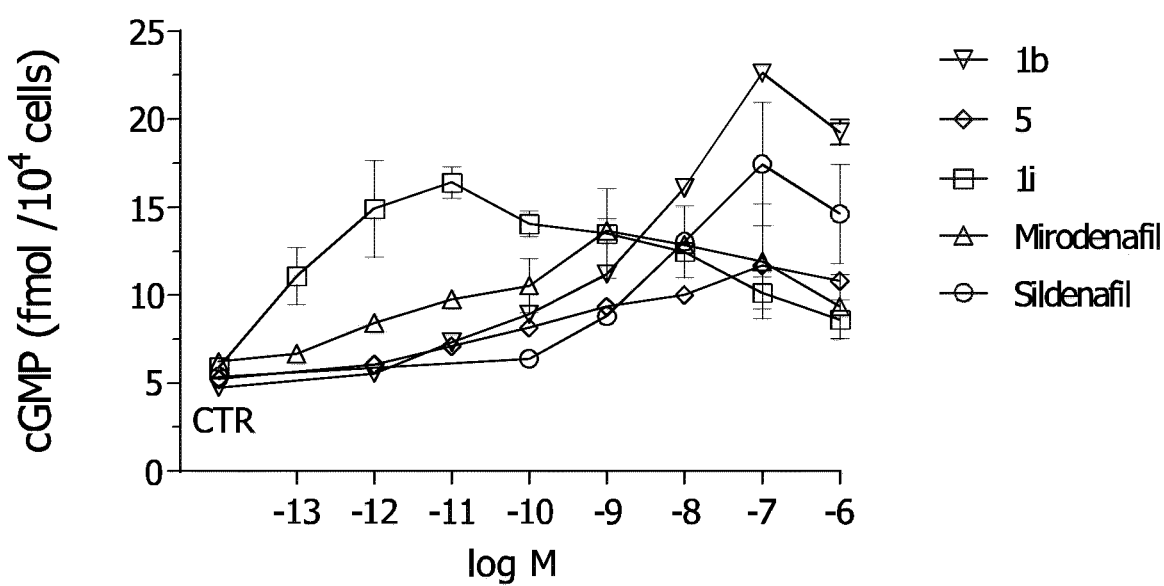
FIG. 3: Concentration dependent measurements of cyclic guanosine 3'-5'-monophosphate (cGMP) in human pulmonary artery smooth muscle cells (hPASMC) incubated in presence of the compounds of the inventions or the reference PDE5 inhibitor sildenafil and mirodenafil.

Measurements of intracellular cGMP were performed using the Amersham cGMP EIA System (GE Healthcare, RPN226) following the instructions of the manufacturer. The assay has a sensitivity of 2 fmol cGMP per well. Briefly, incubations were terminated by adding Amersham's lysis buffer 1 and cells left for 10 min under agitation to ensure complete lysis. cGMP in samples was then acetylated using triethylamine and acetic anhydride and determined by a competitive ELISA. The ELISA is based on the competition between acetylated cGMP in cell culture lysates and a peroxidase-labelled cGMP conjugate for limited binding sites on a cGMP specific antiserum immobilized on pre-coated 96 well MTP. cGMP was determined based on a standard curve. Results were expressed as fmol cGMP in $10^4$ cells as means+/−SE from 3 independent experiments in triplicates (FIG. 3). Surprisingly, the inventive compounds 1b and 1i show a significantly higher efficacy in increasing cGMP level as compared to the reference inhibitor sildenafil, mirodenafil or compound 5, which is a much more potent PDE5 inhibitor (see Table 1, Example 110) compared to the inventive compounds 1b and 1i.

The invention claimed is:

1. A compound of formula I

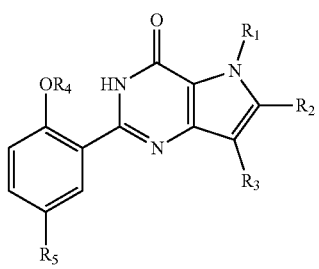

or pharmaceutically acceptable salt, solvate or hydrate thereof, wherein $R_1$ is $C_1$-$C_3$alkyl optionally substituted with F;

$R_2$ is H, $C_1$-$C_3$alkyl optionally substituted with OH; CHO, CN, or $CR_8$=N—$OR_9$;

$R_3$ is $C_1$-$C_4$alkyl optionally substituted with F, $C_1$-$C_3$alkoxy, or $C_3$-$C_6$cycloalkyl;

$R_4$ is $C_1$-$C_6$alkyl optionally substituted with $C_1$-$C_6$alkoxy;

$R_5$ is $SO_2NR_{13}NR_{14}$;

$R_8$ is H, $CH_3$ or $C_2H_5$;

$R_9$ is H or $C_1$-$C_3$ alkyl optionally substituted with OH;

$R_{13}$ and $R_{14}$, together with the nitrogen atom to which they are attached, form a heterocyclic ring, wherein said heterocyclic ring is substituted with at least one $R_{15}$; and $R_{15}$ is $C_1$-$C_6$alkyl substituted with at least one ONO or $ONO_2$, and is optionally substituted with OH.

2. The compound according to claim 1, wherein $R_1$ is $C_1$-$C_3$alkyl.

3. The compound according to claim 1, wherein $R_2$ is H.

4. The compound according to claim 1, wherein $R_3$ is $C_1$-$C_4$alkyl.

5. The compound according to claim 1, wherein $R_4$ is $C_1$-$C_4$alkyl optionally substituted with $C_1$-$C_3$alkoxy.

6. The compound according to claim 1, wherein $R_{15}$ is $C_1$-$C_4$alkyl substituted with at least one ONO or $ONO_2$, and is optionally substituted with OH.

7. The compound according to claim 1, wherein said compound of formula I is a compound of formula I*, or pharmaceutically acceptable salt, solvate or hydrate thereof, wherein

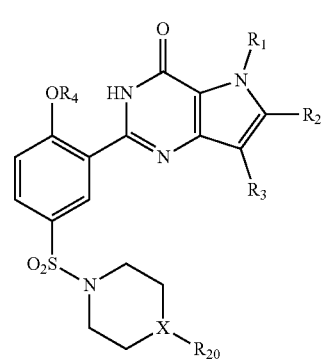

wherein $R_1$, $R_2$, $R_3$, and $R_4$, are as defined in claim 1; and wherein

X is $CR_{21}$ or N;

$R_{20}$ is $C_1$-$C_4$alkyl substituted with at least one ONO or $ONO_2$, and is optionally substituted with OH; and $R_{21}$ is H or $C_1$-$C_4$alkyl optionally substituted with OH, ONO, or $ONO_2$.

8. The compound according to claim 7, wherein $R_1$ is $C_1$-$C_3$alkyl;

$R_2$ is H, $C_1$-$C_3$alkyl optionally substituted with CHO, CN, or $CR_8$=N—$OR_9$;

$R_8$ is independently H or $CH_3$;

$R_9$ is H or $C_1$-$C_3$alkyl optionally substituted with OH;

$R_3$ is $C_1$-$C_4$alkyl;

$R_4$ is $C_1$-$C_4$alkyl optionally substituted with $C_1$-$C_3$alkoxy;

$R_{20}$ is $C_1$-$C_4$alkyl substituted with at least one ONO or $ONO_2$, and is optionally substituted with OH; and $R_{21}$ is H or $C_1$-$C_4$alkyl optionally substituted with halogen, OH, ONO, or $ONO_2$.

9. The compound according to claim 7, wherein $R_1$ is $C_1$-$C_2$alkyl;

$R_2$ is H, $C_1$-$C_3$alkyl optionally substituted with OH; CHO, or $CR_8$=N—$OR_9$;

$R_8$ is H or $CH_3$;

$R_9$ is H or $C_1$-$C_3$alkyl optionally substituted with OH;

$R_3$ is $C_2$-$C_3$alkyl;

$R_4$ is $C_2$-$C_3$alkyl;

$R_{20}$ is $C_1$-$C_3$alkyl substituted with one, two or three substituents selected from OH, ONO and $ONO_2$ wherein $R_{20}$ is substituted with at least one $ONO_2$ or ONO moiety; and $R_{21}$ is H or $C_1$-$C_3$alkyl substituted with one or two substituents selected from OH, ONO and $ONO_2$.

10. The compound according to claim 1, wherein said compound of formula I is a compound of formula I**, or pharmaceutically acceptable salt, solvate or hydrate thereof, wherein at least one of $R_{22}$, $R_{23}$ or $R_{24}$ independently of each other comprises at least one $ONO_2$ or ONO moiety;

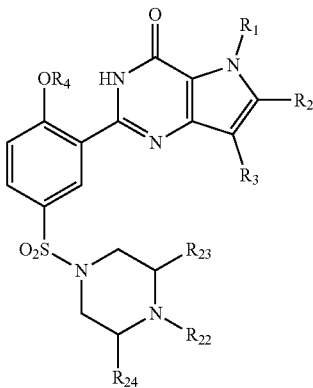

wherein $R_1$, $R_2$, $R_3$, and $R_4$, are as defined in claim 1; and wherein $R_{22}$ is H or $C_1$-$C_4$alkyl optionally substituted with OH, ONO, or $ONO_2$; and $R_{23}$ and $R_{24}$ are each independently $C_1$-$C_4$alkyl optionally substituted with OH, ONO, or $ONO_2$.

11. The compound according to claim 10, wherein said $R_{22}$ is $C_1$-$C_2$alkyl; and $R_{23}$ and $R_{24}$ are each independently $C_1$-$C_3$alkyl substituted with OH, ONO or $ONO_2$ wherein at least one of $R_{23}$ and $R_{24}$ is substituted with ONO or $ONO_2$.

12. The compound according to claim 1, wherein $R_{13}$ and $R_{14}$ together with the nitrogen atom to which they are attached form a heterocyclic ring, wherein said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, and wherein said heterocyclic ring is optionally substituted with $R_{15}$.

13. The compound according to claim 1, wherein $R_8$ is H or $CH_3$.

14. The compound according to claim 10, wherein said $R_{22}$ is methyl; and $R_{23}$ and $R_{24}$ are each independently $C_1$-$C_3$alkyl substituted with ONO or $ONO_2$.

15. The compound according to claim 1, wherein $R_2$ is CHO.

16. The compound according to claim 1, wherein $R_2$ is CH=N—$OR_9$, wherein $R_9$ is H.

17. The compound according to claim 1, wherein said compound is 2-(4-((3-(5-ethyl-4-oxo-7-propyl-4,5-dihydro-3H-pyrrolo[3,2-d]pyrimidin-2-yl)-4-propoxyphenyl)sulfonyl)piperazin-1-yl)ethyl nitrate, or a pharmaceutically acceptable salt or hydrate thereof.

18. The compound of claim 1, wherein said compound is (1-((3-(5-ethyl-4-oxo-7-propyl-4,5-dihydro-3H-pyrrolo[3,2-d]pyrimidin-2-yl)-4-propoxyphenyl)sulfonyl)piperidine-4,4-diyl)bis(ethane-2,1-diyl) dinitrate, or a pharmaceutically acceptable salt or hydrate thereof.

19. A pharmaceutical composition comprising at least one compound of formula I of claim 1, or a pharmaceutically acceptable salt, solvate or hydrate thereof, and a pharmaceutically acceptable excipient, adjuvant, or carrier.

20. A pharmaceutical composition comprising the 2-(44 (3-(5-ethyl-4-oxo-7-propyl-4,5-dihydro-3H-pyrrolo[3,2-d]pyrimidin-2-yl)-4-propoxyphenyl)sulfonyl)piperazin-1-yl) ethyl nitrate of claim 17, or a pharmaceutically acceptable salt or hydrate thereof, and a pharmaceutically acceptable excipient, adjuvant, or carrier.

21. A pharmaceutical composition comprising the (14(3-(5-ethyl-4-oxo-7-propyl-4,5-dihydro-3H-pyrrolo[3,2-d]pyrimidin-2-yl)-4-propoxyphenyl)sulfonyl)piperidine-4,4-diyl)bis(ethane-2,1-diyl) dinitrate of claim 18, or a pharmaceutically acceptable salt or hydrate thereof, and a pharmaceutically acceptable excipient, adjuvant, or carrier.

\* \* \* \* \*

UNITED STATES PATENT AND TRADEMARK OFFICE
CERTIFICATE OF CORRECTION

PATENT NO. : 11,905,293 B2
APPLICATION NO. : 17/477122
DATED : February 20, 2024
INVENTOR(S) : Reto Naef and Hermann Tenor Page 1 of 1

It is certified that error appears in the above-identified patent and that said Letters Patent is hereby corrected as shown below:

In the Claims

Claim 8, Column 158, Lines 34-35 replace "$R_2$ is H, $C_1$-$C_3$alkyl optionally substituted with CHO, CN, or $CR_8$=N-$OR_9$" with -- $R_2$ is H, $C_1$-$C_3$alkyl optionally substituted with OH, CHO, CN, or $CR_8$=N-$OR_9$; --

Claim 20, Column 160, Lines 24-26 replace "A pharmaceutical composition comprising the 2-(44(3-(5-ethyl-4-oxo-7-propyl-4,5-dihydro-3H-pyrrolo[3,2-d]pyrimidin-2-yl)-4-propoxyphenyl)sulfonyl)piperazin-1-yl)" with -- A pharmaceutical composition comprising the 2-(4-(3-(5-ethyl-4-oxo-7-propyl-4,5-dihydro-3H-pyrrolo[3,2-d]pyrimidin-2-yl)-4-propoxyphenyl)sulfonyl)piperazin-1-yl) --

Claim 21, Column 160, Lines 30-33 replace "A pharmaceutical composition comprising the (14(3-(5-ethyl-4-oxo-7-propyl-4,5-dihydro-3H-pyrrolo[3,2-d]pyrimidin-2-yl)-4-propoxyphenyl)sulfonyl)piperidine-4,4-diyl)bis(ethane-2,1-diyl) dinitrate of claim 18, or a" with -- A pharmaceutical composition comprising the (1-((3-(5-ethyl-4-oxo-7-propyl-4,5-dihydro-3H-pyrrolo[3,2-d]pyrimidin-2-yl)-4-propoxyphenyl)sulfonyl)piperidine-4,4-diyl)bis(ethane-2,1-diyl) dinitrate of claim 18, or a --

Signed and Sealed this
Eighteenth Day of June, 2024

Katherine Kelly Vidal
*Director of the United States Patent and Trademark Office*